(12) United States Patent
Wittwer et al.

(10) Patent No.: US 10,900,074 B2
(45) Date of Patent: Jan. 26, 2021

(54) EXTREME REVERSE TRANSCRIPTION PCR

(71) Applicant: University of Utah Research Foundation, Salt Lake City, UT (US)

(72) Inventors: Carl T. Wittwer, Salt Lake City, UT (US); John Francis Quackenbush, Salt Lake City, UT (US); Jessica Anne Houskeeper, Wellington, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 44 days.

(21) Appl. No.: 15/771,968

(22) PCT Filed: Nov. 4, 2016

(86) PCT No.: PCT/US2016/060650
§ 371 (c)(1),
(2) Date: Apr. 27, 2018

(87) PCT Pub. No.: WO2017/079636
PCT Pub. Date: May 11, 2017

(65) Prior Publication Data
US 2019/0002954 A1    Jan. 3, 2019

Related U.S. Application Data

(60) Provisional application No. 62/251,400, filed on Nov. 5, 2015.

(51) Int. Cl.
*C12Q 1/686* (2018.01)
*B01L 7/00* (2006.01)

(52) U.S. Cl.
CPC .............. *C12Q 1/686* (2013.01); *B01L 7/525* (2013.01); *B01L 7/5255* (2013.01); *B01L 2300/185* (2013.01)

(58) Field of Classification Search
CPC .............. C12Q 1/686; C12Q 2521/107; C12Q 2527/113; C12Q 2527/125; C12Q 2527/143; C12Q 2527/149; B01L 2300/185; B01L 7/525; B01L 7/5255
See application file for complete search history.

(56) References Cited

U.S. PATENT DOCUMENTS

| | | |
|---|---|---|
| 5,436,149 A | 7/1995 | Barnes |
| 6,020,130 A | 2/2000 | Gold et al. |
| 6,210,882 B1 | 4/2001 | Landers et al. |
| 6,706,617 B2 | 3/2004 | Park |
| 8,003,370 B2 | 8/2011 | Maltezos et al. |
| 2008/0248535 A1 | 10/2008 | Ankenbauer et al. |
| 2009/0269766 A1 | 10/2009 | Heindl et al. |
| 2009/0325169 A1 | 12/2009 | Walder et al. |
| 2010/0124765 A1 | 5/2010 | Lao et al. |
| 2011/0039305 A1 | 2/2011 | Termaat, Jr. et al. |
| 2012/0003645 A1 | 1/2012 | Yim et al. |
| 2012/0214207 A1 | 8/2012 | Gunter et al. |
| 2014/0141422 A1 | 5/2014 | Wang et al. |
| 2014/0199699 A1 | 7/2014 | Lee et al. |
| 2015/0118715 A1 | 4/2015 | Wittwer et al. |

FOREIGN PATENT DOCUMENTS

| | | |
|---|---|---|
| CN | 101407850 | 4/2009 |
| EP | 0 511 712 A1 | 11/1992 |
| WO | WO 95/04161 A1 | 2/1995 |
| WO | WO 97/11085 A1 | 3/1997 |
| WO | WO 2015/069743 A1 | 5/2015 |

OTHER PUBLICATIONS

Extended European Search Report corresponding to European Patent Application No. 16863087.9 (17 pages) (dated Feb. 5, 2019).
Gerard et al. "Reverse Transcriptase (EC 2.7.7.49)" *Methods in Molecular Biology* 16(Chapter 6):73-93 (1993).
International Search Report and the Written Opinion of the International Searching Authority corresponding to International Patent Application No. PCT/US16/60650 (17 pages) (dated Jan. 24, 2017).
Promega "GoTaq® 1-Step RT-qPCR System" *Technical Manual* (13 pages) (2014).
Agarwal et al. "Effect of Ramp Rates During Rapid Thermal Annealing of Iron Implanted Boron for Formation of Ultra-Shallow Junctions" *Journal of Electronic Materials* 28(12):1333-1339 (1999).
Agrawal et al. "A Pocket-Sized Convective PCR Thermocycler" *Angewandte Chemie (International ed. in English)* 46:4316-4319 (2007).
Belgrader et al. "Rapid pathogen detection using a microchip PCR array instrument" *Clinical Chemistry* 44(10):2191-2194 (1998).
Brown et al. "Rapid Cycle Amplification for Construction of Competitive Templates" *Genetic Engineering with PCR* pp. 57-70 (1998).
Brownie et al. "The elimination of primer-dimer accumulation in PCR" *Nucleic Acids Research* 25(16):3235-3241 (1997).
Bustin et al. "Variability of the Reverse Transcription Step: Practical Implications" *Clinical Chemistry* 61(1):202-212 (2015).
Carninci et al. "Thermostabilization and thermoactivation of thermolabile enzymes by trehalose and its application for the synthesis of full length cDNA" *Proceedings of the National Academy of Sciences USA* 95:520-524 (1998).
Chandler et al. "Reverse Transcriptase (RT) Inhibition of PCR at Low Concentrations of Template and Its Implications for Quantitative RT-PCR" *Applied and Environmental Microbiology* 64(2):669-677 (1998).
Chen et al. "Selection of high-affinity RNA ligands to reverse transcriptase: inhibition of cDNA synthesis and RNase H activity" *Biochemistry* 33(29):8746-8756 (1994) (Abstract only).

(Continued)

*Primary Examiner* — Cynthia B Wilder
(74) *Attorney, Agent, or Firm* — Myers Bigel, P.A.

(57) ABSTRACT

Methods, kits and mixtures are provided for performing RT-PCR with an RT incubation of no more than one minute and PCR cycles in <20 seconds per cycle.

19 Claims, 67 Drawing Sheets
Specification includes a Sequence Listing.

(56) References Cited

OTHER PUBLICATIONS

Chen et al. "Electrokinetically Synchronized Polymerase Chain Reaction Microchip Fabricated in Polycarbonate" *Analytical Chemistry* 77:658-666 (2005).

Cheng et al. "Chip PCR. II. Investigation of different PCR amplification systems in microfabricated silicon-glass chips" *Nucleic Acids Research* 24(2):380-385 (1996).

Chiou et al. "Thirty-Cycle Temperature Optimization of a Closed-Cycle Capillary PCR Machine" *BioTechniques* 33:557-564 (2002).

Crews et al. "Continuous-flow thermal gradient PCR" *Biomedical Microdevices* 10:187-195 (2008).

Czerny, Thomas "High primer concentration improves PCR amplification from random pools" *Nucleic Acids Research* 24(5):985-986 (1996).

Dang et al. "Oligonucleotide inhibitors of Taq DNA polymerase facilitate detection of low copy number targets by PCR" *Journal of Molecular Biology* 264(2):268-278 (1996) (Abstract only).

Di Giusto et al. "Single Base Extension (SBE) with Proofreading. Polymerases and Phosphorothioate Primers: Improved Fidelity in Single-Substrate Assays" *Nucleic Acids Research* 31(3):1-12 (2003).

Elenitoba-Johnson et al. "Plastic versus glass capillaries for rapid-cycle PCR" *BioTechniques* 44:487-492 (2008).

Erlich, Henry A. "The Design and Optimization of the PCR" *PCR Technology: Principles and Applications for DNA Amplification* Chapter 1:8-16 (1989).

Farrar et al. "Extreme PCR: Efficient and Specific DNA Amplification in 15-60 Seconds" *Clinical Chemistry* 61(1):145-153 (2015).

Frey et al. "Autonomous microfluidic multi-channel chip for real-time PCR with integrated liquid handling" *Biomedical Microdevices* 9:711-718 (2007).

Friedman et al. "Capillary Tube Resistive Thermal Cycling" *Analytical Chemistry* 70:2997-3002 (1998).

Fuchiwaki et al. "A Practical Liquid Plug Flow-through Polymerase Chain-Reaction System Based on a Heat-Resistant Resin Chip" *Analytical Sciences* 27:225-230 (2011).

Fuchiwaki et al. "Study of DNA Amplification Efficiency Based on Temperature Analyses of the Moving Fluid in a Liquid-Plug Flow PCR System" *Bulletin of the Chemical Society of Japan* 84(10):1075-1081 (2011).

Fuchiwaki et al. "Ultra-rapid flow-through polymerase chain reaction microfluidics using vapor pressure" *Biosensors and Bioelectronics* 27:88-94 (2011).

Gerard et al. "Reverse Transcriptase (EC 2.7.7.49): The Use of Cloned Moloney Leukemia Virus Reverse Transcriptase to Synthesize DNA from RNA" *Methods in Molecular Biology* 16(chapter 6):73-93 (1993).

Giordano et al. "Polymerase Chain Reaction in Polymeric Microchips: DNA Amplification in Less Than 240 Seconds" *Analytical Biochemistry* 291:124-132 (2001).

Gundry et al. "Obtaining Maximum PCR Sensitivity and Specificity" *PCR Troubleshooting and Optimization: The Essential Guide* Chapter 4:79-96 (2011).

Hashimoto et al. "Rapid PCR in a continuous flow device" *Lab Chip* 4:638-645 (2004).

Heap et al. "PCR Amplification Using Electrolytic Resistance for Heating and Temperature Monitoring" *Bio Techniques* 29:1006-1012 (2000).

Herrmann et al. "Amplicon DNA Melting Analysis for Mutation Scanning and Genotyping: Cross-Platform Comparison of Instruments and Dyes" *Clinical Chemistry* 52(3):494-503 (2006).

Herrmann et al. "Expanded Instrument Comparison of Amplicon DNA Melting Analysis for Mutation Scanning and Genotyping" *Clinical Chemistry* 53(8):1544-1548 (2007).

Innis et al. "DNA sequencing with *Thermus aquaticus* DNA polymerase and direct sequencing of polymerase chain reaction-amplified DNA" *Proceedings of the National Academy of Sciences* 85:9436-9440 (1988).

Innis et al. "Optimization of PCRs" *PCR Protocols: A Guide to Methods and Applications* Chapter 1:3-12 (1990).

International Preliminary Report on Patentability corresponding to International Patent Application no. PCT/US2016/060650 (17 pages) (dated Jun. 1, 2018).

Kim et al. "Nanodroplet real-time PCR system with laser assisted heating" *Optics Express* 17(1):218-227 (2009).

Kopp et al. "Chemical Amplification: Continuous-Flow PCR on a Chip" *Science* 280(5366):1046-1048 (1998).

Lao et al. "A Non-Contact Micro Thermocycling Chip for Polymerase Chain Reactions" *International Journal of Computational Engineering Science* 4(3):651-654 (2003) (Abstract only).

Lawyer et al. "High-level Expression, Purification, and Enzymatic Characterization of Full-length *Thermus aquaticus* DNA Polymerase and a Truncated Form Deficient in 5' to 3' Exonuclease Activity" *Genome Research* 2:275-287 (1993).

Lin et al. "Inhibition of multiple thermostable DNA polymerases by a heterodimeric aptamer" Journal of Molecular Biology 271(1):100-111 (1997) (Abstract only).

Maltezos et al. "Exploring the limits of ultrafast polymerase chain reaction using liquid for thermal heat exchange: A proof of principle" *Applied Physics Letters* 97:264101 (2010).

Mijatovic-Rustempasic et al. "Sensitive and Specific Quantitative Detection of Rotavirus a by One-Step Real-Time Reverse Transcription-PCR Assay without Antecedent Double-Stranded-RNA Denaturation" *Journal of Clinical Microbiology* 51(9):3047-3054 (2013).

Montgomery et al. "Stopped-flow DNA polymerase assay by continuous monitoring of dNTP incorporation by fluorescence" *Analytical Biochemistry* 441:133-139 (2013).

Montgomery et al. "Influence of PCR Reagents on DNA Polymerase Extension Rates Measured on Real-Time PCR Instruments" *Clinical Chemistry* 60(2):334-340 (2014).

Neuzil et al. "Ultra fast miniaturized real-time PCR: 40 cycles in less than six minutes" *Nucleic Acids Research* 34(11):e77 (2006).

Noma et al. "Aptamer selection based on inhibitory activity using an evolution-mimicking algorithm" *Biochemical and Biophysical Research Communications* 347(1):226-231 (2006) (Abstract only).

Obeid et al. "Microfabricated Device for DNA and RNA Amplification by Continuous-Flow Polymerase Chain Reaction and Reverse Transcription-Polymerase Chain Reaction with Cycle Number Selection" *Analytical Chemistry* 75:288-295 (2003).

Oda et al. "Infrared-Mediated Thermocycling for Ultrafast Polymerase Chain Reaction Amplification of DNA" *Analytical Chemistry* 70:4361-4368 (1998).

Pal et al. "A power-efficient thermocycler based on induction heating for DNA amplification by polymerase chain reaction" *Review of Scientific Instruments* 75(9):2880-2883 (2004).

Raja et al. "Temperature-controlled Primer Limit for Multiplexing of Rapid, Quantitative Reverse Transcription-PCR Assays: Application to Intraoperative Cancer Diagnostics" *Clinical Chemistry* 48(8):1329-1337 (2002).

Ririe et al. "Product Differentiation by Analysis of DNA Melting Curves during the Polymerase Chain Reaction" *Analytical Biochemistry* 245:154-160 (1997).

Roper et al. "Advances in Polymerase Chain Reaction on Microfluidic Chips" *Analytical Chemistry* 77:3887-3894 (2005).

Roper et al. "Infrared Temperature Control System for a Completely Noncontact Polymerase Chain Reaction in Microfluidic Chips" *Analytical Chemistry* 79:1294-1300 (2007).

Schoder et al. "Novel Approach for Assessing Performance of PCR Cyclers Used for Diagnostic Testing" *Journal of Clinical Microbiology* 43(6):2724-2728 (2005).

Sellner et al. "Reverse transcriptase inhibits Taq polymerase activity" *Nucleic Acids Research* 20(7):1487-1490 (1992).

Shen et al. "Multiplexed Quantification of Nucleic Acids with Large Dynamic Range Using Multivolume Digital RT-PCR on a Rotational SlipChip Tested with HIV and Hepatitis C Viral Load" *Journal of the American Chemical Society* 133:17705-17712 (2011).

Smith, Caitlin "Fast PCR: A Relay Between Instrument and Enzyme" *Biocompare Editorial Article* (3 pages) (Jan. 21, 2008).

Sun et al. "A circular ferrofluid driven microchip for rapid polymerase chain reaction" *Lab Chip* 7:1012-1017 (2007).

Suslov et al. "PCR inhibition by reverse transcriptase leads to an overestimation of amplification efficiency" *Nucleic Acids Research* 33(20):1-12 (2005).

(56) References Cited

OTHER PUBLICATIONS

"TaqMan® EZ RT-PCR Kit: Protocol" 50 pages (2002).
"Taq PCR Kit: Instruction Manual" 16 pages (2009).
Terazono et al. "Development of 1480 nm Photothermal High-Speed Real-Time Polymerase Chain Reaction System for Rapid Nucleotide Recognition" *Japanese Journal of Applied Physics* 47(6):5212-5216 (2008).
Terazono et al. "Development of a High-Speed Real-Time Polymerase Chain Reaction System Using a Circulating Water-Based Rapid Heat-Exchange" *Japanese Journal of Applied Physics* 49:1-5 (2010).
Von Ahsen et al. "Oligonucleotide Melting Temperatures under PCR Conditions: Nearest-Neighbor Corrections for $Mg^{2+}$, Deoxynucleotide Triphosphate, and Dimethyl Sulfoxide Concentrations with Comparison to Alternative Empirical Formulas" *Clinical Chemistry* 47(11):1956-1961 (2001).
Von Kanel et al. "Sample Number and Denaturation Time are Crucial for the Accuracy of Capillary-Based LightCyclers" *Clinical Chemistry* 53(7):1392-1394 (2007).
Weis et al. "Detection of rare mRNAs via quantitative RT-PCR" *Trends in Genetics* 8(8):263-264 (1992).
Wheeler et al. "Convectively Driven Polymerase Chain Reaction Thermal Cycler" *Analytical Chemistry* 76:4011-4016 (2004).
Wheeler et al. "Under-three minute PCR: Probing the limits of fast amplification" *Analyst* 136:3707-3712 (2011).
Whitney, Scott E. "Analysis of Rapid Thermocycling for the Polymerase Chain Reaction" *Dissertation* (267 pages) (May 2004).
Wilhelm et al. "Influence of Dna Target Melting Behavior on Real-Time PCR Quantification" *Clinical Chemistry* 46(11):1738-1743 (2000).
Wittwer et al. "Automated polymerase chain reaction in capillary tubes with hot air" *Nucleic Acids Research* 17(11):4353-4357 (1989).
Wittwer et al. "Minimizing the Time Required for DNA Amplification by Efficient Heat Transfer to Small Samples" *Analytical Biochemistry* 186:328-331 (1990).
Wittwer et al. "Rapid Cycle DNA Amplification: Time and Temperature Optimization" *BioTechniques* 10(1):76-83 (1991).
Wittwer et al. "Rapid Cycle Allele-Specific Amplification: Studies with the Cystic Fibrosis $\Delta F_{508}$ Locus" *Clinical Chemistry* 39(5):804-809 (1993).
Wittwer et al. "Rapid Cycle DNA Amplification" *The Polymerase Chain Reaction* 15:174-181 (1994).
Wittwer et al. "Continuous Fluorescence Monitoring of Rapid Cycle DNA Amplification" *BioTechniques* 22:130-138 (1997).
Wittwer et al. "The LightCycler™: A Microvolume Multisample Fluorimeter with Rapid Temperature Control" *BioTechniques* 22:176-181 (1997).
Wittwer et al. "Fluorescence Monitoring of Rapid Cycle PCR for Quantification" *Gene Quantification* pp. 129-144 (1998).
Wittwer et al. "Rapid Thermal Cycling and PCR Kinetics" *PCR Methods Manual* 14:211-229 (1999).
Wittwer et al. "High-Resolution Genotyping by Amplicon Melting Analysis Using LCGreen" *Clinical Chemistry* 49(6):853-860 (2003).
Wittwer et al. "Rapid polymerase chain reaction and melting analysis" *The PCR Revolution: Basic Technologies and Applications* (pp. 48-69) (2010).
Woolley et al. "Functional Integration of PCR Amplification and Capillary Electrophoresis in a Microfabricated DNA Analysis Device" *Analytical Chemistry* 68:4081-4086 (1996).
Zhang et al. "PCR microfluidic devices for DNA amplification" *Biotechnology Advances* 24:243-284 (2006).
Zhang et al. "Miniaturized PCR chips for nucleic acid amplification and analysis: latest advances and future trends" *Nucleic Acids Research* 35(13):4223-4237 (2007).
Zuna et al. "Temperature Non-homogeneity in Rapid Airflow-Based Cycler Significantly Affects Real-Time PCR" *Bio Techniques* 33:508-512 (2002).

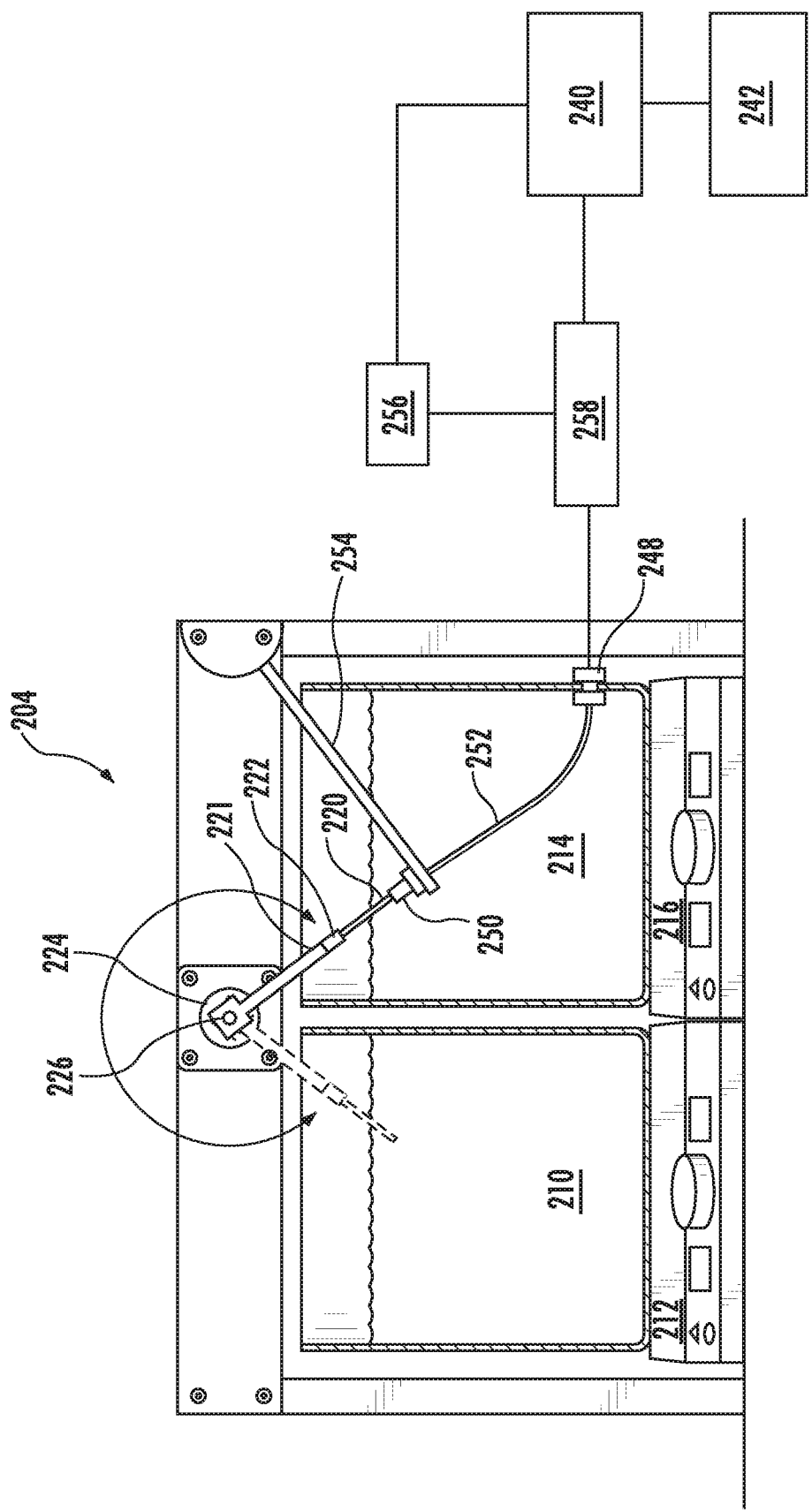

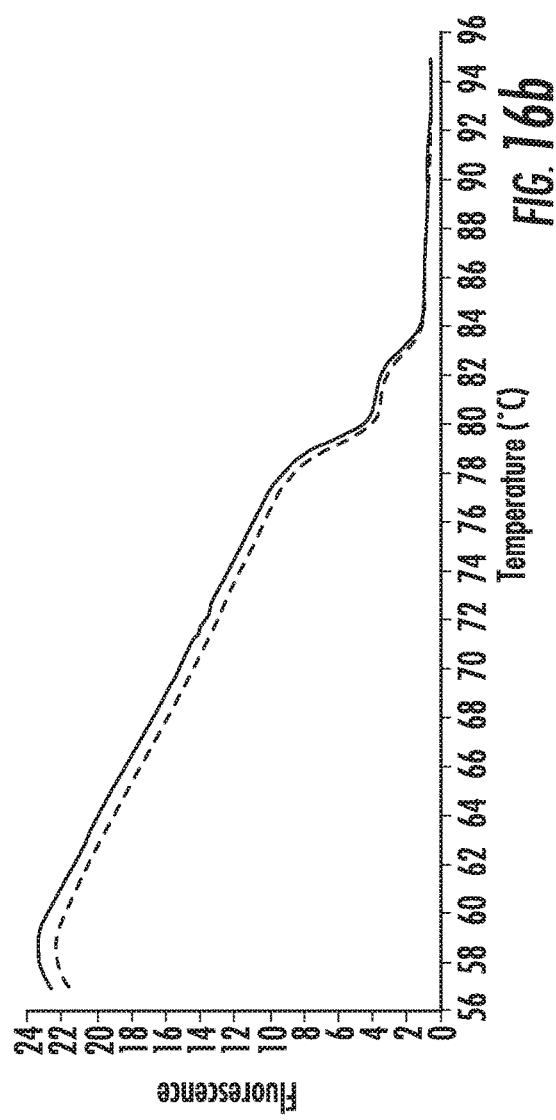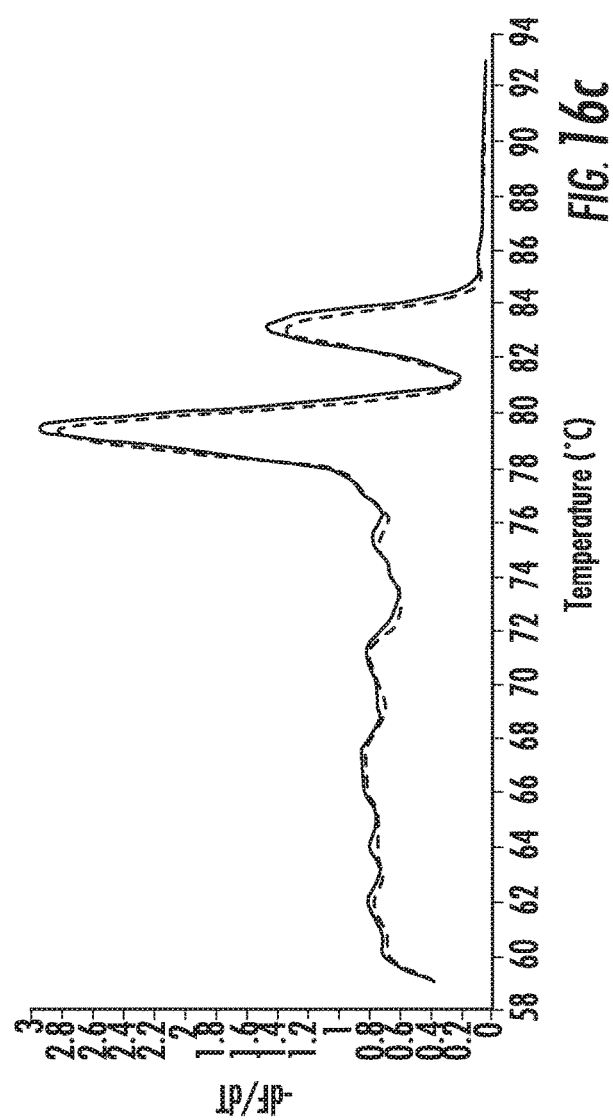

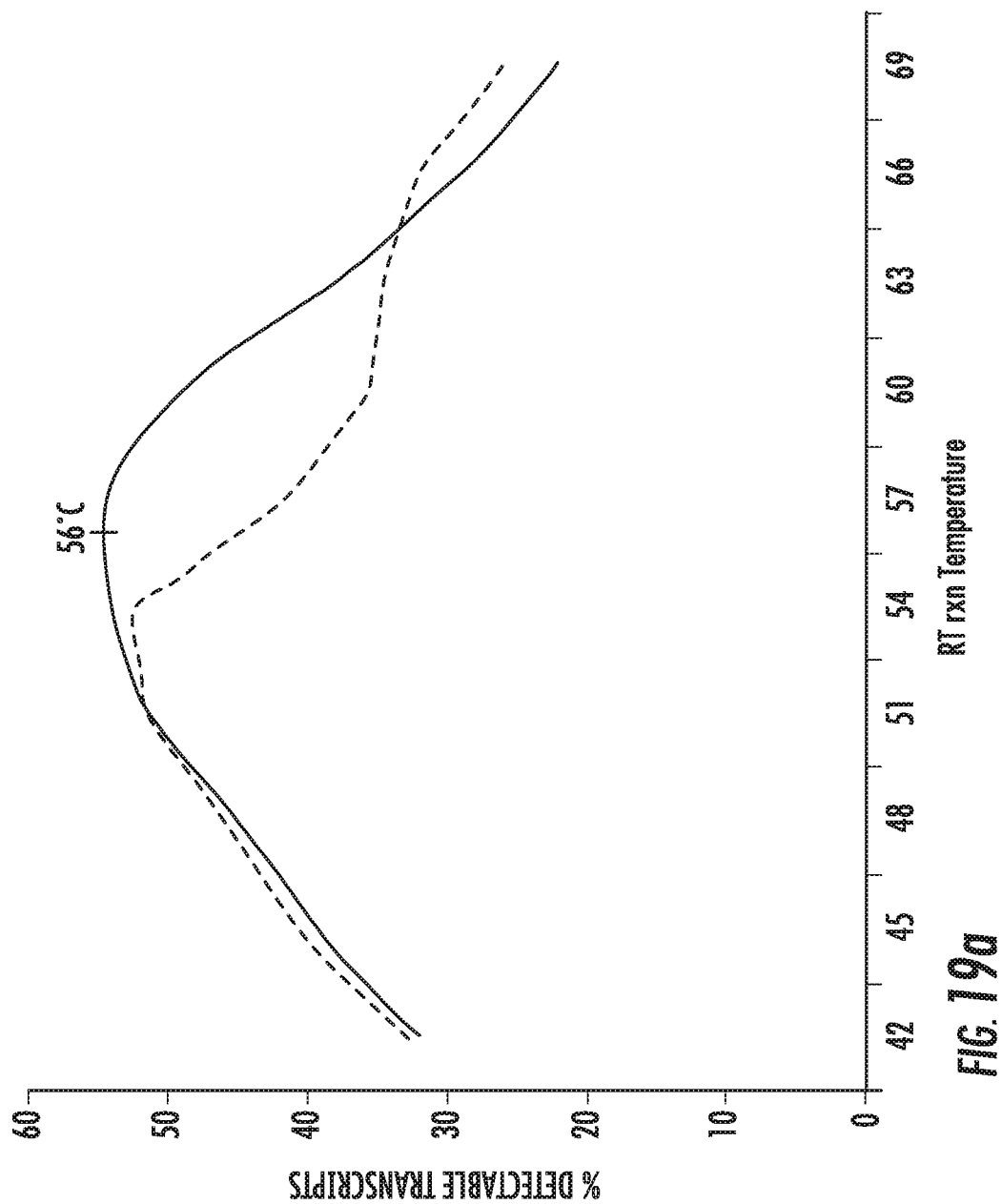

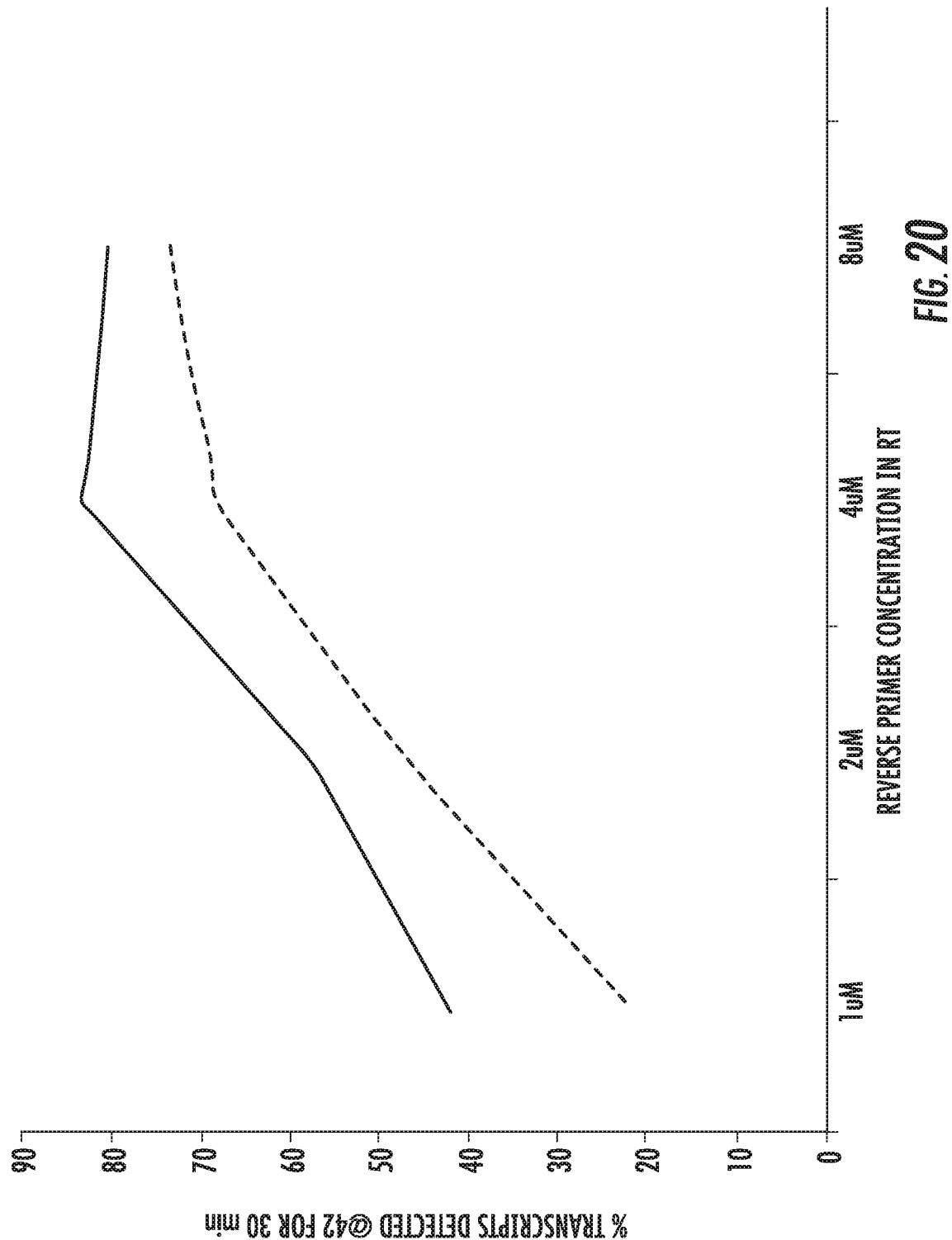

SEQUENCE LISTING

```
<160> NUMBER OF SEQ ID NOS: 42

<210> SEQ ID NO 1
<211> LENGTH: 24
<212> TYPE: DNA
<213> ORGANISM: Homo sapiens

<400> SEQUENCE: 1
cccattcaac gtctacatcg agtc                                          24

<210> SEQ ID NO 2
<211> LENGTH: 19
<212> TYPE: DNA
<213> ORGANISM: Homo sapiens

<400> SEQUENCE: 2
tccttctctt gccaggcat                                                19

<210> SEQ ID NO 3
<211> LENGTH: 45
<212> TYPE: DNA
<213> ORGANISM: Homo sapiens
<220> FEATURE:
<221> NAME/KEY: mutation
<222> LOCATION: (23)..(23)
<223> OTHER INFORMATION: G or A residue

<400> SEQUENCE: 3
cccattcaac gtctacatcg agtccgatgc ctggcaagag aagga                   45

<210> SEQ ID NO 4
<211> LENGTH: 20
<212> TYPE: DNA
<213> ORGANISM: Homo sapiens

<400> SEQUENCE: 4
ctacagtggg agtcacctgc                                               20

<210> SEQ ID NO 5
<211> LENGTH: 25
<212> TYPE: DNA
<213> ORGANISM: Homo sapiens

<400> SEQUENCE: 5
ggtactgagc tgtgaaagtc aggtt                                         25
```

<210> SEQ ID NO 6
<211> LENGTH: 58
<212> TYPE: DNA
<213> ORGANISM: Homo sapiens
<220> FEATURE:
<221> NAME/KEY: mutation
<222> LOCATION: (28)..(28)
<223> OTHER INFORMATION: A or G residue

<400> SEQUENCE: 6
ctacagtggg agtcacctgc ttttgccaaa gggaacctga ctttcacagc tcagtacc        58

<210> SEQ ID NO 7
<211> LENGTH: 20
<212> TYPE: DNA
<213> ORGANISM: Homo sapiens

<400> SEQUENCE: 7
gggagtcacc tgcttttgcc        20

<210> SEQ ID NO 8
<211> LENGTH: 25
<212> TYPE: DNA
<213> ORGANISM: Homo sapiens

<400> SEQUENCE: 8
tactgagctg tgaaagtcag gttcc        25

<210> SEQ ID NO 9
<211> LENGTH: 49
<212> TYPE: DNA
<213> ORGANISM: Homo sapiens

<400> SEQUENCE: 9
gggagtcacc tgcttttgcc aaagggaacc tgactttcac agctcagta        49

<210> SEQ ID NO 10
<211> LENGTH: 34
<212> TYPE: DNA
<213> ORGANISM: Homo sapiens

<400> SEQUENCE: 10
ctctgtgctt tctgtatcct cagagtggca ttct        34

<210> SEQ ID NO 11
<211> LENGTH: 28
<212> TYPE: DNA
<213> ORGANISM: Homo sapiens

<400> SEQUENCE: 11
cgtctgctgg agtgtgccca atgctata        28

<210> SEQ ID NO 12
<211> LENGTH: 60
<212> TYPE: DNA
<213> ORGANISM: Homo sapiens
<220> FEATURE:
<221> NAME/KEY: misc_feature
<222> LOCATION: (1)..(41)
<223> OTHER INFORMATION: 5' standard synthetic region

<400> SEQUENCE: 12
acacacacac acacacacac acacacacac acacacaaaa attcagtggc attaaatacg        60

<210> SEQ ID NO 13
<211> LENGTH: 67
<212> TYPE: DNA
<213> ORGANISM: Homo sapiens
<220> FEATURE:
<221> NAME/KEY: misc_feature
<222> LOCATION: (1)..(50)
<223> OTHER INFORMATION: 5' standard synthetic region

<400> SEQUENCE: 13
gagagagaga gagagagaga gagagagaga gagagagaga gagagaaaaa ccagagctaa      60
agggaag                                                               67

<210> SEQ ID NO 14
<211> LENGTH: 66
<212> TYPE: DNA
<213> ORGANISM: Homo sapiens
<220> FEATURE:
<221> NAME/KEY: misc_feature
<222> LOCATION: (1)..(41)
<223> OTHER INFORMATION: 5' standard synthetic region

<400> SEQUENCE: 14
acacacacac acacacacac acacacacac acacacaaaa agctggtgtc tgctatagaa      60
ctgatt                                                                66

<210> SEQ ID NO 15
<211> LENGTH: 72
<212> TYPE: DNA
<213> ORGANISM: Homo sapiens
<220> FEATURE:
<221> NAME/KEY: misc_feature
<222> LOCATION: (1)..(50)
<223> OTHER INFORMATION: 5' standard synthetic region

<400> SEQUENCE: 15
gagagagaga gagagagaga gagagagaga gagagagaga gagagaaaaa gttgccagag      60
ctaaagggaa gg                                                         72

<210> SEQ ID NO 16
<211> LENGTH: 41
<212> TYPE: DNA
<213> ORGANISM: Artificial Sequence
<220> FEATURE:
<223> OTHER INFORMATION: Synthetic common primer

<400> SEQUENCE: 16
acacacacac acacacacac acacacacac acacacaaaa a                         41

<210> SEQ ID NO 17
<211> LENGTH: 50
<212> TYPE: DNA
<213> ORGANISM: Artificial Sequence
<220> FEATURE:
<223> OTHER INFORMATION: Synthetic common primer

<400> SEQUENCE: 17
gagagagaga gagagagaga gagagagaga gagagagaga gagagaaaaa                50

<210> SEQ ID NO 18
<211> LENGTH: 24
<212> TYPE: DNA
<213> ORGANISM: Artificial Sequence
<220> FEATURE:
<223> OTHER INFORMATION: Synthetic common primer

<400> SEQUENCE: 18
actcgcacga actcaccgca ctcc                                              24

<210> SEQ ID NO 19
<211> LENGTH: 24
<212> TYPE: DNA
<213> ORGANISM: Artificial Sequence
<220> FEATURE:
<223> OTHER INFORMATION: Synthetic common primer

<400> SEQUENCE: 19
actcgcacga actcaccgca ctcc                                              24

<210> SEQ ID NO 20
<211> LENGTH: 100
<212> TYPE: DNA
<213> ORGANISM: Artificial Sequence
<220> FEATURE:
<223> OTHER INFORMATION: Synthetic template

<400> SEQUENCE: 20
actcgcacga actcaccgca ctccggatgg attgtgaaga ggcccaagat actggtcata      60
ttatcctttg atctagctct cactcgcact ctcacgcaca                           100

<210> SEQ ID NO 21
<211> LENGTH: 200
<212> TYPE: DNA
<213> ORGANISM: Artificial Sequence
<220> FEATURE:
<223> OTHER INFORMATION: Synthetic template

<400> SEQUENCE: 21
actcgcacga actcaccgca ctcctcaatg ctgacaaatc gaaagaatag gaatagcgta      60
attactagag gactccaata tagtatatta ccctggtgac cgcctgtact gtaggaacac     120
taccgcggtt atattgacag cttagcaatc taccctgttg ggatctgttt aagtggctct     180
cactcgcact ctcacgcaca                                                 200

<210> SEQ ID NO 22
<211> LENGTH: 300
<212> TYPE: DNA
<213> ORGANISM: Artificial Sequence
<220> FEATURE:
<223> OTHER INFORMATION: Synthetic template

<400> SEQUENCE: 22
actcgcacga actcaccgca ctccccttcg aatataaagt acgacattac tagcaatgac      60
agttccagga tttaagaaag tagtgttcca catcaatgca tatccagtga aagcataacg     120
tcaaaaaaag cctggcaccg ttcgcgatct ggacttactt agatttgttg tagtcaagcc     180
ggctatcagc gatttatccc ggaaacacat actagtgagt tatttgtatg ttacctagaa     240
tagctgtcac gaatcactaa tacattcacc caccagctct cactcgcact ctcacgcaca     300

<210> SEQ ID NO 23
<211> LENGTH: 400
<212> TYPE: DNA
<213> ORGANISM: Artificial Sequence
<220> FEATURE:
<223> OTHER INFORMATION: Synthetic template

<400> SEQUENCE: 23

```
actcgcacga actcaccgca ctcctgaata caagacgaca gtcctgatta tattttcatt    60
taattacgcc aatttaatta tgatgaatat taacggaatt aaatatgtat tgataagtac   120
taagtaatgg tttacccacg gcgatctata tgcaagggaa acattaacaa atttaaacat   180
ctgatgtgga caaaacttgt aatgtggtat agttaaaaat ataggtttca gggacacgta   240
agtatctatc ttgaatgttt aagtaggtcc tgtctaccat tctgaaattt agaaaatcgc   300
gttcatcggg ctgtcggcta cacctcagaa aaccatttcg tgttgcacag gaggaacttt   360
cgagggttcg tatgagctct cactcgcact ctcacgcaca                         400

<210> SEQ ID NO 24
<211> LENGTH: 500
<212> TYPE: DNA
<213> ORGANISM: Artificial Sequence
<220> FEATURE:
<223> OTHER INFORMATION: Synthetic template

<400> SEQUENCE: 24
actcgcacga actcaccgca ctccaccgct tgacgacgta gggtatttgg tatctgaatc    60
tactcattta cctacatact gaagattttg cgatcgtcta atatattgga ctaatgcccg   120
atttctgatc aattactcta ggcgatactt catcgctggc cttatttgga ttttgctcaa   180 gtgctaaaact ctctgcgcgt caatactagt ctgacatcag tcaagacctg ctatctgaaa   240
actactagag agatataacct aacaacttta gtggataaaat caggtctgga gattgtcata   300
taatgccact agggtcagaa ggctgtgtca agttagtgg ttagtaggtc tccgctctgc   360
ggtactattc ttatattctc ttactatgca tcaaacaaaa tagaatgcat agacaaaccg   420
cctgccaagt ttacaagata acttgcgtat aggtttataa gggttcttct gtatcgctct   480
cactcgcact ctcacgcaca                                              500

<210> SEQ ID NO 25
<211> LENGTH: 31
<212> TYPE: DNA
<213> ORGANISM: Homo sapiens

<400> SEQUENCE: 25
gcttggaaga ttgctaaaat gatagtcagt g                                  31

<210> SEQ ID NO 26
<211> LENGTH: 26
<212> TYPE: DNA
<213> ORGANISM: Homo sapiens

<400> SEQUENCE: 26
ttgatcatac tgagcctgct gcataa                                        26

<210> SEQ ID NO 27
<211> LENGTH: 60
<212> TYPE: DNA
<213> ORGANISM: Homo sapiens
<220> FEATURE:
<221> NAME/KEY: mutation
<222> LOCATION: (34)..(34)
<223> OTHER INFORMATION: A or G residue

<400> SEQUENCE: 27
gcttggaaga ttgctaaaat gatagtcagt gacattatgc agcaggctca gtatgatcaa    60

<210> SEQ ID NO 28
<211> LENGTH: 17
```

```
<212> TYPE: DNA
<213> ORGANISM: Homo sapiens

<400> SEQUENCE: 28
ttcctgggca tggagtc                                                    17

<210> SEQ ID NO 29
<211> LENGTH: 17
<212> TYPE: DNA
<213> ORGANISM: Homo sapiens

<400> SEQUENCE: 29
caggtctttg cggatgc                                                    17

<210> SEQ ID NO 30
<211> LENGTH: 21
<212> TYPE: DNA
<213> ORGANISM: respiratory syncytial virus

<400> SEQUENCE: 30
tggggcaaat atgtcacgaa g                                               21

<210> SEQ ID NO 31
<211> LENGTH: 27
<212> TYPE: DNA
<213> ORGANISM: respiratory syncytial virus

<400> SEQUENCE: 31
ccatttaagc aatgacctcg aatttca                                         27

<210> SEQ ID NO 32
<211> LENGTH: 20
<212> TYPE: DNA
<213> ORGANISM: Zika virus

<400> SEQUENCE: 32
caggttggag tgggagtcat                                                 20

<210> SEQ ID NO 33
<211> LENGTH: 20
<212> TYPE: DNA
<213> ORGANISM: Zika virus

<400> SEQUENCE: 33
tttgtaacgt gccacatggt                                                 20

<210> SEQ ID NO 34
<211> LENGTH: 30
<212> TYPE: DNA
<213> ORGANISM: Artificial Sequence
<220> FEATURE:
<223> OTHER INFORMATION: Synthetic aptamer

<400> SEQUENCE: 34
caagacgggc gggtgtggta ggcgcccgtg                                      30

<210> SEQ ID NO 35
<211> LENGTH: 30
<212> TYPE: DNA
<213> ORGANISM: Artificial Sequence
<220> FEATURE:
<223> OTHER INFORMATION: synthetic aptamer

<400> SEQUENCE: 35
```
acttgatggc gggtgtggta ggcgccatct                                30

<210> SEQ ID NO 36
<211> LENGTH: 30
<212> TYPE: DNA
<213> ORGANISM: Artificial Sequence
<220> FEATURE:
<223> OTHER INFORMATION: Synthetic aptamer

<400> SEQUENCE: 36
aagaccagac aatgtacagt attggcctga                                30

<210> SEQ ID NO 37
<211> LENGTH: 27
<212> TYPE: DNA
<213> ORGANISM: Artificial Sequence
<220> FEATURE:
<223> OTHER INFORMATION: Synthetic aptamer

<400> SEQUENCE: 37
gccggccaat gtacagtatt ggccggc                                   27

<210> SEQ ID NO 38
<211> LENGTH: 26
<212> TYPE: DNA
<213> ORGANISM: Artificial Sequence
<220> FEATURE:
<223> OTHER INFORMATION: Synthetic aptamer

<400> SEQUENCE: 38
ccggacaatg tacagtattg gcccgg                                    26

<210> SEQ ID NO 39
<211> LENGTH: 33
<212> TYPE: RNA
<213> ORGANISM: Artificial Sequence
<220> FEATURE:
<223> OTHER INFORMATION: Synthetic aptamer

<400> SEQUENCE: 39
uuaccacgcg cucuuaacug cuagcgccau ggc                            33

<210> SEQ ID NO 40
<211> LENGTH: 41
<212> TYPE: RNA
<213> ORGANISM: Artificial Sequence
<220> FEATURE:
<223> OTHER INFORMATION: Synthetic aptamer

<400> SEQUENCE: 40
cuuaccacgc gcucuuaacu gcuagcgcca uggccaaaac u                   41

<210> SEQ ID NO 41
<211> LENGTH: 21
<212> TYPE: DNA
<213> ORGANISM: Homo sapiens

<400> SEQUENCE: 41
aggtaggtga ggagacttaa g                                         21

<210> SEQ ID NO 42
<211> LENGTH: 17

```
<212> TYPE: DNA
<213> ORGANISM: Homo sapiens

<400> SEQUENCE: 42
taaccagctg gtggtga                                            17
```

EXTREME REVERSE TRANSCRIPTION PCR

STATEMENT OF PRIORITY

This application is a 35 U.S.C. § 371 national phase application of International Application Serial No. PCT/US2016/060650, filed Nov. 4, 2016, which claims the benefit, under 35 U.S.C. § 119(e), of U.S. Provisional Application Ser. No. 62/251,400, filed Nov. 5, 2015, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 1267-13_ST25.txt, 9,818 bytes in size, generated on Jul. 31, 2018 and filed via EFS-Web, is provided in lieu of a paper copy. This Sequence Listing is incorporated by reference into the specification for its disclosures.

BACKGROUND OF THE INVENTION

Polymerase chain reaction (PCR) is a technique widely used in molecular biology. It derives its name from one of its key components, a DNA polymerase used to amplify a piece of DNA by in vitro enzymatic replication. As PCR progresses, the DNA generated (the amplicon) is itself used as a template for replication. This sets in motion a chain reaction in which the DNA template is exponentially amplified. With PCR, it is possible to amplify a single or few copies of a piece of DNA across several orders of magnitude, generating millions or more copies of the DNA piece. PCR employs a thermostable polymerase, dNTPs, and a pair of primers.

PCR is conceptually divided into 3 reactions, each usually assumed to occur over time at each of three temperatures. Such an "equilibrium paradigm" of PCR is easy to understand in terms of three reactions (denaturation, annealing, and extension) occurring at 3 temperatures over 3 time periods each cycle. However, this equilibrium paradigm does not fit well with physical reality. Instantaneous temperature changes do not occur; it takes time to change the sample temperature. Furthermore, individual reaction rates vary with temperature, and once primer annealing occurs, polymerase extension immediately follows. More accurate, particularly for rapid PCR, is a kinetic paradigm where reaction rates and temperature are always changing. Holding the temperature constant during PCR is not necessary as long as the products denature and the primers anneal. Under the kinetic paradigm of PCR, product denaturation, primer annealing, and polymerase extension may temporally overlap and their rates continuously vary with temperature. Under the equilibrium paradigm, a cycle is defined by 3 temperatures each held for a time period, whereas the kinetic paradigm requires transition rates and target temperatures. Illustrative time/temperature profiles for the equilibrium and kinetic paradigms are shown in FIGS. 15a-15b. However, it is understood that these temperature profiles are illustrative only and that in some implementations of PCR, the annealing and extension steps are combined so that only 2 temperatures are needed.

Paradigms are not right or wrong, but they vary in their usefulness. The equilibrium paradigm is simple to understand and lends itself well to the engineering mindset and instrument manufacture. The kinetic paradigm is more relevant to biochemistry, rapid cycle PCR, and melting curve analysis.

When PCR was first popularized in the late 1980s, the process was slow. A typical protocol was 1 minute for denaturation at 94° C., 2 minutes for annealing at 55° C., and 3 minutes for extension at 72° C. When the time for transition between temperatures was included, 8 minute cycles were typical, resulting in completion of 30 cycles in 4 hours. Twenty-five percent of the cycling time was spent in temperature transitions. As cycling speeds increased, the proportion of time spent in temperature transitions also increased and the kinetic paradigm became more and more relevant. During rapid cycle PCR, the temperature is usually changing. For rapid cycle PCR of short products (<100 bps), 100% of the time may be spent in temperature transition and no holding times are necessary. For rapid cycle PCR of longer products, a temperature hold at an optimal extension temperature may be included.

In isolation, the term "rapid PCR" is both relative and vague. A 1 hour PCR is rapid compared to 4 hours, but slow compared to 15 minutes. Furthermore, PCR protocols can be made shorter if one starts with higher template concentrations or uses fewer cycles. A more specific measure is the time required for each cycle. Thus, "rapid cycle PCR" (or "rapid cycling") was defined in 1994 as 30 cycles completed in 10-30 minutes (1), resulting in cycles of 20-60 seconds each. This actual time of each cycle is longer than the sum of the times often programmed for denaturation, annealing and extension, as time is needed to ramp the temperatures between each of these stages. Initial work in the early 1990s established the feasibility of rapid cycling using capillary tubes and hot air for temperature control. Over the years, systems have become faster, and the kinetic requirements of denaturation, annealing, and extension have become clearer.

In one early rapid system, a heating element and fan from a hair dryer, a thermocouple, and PCR samples in capillary tubes were enclosed in a chamber (2). The fan created a rapid flow of heated air past the thermocouple and capillaries. By matching the thermal response of the thermocouple to the sample, the temperature of the thermocouple closely tracked the temperature of the samples, even during temperature changes. Although air has a low thermal conductivity, rapidly moving air against the large surface area exposed by the capillaries was adequate to cycle the sample between denaturation, annealing, and extension temperatures. Electronic controllers monitored the temperature, adjusted the power to the heating element, and provided the required timing and number of cycles. For cooling, the controller activated a solenoid that opened a portal to outside air, introducing cooling air to the otherwise closed chamber.

Temperatures could be rapidly changed using the capillary/air system. Using a low thermal mass chamber, circulating air, and samples in glass capillaries, PCR products >500 bp were visualized on ethidium bromide stained gels after only 10 minutes of PCR (30 cycles of 20 seconds each) (3). Product yield was affected by the extension time and the concentration of polymerase. With 30 second cycle times (about 10 seconds between 70 and 80° C. for extension), the band intensity increased as the polymerase concentration was increased from 0.1 to 0.8 Units per 10 µl reaction. It is noted that polymerase Unit definitions can be confusing. For native Taq polymerase, 0.4 U/10 µl is about 1.5 nM under typical rapid cycling conditions (50).

Rapid protocols use momentary or "0" second holds at the denaturation and annealing temperatures. That is, the temperature-time profiles show temperature spikes for denaturation and annealing, without holding the top and bottom temperatures. Denaturation and annealing can occur very quickly.

Rapid and accurate control of temperature allowed analytical study of the required temperatures and times for PCR. For an illustrative 536 bp fragment of human genomic DNA (β-globin), denaturation temperatures between 91° C. and 97° C. were equally effective, as were denaturation times from <1 second to 16 seconds. However, it was found that denaturation times longer than 16 seconds actually decreased product yield. Specific products in good yield were obtained with annealing temperatures of 50-60° C., as long as the time for primer annealing was limited. That is, best specificity was obtained by rapid cooling from denaturation to annealing and an annealing time of <1 second. Yield was best at extension temperatures of 75-79° C., and increased with extension time up to about 40 seconds.

Conclusions from this early work were: 1) denaturation of PCR products is very rapid with no need to hold the denaturation temperature, 2) annealing of primers can occur very quickly and annealing temperature holds may not be necessary, and 3) the required extension time depends on PCR product length and polymerase concentration. Also, rapid cycle PCR is not only faster, but better in terms of specificity and yield (4, 5) as long as the temperature was controlled precisely. PCR speed is not limited by the available biochemistry, but by instrumentation that does not control the sample temperature closely or rapidly.

However, most current laboratory PCR instruments perform poorly with momentary denaturation and annealing times, and many don't even allow programming of "0" second holding periods. Time delays from thermal transfer through the walls of conical tubes, low surface area-to-volume ratios, and heating of large samples force most instruments to rely on extended times at denaturation and annealing to assure that the sample reaches the desired temperatures. With these time delays, the exact temperature vs. time course becomes indefinite. The result is limited reproducibility within and high variability between commercial products (6). Many instruments show marked temperature variance during temperature transitions (7, 8). Undershoot and/or overshoot of temperature is a chronic problem that is seldom solved by attempted software prediction that depends on sample volume. Such difficulties are compounded by thermal properties of the instrument that may change with age.

Over time, conventional heat block instruments have become faster, with incremental improvements in "thin wall" tubes, more conductive heat distribution between samples, low thermal mass blocks and other "fast" modifications. Nevertheless, it is unusual for these systems to cycle rapidly enough to complete a cycle in less than 60 seconds. A few heat block systems can achieve <60 second cycles, usually restricted to 2-temperature cycling between a limited range of temperatures. By flattening the sample container, rapid cycling can be achieved by resistive heating and air cooling (9), or by moving the sample in a flexible tube between heating zones kept at a constant temperature (U.S. Pat. No. 6,706,617).

Commercial versions of the air/capillary system for PCR have been available since 1991 (1) and for real-time PCR since 1996 (10, 11). Rapid cycling capabilities of other instruments are often compared against the air/capillary standard that first demonstrated 20-60 second cycles. Oddly enough, there has been a trend to run the capillary/air systems slower over the years, perhaps reflecting discomfort with "0" second denaturation and annealing times by many users. Also, heat-activated enzymes require long activation periods, often doubling run times even when "fast" activation enzymes are used. Another compromise away from rapid cycling is the use of plastic capillaries. These capillaries are not thermally matched to the instrument, so 20 second holds at denaturation and annealing are often required to reach the target temperatures (12).

Some progress in further decreasing the cycle times for PCR has occurred in microsystems, where small volumes are naturally processed (13, 14). However, even with high surface area-to-volume sample chambers, cycles may be long if the heating element has a high thermal mass and is external to the chamber (15). With thin film resistive heaters and temperature sensors close to the samples, 10-30 minute amplification can be achieved (16, 17).

While cooling of low thermal mass systems is usually by passive thermal diffusion and/or by forced air, several interesting heating methods have been developed. Infrared radiation can be used for heating (18) with calibrated infrared pyrometry for temperature monitoring (19). Alternatively, thin metal films on glass capillaries can serve as both a resistive heating element and a temperature sensor for rapid cycling (20). Finally, direct Joule heating and temperature monitoring of the PCR solution by electrolytic resistance is possible and has been implemented in capillaries (21). All of the above methods transfer heat to and from fixed samples.

Instead of heat transfer to and from stationary samples, the samples can be physically moved to different temperature baths, or through channels with fixed temperature zones. Microfluidic methods have become popular, with the PCR fluid passing within channels through different segments kept at denaturation, annealing, and extension temperatures. Continuous flow PCR has been demonstrated within serpentine channels that pass back and forth through 3 temperature zones (22) and within loops of increasing or decreasing radius that pass through 3 temperature sectors (23). A variant with a serpentine layout uses stationary thermal gradients instead of isothermal zones, to more closely fit the kinetic paradigm of PCR (24). To limit the length of the microchannel necessary for PCR, some systems shuttle samples back and forth between temperature zones by bi-directional pressure-driven flow (25), pneumatics (26), or electrokinetic forces (27). Instead of linear shuttling of samples, a single circular channel can be used with sample movement driven as a magnetic ferrofluid (28) or by convection (29). One potential advantage of microsystem PCR, including continuous flow methods, is cycling speed.

Although some microsystems still require >60 second cycles, many operate in the 20-60 second cycle range of rapid cycle PCR (13, 30). Minimum cycle times ranging from 16-37 seconds have been reported for infrared heating (18, 19). Metal coated capillaries have achieved 40 second PCR cycles (20), while direct electrolytic heating has amplified with 21 second cycles (20). Minimum cycle times reported for closed loop convective PCR range from 24-42 seconds (29, 31). Several groups have focused on reducing PCR cycle times to <20 seconds, faster than the original definition of rapid cycle PCR that was first demonstrated in 1990. Thin film resistive heating of stationary samples has reduced cycle times down to 17 seconds for 25 μl samples (32) and 8.5 seconds for 100 nl samples (17). Continuous flow systems have achieved 12-14 second cycles with thermal gradient PCR (24) and sample shuttling (26), while a ferrofluid loop claims successful PCR with 9 second cycles (28). Continuous flow systems through glass and plastic substrates have achieved cycle times of 6.9 seconds (22) and 5.2 seconds (23) for various size PCR products. Alternating hot and cool water conduction through an aluminum substrate amplified 1 µl droplets under oil with 5.25 second cycles (33). Similarly, water conduction through a porous copper block amplified 5 µl samples with 4.6 second cycles (34). A continuous flow device of 1 µl reaction plugs augmented by vapor pressure achieved 3 second cycles (35). Additionally, there are reports that claim to amplify an 85 bp fragment of the Stx bacteriophage of *E. coli* in capillaries with 2.7 second cycles by immersion of the capillaries in gallium sandwiched between Peltier elements (36). Alternatively, PCR amplification in capillaries cycled by pressurized hot and cool gases obtained 2.6 second cycles (48).

Table 1 summarizes work to minimize PCR cycle times to less than the 20 second cycles that originally defined "Rapid PCR". Over the past 20 years, new prototype instruments have been developed that incrementally improve cycling speed. However, practical PCR performance (efficiency and yield) is often poor. As a general rule, as cycles become increasingly shorter, claims for successful PCR correlate with lower complexity targets (bacteria, phage, multicopy plasmids, or even PCR products) that are used at higher starting concentrations (see, e.g., U.S. Pat. No. 6,210,882, wherein 5 ng of amplicon was used as the starting sample). Indeed, none of the studies listed in Table 1 with <20 second cycles used complex eukaryotic DNA such as human DNA. The starting copy number of template molecules is often very high (e.g., 180,000,000 copies of lambda phage/µl), so that little amplification is needed before success is claimed. Furthermore, the lack of no template controls in many studies raises questions regarding the validity of positive results, especially in an environment with high template concentrations. One instrument-oriented report focuses extensively on the design and modeling of the thermal cycling device, with a final brief PCR demonstration using a high concentration of a low complexity target. Heating and cooling rates (up to 175° C./s) have been reported based on modeling and measurements without PCR samples present (17).

TABLE 1

| Fastest Cycle Time (s) | [Template] (Copies/μl) | Template Form | Total [Primers] (nM) | Polymerase | [Polymerase] (nM) | Product Length (bp) | Quantification | Trend | Method | No Template Control? | Reference |
|---|---|---|---|---|---|---|---|---|---|---|---|
| 20 | 1,600 | Human DNA | 1000 | 0.08 U/μl Taq | 3 | 536 | Faint Gel Band | Increases with [Polymerase] | Capillary Air Cycling | No | 3 |
| 12 | 40,000 | Lambda phage | 400 | 0.2 U/μl Taq | 7.5 | 500 | Capillary Electrophoresis | ? | IR Heating, Pressurized Air Cooling | No | 56 |
| 12 | 1,000,000 | 230 bp PCR product | 1000 | 0.5 U/μl Taq | 19 | 230 | Good gel band | Dependent on cycle # and copy # | Continuous Flow | Yes | 55 |
| 9.25 | 4,700-470,000 | 18S rDNA (human genomic) | 1800 | Taq Gold | ? | 187 | ? | ? | IR Heating of droplets in oil | No | 54 |
| 9 | 18,000,000 | Lambda phage | 2000 | 0.025 U/μl Taq | 0.94 | 500 | OK gel band | Intensity increases with cycle time | Continuous Flow with a Ferrous Particle Plug | No | 28 |
| 8.5 | ? | cDNA | 1800 | ? | ? | 82 | 80% efficiency | Decreasing efficiency at faster cycles | Micromachined cantilever | ? | 17 |
| 7.0 | 10,000,000 | 1 KB PCR product | 2000 | 0.25 U/μl Taq | 9.4 | 176 | 7% of control | 50% at 15 s cycles | Continuous Flow | Yes | 22 |
| 6.3 | 10,000 | Plasmids (*B. anthracis*) | 1200 | 0.05 U/μl Ex Taq HS | ? | 134 | 55% of control | ? | Plug Continuous Flow | Yes | 53 |
| 5.2/9.7 | 180,000,000 | Lambda phage | 400 | 0.07 U/μl Taq | 2.6 | 500/997 | Faint gel bands | Dependent on cycle times | Continuous Flow | No | 23 |
| 5.25 | 1,400,000 | *B. subtilis* (bacterial DNA) | 500 | 0.025 U/μl KOD plus | ? | 72 | 90% efficiency (SYBR) | Single run | Water pumped against aluminum plate | Yes | 33 |
| 4.6 | 34,000 | *E. herbicola* (bacterial DNA) | 800 | 0.04 U/μl KAPA2G | 4 | 58/160 | Faint gel bands | Yield increases with # cycles | Water pumped through porous copper | No | 31 |
| 4.2 | 50[1] | *B. subtilis* (bacterial DNA) | ? | KOD plus | ? | 72 | Cq = 33 (SYBR) | Higher copy # reduces Cq | IR laser | ?[2] | 51 |
| 3.0 | 10,000 | Plasmids (*B. anthracis*) | 1200 | 0.05 U/μl Ex Taq HS | ? | 134 | 15% of control | 80% at 7.5 s cycles | Constant flow with vapor pressure | Yes (5% signal) | 35 |
| 2.7 | ? | stx phage (*E. coli*) | ?[3] | KOD | ? | 85 | Barely visible band | Decreasing yield from 3.06 s to 2.69 s cycles | Gallium transfer from Peltiers to capillaries | No | 36 |
| 2.6 | ?[4] | stx phage (*E. coli*) | ?[5] | 0.5 U/μl Taq | 19 | 85 | Very dim band | Constant from 2.8 to 2.6 cycles | Pressurized gas and capillaries | No | 48 |

[1] Presumed single copy in a 20 nl droplet with Cq of 33 under SYBR Green monitoring, but no gel or melting analysis to confirm PCR product identity.
[2] A "Blank" sample was run, but it is not clear if this was a no template control.
[3] Article says [primer] is 0.5 mmol, patent application (US 2009/0275014 A1) says [primer] is 0.01-0.5 μM.
[4] Two pg *E. coli* DNA/μl, but copy number of phage in the DNA preparation is unknown.
[5] Dissertation says 0.5 μmol/10 μl (50 mM), patent (U.S. Pat. No. 6,472,186) says 50 pmol/10 μl (5 μM).

One way to decrease cycle time is to introduce variations to the PCR protocol to ease the temperature cycling requirements. Longer primers with higher Tms allow higher annealing temperatures. By limiting the product length and its Tm, denaturation temperatures can be lowered to just above the product Tm. In combination, higher annealing and lower denaturation temperatures decrease the temperature range required for successful amplification. Reducing 3-step cycling (denaturation, annealing, and extension) to 2-steps (denaturation and a combined annealing/extension step) also simplifies the temperature cycling requirements. Both decreased temperature range and 2-step cycling are typical for the studies in Table 1 with cycle times <20 seconds. Two-step cycling can, however, compromise polymerase extension rates if the combined annealing/extension step is performed at temperatures lower than the 70 to 80° C. temperature optimum where the polymerase is most active. Polymerase extension rates are log-linear with temperature until about 70-80° C., with a reported maximum of 60-120 bp/s (50).

Even with protocol variations, amplification efficiency and yield are often poor when cycle times are <20 seconds when compared to control reactions (22, 23). These efforts towards faster PCR appear dominated by engineering with little focus on the biochemistry. As cycle times decrease from 20 seconds towards 2 seconds, PCR yield decreases and finally disappears, reflecting a lack of robustness even with simple targets at high copy number.

The instrumentation in various references disclosed in Table 1 may be suitable for extremely fast PCR, if reaction conditions are compatible. As disclosed herein, a focus on increased concentrations of primers, polymerase, and Mg++ allows for "extreme PCR" (PCR with <20 second cycles (30 cycles in <10 min)), while retaining reaction robustness and yield. Also as disclosed herein, a focus on increased concentrations of primers, reverse transcriptase, and the inclusion of a sugar such as trehalose allows for faster reverse transcription (RT) for use in reverse-transcription PCR (RT-PCR).

SUMMARY OF THE INVENTION

In one embodiment of the present invention, methods are provided for amplifying a target RNA in a biological sample during amplification comprising the steps of providing a reaction mixture comprising the biological sample, a reverse transcription enzyme, a thermostable polymerase and primers configured for amplification of the target RNA to the biological sample, wherein the polymerase is provided at a concentration of at least 0.5 µM and primers are each provided at a concentration of at least 2 µM; reverse transcribing the RNA to DNA by incubating for no longer than 5 minutes, and amplifying the DNA by polymerase chain reaction by thermally cycling the biological sample between at least a denaturation temperature and an elongation temperature through a plurality of amplification cycles using an extreme temperature cycling profile, wherein each cycle is completed in a cycle time less than 20 seconds per cycle.

Kits and reaction mixtures are also provided herein.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 1b is an illustrative device for performing extreme PCR with real-time capabilities for monitoring one sample tube in a water bath.

FIG. 5b is the extreme PCR temperature trace used in FIG. 5a.

FIG. 5c shows negative derivative melting curves of the 4 µM KLENTAQ® polymerase (KT POL) products from FIG. 5a.

FIG. 5d is an agarose gel showing results of extreme PCR using varying polymerase concentrations at 10 µM primer concentrations from FIG. 5a.

FIG. 6b is a gel of the PCR products produced by the extreme temperature cycles of FIG. 6a.

FIG. 12b is a gel of the PCR products shown in the negative derivative melting curves of FIG. 12a.

FIG. 13b is a gel of the PCR products shown in the negative derivative melting curves of FIG. 13a.

FIG. 14b is a gel of the PCR products shown in the negative derivative melting curves of FIG. 14a.

FIGS. 16a-16c show an amplification profile (FIG. 16a), a melting profile (FIG. 16b), and melting peaks (FIG. 16c) of AKAP10 and ACTB in a duplex RT-PCR protocol. Two runs are shown.

FIGS. 19a-19b are graphs that show the effect of 0.6 M trehalose on the RT step at various RT incubation temperatures, using the enzyme ISCRIPT™ with trehalose (————) and without trehalose (- - - - -) (FIG. 19a), and with the enzyme ISCRIPT™ (————) and the enzyme ROCKETSCRIPT™ (- - - - -) both with trehalose (FIG. 19b).

FIG. 20 is a graph that shows the effects of reverse primer concentration on two-step RT-PCR, with an incubation of 20 seconds (- - - - -) and 60 seconds (————).

DETAILED DESCRIPTION

Figure 1A:
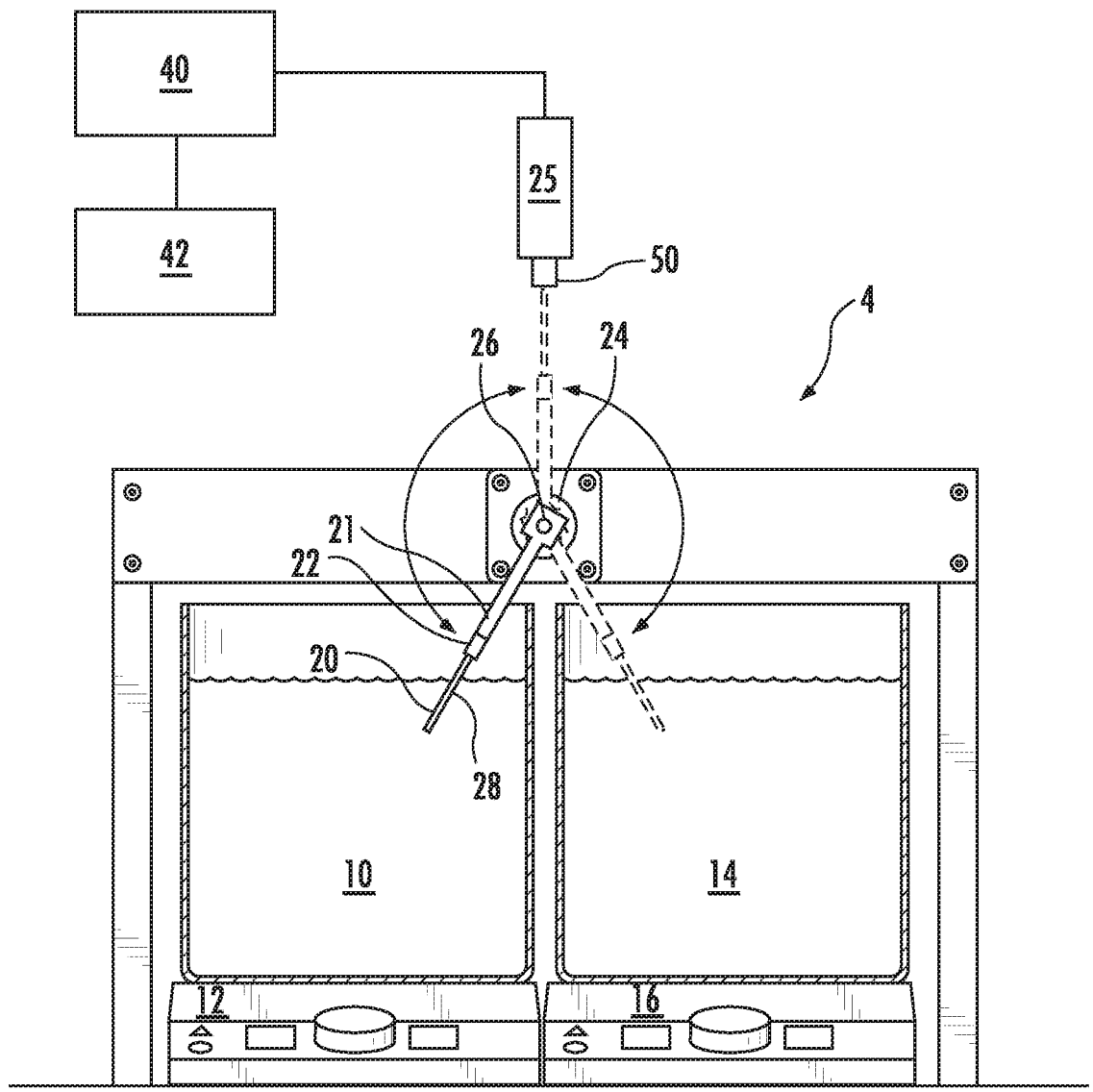
FIG. 1a shows a schematic for performing extreme PCR.

As used herein, the terms "a," "an," and "the" are defined to mean one or more and include the plural unless the context is inappropriate. Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim of this invention is not intended to be interpreted to be equivalent to "comprising".

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); or a solution containing a naturally or non-naturally occurring nucleic acid, which is assayed as described herein. A sample may also be any body fluid or excretion (for example, but not limited to, blood, urine, stool, saliva, tears, bile) that contains cells, cell components, or nucleic acids.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU, dUTP, 7-deaza-dGTP), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

By "probe," "primer," or "oligonucleotide" is meant a single-stranded DNA or RNA molecule of defined sequence that can base-pair to a second DNA or RNA molecule that contains a complementary sequence (the "target"). The stability of the resulting hybrid depends upon the length, GC content, nearest neighbor stacking energy, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes (dyes that fluoresce more strongly when bound to double-stranded DNA than when bound to single-stranded DNA or free in solution) may be used to detect dsDNA. It is understood that a "primer" is specifically configured to be extended by a polymerase, whereas a "probe" or "oligonucleotide" may or may not be so configured.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant typically occur at about melting temperature (Tm) minus 5° C. (i.e. 5° below the Tm of the probe). Functionally, high stringency conditions are used to identify nucleic acid sequences having at least 80% sequence identity.

In an illustrative embodiment, methods and kits are provided for PCR with <20 second cycle times, with some embodiments using <10 second, <5 second, <2 second, <1 second, and <0.5 second cycle times. With these cycle times, a 30 cycle PCR is completed in <10 min, <5 min, <2.5 min, <1 min, <30 seconds, and <15 seconds, respectively. As PCR speeds become increasingly faster, the primer or polymerase concentrations, or both, are increased, thereby retaining PCR efficiency and yield.

Compromising any of the 3 component reactions of PCR (primer annealing, polymerase extension, and template denaturation) can limit the efficiency and yield of PCR. For example, if primers anneal to only 95% of the template, the PCR efficiency cannot be greater than 95%, even if 100% of the templates are denatured and 100% of the primed templates are extended to full length products. Similarly, if extension is only 95% efficient, the maximum possible PCR efficiency is only 95%. In order for the PCR product concentration to double each cycle, all the components must reach 100% completion. Denaturation, annealing and extension will be considered sequentially in the following paragraphs.

Inadequate denaturation is a common reason for PCR failure, in slow (>60 second cycles), rapid (20-60 second cycles), and extreme (<20 second cycles) PCR temperature cycling. The goal is complete denaturation each cycle, providing quantitative template availability for primer annealing. Initial denaturation of template before PCR, particularly genomic DNA, usually requires more severe conditions than denaturation of the amplification product during PCR. The original optimization of rapid cycle PCR (4) was performed after boiling the template, a good way to assure initial denaturation of genomic DNA. Incomplete initial denaturation can occur with high Tm targets, particularly those with flanking regions of high stability (37). This can compromise quantitative PCR, illustratively for genomic insertions or deletions, particularly if minor temperature differences during denaturation affect PCR efficiency (37-39). If prior boiling or restriction digestion (37) is not desired, and higher denaturation temperatures compromise the polymerase, adjuvants that lower product Tm can be used to help with denaturation.

Although 94° C. is often used as a default target temperature for denaturation, it is seldom optimal. PCR products melt over a 40° C. range, depending primarily on GC content and length (43). Low denaturation target temperatures have both a speed and specificity advantage when the PCR product melts low enough that a lower denaturation temperature can be used. The lower the denaturation temperature, the faster the sample can reach the denaturation temperature, and the faster PCR can be performed. Added specificity arises from eliminating all potential products with higher denaturation temperatures, as these potential products will remain double-stranded and will not be available for primer annealing. To amplify high Tm products, the target temperature may need to be increased above 94° C. However, most current heat stable polymerases start to denature above 97° C. and the PCR solution may boil between 95° C. (or lower) and 100° C., depending on the altitude, so there is not much room to increase the temperature. Lowering the monovalent salt and Mg++ concentration lowers product Tm. Similarly, incorporating dUTP and/or 7-deaza-dGTP also lowers product Tm, but may decrease polymerase extension rates. Most proprietary PCR "enhancers" are simple organics that lower product Tm, enabling denaturation (and amplification) of high Tm products. Most popular among these are DMSO, betaine, glycerol, ethylene glycol, and formamide. In addition to lowering Tm, some of these additives also raise the boiling point of the PCR mixture (particularly useful at high altitudes). As the concentration of enhancer increases, product Tms decrease, but polymerase inhibition may increase.

Denaturation, however, need not be rate limiting even under extreme cycling conditions, because DNA unwinding is first order and very fast (10-100 msec), even when the temperature is only slightly above the product Tm. Denaturation occurs so rapidly at 2-3° C. above the Tm of the amplification product that it is difficult to measure, but complete denaturation of the amplicon probably occurs in less than 0.1 second. If the product melts in multiple domains, the target denaturation temperature should be 2-3° C. above the highest melting domain. As long as the sample reaches this temperature, denaturation is very fast, even for long products. Using capillaries and water baths (40), complete denaturation of PCR products over 20 kB occurred in less than one second (52). Product Tms and melting domains are illustratively determined experimentally with DNA dyes and high resolution melting (41). Although Tm estimates can be obtained by software predictions (42), their accuracy is limited. Furthermore, observed Tms strongly depend on local reaction conditions, such as salt concentrations and the presence of any dyes and adjuvants. Thus, observed Tms are usually better matched to the reaction conditions.

Figure 2A:
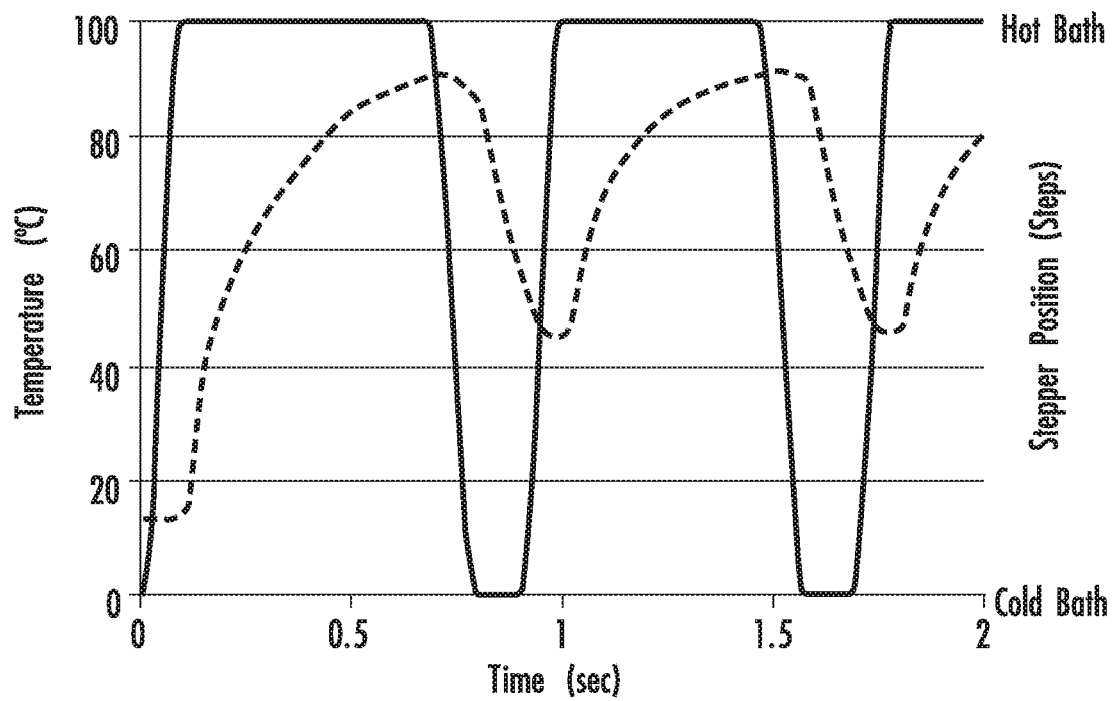
FIG. 2a is a graph that superimposes the location of the sample holder (- - - - -) of FIG. 1b with the temperature of the sample (―――).
Figure 6A:
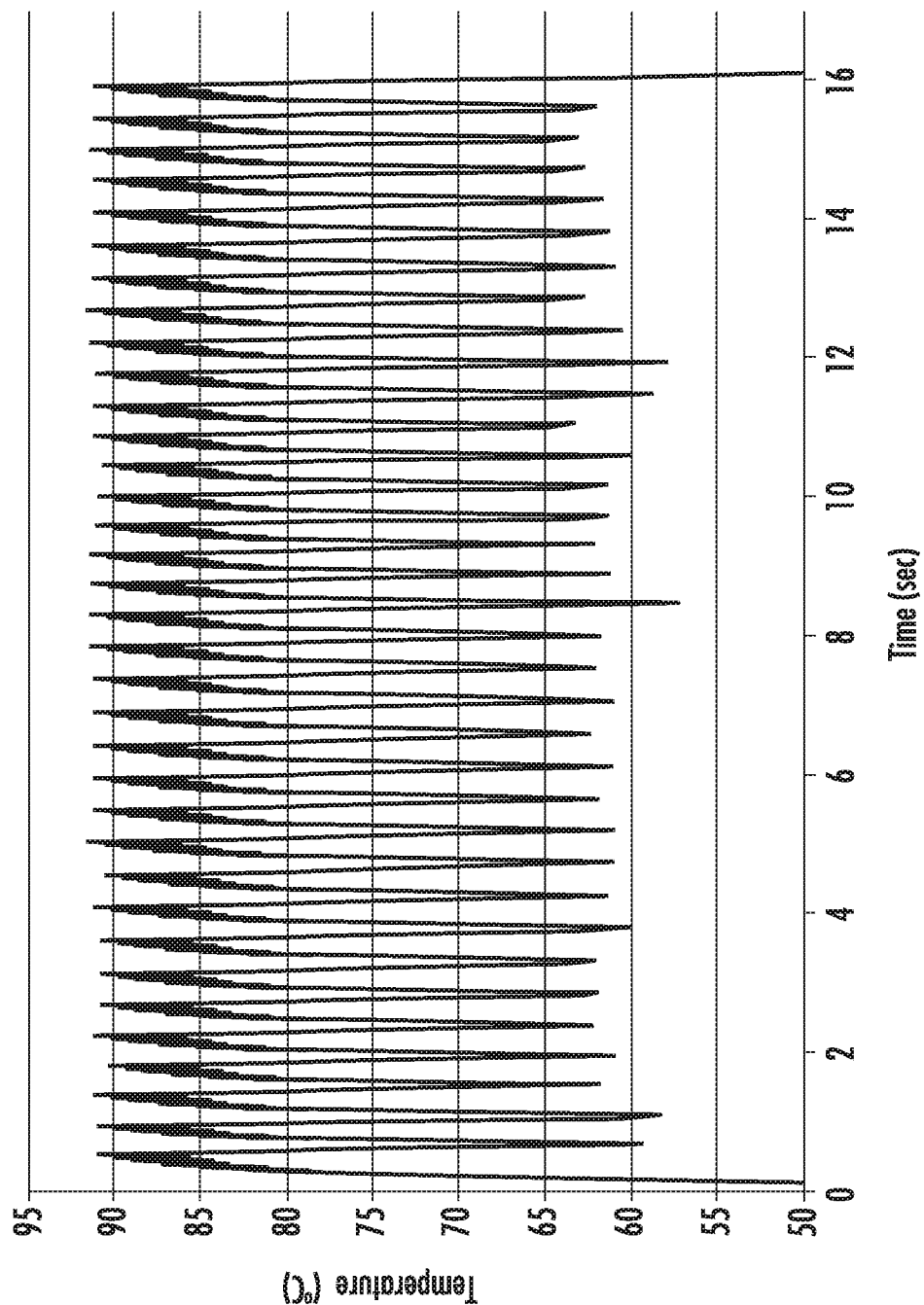
FIG. 6a is a temperature trace of extreme PCR performed in a 19 gauge stainless steel tube.

Without any effect on efficiency, the approach rate to denaturation can be as fast as possible, for example 200-400° C./s, as shown in FIGS. 2a and 6a. At these rates, only about 0.1-0.2 seconds are required to reach denaturation temperatures. However, a slower rate as the target temperature is approached decreases the risk of surpassing the target temperature and avoids possible polymerase inactivation or boiling of the solution. One illustrative method to achieve a slower approach temperature is to submerge the sample in a hot bath that exceeds the target temperature by 5-10° C. The temperature difference between the target and bath temperatures determines the exponential approach curve that automatically slows as the difference decreases. By continuously monitoring the temperature, the next phase (cooling toward annealing) is triggered when the denaturation target is achieved. In summary, complete product denaturation in PCR requires <0.2 s at temperatures 2-3° C. above the highest melting domain temperature of the product and the denaturation temperature can be approached as rapidly as possible, illustratively at 40-400° C./second. Since denaturation is first order, its rate depends only on the product concentration, and the efficiency (or percentage of the product that is denatured) is independent of the product concentration.

Incomplete and/or misdirected primer annealing can result in poor PCR. Low efficiency results if not all template sites are primed. Furthermore, if priming occurs at undesired sites, alternative products may be produced. The goal is essentially complete primer annealing to only the desired sites each cycle, providing quantitative primed template for polymerase extension.

Rapid PCR protocols with 20-60 second cycles suggest an annealing time of <1 second at 5° C. below the Tm with 500 nM primers (52). Primer concentrations for instruments attempting <20 second cycles range from 200-1,000 nM each (Table 1). These concentrations are similar to those used in conventional PCR (>60 second cycles), where long annealing times are used. Lowering the primer concentration is often used to improve specificity, and increasing the primer concentration is seldom considered due to concerns regarding nonspecific amplification. However, with rapid cycling, improved specificity has been attributed to shorter annealing times (5). If this trend is continued, one would expect that very short annealing times of extreme PCR should tolerate high primer concentrations. To promote annealing, an annealing temperature 5° C. below the primer Tm is recommended for 20-60 second cycles. Tms are best measured experimentally by melting analysis using saturating DNA dyes and oligonucleotides under the same buffer conditions used for amplification. The primer is combined with its complementary target with a 5'-extension as a dangling end, to best approximate the stability of a primer annealed to its template, and melting analysis is performed.

In contrast to denaturation, annealing efficiency depends on the primer concentration. Primer annealing can become limiting at very fast cycle speeds. Primer annealing is a second order reaction dependent on both primer and target concentrations. However, during most of PCR, the primer concentration is much higher than the target concentration and annealing is effectively pseudo-first order and dependent only on the primer concentration. In this case, the fraction of product that is primed (the annealing efficiency) depends only on the primer concentration, not the product concentration, so that higher primer concentrations should allow for shorter annealing times. Furthermore, without being bound to theory, it is believed that the relationship is linear. As the annealing time becomes shorter and shorter, increased primer concentrations become necessary to maintain the efficiency and yield of PCR. For example, rapid cycling allows about 1-3 seconds for annealing at temperatures 5° C. below primer Tm (3). If this annealing time (at or below Tm-5° C.) is reduced 10-fold in extreme PCR, a similar priming efficiency would be expected if the primer concentration were increased 10-fold. As the available annealing time becomes increasingly shorter, the primer concentration should be made increasingly higher by approximately the same multiple. Typical rapid PCR protocols use 500 nM each primer. If the annealing time in extreme PCR is reduced 3 to 40-fold, the primer concentrations required to obtain the same priming efficiency are 1,500-20,000 nM each primer. This is equivalent to 3,000-40,000 nM total primers, higher than any primer concentration in Table 1. This suggests that one reason for poor efficiency in prior attempts at <20 second cycling is poor annealing efficiency secondary to inadequate primer concentrations. In extreme PCR, the primer concentrations are increased to 1.5-20 µM each to obtain excellent annealing efficiency despite annealing times of 0.05-0.3 seconds. Ever greater primer concentrations can be contemplated for even shorter annealing times, using increased primer concentrations to offset decreased annealing times to obtain the same annealing efficiency. It is noted that most commercial instruments require a hold time of at least 1 second, while a few instruments allow a hold time of "0" seconds, but no commercial instrument allows a hold time of a fractional second. For some illustrative examples of extreme PCR, hold times in increments of 0.1 or 0.01 seconds may be desirable.

Another way to increase the annealing rate and shorten annealing times without compromising efficiency is to increase the ionic strength, illustratively by increasing the Mg++ concentration. Annealing rates are known in the art to increase with increasing ionic strength, and divalent cations are particularly effective for increasing rates of hybridization, including primer annealing.

Illustratively, the approach rate to the annealing target temperature may be as fast as possible. For example, at 200-800° C./s (FIGS. 2a and 6a), annealing temperatures can be reached in 0.05-0.2 seconds. Rapid cooling also minimizes full length product rehybridization. To the extent that duplex amplification product forms during cooling, PCR efficiency is reduced because primers cannot anneal to the duplex product. Although this is rare early in PCR, as the product concentration increases, more and more duplex forms during cooling. Continuous monitoring with the nucleic acid stain SYBR® GREEN I suggests that such product reannealing can be a major cause of the PCR plateau (44).

Polymerase extension also requires time and can limit PCR efficiency when extension times are short. Longer products are known to require longer extension times during PCR and a final extension of several minutes is often appended at the end of PCR, presumably to complete extension of all products. The usual approach for long products is to lengthen the time for extension. Using lower extension temperatures further increases required times, as in some cases of 2-step cycling where primer annealing and polymerase extension are performed at the same temperature.

Essentially complete extension of the primed template each cycle is required for optimal PCR efficiency. Most polymerase extension rates increase with temperature, up to a certain maximum. For Taq polymerase, the maximum is about 100 nucleotides/s at 75-80° C. and it decreases about 4-fold for each 10° C. that the temperature is reduced (50). For a 536 bp beta-globin product, 76° C. was found optimal in rapid cycle PCR (4). Faster polymerases have recently been introduced with commercial claims that they can reduce overall PCR times, suggesting that they may be able to eliminate or shorten extension holding times for longer products.

As an alternative or complement to faster polymerase extension rates, it has been found that increasing the concentration of polymerase reduces the required extension time. Given a standard Taq polymerase concentration in PCR (0.04 U/µl) or 1.5 nM (49) with 500 nM of each primer, if each primer is attached to a template, there is only enough polymerase to extend 0.15% of the templates at a time, requiring recycling of the polymerase over and over again to new primed templates in order to extend them all. By increasing the concentration of polymerase, more of the available primed templates are extended simultaneously, decreasing the time required to extend all the templates, presumably not by faster extension rates, but by extending a greater proportion of the primed templates at any given time.

To a first approximation, for small PCR products (<100 bp), the required polymerization time appears to be directly proportional to the polymerization rate of the enzyme (itself a function of temperature) and the polymerase concentration. The required time is also inversely proportional to the length of template to be extended (product length minus the primer length). By increasing the polymerase activity 20-300 fold over the standard activity of 0.04 U/µl in the PCR, extreme PCR with <20 second cycles can result in high yields of specific products. That is, activities of 0.8-12 U/µl (1-16 µM of KLENTAQ®, a DNA polymerase) enable two-step extreme PCR with combined annealing/extension times of 0.1-1.0 second. The highest polymerase activity used previously was 0.5 U/µl (Table 1). For two-step PCR that is used in illustrative examples of extreme PCR, a combined annealing/extension step at 70-75° C. is advantageous for faster polymerization rates. Furthermore, because it simplifies temperature cycling, two-step PCR is typically used in illustrative examples of extreme cycling (<20 second cycles) and both rapid annealing and rapid extension must occur during the combined annealing/extension step. Therefore, both increased primer concentrations and increased polymerase concentrations are used in illustrative examples, resulting in robust PCR under extreme two-temperature cycling. Illustratively, primer concentrations of 1.5-20 µM each and polymerase concentrations of 0.4-12 U/µl of any standard polymerase (0.5-16 µM of KLENTAQ®, a DNA polymerase) are necessary with combined annealing/extension times of 0.05-5.0 seconds at 50-75° C., as illustrated in the Examples to follow. Because there is only one PCR cycling segment for both annealing and extension, extreme PCR conditions require enhancement of both processes, illustratively by increasing the concentrations of both the primers and the polymerase.

Extreme three-temperature cycling is also envisioned, where the annealing and extension steps are kept separate at different temperatures. In this case, the time allotted to annealing and extension steps can be individually controlled and tailored to specific needs. For example, if only the annealing time is short (0.05-0.2 seconds) and the extension time is kept comparatively long (illustratively for 1, 2, 5, 10 or 15 seconds), only the primer concentrations need to be increased for efficient PCR. Alternatively, if the extension time is short (<1 sec within 70-80° C.), but the annealing time is long, it is believed that only the polymerase concentration needs to be increased to obtain efficient PCR. It is understood that efficient PCR has an illustrative efficiency of at least 70%, more illustratively of at least 80%, and most illustratively of at least 90%, with >95% efficiency achievable in many instances.

For products longer than 100 bp, efficient extension using extreme PCR may need a combination of high polymerase concentration and increased extension time. If the polymerase is in excess, the minimum time illustratively should be the extension length (defined as the product length minus the primer length) in bases divided by the polymerase extension rate in bases/second. However, as previously noted, the polymerase is usually only saturating in the beginning of PCR, before the concentration of template increases to greater than the concentration of polymerase. One way to decrease cycle time is to use two-temperature PCR near the temperature maximum of the polymerase, typically 70-80° C. The required extension time can be determined experimentally using real-time PCR and monitoring the quantification cycle or Cq. For example, at a polymerase extension rate of 100 bases/second at 75° C., a 200 bp product would be expected to require about 2 seconds if the concentration of polymerase is in excess. Similarly, a 400 bp product would be expected to require about 4 seconds using this same polymerase as long as its concentration is greater than the template being extended. If the polymerase is not in excess, adding more polymerase allows more templates to be extended at the same time, decreasing the required extension time in proportion to the concentration of polymerase.

The utility of any DNA analysis method depends on how fast it can be performed, how much information is obtained, and how difficult it is to do. Compared to conventional cloning techniques, PCR is fast and simple. Rapid cycle and extreme PCR focus on continued reduction of the time required. Real-time PCR increases the information content by acquiring data each cycle. Melting analysis can be performed during or after PCR to monitor DNA hybridization continuously as the temperature is increased.

Figure 15B:
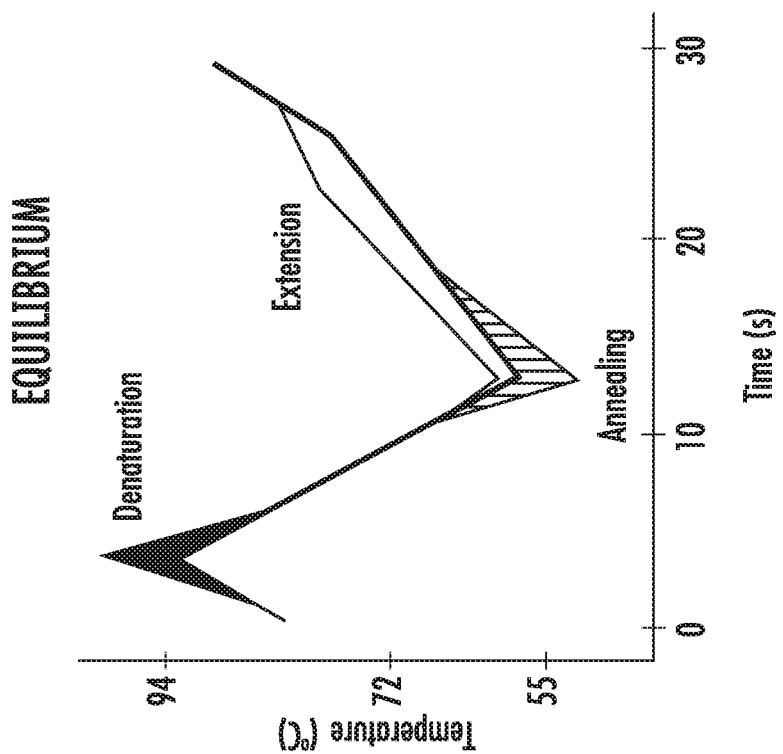
FIGS. 15a-15b show illustrative profiles for an equilibrium paradigm (FIG. 15a) and a kinetic paradigm (FIG. 15b) of PCR. Solid black represents denaturation, striped represents annealing, and solid white represents extension of the nucleic acids during thermal cycling.
Figure 15A:
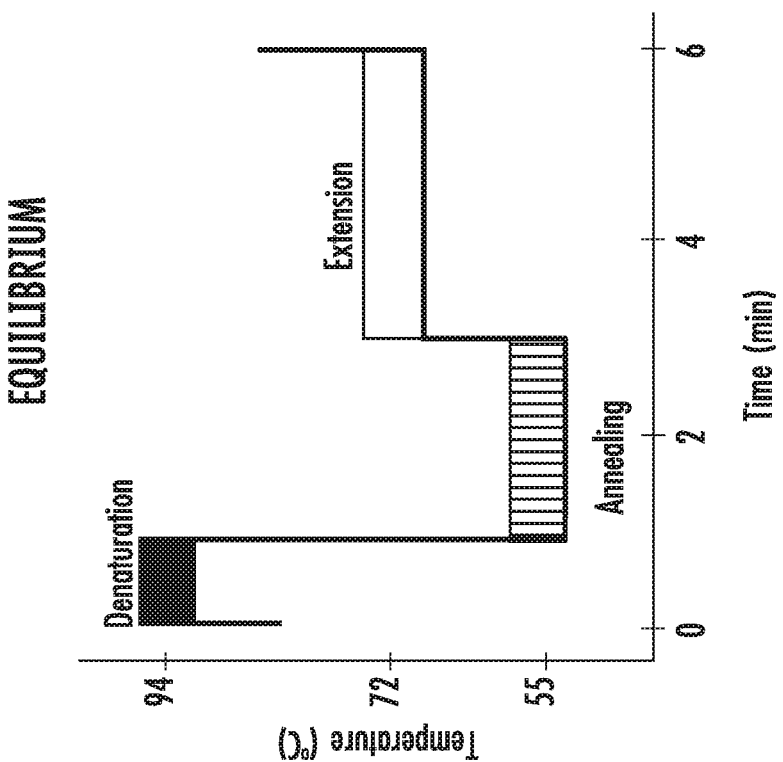

Returning to the equilibrium and kinetic paradigms of PCR (FIG. 15a-15b), extreme PCR of products <100 bps exemplifies a good application of the kinetic model. Temperatures are always changing and rates of denaturation, annealing, and extension depend on temperature, so an adequate assessment of PCR can only be obtained by integrating the rates of the component reactions across temperature. For products greater than 100 bp, longer extension times may be necessary, and components of both the kinetic and equilibrium models are appropriate.

When the reaction conditions are configured according to at least one embodiment herein, it has been found that PCR can be performed at very fast rates, illustratively with some embodiments in less than one minute for complete amplification, with cycle times of less than two seconds. Illustratively, various combinations of increased polymerase and primer concentrations are used for this extreme PCR. Without being bound to any particular theory, it is believed that an excess concentration of primers will allow for generally complete primer annealing, thereby increasing PCR efficiency. Also without being bound to any particular theory, it is believed that an increase in polymerase concentration improves PCR efficiency by allowing more complete extension. Increased polymerase concentration favors binding to the annealed primer, and also favors rebinding if a polymerase falls off prior to complete extension. The examples below show that extreme PCR has been successful, even when starting with complex eukaryotic genomic DNA and single-copy targets.

Although KLENTAQ®, a DNA polymerase, was used in the Examples to follow, it is believed that any thermostable polymerase of similar activity will perform in a similar manner in extreme PCR, with allowances for polymerase extension rates. For example, HERCULASE, KAPA2G FAST, KOD PHUSION™, natural or cloned *Thermus aquaticus* polymerase, PLATINUM™ TAQ, GOTAQ® and FASTSTART™ are commercial preparation of polymerases that should enable extreme PCR when used at the increased concentrations presented here, illustratively adjusted for differences in enzyme activity rates.

Because no current commercial PCR instrument allows for two second cycle times, a system 4 was set up to test proof of concept for extreme PCR. However, it is understood that the system 4 is illustrative and other systems that can thermocycle rapidly are within the scope of this disclosure. As shown in FIG. 1a, a hot water bath 10 of 95.5° C. (the temperature of boiling water in Salt Lake City, Utah, the location where the present examples were performed), and a cool water bath 14 of 30-60° C. are used to change the temperature of 1-5 µl samples contained in a sample container 20. The illustrative water baths 10, 14 are 4.5 quart stainless steel dressing jars (Lab Safety Supply, #41634), although 500 ml glass beakers were used in some examples, and are heated on electric hotplates 12, 16 with magnetic stirring (Fisher Scientific Isotemp Digital Hotplates (#11-300-49SHP). However, it is understood that other embodiments may be used to heat and cool the samples. In the embodiment shown in FIG. 1a, the sample container 20 is a composite glass/plastic reaction tube (BioFire Diagnostics #1720, 0.8 mm ID and 1.0 mm OD). However, in other examples, hypodermic needles (Becton Dickenson #305187, 0.042" ID, 0.075" OD) and composite stainless steel/plastic reaction tubes constructed from stainless steel tubing (Small Parts, 0.042" ID/0.075" OD, 0.035" ID/0.042" OD, or 0.0265" ID/0.035" OD) and fit into the plastic tops of the BioFire tubes were used as the sample container 20. While other sample containers are within the scope of this invention, it is desirable that the sample containers have a large surface area to volume ratio and have a fast heat transfer rate. For certain embodiments, the open end of the metal tubing was sealed by heating to a red-white color using a gas flame and compressing in a vise. For real-time PCR, tubes that are optically clear or have an optically clear portion are desirable. Samples were spun down to the bottom of each tube by brief centrifugation.

The sample container 20 is held by a tube holder 22 attached to a stepper motor shaft 26 by arm 21. The tube holder 22 was machined from black Delrin plastic to hold 2-5 sample containers 20 (only one sample container 20 is visible in FIG. 1a, but a row of such sample containers 20 may be present) so that the reaction solutions were held at a radius of 6.5-7.5 cm. While not visible in FIG. 1a, a thermocouple (Omega type T precision fine wire thermocouple #5SRTC-TT-T-40-36, 36" lead, 0.003' diameter with Teflon insulation) may be used to measure temperature. With reference to FIG. 1d, which shows a similar tube holder and arm of FIG. 1b with like numbers representing similar components, a tube holder 222 designed to hold two sample containers is present, with one location in tube holder 222 occupied by a thermocouple 228. It is understood that any number of sample containers 20 or 220 may be used in any of the embodiments described herein, with or without a thermocouple, as shown in FIG. 1d. Thermocouple amplification and linearization is performed with an Analog Devices AD595 chip (not shown). The thermocouple voltage was first calculated from the AD595 output as Type T voltage=(AD595 output/247.3)−11 µV. Then, the thermocouple voltage was converted to temperature using National Institute of Standards and Technology coefficients for the voltage/temperature correlation of Type T thermocouples. The analog signal was digitized (PCIe-6363 acquisition board) and processed by LabView software (version 2010, National Instruments) installed on CPU 40 and viewed on user interface 42. Stepper motion illustratively is triggered dynamically at 87-92° C. and 60-75° C. or may be held in each water bath for a computer-controlled period of time. Thirty to fifty cycles are typically performed.

The stepper motor 24 (Applied Motion Products, #HT23-401, 3V,3A) is positioned between the water baths 10 and 14 so that all sample containers 20 in the tube holder 22 could flip between each water bath 10 and 14, so that the portion of each sample container 20 containing samples are completely submerged. The stepper motor 24 is powered illustratively by a 4SX-411 nuDrive (National Instruments, not shown) and controlled with a PCI-7344 motion controller and NI-Motion Software (version 8.2, National Instruments) installed on CPU 40. Stepper motor 24 rotates between water baths 10 and 14 in about 0.1 second. FIG. 2a shows a sample temperature trace (- - - - -) juxtaposed over a trace of the position of the sample container 20 (———————), for a run where stepper motion was triggered at 90° C. and 50° C. As can be seen in FIG. 2a, there is some overshoot to a temperature lower than 50° C., presumably due do the time required to move the sample container 20 out of water bath 14. Thus, as discussed above, it may be desirable to trigger stepper motor 24 at a somewhat higher temperature. In the examples below, the temperatures given are for the sample temperature reached, not the trigger temperature. The maximum heating rate calculated from FIG. 2a is 385° C./s and maximum cooling rate 333° C./s. Illustratively, extreme PCR may be performed with ramp rates of at least 200° C./s. In other embodiments, the ramp rate may be 300° C./s or greater.

In some examples, system 4 is also configured for real-time monitoring. As shown in FIG. 1a, for real time monitoring, a fiber optics tip 50 of optics block 25 is mounted above sample container 20, such that when sample container 20 is being moved from hot water bath 10 to the cold water bath by stepper motor 24, sample container 20 passes by the fiber optics tip 50, with or without a hold in this monitoring position. In this illustrative embodiment, fiber optics tip is provided in air above the water baths. Thermocycling device 4 may be controlled by CPU 40 and viewed on user interface 42.

FIG. 1b shows an embodiment similar to FIG. 1a. Hot plates 212 and 216 are provided for controlling temperature of hot water bath 210 and cold water bath 214. A stepper motor 224 is provided for moving sample container 220 and thermocouple 228 (shown in FIG. 1d), by moving arm 221 and tube holder 222, which is illustratively made of aluminum. However, in this embodiment, the tip 250 of the fiber optics cable 252 is held in water bath 214 by positioning block 254. Fiber optics cable 252 enters water bath 214 through port 248 and provides signal to optics block 225. Thermocycling device 204 may be controlled by CPU 240 and viewed on user interface 242

Light from an Ocean Optics LLS-455 LED Light Source 256 was guided by fiber optics cable 252 (Ocean Optics P600-2-UV-VIS, 600 µm fiber core diameter) into a Hamamatsu Optics Block 258 with a 440+/−20 nm excitation interference filter, a beamsplitting 458 nm dichroic and a 490+/−5 nm emission filter (all from Semrock, not shown). Epifluorescent illumination of the capillary was achieved with another fiber optic cable (not shown) placed approximately 1-2 mm distant from and in-line with the one sample capillary when positioned in the cooler water bath. Emission detection was with a Hamamatsu PMT 62.

Figure 1C:
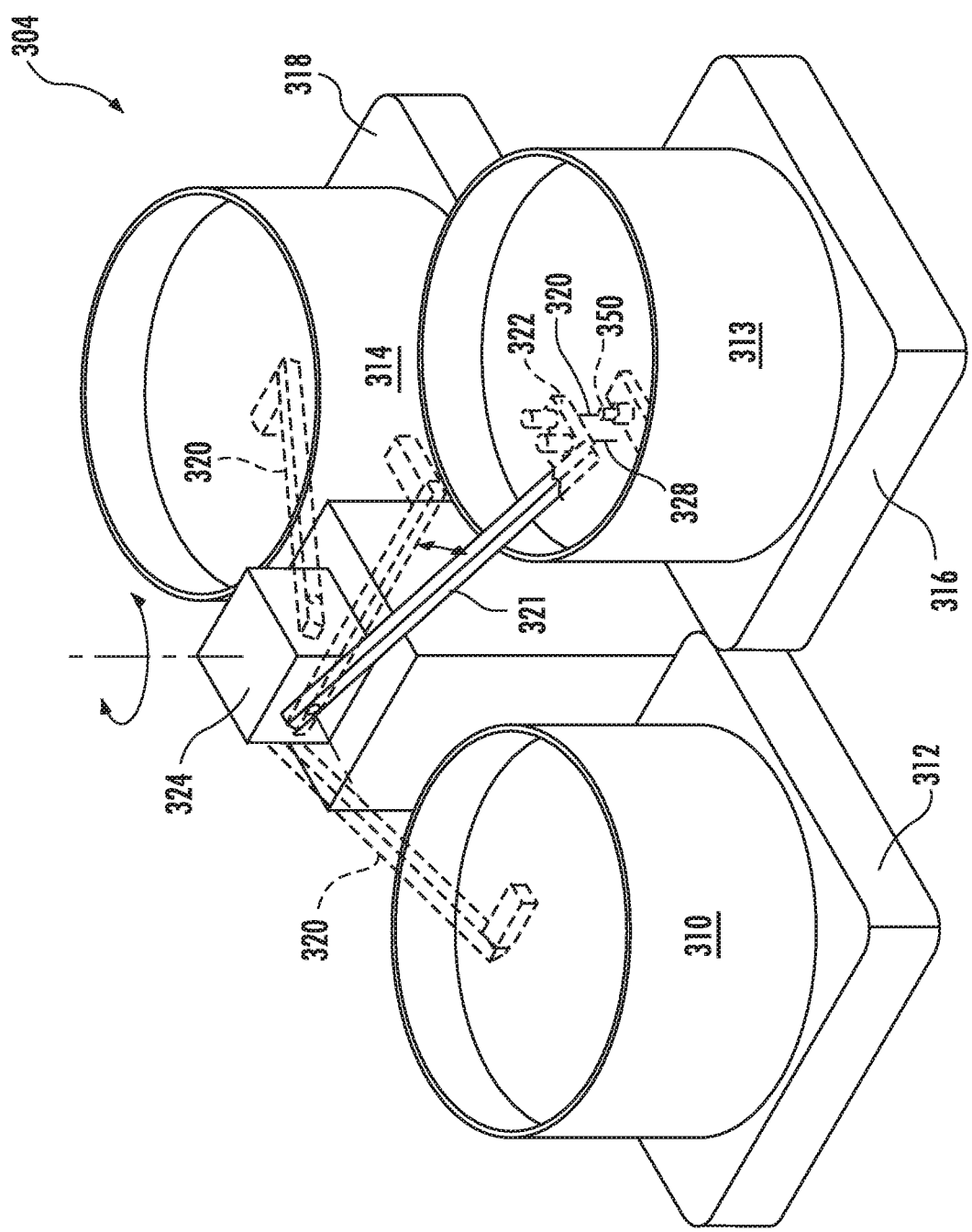
FIG. 1c is an illustrative device for performing extreme PCR with three-temperature cycling.
Figure 1D:
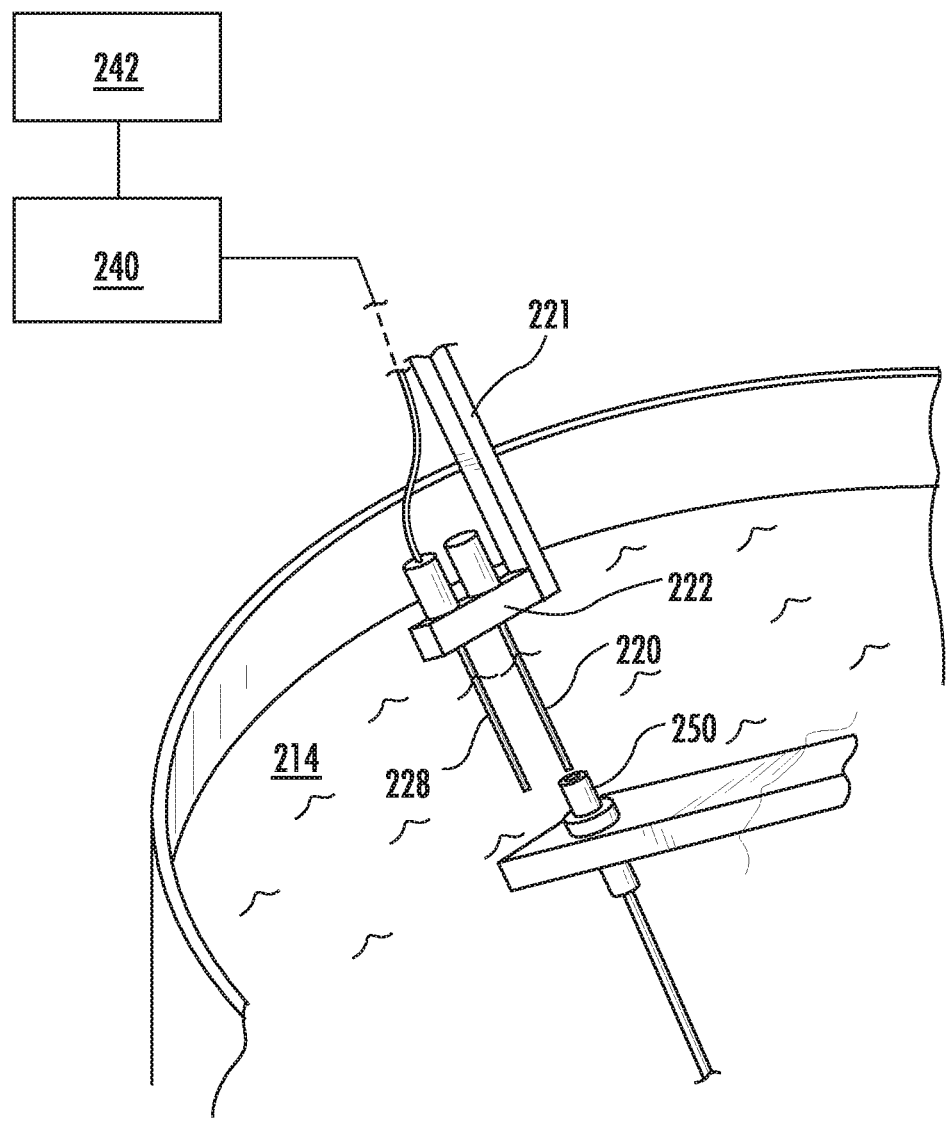
FIG. 1d is a close up view of the optics of the device in FIG. 1b that also shows the temperature reference capillary.

FIG. 1c shows an illustrative system 304 for three-temperature PCR. A hot water bath 310 of 95.5° C., a cool water bath 314 of 30-60° C., and a medium water bath 313 of 70-80° C. are used to change the temperature of 1-5 µl samples contained in a sample container 320, and are heated on three electric hotplates 312, 316, and 318 with magnetic stirring. The sample container 320 is held by a tube holder 322 attached to a stepper motor 324 by arm 321. Thermocouple 328 is also held by tube holder 322. Arm 321 may be raised as stepper motor 324 rotates. A fiber optics tip 350 is illustratively provided in medium water bath 313, although it is understood that it may be placed in air, as with FIG. 1a. Due to the set-up of this illustrative embodiment, it was not possible to place the three water baths, 310, 313, and 314 equidistant from one another. Accordingly, the largest space was placed between hot water bath 310 and cool water bath 314, as cooling of the sample between these baths is desirable, whereas the sample moves between the other water baths to be heated. However, it is understood that this configuration is illustrative only and that other configurations are within the spirit of this disclosure. Because two stepper motors are used simultaneously (one to raise the capillary out of the water and one to transfer between water baths) the angular motion of each can be minimized to decrease the time of movement between baths. In the 2 water bath system, the required angular motion of the stepper to transfer the sample between baths is greater than 270 degrees. However, in the 3 water bath system, the stepper motor that raises the samples needs to traverse less than 45 degrees while the stepper moving the samples between water baths needs to move only 90 degrees or less. The water baths can also be configured as sectors of a circle (pie-shaped wedges) to further limit the angular movement required. Minimizing the angular movement decreases the transfer time between water baths. Transfer times less than 100 msec or even less than 50 msec are envisioned. Other components of this system 304 are similar to the systems 4, 204 shown in FIGS. 1a-b and are not shown in FIG. 1c. Extension to a 4 water bath system is also envisioned. Uses for the fourth water bath include an ice water bath to ensure a cold start to limit the amount of extension before initial PCR denaturation, and a water bath at 37-56° C. for reverse transcription prior to PCR (RT-PCR). If both a cold start and a reverse transcription were needed, a 5 water bath system could be used.

EXAMPLES

Example 1

Unless otherwise indicated, PCR was performed in 5 µl reaction volumes containing 50 mM Tris (pH 8.3, at 25° C.), 3 mM MgCl$_2$, 200 µM each dNTP (dATP, dCTP, dGTP, dTTP), 500 µg/ml non-acetylated bovine serum albumin (Sigma), 2% (v/v) glycerol (Sigma), 50 ng of purified human genomic DNA, and 1×LCGreen® Plus (BioFire Diagnostics). The concentration of the primers and the polymerase varied according to the specific experimental protocols. KLENTAQ1™ DNA polymerase was obtained from either AB Peptides, St. Louis, Mo., or from Wayne Barnes at Washington University (St. Louis). The molecular weight of KLENTAQ®, a DNA polymerase, is 62.1 kD with an extinction coefficient at 280 nm of 69,130 M-1 cm-1, as calculated from the sequence (U.S. Pat. No. 5,436,149). Mass spectrometry confirmed a predominate molecular weight of 62 kD, and denaturing polyacrylamide gels showed that the major band was greater than 80% pure by integration. Using the absorbance and purity to calculate the concentration indicated an 80 µM stock in 10% glycerol. Final polymerase concentrations were typically 0.25-16 µM. One µM KLENTAQ®, a DNA polymerase, is the equivalent of 0.75 U/µl, with a unit defined as 10 nmol of product synthesized in 30 min at 72° C. with activated salmon sperm DNA. Primers were synthesized by the University of Utah core facility, desalted, and concentrations determined by A260. The final concentrations of each primer typically varied from 2.5-20 µM.

A 45 bp fragment of KCNE1 was amplified from human genomic DNA using primers CCCATTCAACGTCTA-CATCGAGTC (SEQ ID NO:1) and TCCTTCTCTTGCCAGGCAT (SEQ ID NO:2). The primers bracketed the variant rs #1805128 (c.253G>A) and amplified the sequence:

(SEQ ID NO: 3)
CCCATTCAACGTCTACATCGAGTCC(G/A)ATGCCTGGCAAGAGAAGGA.

Figure 2B:
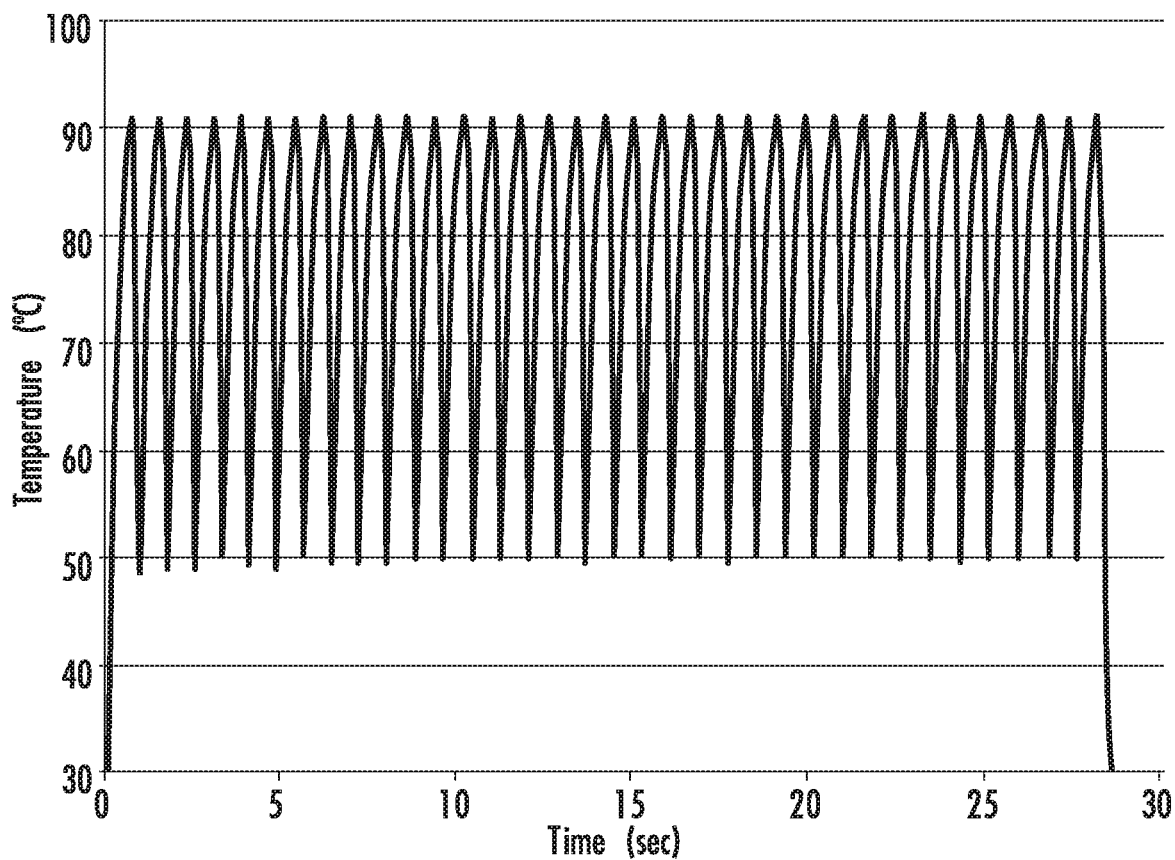
FIG. 2b is a temperature graph of extreme PCR using the device shown in FIG. 1b.
Figure 2C:
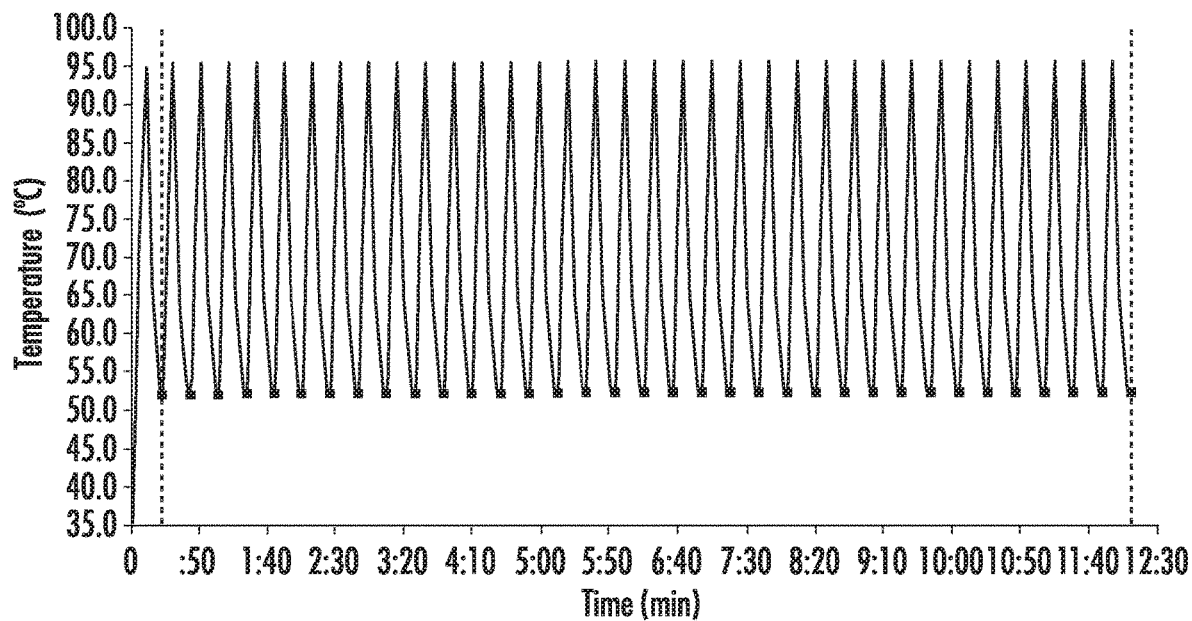
FIG. 2c is a temperature graph of rapid cycle PCR using a carousel LightCycler (Roche) shown for comparison against FIG. 2b.
Figure 3A:
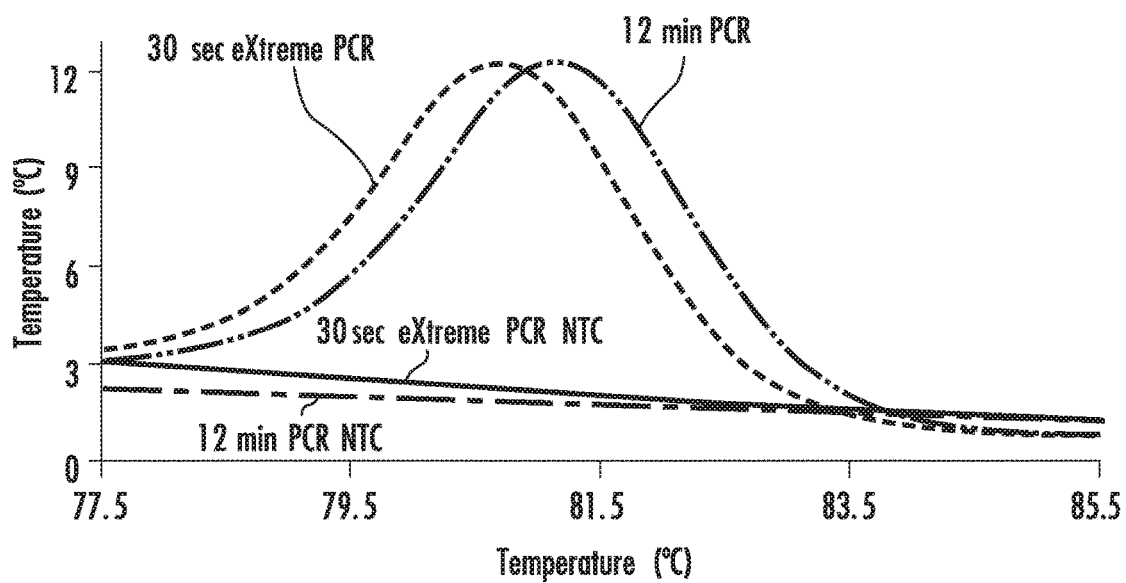
FIG. 3a shows derivative melting curves of extreme PCR products (- - - - -) and rapid cycle PCR products (――• •――), with negative controls for extreme (―――) and rapid (―― ――) cycling, amplified using the temperature profile of FIG. 2b.
Figure 3B:
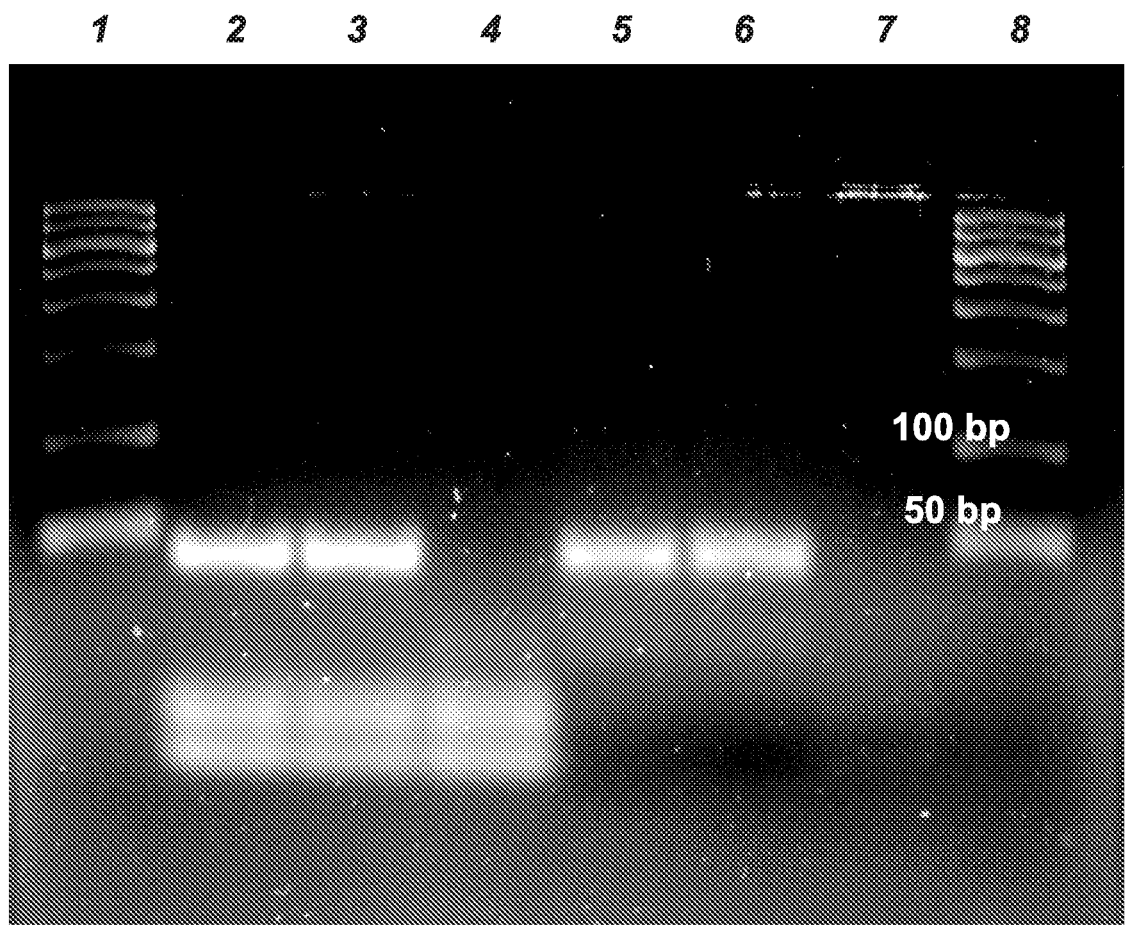
FIG. 3b is a 2% SEAKEM® LE agarose gel of the same samples of FIG. 3a, lanes 1 and 8 are size markers, lanes 2 and 3 are products resulting from 30 sec extreme PCR, lane 4 is a no template control for 30 sec extreme PCR, lanes 5 and 6 are products resulting from 12 min PCR, and lane 7 is the no template control for 12 min PCR.

FIG. 3a shows a melting curve of the PCR product generated by extreme PCR using the device shown in FIG. 1a, where 0.64 µM KLENTAQ®, a DNA polymerase, and 10 µM of each primer were used, and cycled between 91° C. and 50° C., as shown in FIG. 2b, for 35 cycles and a total amplification time of 28 seconds. Each cycle required 0.8 seconds. Also shown in FIG. 3a is a melting curve of the same amplicon generated by rapid cycling in the LightCycler, where 0.064 µM KLENTAQ®, a DNA polymerase, and 0.5 µM of each primer were used, and cycling was between 90° C. and 50° C. for 35 cycles and a total amplification time of 12 minutes (FIG. 2c). Each cycle required 10.3 seconds. Note that because of the different time scales in FIGS. 2b and 2c, the entire extreme PCR protocol of FIG. 2b is completed in less than 2 cycles of its rapid cycle counterpart. Both reactions produced amplicons having similar Tms and strong bands on gel electrophoresis (FIG. 3b), whereas neither negative control showed amplification by either melting analysis or gel electrophoresis. In this illustrative example, extreme PCR conditions showed greater yield than rapid cycle PCR conditions when analyzed on gels (FIG. 3b). The 0.5° C. difference in Tm on the melting curves is believed to be due to the different amounts of glycerol in each reaction, arising from the glycerol content in the polymerase storage buffer (final concentration of glycerol in the PCR was 1.3% under extreme conditions and 0.1% under rapid conditions). FIG. 3b also confirms that the size of the amplicons were similar and as predicted. In addition, despite the high concentrations of polymerase and primers, the reaction appears specific with no indication of nonspecific products. However, high resolution melting analysis was unable to distinguish the 3 genotypes. The stoichiometric percentage of polymerase to total primer concentration was 3% for extreme PCR and 6.4% for rapid cycle PCR.

Figure 3C:
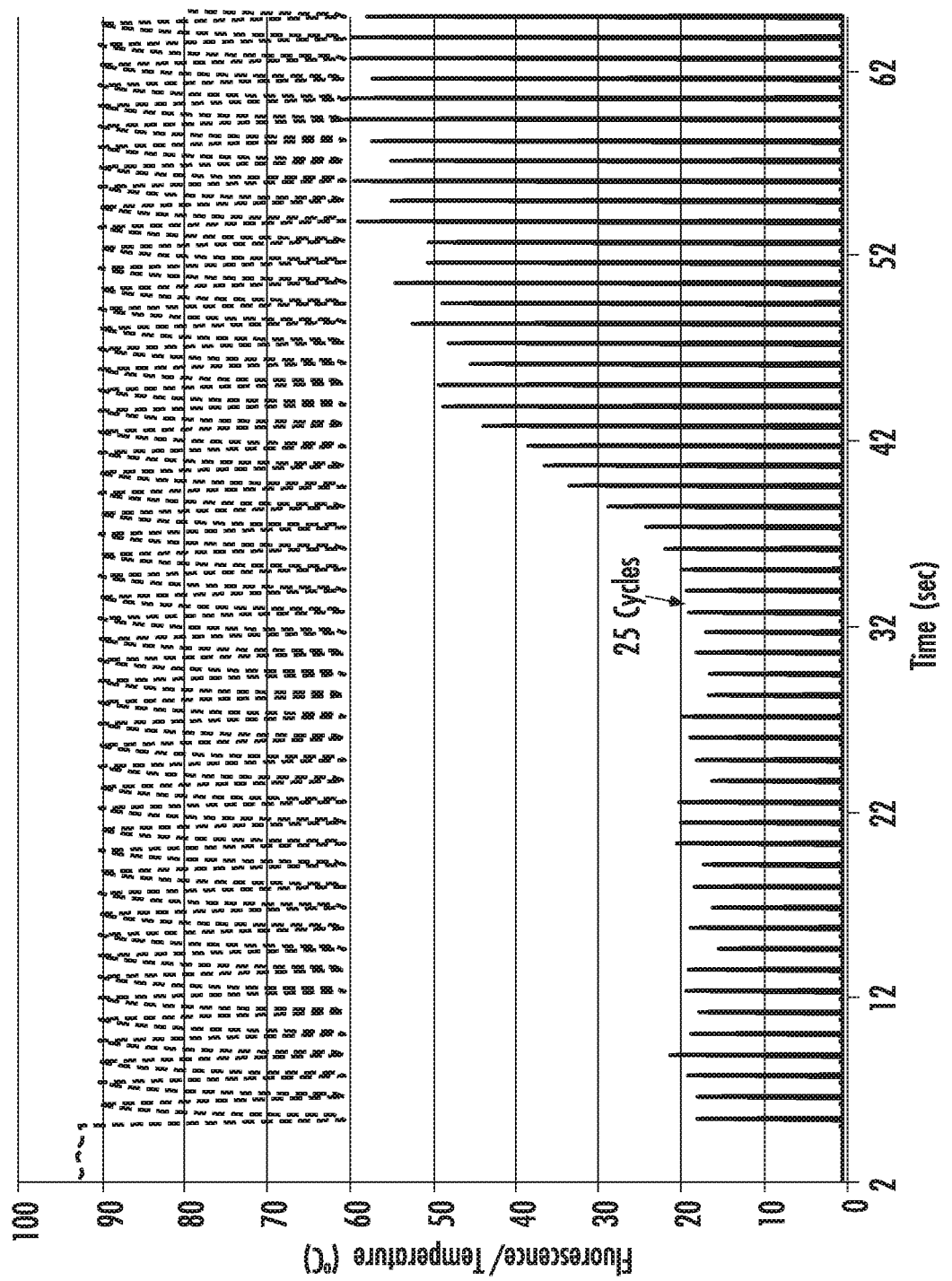
FIG. 3c shows an extreme PCR temperature trace (- - - - -) that amplified the same products shown in FIGS. 3a and 3b, along with real-time monitoring (―――) of the same reaction.

Real-time monitoring of the 45 bp KCNE1 reaction was performed using 1 µM polymerase, 10 µM of each primer, and 1.3% glycerol. The sample was monitored each cycle in air between the 2 water baths using the device of FIG. 1a. The enclosed chamber air temperature was held at 70° C. and the sample was interrogated for 0.2 seconds each cycle. As measured by the temperature reference capillary, samples were cycled between 60 and 90° C., as shown in FIG. 3c. The cycle time increased from 0.8 seconds to 1.12 seconds because of the added time for positioning and measuring. Thus, fifty cycles were completed in 56 seconds. Amplification was apparent from an increase in fluorescence at about 30 cycles or after about 34 seconds (FIG. 3c). The temperature remained near 60° C. while the sample was in air for measurement, limiting the extension rate of the polymerase.

As seen in FIG. 3c, this reaction has a quantification cycle (Cq) of about 25 cycles, but it does not seem to plateau until at least 50 cycles. Also, because the reaction was stopped after 64 cycles, it is possible that the quantity of amplicon may continue to increase and not plateau until significantly later. Without being bound to theory, it is believed that the increase in primer concentration allows for improved yield and delayed plateau, illustratively 20 cycles after Cq, and more illustratively 25 cycles or more after Cq.

Example 2

Figure 4A:
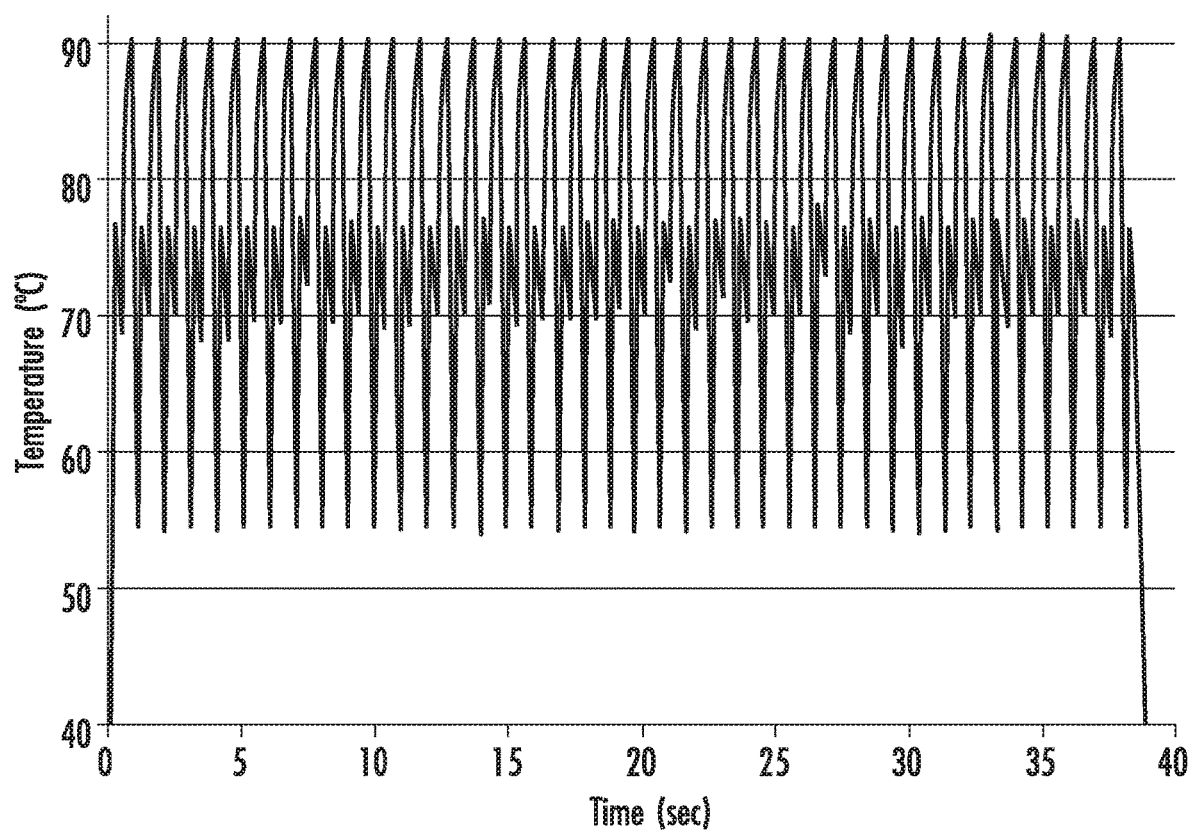
FIG. 4a shows an extreme PCR temperature trace that increases the extension rate by temperature control.
Figure 4B:
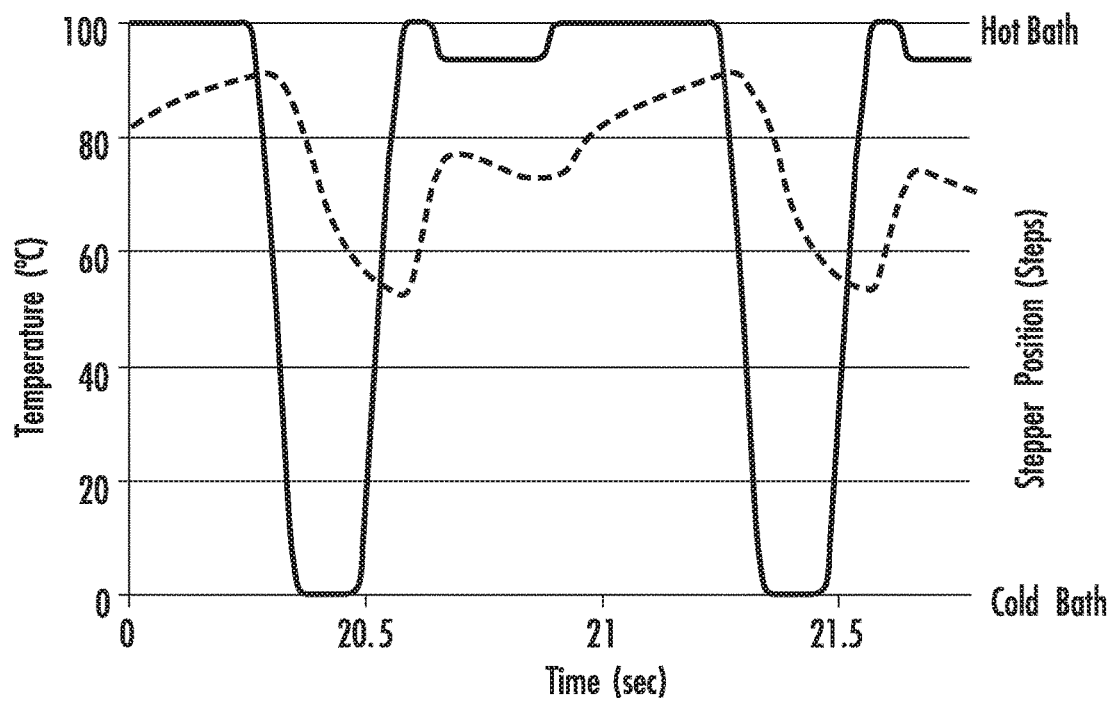
FIG. 4b shows a magnified portion of FIG. 4a, superimposing the location of the sample holder (―――) of FIG. 1b with the temperature of the sample (- - - - -).
Figure 4C:
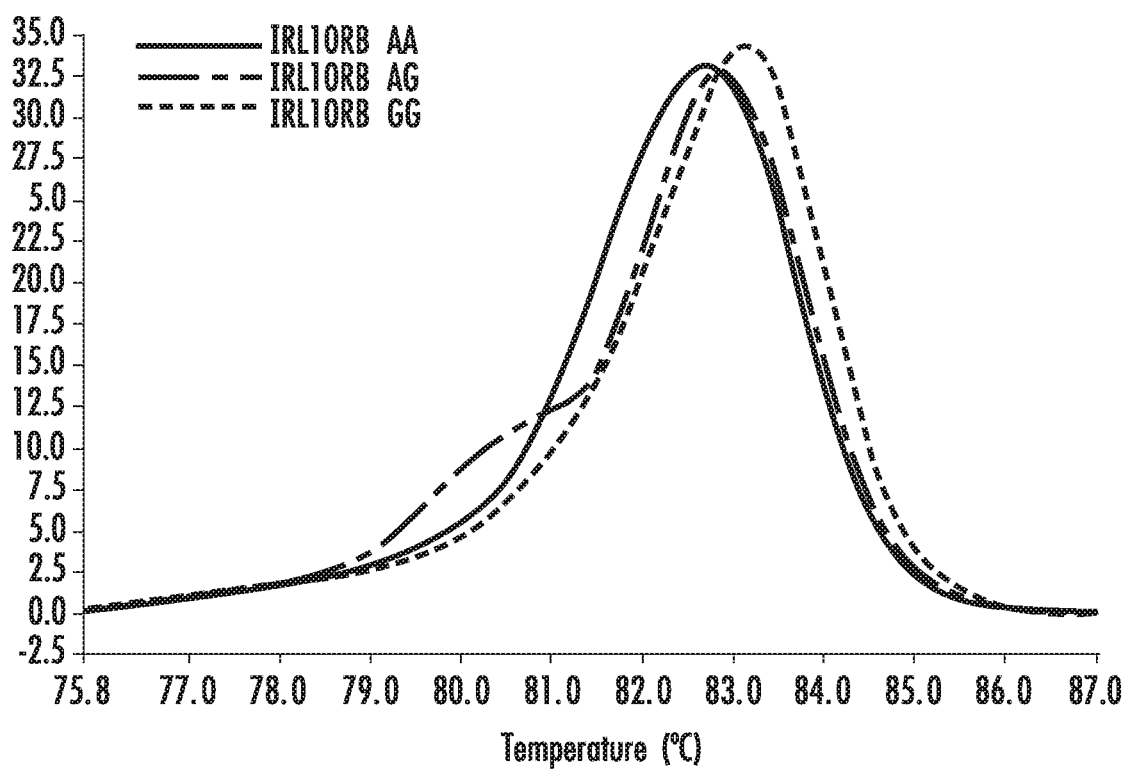
FIG. 4c is a negative derivative melting curve (-dF/dT) of a 58 bp amplicon of IRL10RB, wherein AA (―――), AG (―― ――), and GG (- - - - -) genotypes are shown.

In this example, a 58 bp fragment bracketing an A>G variant (rs #2834167) in the interleukin 10 beta receptor was amplified with primers CTACAGTGGGAGTCACCTGC (SEQ ID NO:4) and GGTACTGAGCTGT-GAAAGTCAGGTT (SEQ ID NO:5) to generate the following amplicon: CTACAGTGGGAGT-CACCTGCTTTTGCC(A/G)AAGGGAACCTGACTTTCACAGCTC AGTACC (SEQ ID NO:6). Extreme PCR was performed as described in Example 1 using the instrument shown in FIG. 1a. One µM polymerase, 10 µM each primer and 1.3% glycerol were used (polymerase to total primer percentage=5%). In order to increase the temperature for polymerase extension to 70-80° C., where the polymerase has higher extension rates, a different positioning protocol was used. After reaching the annealing temperature, instead of immediately positioning in air for monitoring, the sample was transferred to the hot water bath until the extension temperature was reached. Then the sample was positioned in air just above the hot water bath, producing the temperature cycles shown in FIGS. 4a and 4b, and enabling faster polymerase extension at optimal temperatures between 70 and 77° C. The 3 different genotypes were each amplified by extreme PCR using 0.97 second cycles, completing 39 cycles in 38 seconds. After extreme PCR, high resolution melting curves were obtained for each genotype on an HR-1 instrument modified to accept LC24 capillaries. FIG. 4c reveals that all three genotypes were amplified and distinguished, as expected.

Example 3

The reaction mixtures in Example 1 were the same for both the extreme PCR and rapid cycle PCR, except for the amounts of polymerase and primers, and a minor difference in glycerol concentration that apparently caused the shift in Tm seen in FIG. 3a. In this and all future examples, the glycerol concentration was held at 2% by equalizing its concentration as necessary. For extreme PCR, 1 µM polymerase and 10 µM of each primer were used, while for rapid cycle PCR, 0.064 µM polymerase and 0.5 µM of each primer were used. As discussed above, it is believed that faster annealing times provide for improved primer specificity. With this improved specificity, increased concentrations of primers may be used, which is believed to favor primer binding and allow reduced annealing times. Similarly, increased polymerase concentrations favor binding to the annealed primer, and also favor rebinding to the incomplete amplicon if a polymerase falls off prior to complete extension. In addition, because of the higher polymerase concentration, a greater proportion of the primed templates can be extended at once even late in PCR, reducing the number of templates that a single polymerase must extend and reducing the overall extension time.

Figure 5A:
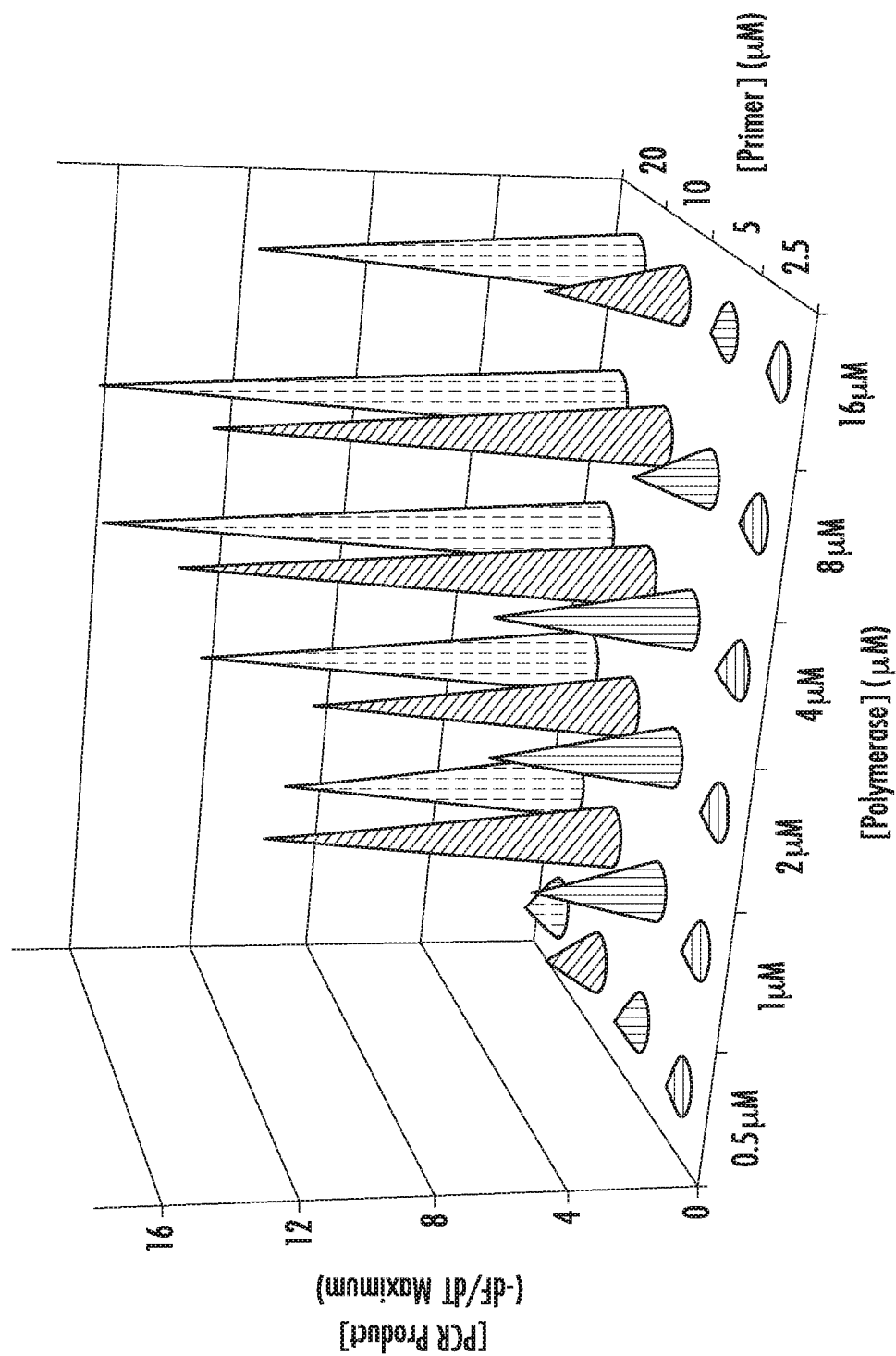
FIG. 5a is a three dimensional graph plotting polymerase concentration vs. primer concentration vs. concentration of PCR product, using extreme PCR.
Figure 5B:
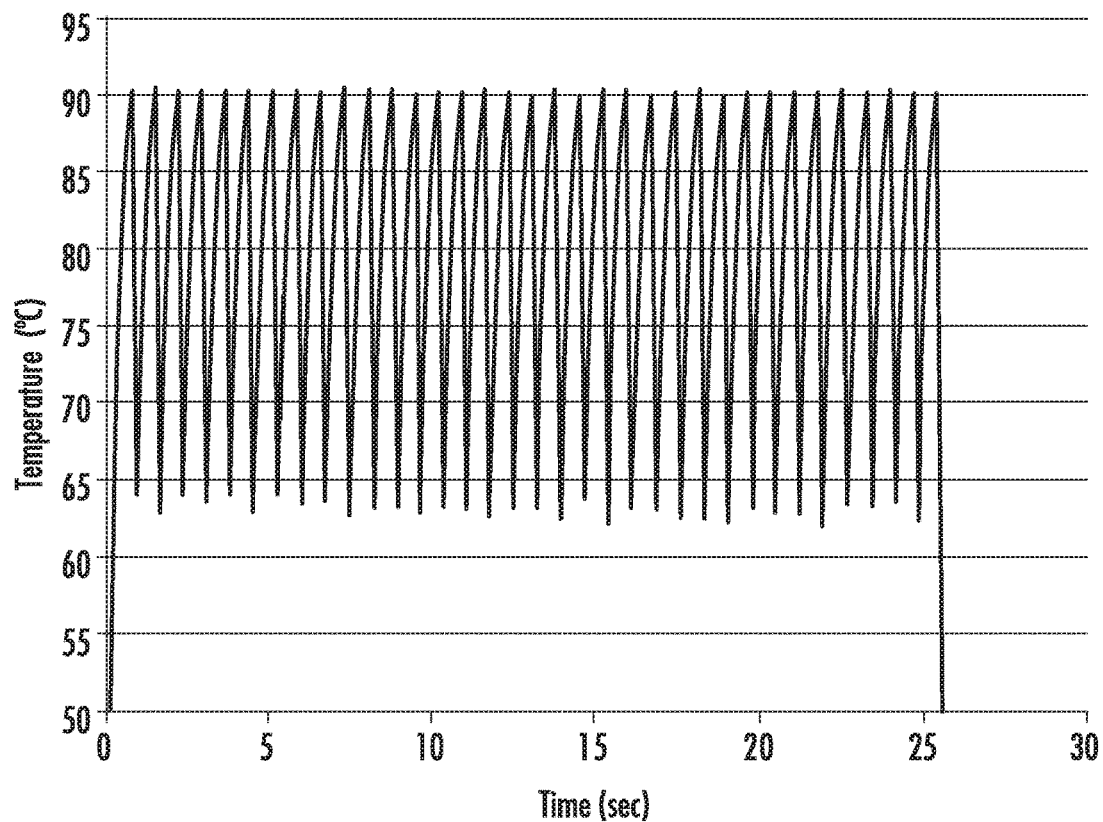

FIG. 5a summarizes the results of extreme PCR cycling with various polymerase and primer concentrations. In this example, a 49 bp fragment of the interleukin 10 beta receptor was amplified with primers GGGAGT-CACCTGCTTTTGCC (SEQ ID NO:7) and TACT-GAGCTGTGAAAGTCAGGTTCC (SEQ ID NO:8) and 3 mM $MgCl_2$, to generate: GGGAGTCACCTGCTTTTGC-CAAAGGGAACCTGACTTTCACAGCTCAGTA (SEQ ID NO:9). For each extreme PCR reaction, the device shown in FIG. 1b was used without real time monitoring. The temperature was cycled between 90° C. and 63° C. for 35 cycles, for a total reaction time of just under 26 seconds (0.73 second cycles) as shown in FIG. 5b. Reaction conditions were as discussed in Example 1, except that the amounts of polymerase and primers were varied, as shown in FIG. 5a. The vertical axis in FIG. 5a is quantified as the peak of the negative derivative plot of the melting curve, obtained without normalization on the HR-1 instrument. At 0.5 µM polymerase, virtually no amplification was seen at any level of primer concentration. However, at 1.0 µM polymerase, discernible levels of amplification were seen at primer concentrations of 5 µM and above. As the polymerase levels increase, so do the amount of amplicon, up to levels of about 4 µM. At 8 polymerase, the amount of amplicon plateaued or dropped off, depending on the primer concentration, with a significant drop off at 16 µM at lower primer concentrations. It appears that under these extreme temperature cycling conditions for a 49 bp product, the polymerase has a favored concentration range between about 1 and 8 and more specifically between 2 and 8 depending on the primer concentration.

Figure 5C:
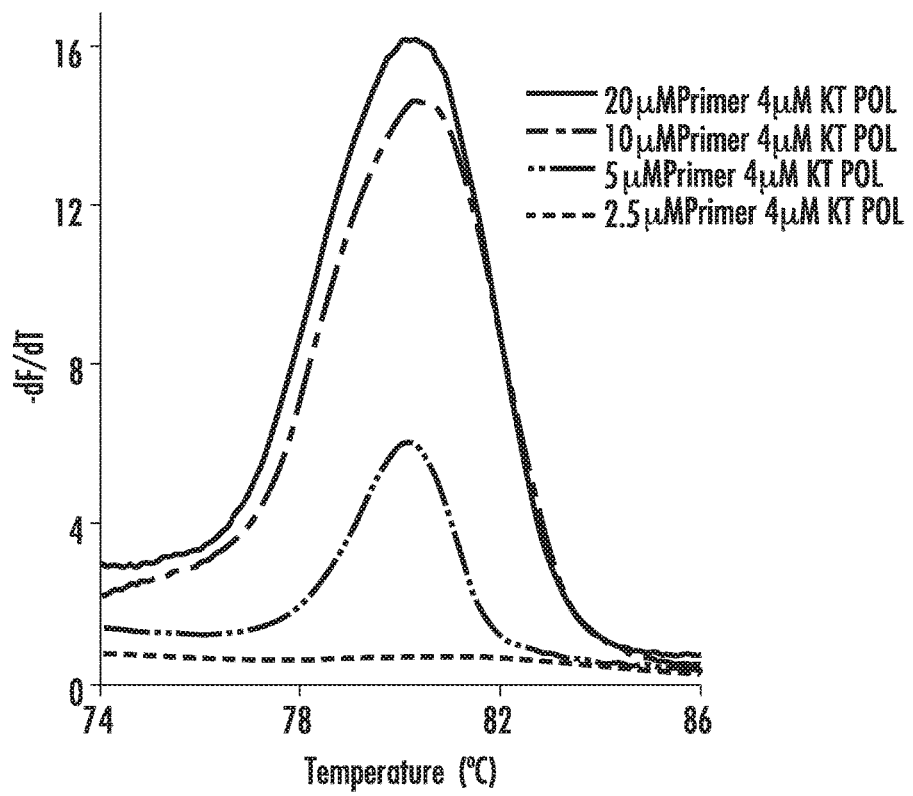
Figure 5D:
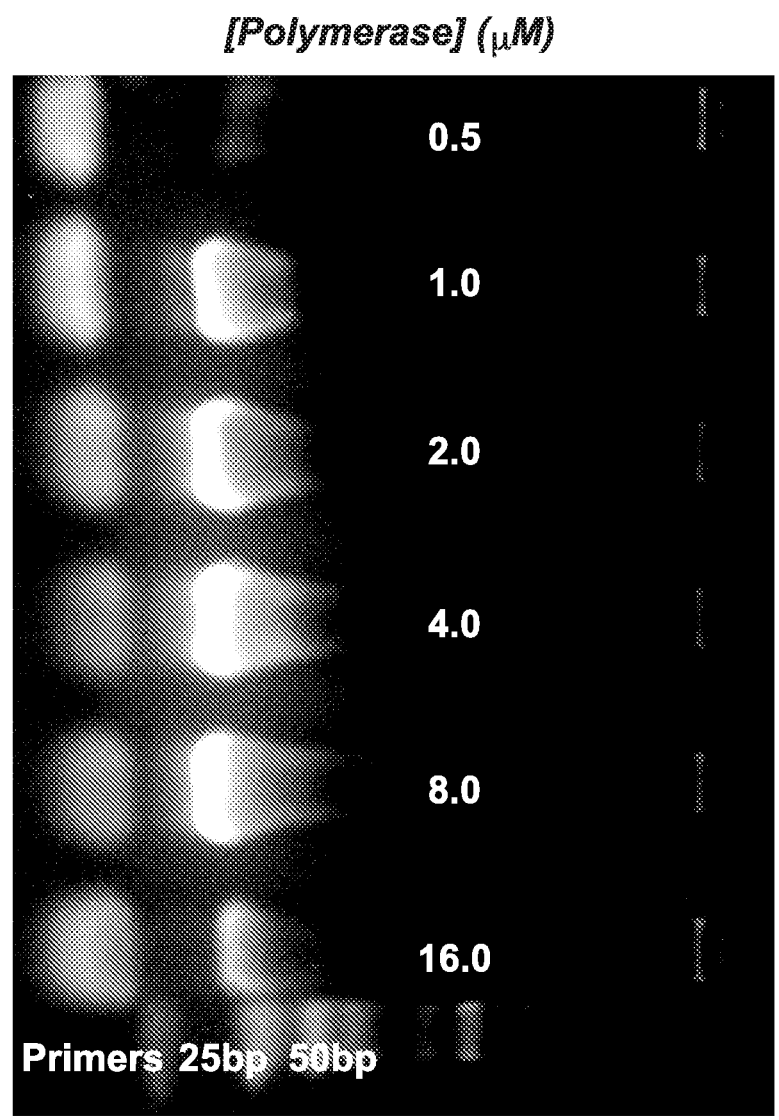

Similarly, little amplification was seen with primer concentrations of 2.5 µM. However, amplification was successful at 5 µM primer, with KLENTAQ®, a DNA polymerase, concentrations of 2-8 and amplification continued to improve with increasing concentrations. Excellent amplification was achieved with primer concentrations of about 10-20 µM primer. FIG. 5c shows melting curves for various primer concentrations at 4 µM KLENTAQ®, a DNA polymerase, while FIG. 5d verifies the size of the product as the polymerase concentration varies while the primer concentration is held at 10 µM. Despite the high concentrations of polymerase and primers, no nonspecific amplification is seen.

Without being bound to theory, it appears that the ratio between the amount of enzyme and amount of primer is important for extreme PCR cycling, provided that both are above a threshold amount. It is noted that the above amounts are provided based on each primer. Given that the polymerase binds to each of the duplexed primers, the total primer concentration may be the most important. For KLENTAQ®, a DNA polymerase, suitable ratios are 0.03-0.4 (3-40% enzyme to total primer concentration), with an illustrative minimum KLENTAQ® concentration of about 0.5 and more illustratively about 1.0 for extreme PCR. The primers may be provided in equimolar amounts, or one may be provided in excess, as for asymmetric PCR. The optimal polymerase:primer percentage may also depend on the temperature cycling conditions and the product size. For example, standard (slow) temperature cycling often uses a much lower polymerase to primer percentage, typically 1.5 nM (0.04 U/µl) polymerase (49) and 1,000 nM total primer concentration, for a percentage of 0.15%, over 10 times lower than the percentages found effective for extreme PCR.

Example 4

Figure 6B:
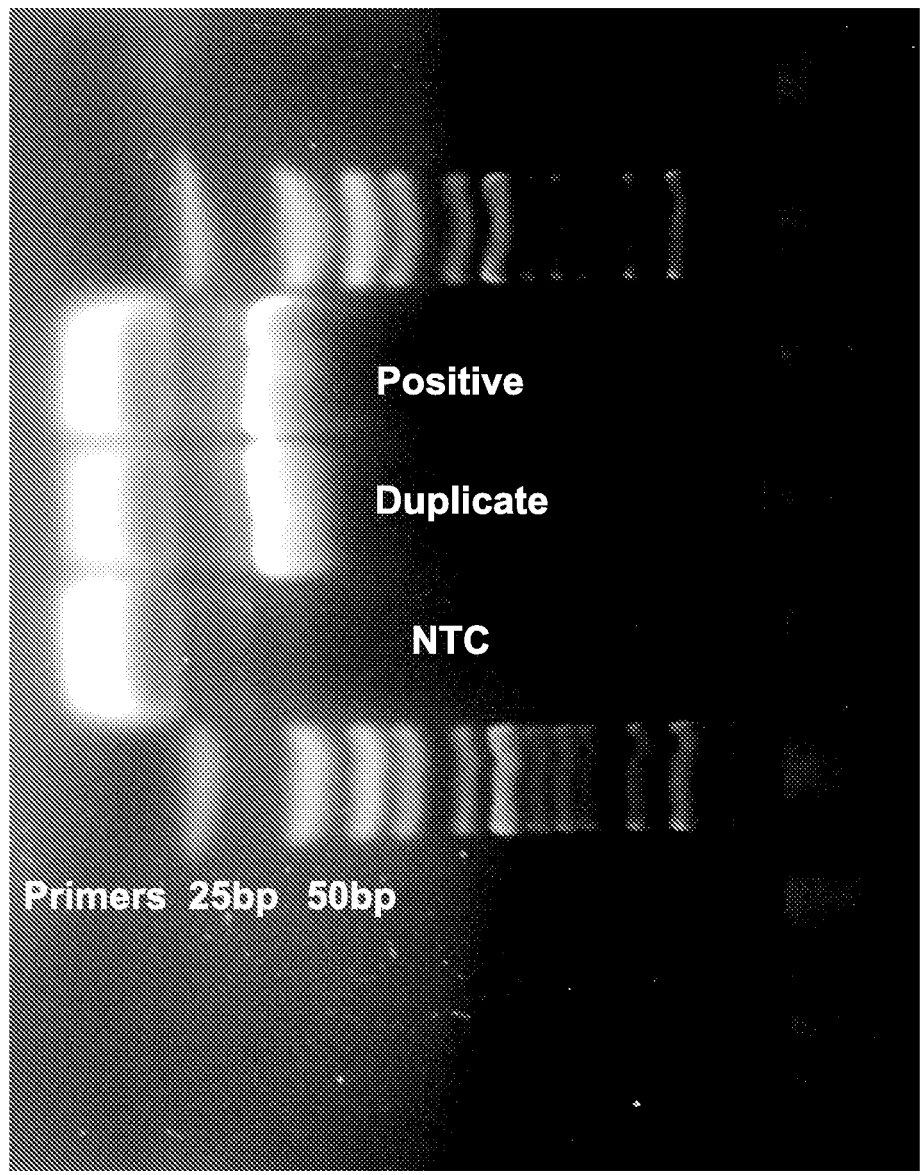

The same PCR target as in Example 3 was amplified with 8 µM polymerase and 20 µM each primer in a 19 gauge steel hypodermic needle, to increase thermal transfer and cycling speeds. The polymerase to total primer percentage was 20%. Amplification was performed on the instrument of FIG. 1b and was completed in 16 seconds using 35 cycles of 0.46 seconds each (FIG. 6a), cycling between 91° C. and 59-63° C. The maximum heating rate during cycling was 407° C./s and the maximum cooling rate was 815° C./s, demonstrating that PCR can occur with ramp rates of greater than 400° C./s with no holds. Analysis of the products on a 4% NuSieve 3:1 agarose gel revealed strong specific bands of the correct size (FIG. 6b). The no template control showed no product at 49 bp, but did show a prominent primer band similar to the positive samples.

Example 5

Figure 7A:
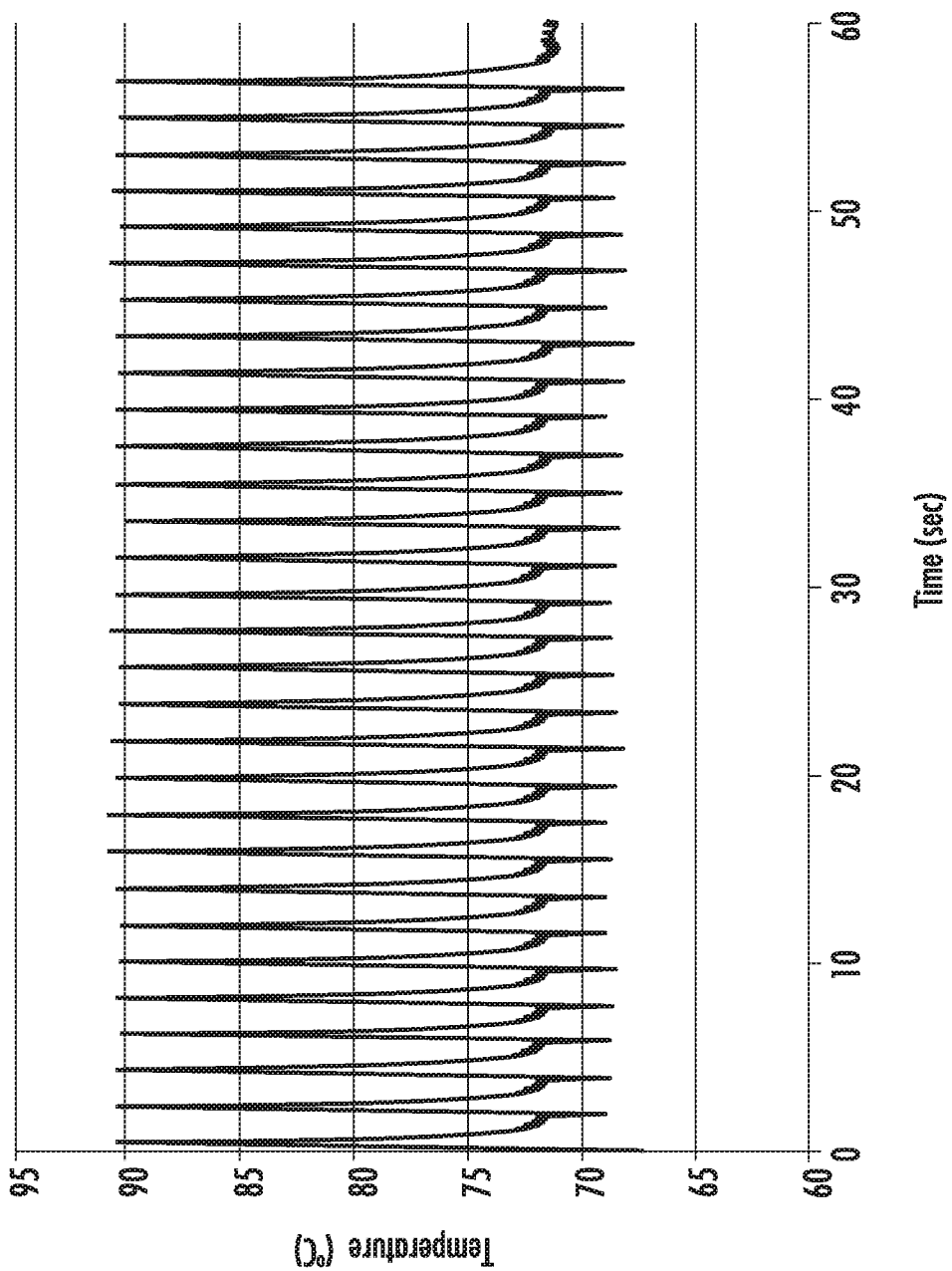
FIG. 7a is an extreme PCR temperature trace with a long (1 second) combined annealing/extension step.
Figure 7B:
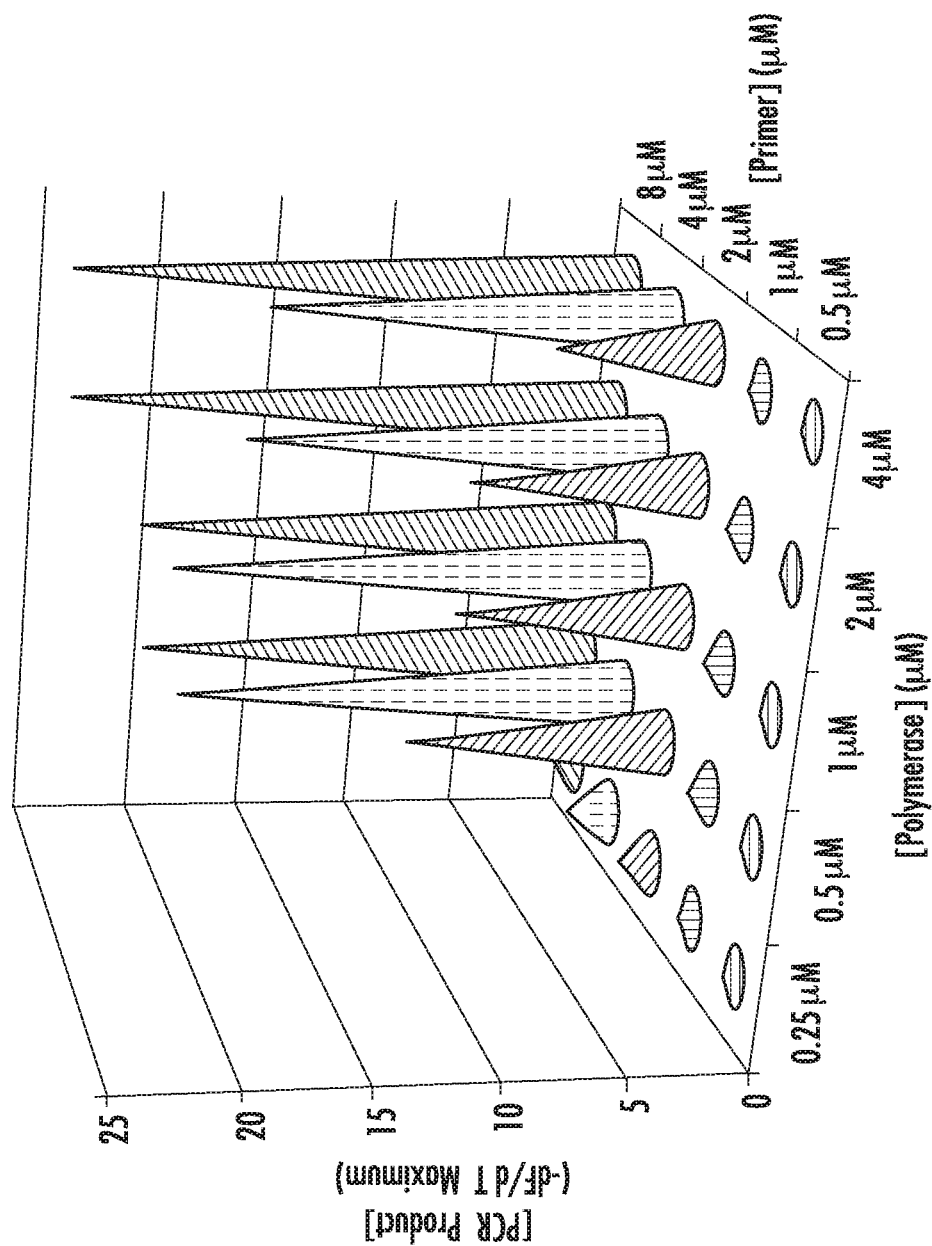
FIG. 7b is a three dimensional graph plotting polymerase concentration vs. primer concentration vs. concentration of PCR product, using extreme PCR for a 102 bp product.

A 102 bp fragment of the NQO1 gene was amplified using primers CTCTGTGCTTTCTGTATCCTCAGAGTGGCAT-TCT (SEQ ID NO:10) and CGTCTGCTGGAGTGTGCC-CAATGCTATA (SEQ ID NO:11) and the instrument of FIG. 1b without the real-time components. The polymerase concentration was varied between 0.25 and 4 while each primer concentration was varied between 0.5 and 8 µM. The primers were designed to anneal at higher temperatures (low 70s) so that extension at a combined annealing/extension phase would be at a more optimal temperature for the polymerase. Greater polymerization rates at these temperatures were expected to enable amplification of longer products. The cooler water bath was controlled at 72° C. and the end of the annealing/extension phase triggered by time (1 second), rather than temperature. Cycling between 72 and 90° C. for 30 cycles required 58 seconds using 1.93 second cycles (FIG. 7a). As seen in FIG. 7a, the sample temperature drops about 3° C. below the annealing/extension temperature while it travels through the air to the hot water bath. FIG. 7b shows the amount of product amplified by quantifying the melting curves as in FIG. 5a. Melting curve analysis showed only a single product of Tm 84° C. Very little product was observed at 0.25 µM polymerase or at 1 µM each primer. Some amplification occurs at 2 each primer, with the best amplification at 2-4 µM polymerase and 8 µM each primer. At primer concentrations of 2-4 yield decreases as the polymerase concentration increases, although this was not seen at 8 µM primer concentration. Although the thermal cycling and target length are different from Example 3, the best amplification occurs at polymerase to total primer concentrations of 3.1 to 50%.

Example 6

Extreme PCR was used to amplify 135 bp and 337 bp fragments of the BBS2 gene using the instrument shown in FIG. 1b with real time monitoring. In order to study the effect of product length on extreme PCR and control for possible confounding effects of different primers, the fragments were first amplified from genomic DNA using primers with common 5'-end extensions. For the 135 bp fragment the primers were ACACACACACACACACACACACACACACAC ACACACAAAAATTCAGTGGCATT AAATACG (SEQ ID NO:12) and GAGAGAGAGAGAGAGAGAGAGAGAGAGAG AGAGAGAGAGAGAGAGAAAAAC CAGAGCTAAAGGGAAG (SEQ ID NO:13). For the 337 bp fragment the primers were ACACACACACACACACACACACACACACAC ACACACAAAAAGCTGGTGTCTGC TATAGAACT-GATT (SEQ ID NO:14) and GAGAGAGAGAGAGAGAGAGAGAGAGAGA GAGAGAGAGAGAGAGAGAAAAAG TTGCCAGAGCTAAAGGGAAGG (SEQ ID NO:15). After standard PCR amplification from genomic DNA, primers and dNTPs were degraded by ExoSAP-IT (Affymetrix, CA), followed by PCR product purification using the QUICKSTEP™ 2 PCR Purification Kit (Catalog #33617, Edge BioSystems, Gaithersburg, Md.). PCR products were diluted approximately 1 million-fold and adjusted to equal concentrations by equalizing the Cq obtained by standard real-time PCR to obtain a Cq of 25 cycles (approximately 10,000 copies/10 µl reaction).

Figure 8A:
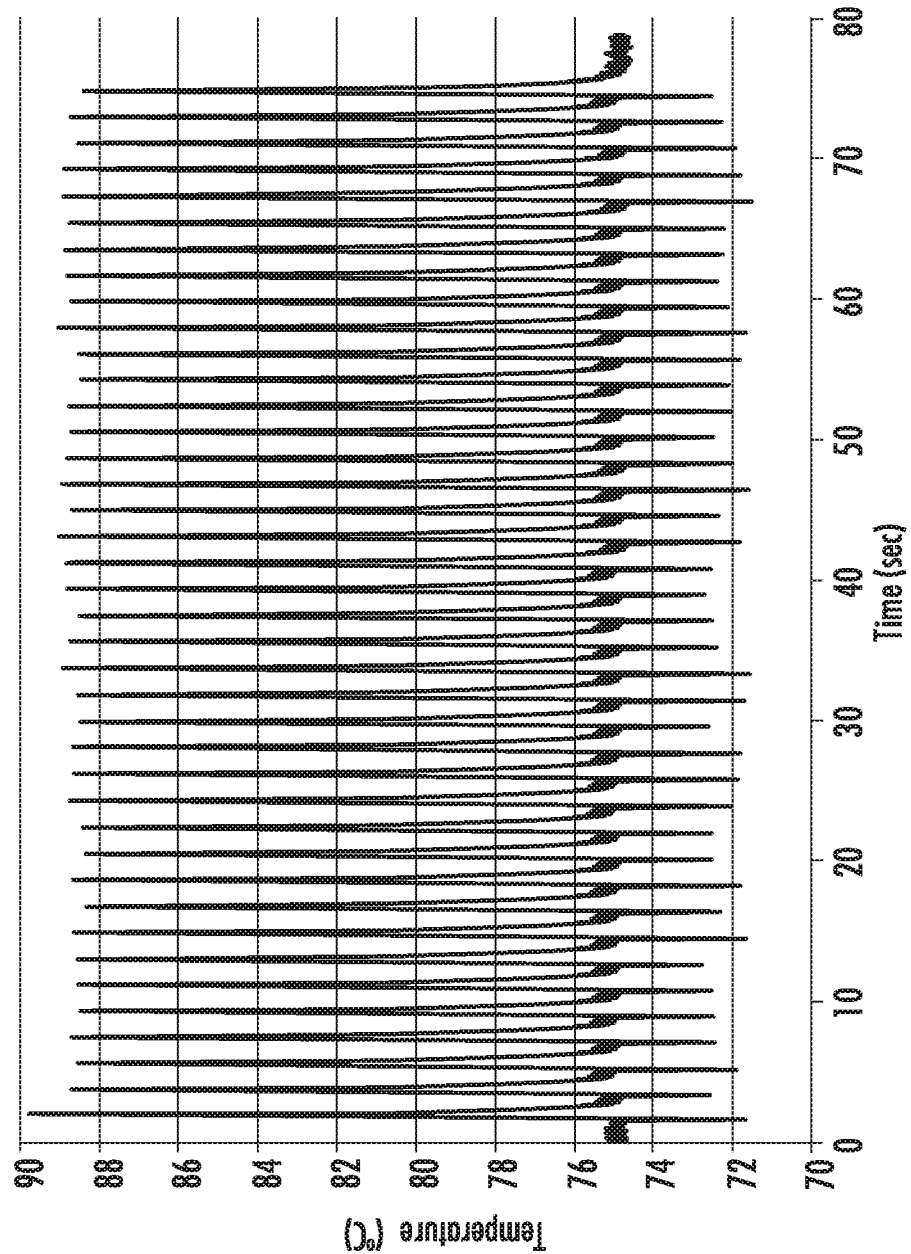
FIG. 8a shows an extreme PCR temperature profile used to amplify a 226 bp product, using a one second combined annealing/extension step.
Figure 8B:
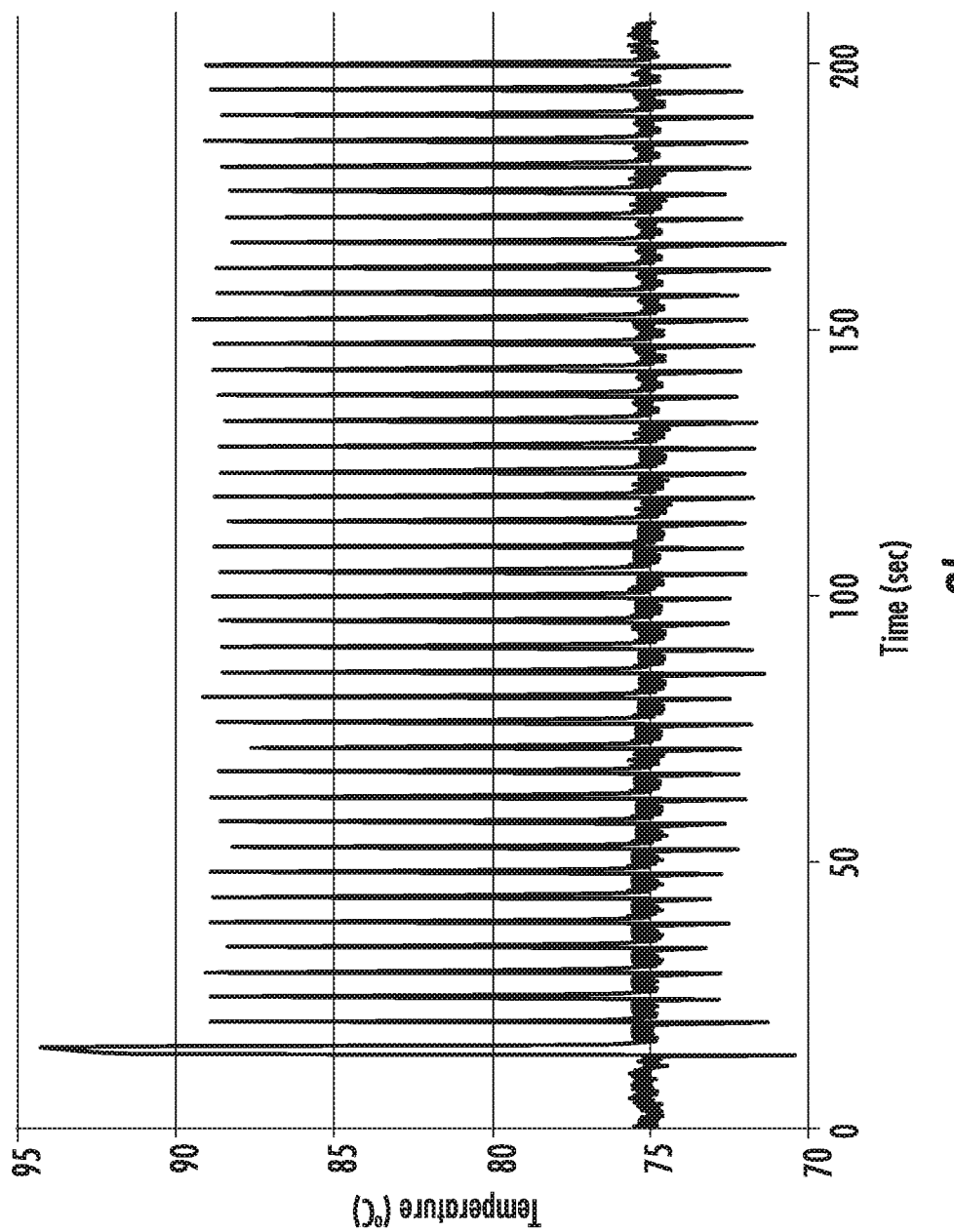
FIG. 8b shows an extreme PCR temperature profile used to amplify a 428 bp product, using a four second combined annealing/extension step.
Figure 8C:
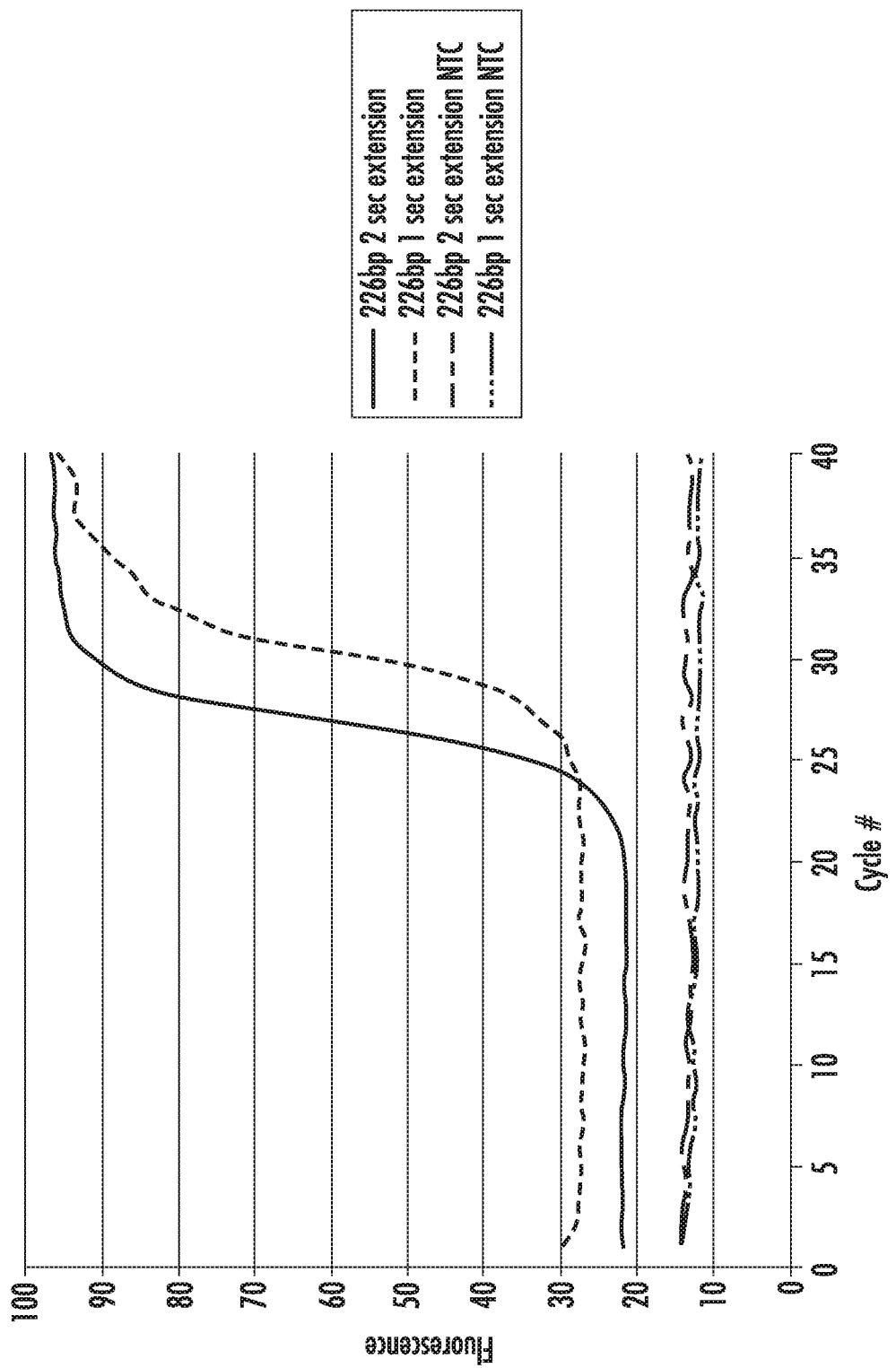
FIG. 8c shows the real time results obtained from FIG. 8a and a similar temperature trace using a 2 second annealing/extension step, including no template controls for each.
Figure 8D:
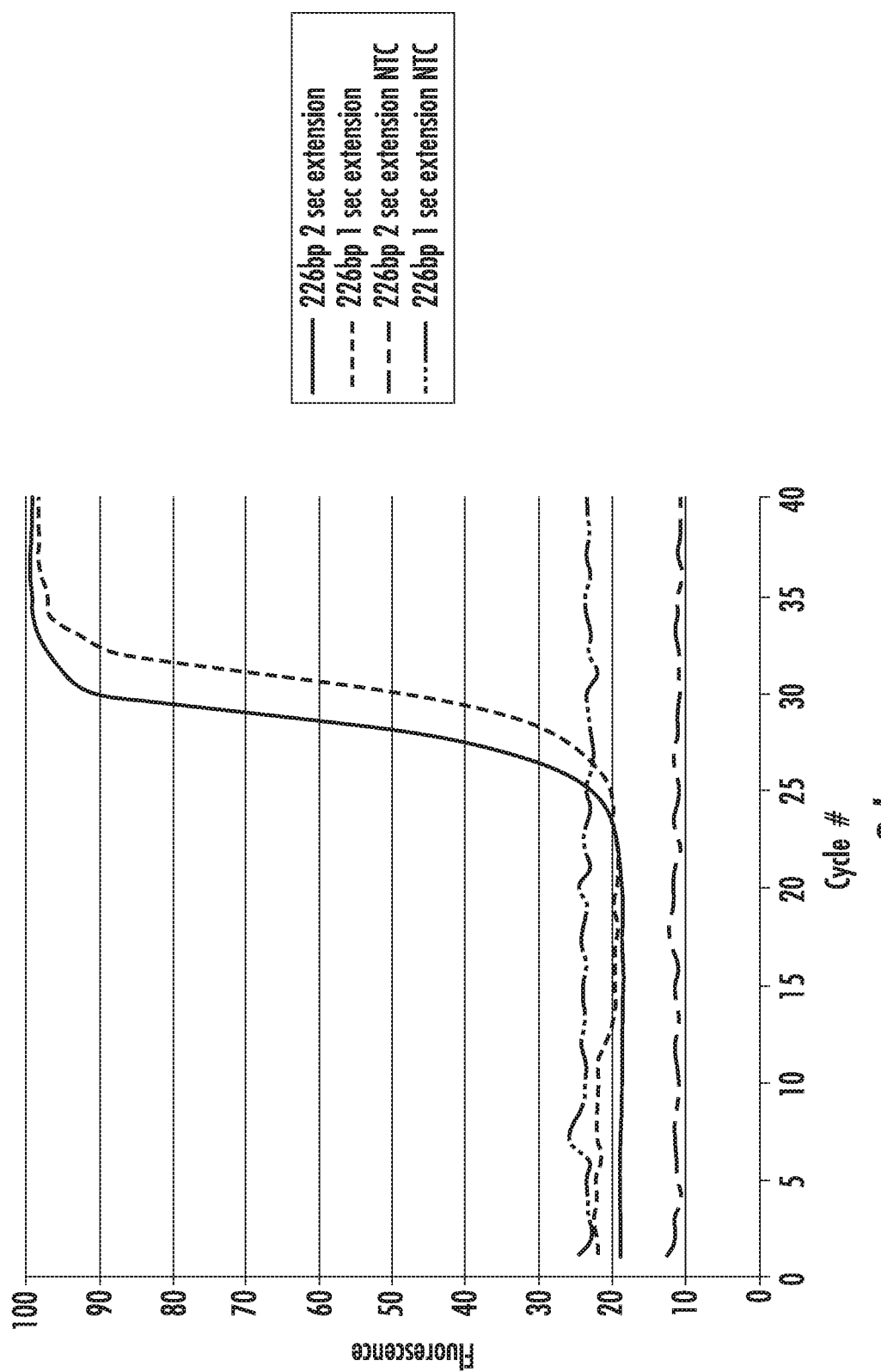
FIG. 8d shows the real time results obtained from FIG. 8b and a similar temperature trace using a 5 second annealing/extension step, including no template controls for each.

Extreme PCR was performed on 1,000 copies of the amplified templates in a total volume of 5 µl using the common primers ACACACACACACACACACACACACACACAC ACACACAAAAA (SEQ ID NO:16) and GAGAGAGAGAGAGAGAGAGAGAGAGAGA GAGAGAGAGAGAGAGAAAAA (SEQ ID NO:17) each at 2 µM with 2 µM polymerase and 2% glycerol. The 135 bp BBS2 fragment resulted in a 226 bp product requiring extension of 176 or 185 bases (depending on the primer), while the 337 bp BBS2 fragment resulted in a 428 bp PCR product requiring extension of 378 or 387 bases. Specific amplification was verified on agarose gels and by melting analysis. The extreme PCR temperature profile used for the 226 bp product is shown in FIG. 8a, which included a 1 second combined annealing/extension at 75° C. and denaturation at 87° C. Also performed was a 2 second annealing/extension phase at the same temperature (trace not shown). Real time PCR results for these amplifications are shown in FIG. 8c, revealing about a 5 cycle shift to higher Cq with the 1 second extension as compared to the 2 second extension, presumably reflecting a decrease in efficiency as the extension time is decreased. The extreme PCR temperature profile used for the 428 bp product is shown in FIG. 8b, showing a 4 second combined annealing/extension at 75° C. and denaturation at 87° C. Also performed was a 5 second annealing/extension phase at the same temperature (trace not shown). Real time PCR results for these amplifications are shown in FIG. 8d, revealing about a 2 cycle shift to higher Cq with the 4 second extension as compared to the 5 second extension, presumably reflecting a decrease in efficiency as the extension time is decreased.

Example 7

Figure 9A:
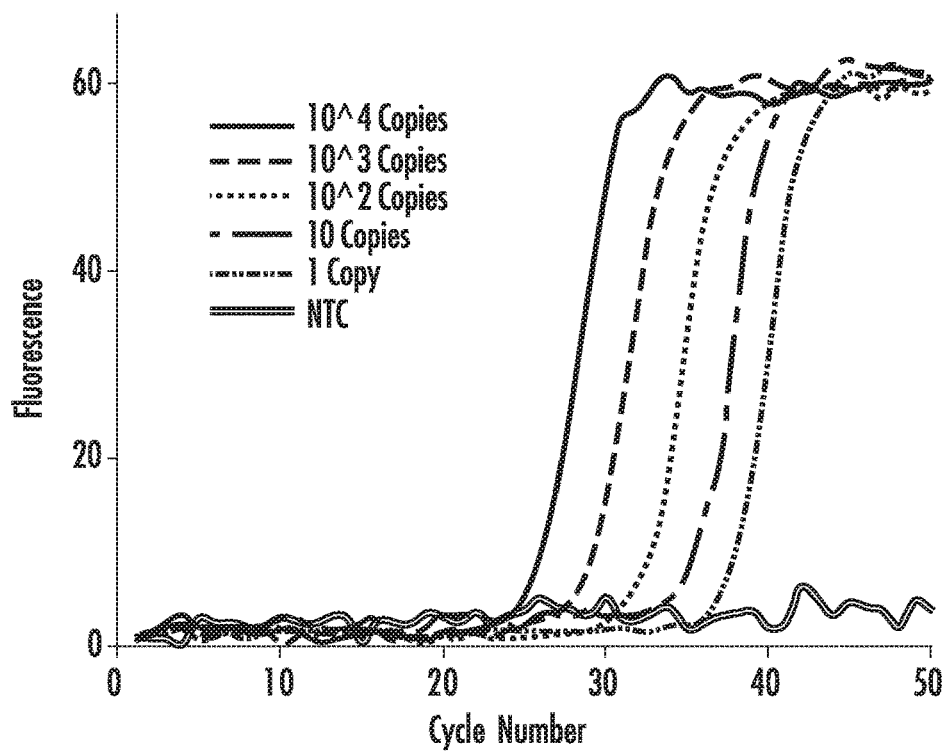
FIG. 9a shows amplification curves of a 45 bp fragment of KCNE1 at different starting concentrations.
Figure 9B:
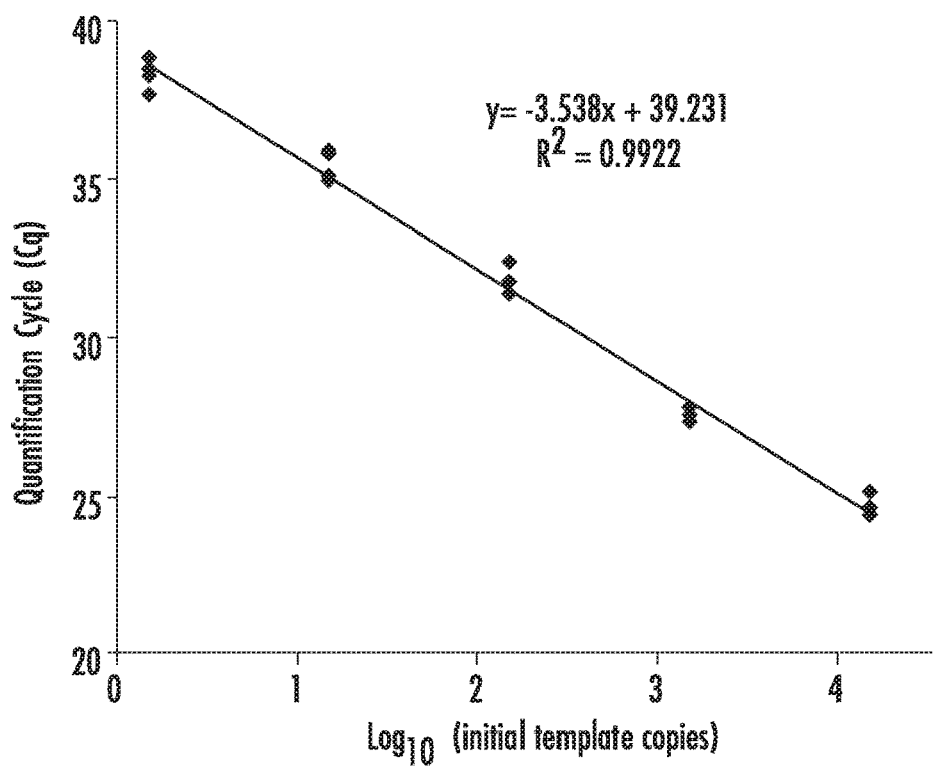
FIG. 9b is a plot of Cq versus log-10 (initial template copies) of the data from FIG. 9a. Reactions were performed in quintuplicate.
Figure 9C:
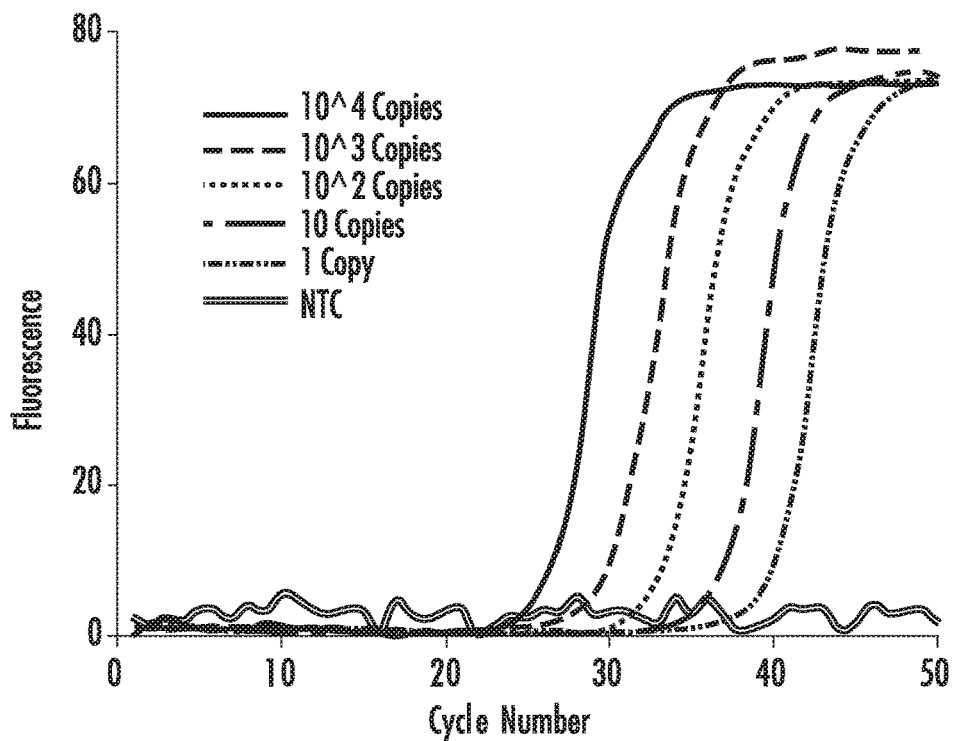
FIGS. 9c-9d are similar to FIGS. 9a-9b, except showing amplification of a 102 bp fragment of NQO1.
Figure 9D:
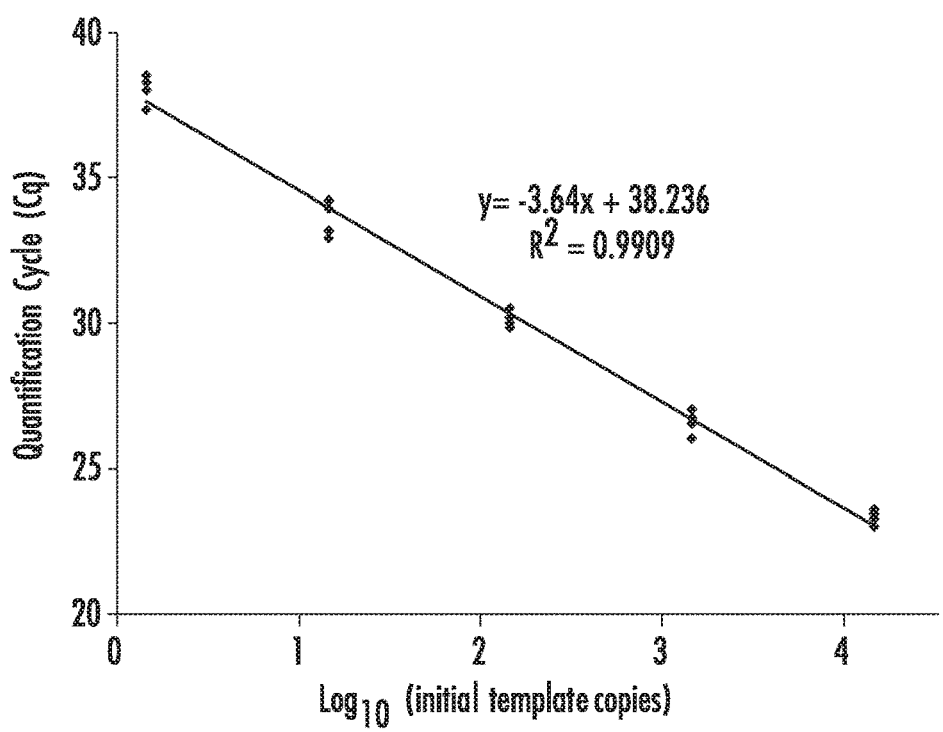

Quantitative performance of PCR was assessed using the real-time instrument of FIG. 1b for the 102 bp fragment of NQO1 of Example 5 and the 45 bp fragment of KCNE1 of Example 1 using a dilution series of human genomic DNA, using 2 µM KLENTAQ® (a DNA polymerase) and 8 µM each primer for NQO1 and 8 µM KLENTAQ® (a DNA polymerase) and 20 µM each primer for KNCE1. With a dynamic range of at least 4 decades, as seen in FIGS. 9a and 9b, the amplification efficiencies calculated from the standard curves were 95.8% for NQO1 and 91.7% for KCNE1. Control reactions without template did not amplify after 50 cycles and single copy replicates (mean copy number of 1.5 copies per reaction) were similar in amplification curve shape and intensity to higher concentrations (FIGS. 9A and 9C). At a mean copy number of 0.15 copies/reaction, 2 reactions were positive out of 17 (combining both NQO1 and KCNE1 trials), with a calculated expectation of 0.13 copies/reaction by binomial expansion.

Example 8

Figure 10A:
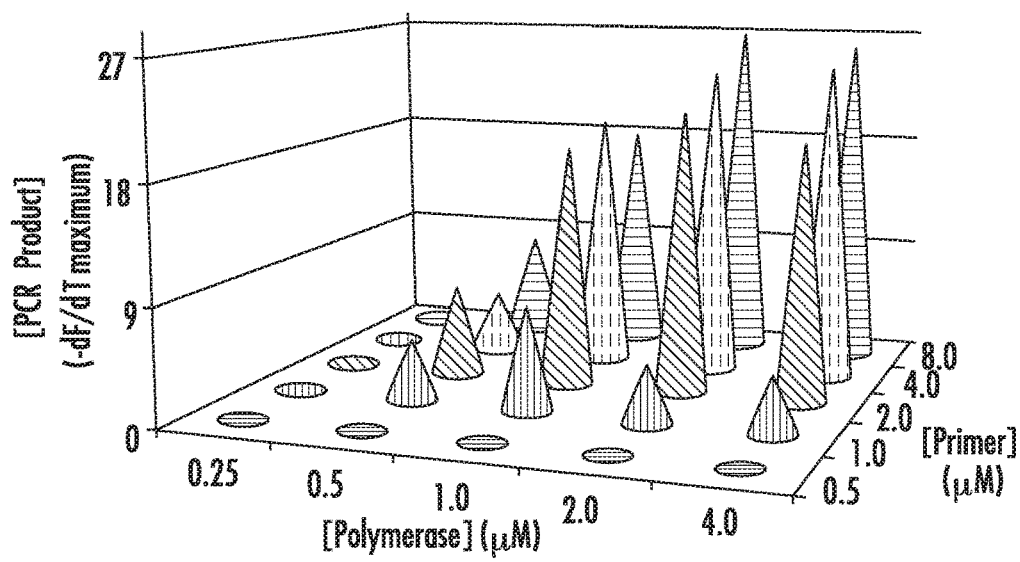
FIG. 10a is a three dimensional graph plotting polymerase concentration vs. primer concentration vs. concentration of PCR product, using extreme PCR for a 300 bp product (20 cycles, 4.9 seconds per cycle).
Figure 10B:
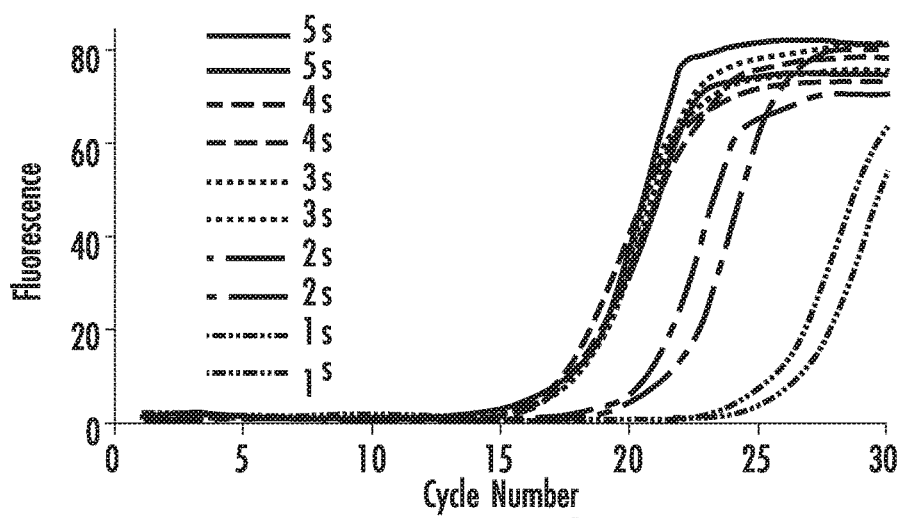
FIG. 10b shows fluorescence versus cycle number plots for PCR amplification of a 500 bp synthetic template using KAPA2G FAST polymerase and 1-5 second extension times.
Figure 10C:
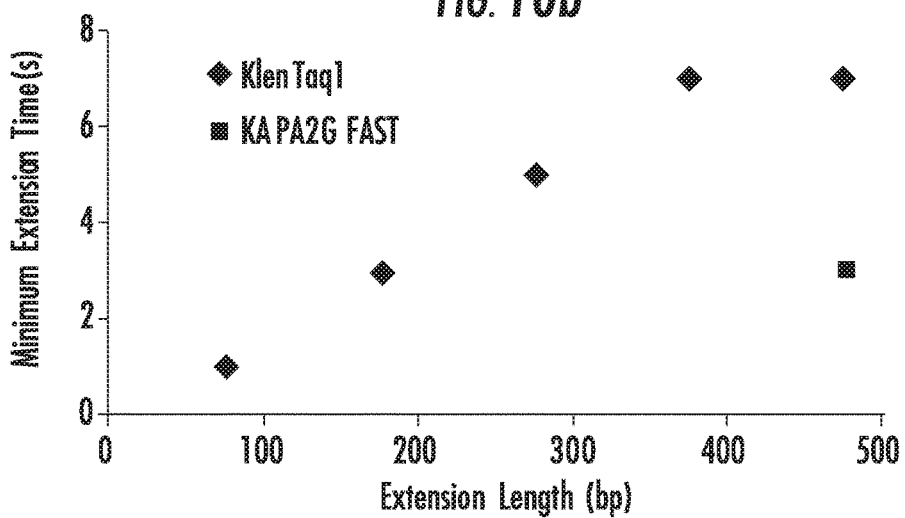
FIG. 10c is a plot of extension length vs. minimum extension time for several KLENTAQ® polymerase concentrations and KAPA2G FAST polymerase.
Figure 11A:
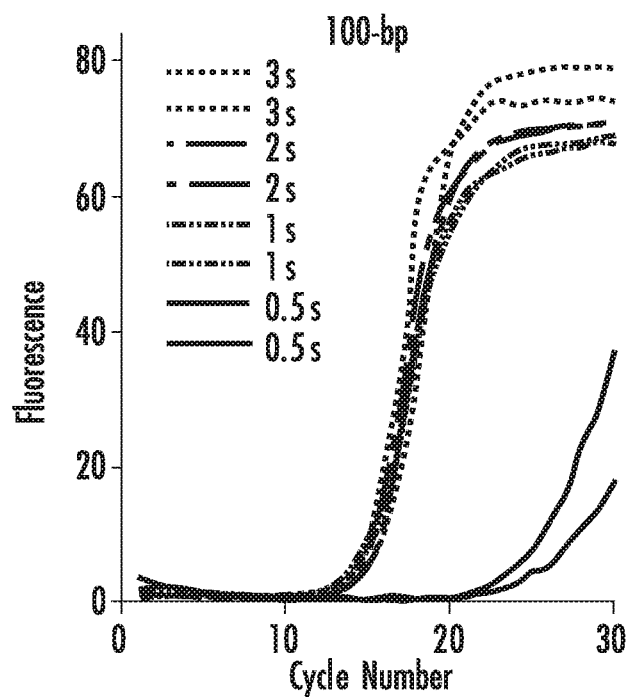
FIGS. 11a-11e show fluorescence versus cycle number plots for PCR amplification of products of size: 100 bp (FIG. 11a), 200 bp (FIG. 11b), 300 bp (FIG. 11c), 400 bp (FIGS. 11d), and 500 bp (FIG. 11e).
Figure 11B:
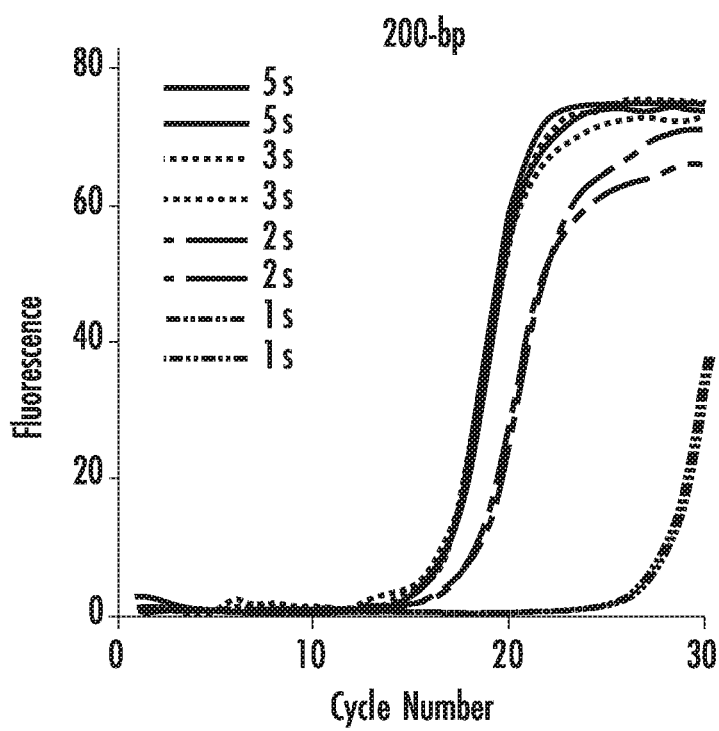
Figure 11C:
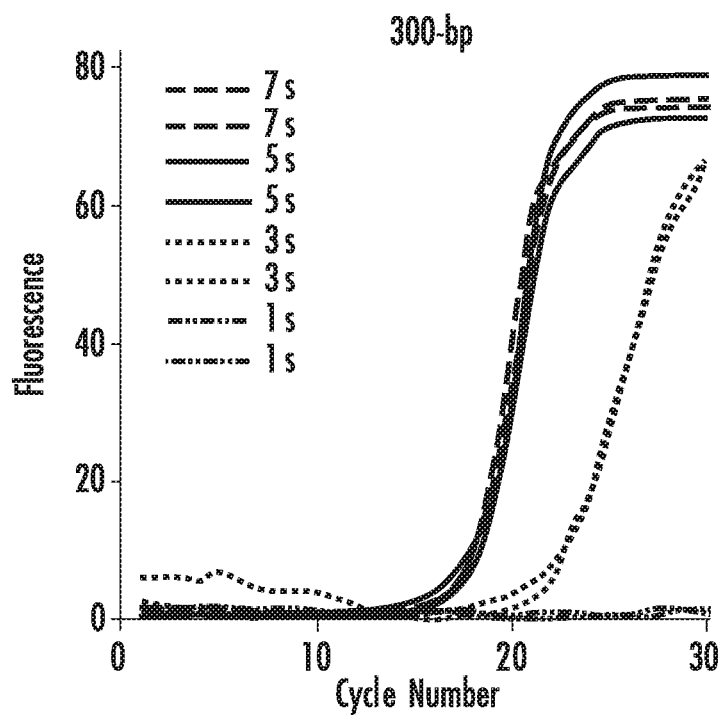
Figure 11D:
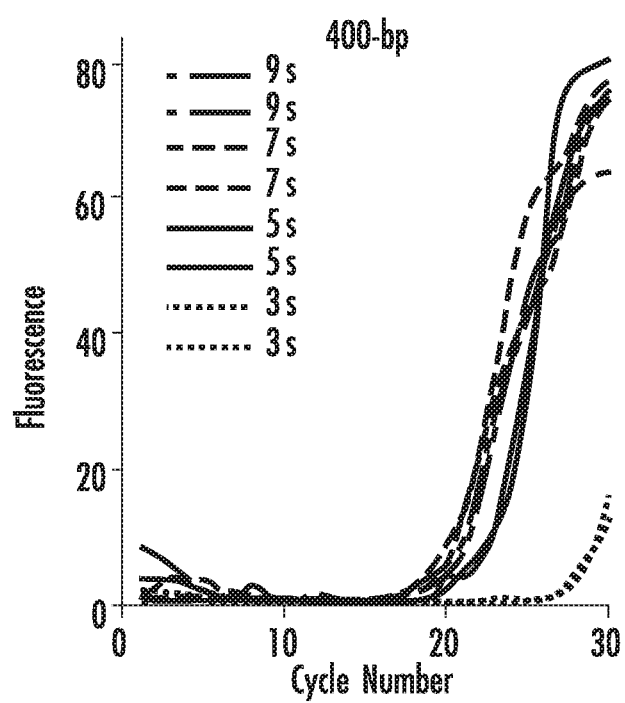
Figure 11E:
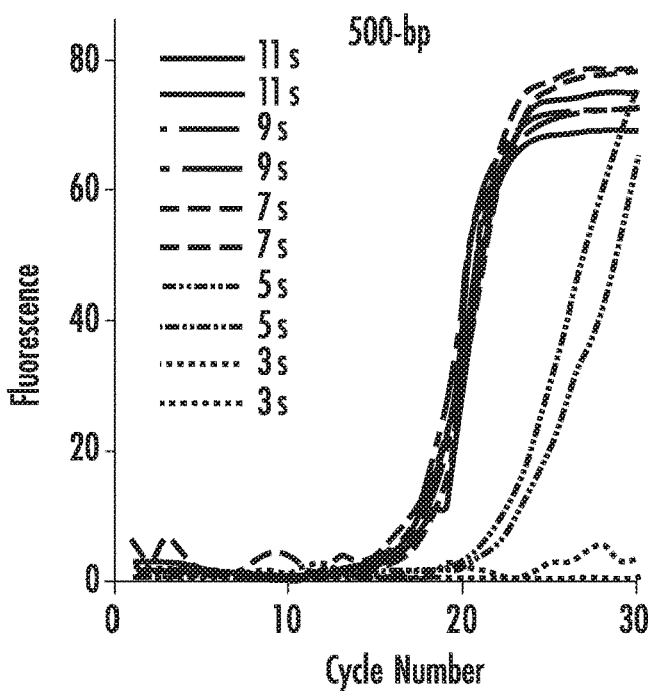

The extension time required for different product lengths using real-time PCR (FIG. 10a-c). To control for the possible confounding effects of different primers, synthetic templates of 100-500 bp using the following common high Tm (77° C.) primers:

```
                                         (SEQ ID NO: 18)
          ACTCGCACGAACTCACCGCACTCC
          and
                                         (SEQ ID NO: 19)
          GCTCTCACTCGCACTCTCACGCACA.
```

The synthetic template sequences were:

100 bp Template:

100 bp Template:
```
                                         (SEQ ID NO: 20)
ACTCGCACGAACTCACCGCACTCCGGATGGATTGTGAAGAGGCCCAAGA

TACTGGTCATATTATCCTTTGATCTAGCTCTCACTCGCACTCTCACGCA

CA.
```

200 bp Template:
```
                                         (SEQ ID NO: 21)
ACTCGCACGAACTCACCGCACTCCTCAATGCTGACAAATCGAAAGAATA

GGAATAGCGTAATTACTAGAGGACTCCAATATAGTATATTACCCTGGTG
```

-continued

ACCGCCTGTACTGTAGGAACACTACCGCGGTTATATTGACAGCTTAGCA

ATCTACCCTGTTGGGATCTGTTTAAGTGGCTCTCACTCGCACTCTCACG

CACA.

300 bp Template:
(SEQ ID NO: 22)
ACTCGCACGAACTCACCGCACTCCCCTTCGAATATAAAGTACGACATTA

CTAGCAATGACAGTTCCAGGATTTAAGAAAGTAGTGTTCCACATCAATG

CATATCCAGTGAAAGCATAACGTCAAAAAAAGCCTGGCACCGTTCGCGA

TCTGGACTTACTTAGATTTGTTGTAGTCAAGCCGGCTATCAGCGATTTA

TCCCGGAAACACATACTAGTGAGTTATTTGTATGTTACCTAGAATAGCT

GTCACGAATCACTAATACATTCACCCACCAGCTCTCACTCGCACTCTCA

CGCACA.

400 bp Template:
(SEQ ID NO: 23)
ACTCGCACGAACTCACCGCACTCCTGAATACAAGACGACAGTCCTGATT

ATATTTTCATTTAATTACGCCAATTTAATTATGATGAATATTAACGGAA

TTAAATATGTATTGATAAGTACTAAGTAATGGTTTACCCACGGCGATCT

ATATGCAAGGGAAACATTAACAAATTTAAACATCTGATGTGGACAAAAC

TTGTAATGTGGTATAGTTAAAAATATAGGTTTCAGGGACACGTAAGTAT

CTATCTTGAATGTTTAAGTAGGTCCTGTCTACCATTCTGAAATTTAGAA

AATCGCGTTCATCGGGCTGTCGGCTACACCTCAGAAAACCATTTCGTGT

TGCACAGGAGGAACTTTCGAGGGTTCGTATGAGCTCTCACTCGCACTCT

CACGCACA.

500 bp Template:
(SEQ ID NO: 24)
ACTCGCACGAACTCACCGCACTCCACCGCTTGACGACGTAGGGTATTTG

GTATCTGAATCTACTCATTTACCTACATACTGAAGATTTTGCGATCGTC

TAATATATTGGACTAATGCCCGATTTCTGATCAATTACTCTAGGCGATA

CTTCATCGCTGGCCTTATTTGGATTTTGCTCAAGTGCTAAACTCTCTGC

GCGTCAATACTAGTCTGACATCAGTCAAGACCTGCTATCTGAAAACTAC

TAGAGAGATATACCTAACAACTTTAGTGGATAAATCAGGTCTGGAGATT

GTCATATAATGCCACTAGGGTCAGAAGGCTGTGTCAAAGTTAGTGGTTA

GTAGGTCTCCGCTCTGCGGTACTATTCTTATATTCTCTTACTATGCATC

AAACAAAATAGAATGCATAGACAAACCGCCTGCCAAGTTTACAAGATAA

CTTGCGTATAGGTTTATAAGGGTTCTTCTGTATCGCTCTCACTCGCACT

CTCACGCACA.

Optimal concentrations of primers and polymerase were first determined for the intermediate length 300-bp product using a 4 second combined annealing/extension segment with 4.9 seconds per cycles (FIG. 10a). Identical primer (4 μM) and polymerase (2 μM) concentrations were then used for all product lengths and minimum extension times were determined (FIG. 11a-e). Depending on the product length, increased extension times resulted in decreased fractional quantification cycles (Cq) until no further change was observed, reflecting the minimum extension time required for efficient PCR. For example, amplification curves using the KAPA2G™ FAST polymerase (Kapa Biosystems) for the 500 bp product are shown in FIG. 10b. The minimum extension time using KAPA2G FAST polymerase was 3 s, compared to 7 s using KLENTAQ1™ (a deletion mutant of Taq polymerase, AB Peptides). When the identity of the polymerase is kept constant, longer products required longer extension times (FIG. 10c). For KLENTAQ1™ polymerase, about 1 second is required for each 60 bps, while for KAPA2G FAST, 1 second is required for each 158 bp. It is noted that these two polymerases were chosen because they are commercially available at sufficient concentrations, while most other polymerases are not commercially available at such high concentrations. It is understood that the required time for extension depends directly and linearly with the length to be extended, and inversely with the concentration of polymerase and the polymerase speed. A proportionality constant (k2) can be defined that relates these 3 parameters:

$$\text{Required Extension Time} = k2*(\text{extension length})/([\text{polymerase}]*(\text{polymerase speed}))$$

Example 9

Extreme PCR times can also be reduced with high Mg++ concentrations. A 60 bp fragment of AKAP10 was amplified with primers: GCTTGGAAGATTGCTAAAATGA-TAGTCAGTG (SEQ ID NO:25) and TTGATCATACT-GAGCCTGCTGCATAA (SEQ ID NO:26), to generate the amplicon GCTTGGAAGATTGCTAAAATGA-TAGTCAGTGAC(A/G)TTATGCAGCAGGCTCAG TAT-GATCAA (SEQ ID NO:27).

Figure 12A:
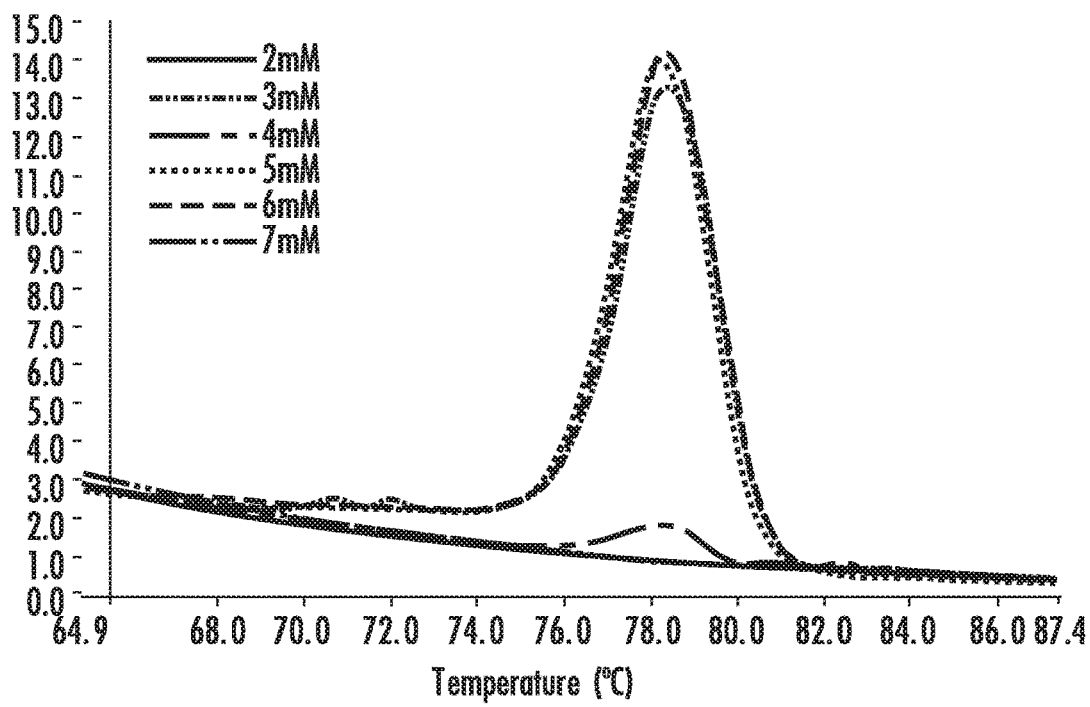
FIG. 12a shows negative derivative melting curves of a 60 bp fragment of AKAP10 after 35 cycles of extreme PCR, using varying magnesium concentrations.
Figure 12B:
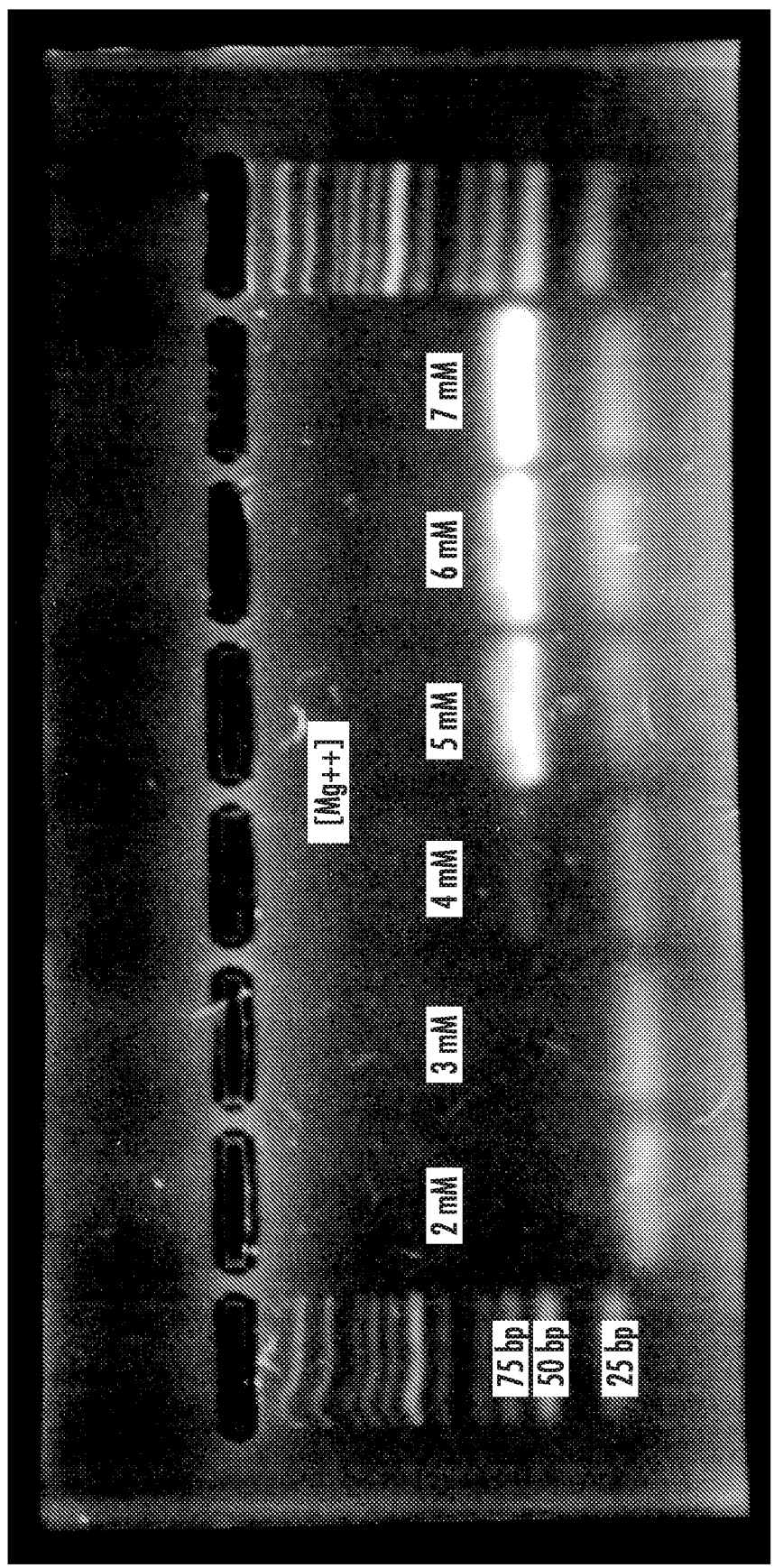
Figure 13A:
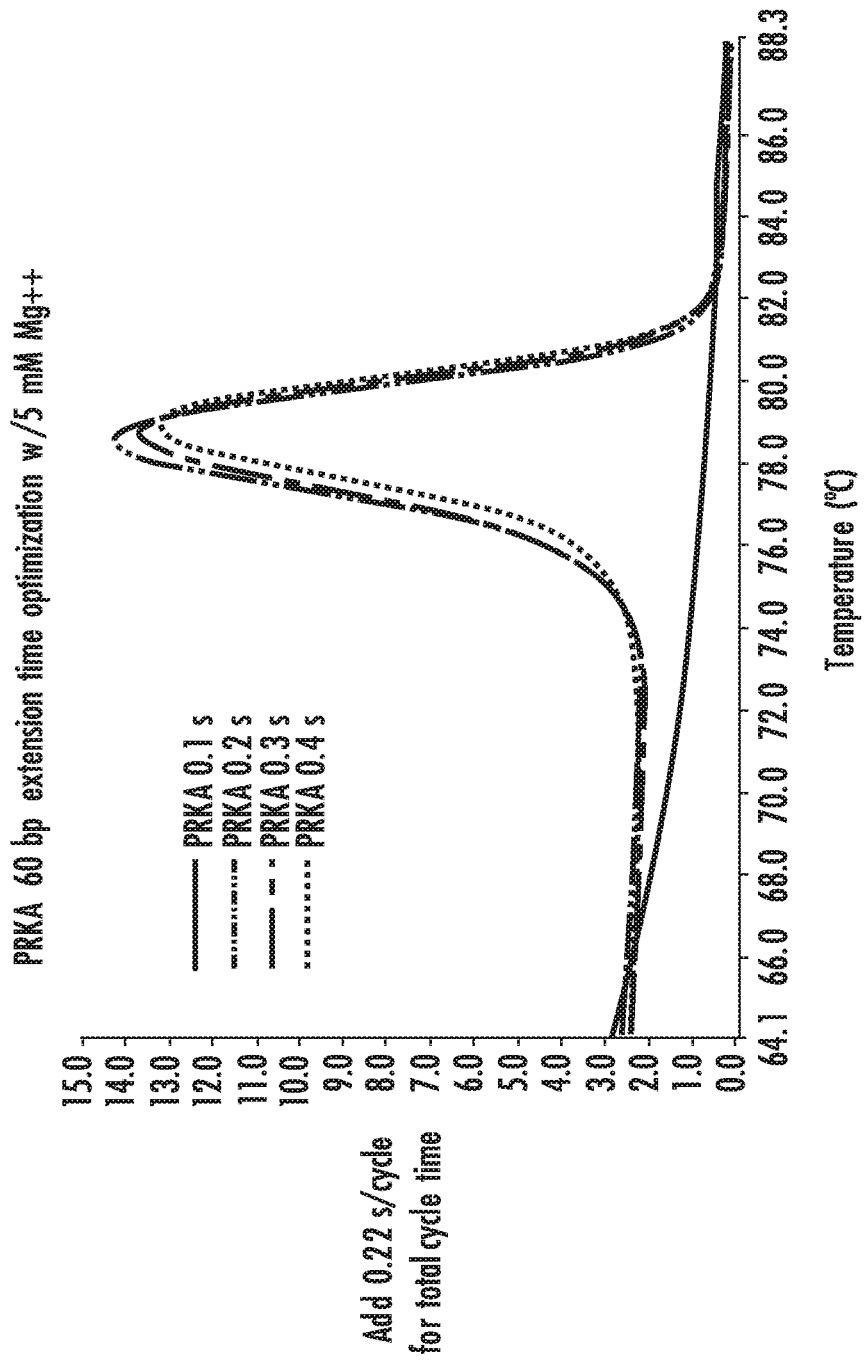
FIG. 13a shows negative derivative melting curves of a 60 bp fragment of AKAP10 after 35 cycles, using varying cycle times with 5 mM Mg++. Cycle times were 0.32 seconds (————), 0.42 seconds (—— • • ——), 0.52 seconds (—— -——), and 0.62 seconds (- - - - -). Cycle times included a 0.1 to 0.4 second hold in a 60° C. bath.
Figure 13B:
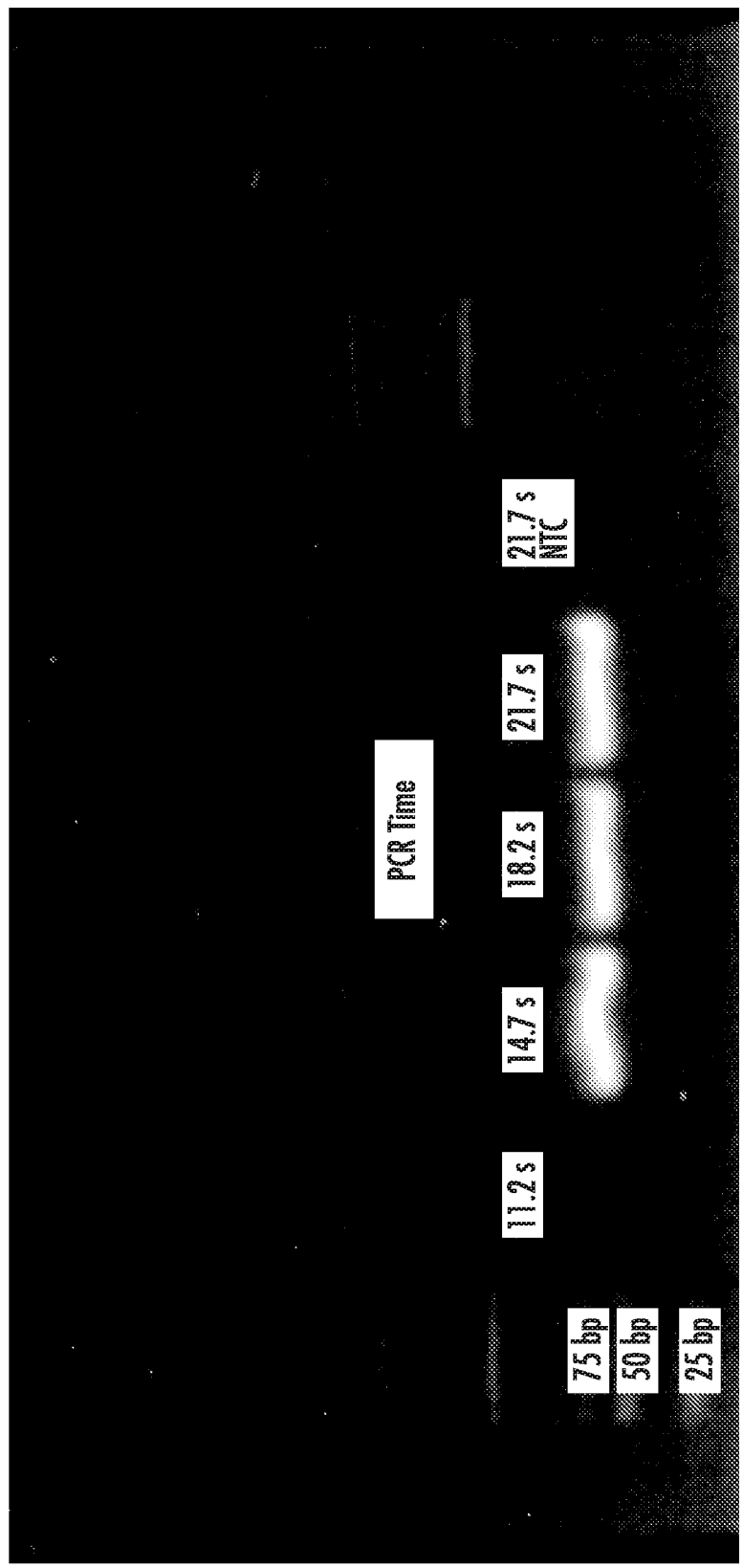

Each reaction was in a 1 μl volume with time based control (0.07 seconds in a 94° C. water bath, 0.1-0.4 seconds in a 60° C. water bath) for 35 cycles using 2-7 mM MgCl2. The sample volume was 1 with 5 ng human genomic DNA, 20 μM primers, and 8 μM polymerase. Using a 0.42 second per cycle protocol, when the MgCl$_2$ was 2-3 mM, no product was observed on melting curves (FIG. 12a) or gels (FIG. 12b). Minimal product was present at 4 mM, but a large amount of product was observed after amplification with 5-7 mM MgCl$_2$. At 5 mM MgCl$_2$, no products were observed on melting curves (FIG. 13a) or gels (FIG. 13b) with cycle times of 0.32 seconds, but large amounts of product were present at cycle times of 0.42 seconds, 0.52 seconds, and 0.62 seconds, demonstrating that specific, high yield 60 bp products can be obtained in PCR performed in under 15 seconds (35 cycles in 14.7 seconds). Thus, illustrative Mg++ concentrations are at least 4 mM, at least 5 mM, at least 6 mM, at least 7 mM, or more, and it is understood that these illustrative Mg++ concentrations may be used with any of the embodiments described herein.

Example 10

Figure 14A:
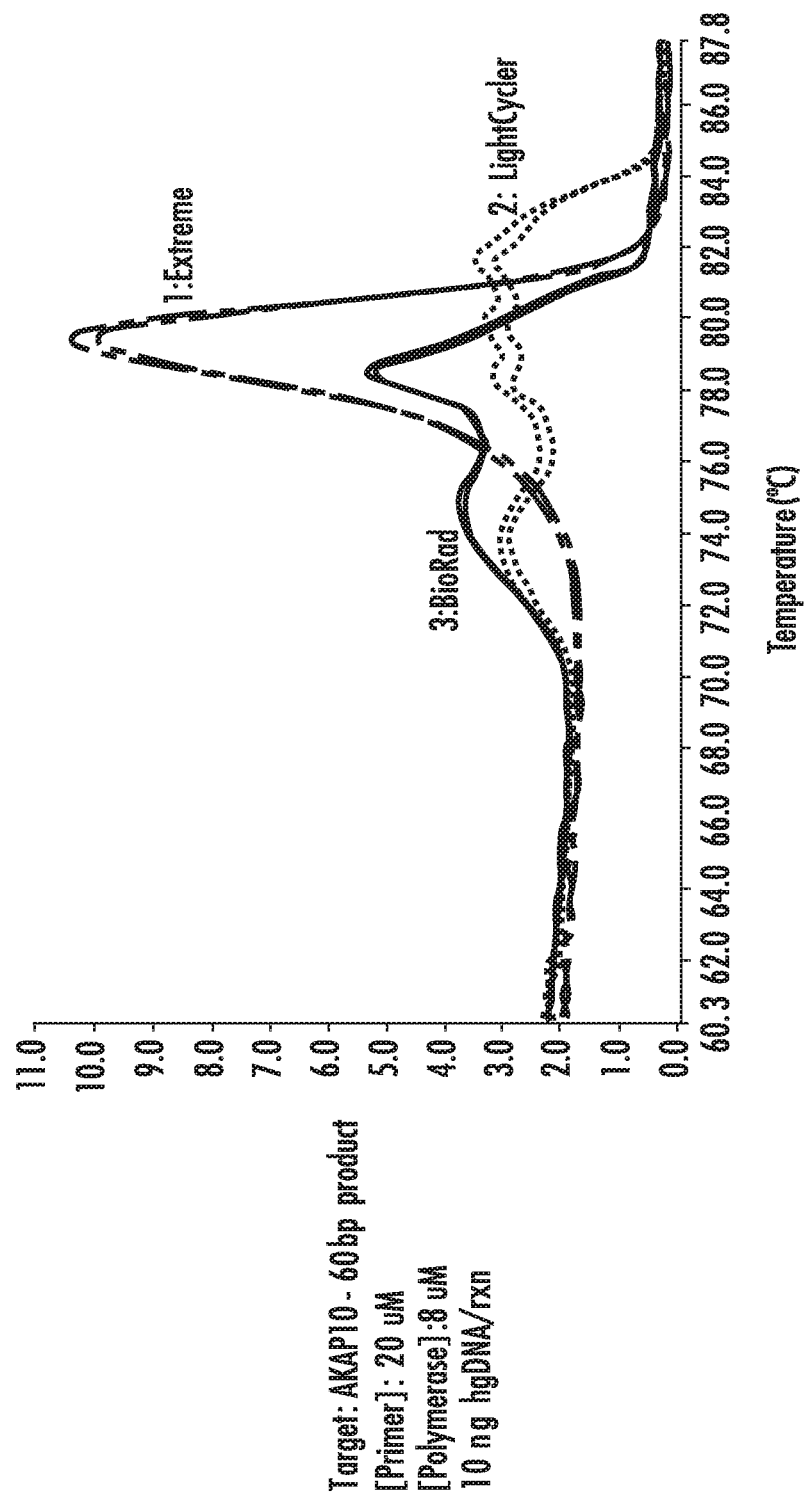
FIG. 14a shows negative derivative melting curves of a 60 bp fragment of AKAP10, as amplified on three different instruments: (1) extreme PCR, (2) LightCycler, and (3) CFX96 (Bio-Rad).
Figure 14B:
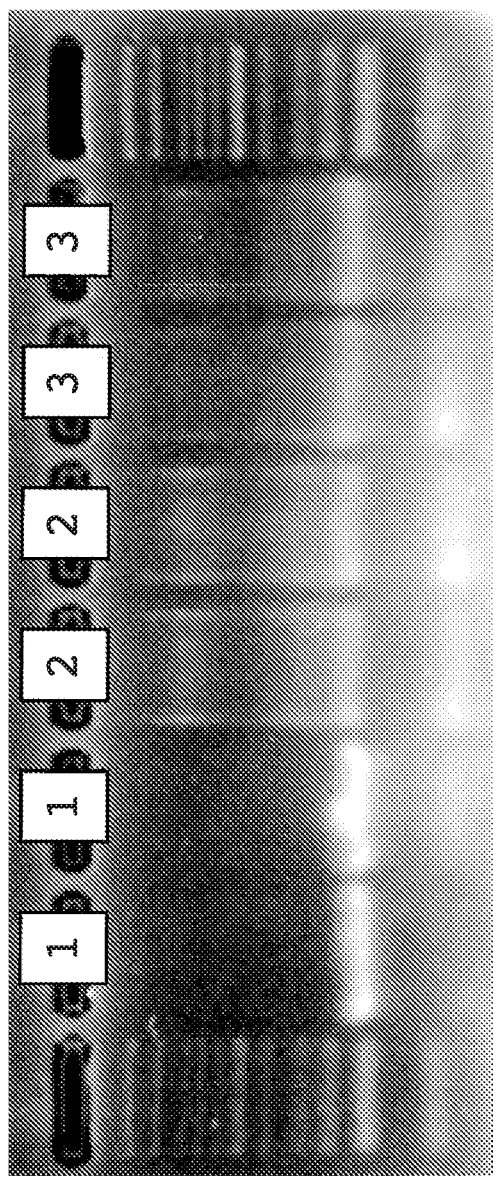

The high concentrations of primer and polymerase used in extreme PCR can have detrimental effects when used at slower cycling speeds. Non-specific products were obtained on rapid cycle or block based instruments that are 32- or 106-fold slower, respectively. FIG. 14a-b shows the results comparing amplification of the AKAP10 60 bp product used in Example 9, wherein amplification was performed using 20 μM of each primer, 8 μM KLENTAQ® (a DNA polymerase) and 10 ng human genomic DNA for 40 cycles using: (1) extreme PCR with set times of 0.5 s at 94° C. and 0.2 seconds at 60° C., giving a total time of approximately 17 seconds, (2) Rapid cycle PCR (Roche LightCycler) using set times of 10 s at 94° C. for an initial denaturation, followed by cycles of 85° C. for 0 seconds, and 60° C. for 0 seconds, giving a total time of approximately 9 minutes, and (3) Legacy (block) temperature cycling (Bio-Rad CFX96) with a 10 s initial denaturation at 94° C., following by temperature cycling for 0 s at 85° C. and 5 s at 60° C. with a total time of approximately 30 minutes. As can be seen, even the rapid cycling of the LightCycler resulted in quite a bit of non-specific amplification, while the extreme cycling conditions resulted in a single melting peak and minimal non-specific amplification on the gel.

It also noted that the yield is enhanced in extreme PCR, resulting from high primer and polymerase concentrations. Extreme PCR produced over 30-fold the amount of product compared to rapid cycle PCR, using quantitative PCR for comparison (data not shown).

Examples 1-17 were all performed using one or more of the devices described in FIGS. 1a-1d, or minor variations on those configurations, with certain steps performed on the LightCycler, to confirm qPCR results. However, it is understood that the methods and reactions described herein may take place in a variety of instruments. The water baths and tubes used in these examples allow for sufficiently rapid temperature change to study the effects of elevated concentrations of primers and polymerase. However, other embodiments may be more suitable commercially. Microfluidics systems, with low volume and high surface area to volume ratios, may be well suited to extreme PCR. Such systems allow for rapid temperature changes required by the high concentrations of primers and polymerase that are used in extreme PCR. Microfluidics systems include micro-flow systems (35, 53) that incorporate miniaturized channels that repeatedly carry the samples through denaturation, annealing, and extension temperature zones. Some of these systems have already demonstrated effective PCR with cycle times as fast as 3 seconds for lower complexity targets. It is expected that more complex targets may be amplified in such systems if the polymerase is provided at a concentration of at least 0.5 µM and primers are each provided at a concentration of at least 2 µM. Stationary PCR chips and PCR droplet systems (54) may also benefit from increased primer and probe concentrations, as the volumes may be as small as 1 nl or smaller and may be low enough to permit very fast cycling. It is understood that the exact instrumentation is unimportant to the present invention, provided that the instrumentation temperature cycles fast enough to take advantage of increased primer and polymerase concentrations without suffering from the loss of specificity associated with higher primer concentrations at slower cycle speeds.

While the above examples all employ PCR, it is understood that PCR is illustrative only, and increased primer and enzyme concentrations combined with shorter amplification times are envisioned for nucleic acid amplification methods other than PCR. Illustrative enzymatic activities whose magnitude may be increased include polymerization (DNA polymerase, RNA polymerase or reverse transcriptase), ligation, helical unwinding (helicase), or exonuclease activity (5' to 3' or 3' to 5'), strand displacement and/or cleavage, endonuclease activity, and RNA digestion of a DNA/RNA hybrid (RNAse H). Amplification reactions include without limitation the polymerase chain reaction, the ligase chain reaction, transcription medicated amplification (including transcription-based amplification system, self-sustained sequence replication, and nucleic acid sequence-based amplification), strand displacement amplification, whole genome amplification, multiple displacement amplification, antisense RNA amplification, loop-mediated amplification, linear-linked amplification, rolling circle amplification, ramification amplification, isothermal oligonucleotide amplification, helicase chain reaction, and serial invasive signal amplification.

In general, as the enzyme activity is varied, the amplification time varies inversely by the same factor. For reactions that include primers, as the primer concentration is varied, the amplification time varies inversely by the same factor. When both primers and enzymes are required for amplification, both enzyme and primer concentrations should be varied in order to maximize the reaction speed. If primer annealing occurs in a unique segment of the amplification cycle (for example, a unique temperature during 3-temperature PCR), then the time required for satisfactory completion of primer annealing in that segment is expected to be inversely related to the primer concentration. Similarly, if the enzyme activity is required in a unique segment of the amplification cycle (for example, a unique temperature during 3-temperature PCR), then the time required for satisfactory completion of the enzymatic process in that segment is expected to be inversely related to the enzyme concentration within a certain range. Varying the primer or enzyme concentrations can be used to change the required times of their individual segments, or if both occur under the same conditions (such as in 2-temperature PCR or during an isothermal reaction process), it is expected that a change in both concentrations may be necessary to prevent one reaction from limiting the reaction speed. Increased Mg++ concentration can also be used in combination with increased enzyme and primer concentrations to further speed amplification processes. Higher Mg++ concentrations both increase the speed of primer annealing and reduce the time for many enzymatic reactions used in nucleic acid amplification.

Higher concentrations of Mg++, enzymes, and primers are particularly useful when they are accompanied by shorter amplification times or segments. When higher concentrations are used without shortening times, non-specific amplification products may occur in some cases, as the "stringency" of the reaction has been reduced. Reducing the amplification time or segment time(s) introduces a higher stringency that appears to counterbalance the loss of stringency from increased reactant concentrations. Conversely, reagent costs can be minimized by reducing the concentration of the reactants if these lower concentrations are counterbalanced by increased amplification times or segment times.

Increasing polymerase concentrations can reduce the time necessary for long-range PCR, illustratively where the target is 5-50 kb. Typically, 10 min to 30 min extension periods are used to amplify large targets because the target is so long that such times are needed: 1) for the polymerase to complete extension of a single target, and 2) for enzyme recycling to polymerize additional primed templates. This recycling of polymerase is not needed at the beginning of PCR, when the available enzyme outnumbers the primed template molecules. However, even before the exponential phase is finished, the number of polymerase molecules often becomes limiting and enzyme recycling is necessary. By increasing the concentration of the polymerase, the required extension period can be reduced to less than 5 minutes and possibly less than 2 minutes, while maintaining increased yield due to the high primer concentration. Although the actual enzyme speed is not increased, less recycling is necessary, affecting the minimum time required, approximately in a linear fashion with the enzyme concentration.

Cycle sequencing times can also be reduced by increasing primer and polymerase concentrations. Typically, standard cycle sequencing primer concentrations are 0.16 μM and the combined annealing/extension period is 10 min at 50-60 degrees C. By increasing the primer and polymerase concentrations by 10-fold, the time required for annealing/extension can be reduced approximately 10-fold. In both long PCR and cycle sequencing, the expected time required is inversely proportional to the polymerase or primer concentration, whichever is limiting.

PCR of fragments with ligated linkers that are used as primers in preparation for massively parallel sequencing can be completed in much less time than currently performed by combining extreme temperature cycling with higher concentrations of primers, polymerase, and/or Mg++.

In all of the above applications, it is expected that the specificity of the reaction is maintained by shorter amplification times. Although high primer and polymerase concentrations are expected by those well versed in the art to cause difficulty from non-specific amplification, minimizing the overall cycle time and/or individual segment times results in high specificity and efficiency of the PCR.

TABLE 2

Extreme PCR conditions for different targets.

| | Target | | | | | | |
|---|---|---|---|---|---|---|---|
| | KCNE1 | KCNE1 | IRL10RB | IRL10RB | IRL10RB | NQO1 | AKAP10 |
| Amplicon Size (bp) | 45 | 45 | 49 | 49 | 58 | 102 | 60 |
| Polymerase | KLEN-TAQ1 ™ | KLEN-TAQ1 ™ | KLEN-TAQ1 ™ | KLEN-TAQ1 ™ | KLEN-TAQ1 ™ | KLEN-TAQ1 ™ | KLEN-TAQ1 ™ |
| [Polymerase] | 1 | 8 | 4 | 8 | 2 | 2 | 8 |
| [Primers] | 10 | 20 | 10 | 20 | 10 | 8 | 20 |
| # Cycles | 35 | RT | 35 | 35 | 39 | 30 | 35 |
| Cycle Time (s) | 0.8 | 0.91 | 0.73 | 0.45 | 0.97 | 1.93 | 0.42 |
| PCR Time (s) | 28 | RT | 26 | 16 | 38 | 58 | 14.7 |
| Hot Water Temp (° C.) | 95.5 | 95.5 | 95.5 | 95.5 | 95.5 | 95.5 | 95.5 |
| Cold Water Temp (° C.) | 20 | 58 | 30 | 30 | 30 | 72 | 59 |
| Hot Trigger Temp (° C.) | 90 | 85 | 90 | 90 | 90 | 90 | Time |
| Cold Trigger Temp (° C.) | 70 | 62 | 70 | 70 | 70 | Time | Time |
| Denaturation (° C.) | 90 | 85 | 90 | 90 | 90 | 90 | (82-85) w/ TC |
| Ann/Ext (° C.) | 60 | 60 | 65 | 65 | 65 | 72 | 60 |
| Ann/Ext Time (s) | 0 | 0 | 0 | 0 | 0 | 1 | 0.1-0.4 |
| FIG. | 9a | 9a | 5a | 5a | 4c | 7a | 12a, |
| Tm | 81 | 81 | 80 | 80 | 83 | 85 | 79 |
| Mg++ | 3 | 3 | 3 | 3 | 3 | 3 | 2-7 |

| | Target | | | | | | |
|---|---|---|---|---|---|---|---|
| | Synthetic | Synthetic | Synthetic | Synthetic | Synthetic | Synthetic | Synthetic |
| Amplicon Size (bp) | 100 | 200 | 300 | 300 | 400 | 500 | 500 |
| Polymerase | KLEN-TAQ1 ™ | KLEN-TAQ1 ™ | KLEN-TAQ1 ™ | KLEN-TAQ1 ™ | KLEN-TAQ1 ™ | KLEN-TAQ1 ™ | KAPA2G FAST |
| [Polymerase] | 2 | 2 | 2 | 2 | 2 | 2 | 2 |
| [Primers] | 4 | 4 | 4 | 4 | 4 | 4 | 4 |
| # Cycles | RT | RT | 20 | RT | RT | RT | RT |
| Cycle Time (s) | 1.9 | 3.9 | 4.9 | 5.9 | 7.9 | 7.9 | 3.9 |
| PCR Time (s) | RT | RT | 98 | RT | RT | RT | RT |
| Hot Water Temp (° C.) | 95.5 | 95.5 | 95.5 | 95.5 | 95.5 | 95.5 | 95.5 |
| Cold Water Temp (° C.) | 76 | 76 | 76 | 76 | 76 | 76 | 76 |
| Hot Trigger Temp (° C.) | 92 | 92 | 92 | 92 | 92 | 92 | 92 |
| Cold Trigger Temp (° C.) | Time | Time | Time | Time | Time | Time | Time |
| Denaturation (° C.) | 92 | 92 | 92 | 92 | 92 | 92 | 92 |
| Ann/Ext (° C.) | 76 | 76 | 76 | 76 | 76 | 76 | 76 |
| Ann/Ext Time (s) | 0.5-3 | 1-5 | 4 | 1-7 | 3-9 | 3-11 | 1-5 |
| FIG. | 11a | 11b | 10a, 11c | 11c | 11d | 11e | 10b |
| Tm | 85 | 85 | 85 | 85 | 81/87 (2 domains) | 84 | 84 |
| Mg++ | 3 | 3 | 3 | 3 | 3 | 3 | 3 |

Time = time-based segment control does not have a temperature trigger
RT = real-time acquisition

TABLE 3

Derivation of rate constants (k1 for primer annealing and k2 for polymerase extension) using A) historical ranges, B), the equation for primer annealing, and C) the equation for polymerase extension.

A)

| | [Primer] (µM) | [Polymerase] (µM) | Polymerase Speed (nt/s) | Extension Length (bp) | Cycle Time (s) | Anneal/Extend Time (s) | [Mg++] |
|---|---|---|---|---|---|---|---|
| Standard | 0.05-0.5 | 0.0026-0.026 | 10-45 | 20-980 | 120-480 | 15-60 | 1.5 |
| Rapid Cycle | 0.2-1.0 | 0.063 | 55-90 | 20-480 | 20-60 | 1-10 | 3 |
| Extreme | 1-16 | 0.5-8 | 50-100 | 20-280 | 0.5-5 | <0.1-5 | 3-7 |
| Opt Extreme #1 | 10 | 2.50 | 60 | 29 | 0.73 | <0.1 | 3 |
| Opt Extreme #2 | 4 | 0.50 | 60 | 82 | 1.93 | 1 | 3 |
| Opt Extreme #3 | 4 | 0.75 | 60 | 280 | 4.9 | 4 | 3 |

B) If Required Annealing time = k1/[primer]

| | [Primer] (µM) | Anneal/Extend Time (s) | k1 (s * µM) | | k1 range (s * µM) |
|---|---|---|---|---|---|
| Min Standard | 0.05 | 15 | 0.75 | Standard | 0.75-30 |
| Max Standard | 0.5 | 60 | 30 | Rapid Cycle | 0.2-10 |
| Min Rapid Cycle | 0.2 | 1 | 0.2 | Extreme | 1-20 |
| Max Rapid Cycle | 1 | 10 | 10 | | |
| Opt Extreme #1 | 10 | 0.1 | 1 | | |
| Opt Extreme #2 | 4 | 1 | 4 | | |
| Opt Extreme #3 | 4 | 5 | 20 | | |

C) If required extension time = k2 * product length/(polymerase speed * [polymerase])

| | [Polymerase] (µM) | Polymerase Speed (nt/s) | Extension Length (bp) | Anneal/Extend Time (s) | k2 (1/µM) |
|---|---|---|---|---|---|
| Opt Extreme #1 | 2.5 | 60 | 29 | 0.1 | 0.52 |
| Opt Extreme #2 | 0.5 | 60 | 82 | 1 | 0.37 |
| Opt Extreme #3 | 0.75 | 60 | 280 | 4 | 0.64 |

Specific conditions for extreme PCR are shown in Table 2. All data are presented except for the simultaneous optimization experiments for polymerase and primer concentrations for 3 of the targets. In Table 3, the quantitative relationships between variables are detailed. The inverse proportionality that relates the required annealing time to the primer concentration is approximately constant (k1) and defined by the equation (Required annealing time)=k1/[primer]. Using a range of typical values for these variables under conditions of legacy (standard) PCR, rapid cycle PCR, and extreme PCR produces ranges for the inverse proportionality constant that largely overlap (legacy 0.75-30, rapid cycle 0.2-10, and extreme 1-20). Because of this constant inverse proportionality, desired annealing times outside of those currently performed can be used to predict the required primer concentrations for the desired time. For example, using a constant of 5 (s*µM), for an annealing time of 0.01 s, a primer concentration of 500 µM can be calculated. Conversely, if a primer concentration of 0.01 µM were desired, the required annealing time would be 500 seconds. Although these conditions are outside the bounds of both legacy and extreme PCR, they predict a relationship between primer concentrations and annealing times that are useful for PCR success. Reasonable bounds for k1 across legacy, rapid cycle and extreme PCR are 0.5-20 (s×µM), more preferred 1-10 (s×µM) and most preferred 3-6 (s×µM).

Similar calculations can be performed to relate desired extension times to polymerase concentration, polymerase speed, and the length of the product to be amplified. However, because of many additional variables that affect PCR between legacy, rapid cycle and extreme PCR (polymerase, Mg++, buffers), performed in different laboratories over time, it may be best to look at the well-controlled conditions of extreme PCR presented here to establish an inverse proportionality between variables. This allows a quantitative expression between polymerase concentration, polymerase speed, product length, and the required extension time under extreme PCR conditions. The defining equation is (Required Extension Time)=k2(product length)/([polymerase]*(polymerase speed)). The experimentally determined k2 is defined as the proportionality constant in the above equation under conditions of constant temperature, Mg++, type of polymerase, buffers, additives, and concentration of dsDNA dye. For the 3 extreme PCR targets with two dimensional optimization of [polymerase] and [primer], the [polymerase] at the edge of successful amplification can be discerned across primer concentrations and related to the other 3 variables. As shown in Table 3, the values of k2 for these 3 different targets vary by less than a factor of 2, from which it is inferred that k2 is a constant and can be used to predict one variable if the others are known. The required extension time is proportional to the extension length (product length minus the primer length) and inversely proportional to the polymerase speed and concentration of polymerase. k2 has units of (1/µM) and an optimal value for the extreme PCR conditions used here of 0.5 (1/µM) with a range of 0.3-0.7 (1/µM). Similar values for k2 could be derived for other reaction conditions that vary in polymerase type, Mg++ concentration or different buffer or dye conditions.

Extreme PCR can be performed in any kind of container, as long as the temperature of the sample(s) can be changed quickly, and preferably homogeneously. Both intra-sample, and inter-sample homogeneity is important in many applications, illustratively for quantitative PCR where different PCR efficiencies of different samples translate directly to quantification errors. In addition to standard tubes and capillaries, micro-droplets of aqueous reactions suspended in an oil stream or thin 2-dimensional wafers provide good thermal contact. Continuous flow PCR of a sample stream (either dispersed as droplets, separated by bubbles, or other means to prevent mixing) past spatial segments at different temperatures is a good method for the temperature control needed for the speeds of extreme PCR. Induction heating, as described in WO 2015/069743, herein incorporated by reference in its entirety, may provide suitable methods and devices for extreme PCR.

Example 11

While PCR is a fundamental method in research and clinical diagnostics for detection and quantification specific DNA fragments, RNA cannot be amplified directly by PCR. RNA must first be reverse transcribed into DNA. Typically, this is done enzymatically by enzymes called "reverse transcriptases". Enzymatic reactions take time, and a typical amount of time recommended for reverse transcription is 30-50 min (see, e.g., Product insert for Superscript II Reverse Transcriptase, MAN0001342, Rev. Date: 20 May 2010, Invitrogen/Life Technology/ThermoFisher).

There are many situations when fast reverse transcription (RT) would be useful, for example in point-of-care clinical diagnostics for RNA viruses where rapid time-to-result increases the value of testing and can be critical for the patient or in singleplex, duplex, or multiplex amplification of a specific mRNA transcript with or without a reference gene. As discussed above, extreme PCR is a technology capable of amplifying DNA in as little as 15 seconds or less. However, PCR in less than a minute is not so helpful when the reverse transcription of an mRNA or viral RNA takes 30 minutes or more. Faster RT-PCR would be desirable, and it would be particularly desirable to have a one-step RT-PCR protocol in which both the RT and PCR steps take place in the same reaction mixture.

Figure 16A:
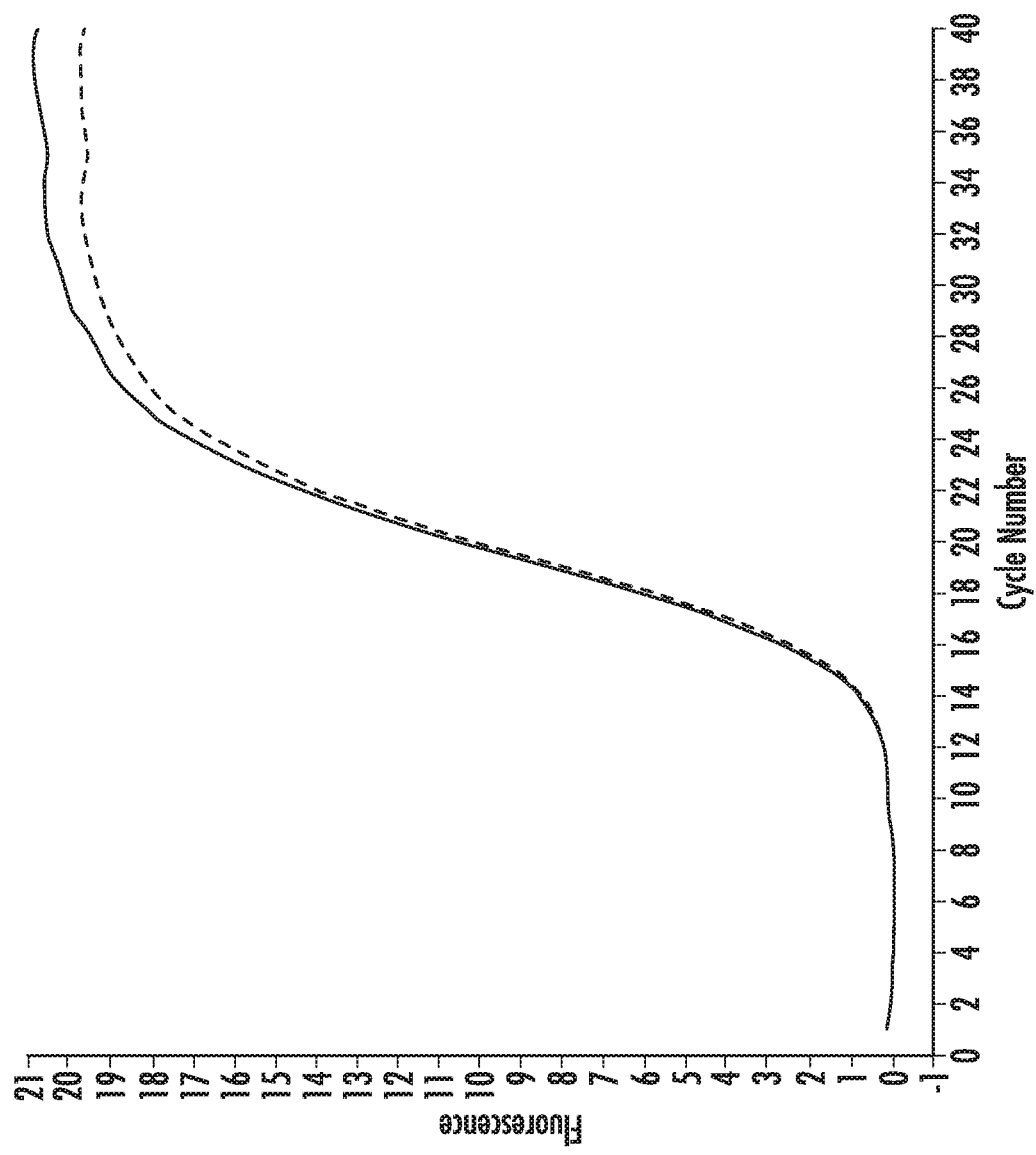

In this example, a rapid one-step RT-PCR duplex reaction with the common reference gene ACTB is performed. Two human transcripts (AKAP10 and ACTB) were reverse transcribed and amplified in one step with primers for AKAP10 (GCTTGGAAGATTGCTAAAATGATAGTCAGTG (SEQ ID NO:25) and TTGATCATACTGAGCCTGCTGCATAA (SEQ ID NO:26)) and ACTB (TTCCTGGGCATGGAGTC (SEQ ID NO:28) and CAGGTCTTTGCGGATGC (SEQ ID NO:29)). Included in the 10 µl reactions were 0.5 µM of each primer, 60 ng of total RNA extracted from human blood leukocytes, 300 Units of Superscript II reverse transcriptase (ThermoFisher), and 0.1 M dithiothreitol in a rapid PCR master solution (1×LCGREEN® PLUS dye, 0.2 µM each dNTP, 3 mM $MgCl_2$, 50 mM Tris, pH 8.3, 25 ng/µl bovine serum albumin, 0.4 U of KLENTAQ®DNA polymerase (AB Peptides) and 64 ng of anti-Taq antibody (eEnzyme). The samples were placed in a LightCycler capillary tube (Roche) incubated at 45° C. for 5 min for reverse transcription, and then cycled for 40 cycles between 94 and 55° C. (no holds) for real time amplification on a carousel LightCycler (FIG. 16a). The samples were then melted in the LightCycler by momentary denaturation at 95° C., cooling to 60° C., and finally fluorescence acquisition by heating to 95° C. at 0.2° C./s (FIGS. 16b-16c). The peak at 79° C. is the AKAP10 amplicon and the peak at 83° C. is ACTB. These results show that faster RT times, times that are much less than 30 minutes (e.g. 5 min) may be used to amplify RNA, including duplex targets.

Example 12

The consistency and quality of RT-PCR depends on many things, including the specific type of RT enzyme (60). Two types of RT enzymes are commonly used for RT-PCR, one from a mouse leukemia virus (Maloney murine leukemia virus—MMLV) and one from a bird virus (avian myeloblastoma virus—AMV), although other RT enzymes are known in the art, and engineered variants of MMLV that have lower (or higher) RNase H activity and increased temperature stability are available commercially. Bustin (60) tested several reverse transcriptases for consistency and yield, and determined that one of the better enzymes is an MMLV sold as ISCRIPT™ (Bio-Rad).

As used herein one "Unit" of RT is the amount of enzyme required to incorporate 1 nmole of dTTP into acid-precipitable material in 10 min at 37° C. using poly(rA)/oligo $(dT)_{25}$ as template/primer. The buffer used for determining MMLV Unit activity is 50 mM Tris, pH 8.3, 75 mM KCl, 3 mM $MgCl_2$, and 10 mM DTT (dithiothreitol). The buffer used for determining AMV Unit activity is 75 mM potassium acetate, 50 mM Tris-HCl (pH 8.3) 8 mM magnesium acetate and 10 mM DTT. The number of Units used for MMLV RT reactions (10 U/µl) is typically 10 times that of AMV RT reactions (1 U/µl). The RT enzymes used here include: 1) native cloned MMLV (New England Biolabs), 2) Superscript II (a modified MMLV with low RNase H activity and increased thermal stability, ThermoFisher), 3) the enzyme ISCRIPT™ (a modified MMLV with strong RNase H activity, Bio-Rad), 4) the enzyme ROCKETSCRIPT™ (a modified MMLV with increased RNase H activity and increased thermal stability, Bioneer), and 5) native cloned AMV (New England Biolabs). For most of these enzymes, the Unit definition and concentration of enzyme are clearly indicated by the manufacturer. Exceptions are the enzyme ROCKETSCRIPT™, where the activity is determined by titration against an enzyme of known activity, and the enzyme ISCRIPT™, where the manufacturer does not disclose the concentration used. However, even in the enzyme ISCRIPT™ case, the suggested procedure (1 µl of enzyme in a RT reaction volume of 20 µl) is identical to the procedures of the other RT enzymes, suggesting that the concentration of the enzyme ISCRIPT™ is a 200 U/µl stock solution, diluted to 10 U/µl in an RT reaction, the concentrations provided and suggested by the other manufacturers.

Figure 17:
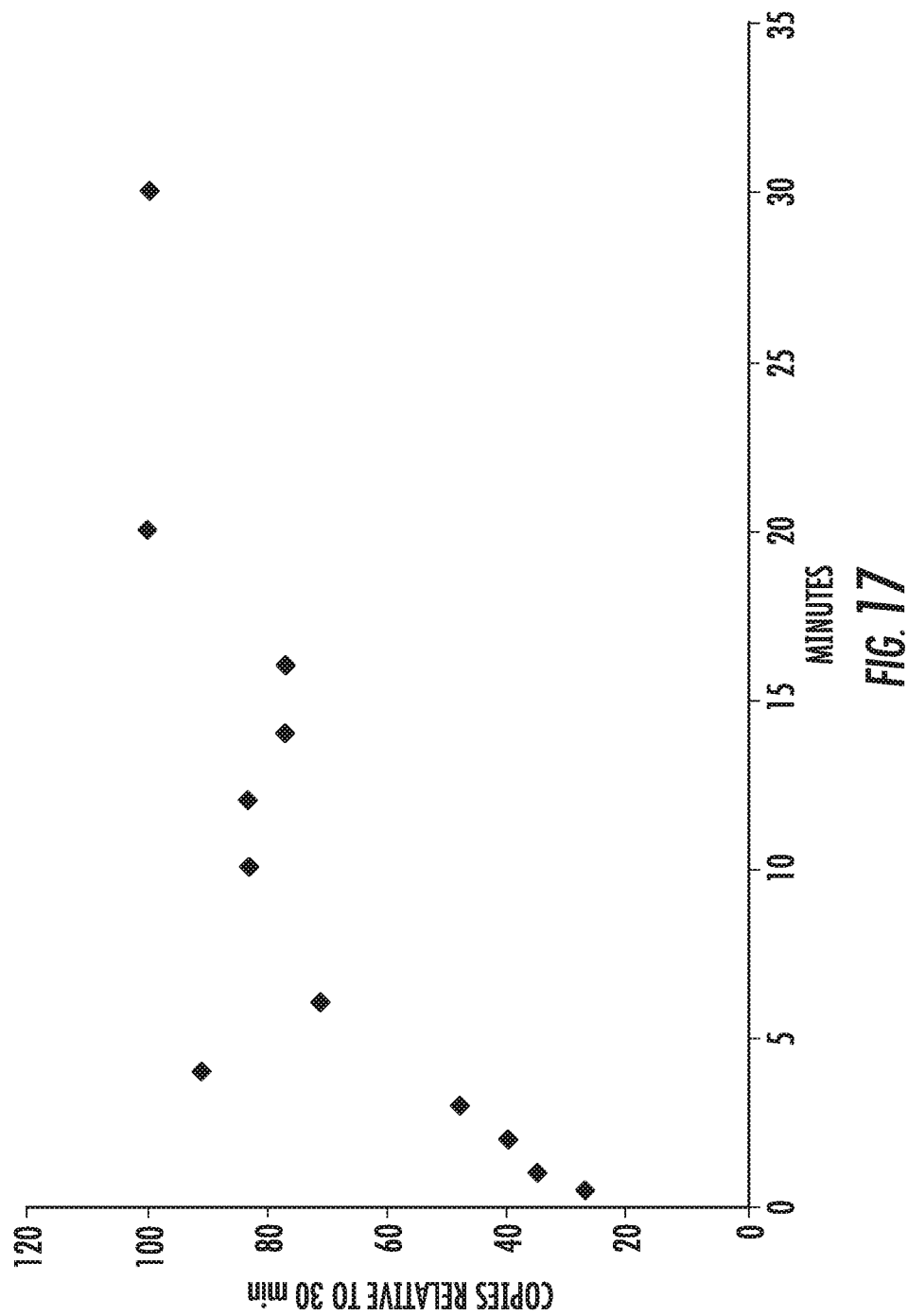
FIG. 17 shows percent RT in shorter incubation times as compared to a 30 minute incubation time.

The recommended incubation time for the enzyme ISCRIPT™ MMLV is 30 minutes. To study the time course of the RT reaction, a two-step RT-PCR was performed. With this two-step method, the RT was performed separately in microfuge tubes in a water bath for different time periods, and then real-time PCR was performed in a capillary LightCycler. The RT step was performed for varying times (1 min to 30 min) at 45° C. with the ACTB reverse primer listed in Example 11. Two µl of the enzyme ISCRIPT™ MMLV (presumptively for a final concentration of 10 U/µl) with RNase inhibitor were combined with a reaction mixture including random hexamers, oligo (dT), stabilizers, dNTPs, and a buffer not otherwise specified. The 40 µl reaction included 256 ng total RNA from leukocytes and the ACTB reverse primer at 0.25 µM. After incubation at 45° C., the reaction was stopped by heating to 85° C. for 5 min, and the mixture was diluted 3-fold with water. The qPCR was performed as in Example 11, except that 2 µl of the diluted cDNA template and only ACTB primers were used. The quantification cycle (Cq) of each curve, relative to the Cq of the 30 min control was used to calculate relative concentrations of ACTB cDNA, assuming an amplification efficiency of 100%. Results are displayed in FIG. 17. Approximately 60% of the cDNA was formed in the first 5 min, with 80% at 10 min, and 100% at 20 min. Additional studies varying the incubation time (0.5, 1, 2, 4, 8, 16, 30 min) and the primer concentration (0.125, 0.25, 0.5, 1 µM) showed that increasing the primer concentration compensates for lower incubation times. It was not possible to study times faster than 0.5 minutes with microfuge tubes because of slow temperature equilibration.

As discussed above, extreme PCR combines rapid temperature cycling with high primer and polymerase concentrations to enable PCR in 2 minutes or less. Annealing times can be reduced because the high primer concentrations drive the reaction faster in direct proportion to increase in primer concentration. Similarly, high enzyme concentration should proportionally speed the extension step when the amount of enzyme is limiting. Analogy to RT suggests that higher primer and enzyme concentrations might also help to speed RT reactions. However, combining both the RT step and the PCR step into one reaction with two different enzymes is difficult. In general, reverse transcriptase and DNA polymerase reaction conditions are not believed to be compatible. For example, KCl is used in RT reactions but is absent from the rapid PCR master solution of Example 11 because KCl inhibits polymerase activity by 80% at 50 mM KCl (61). As shown below, it is believed that KCl concentrations of 0 to 10 mM KCl may be appropriate in a one-step RT-PCR reaction. Higher concentrations of dNTPs (0.5-1.0 mM each (RT) vs. 0.2 mM each (PCR)) and Mg++(3-15 mM (RT) vs. 1.5-5 mM (PCR)) are usually used in RT than are used in PCR. One solution to this problem is to use one enzyme that has both reverse transcriptase and DNA polymerase activity such as rTth, a recombinant heat stabile DNA polymerase that can also use RNA as a template (62). However, such enzymes have their limitations, and, for various reasons, use of two enzymes is often preferred. When two enzymes are combined in one reaction, conditions must be found that work with both enzymes. Conditions for extreme PCR (buffer, [Mg++], salts, [dNTPs], pH, [primers], [enzyme], may not work for RT and vice versa. However, conditions compatible with both RT and PCR are presented herein, and the rapid PCR master solution of Example 11 (sometimes with supplements of Mg++ and dithiothreitol) was used in many of the further examples herein, instead of the reaction mixture sold with the enzyme ISCRIPT™.

Example 13

RNA has more secondary structure than DNA, and strong secondary structure is thought to inhibit RT. Increasing the temperature is one way to release secondary structure in RNA so that it is easier to reverse transcribe. However, commonly used RT enzymes are believed to be thermolabile, so there is a limit to how much one can heat the sample to unfold secondary structure without inactivating the reverse transcriptase. Shorter reaction times would be expected to preserve more of the generated nucleic acid for PCR, both by limiting the time of exposure to any RNases and limiting chemical degradation.

Figure 18:
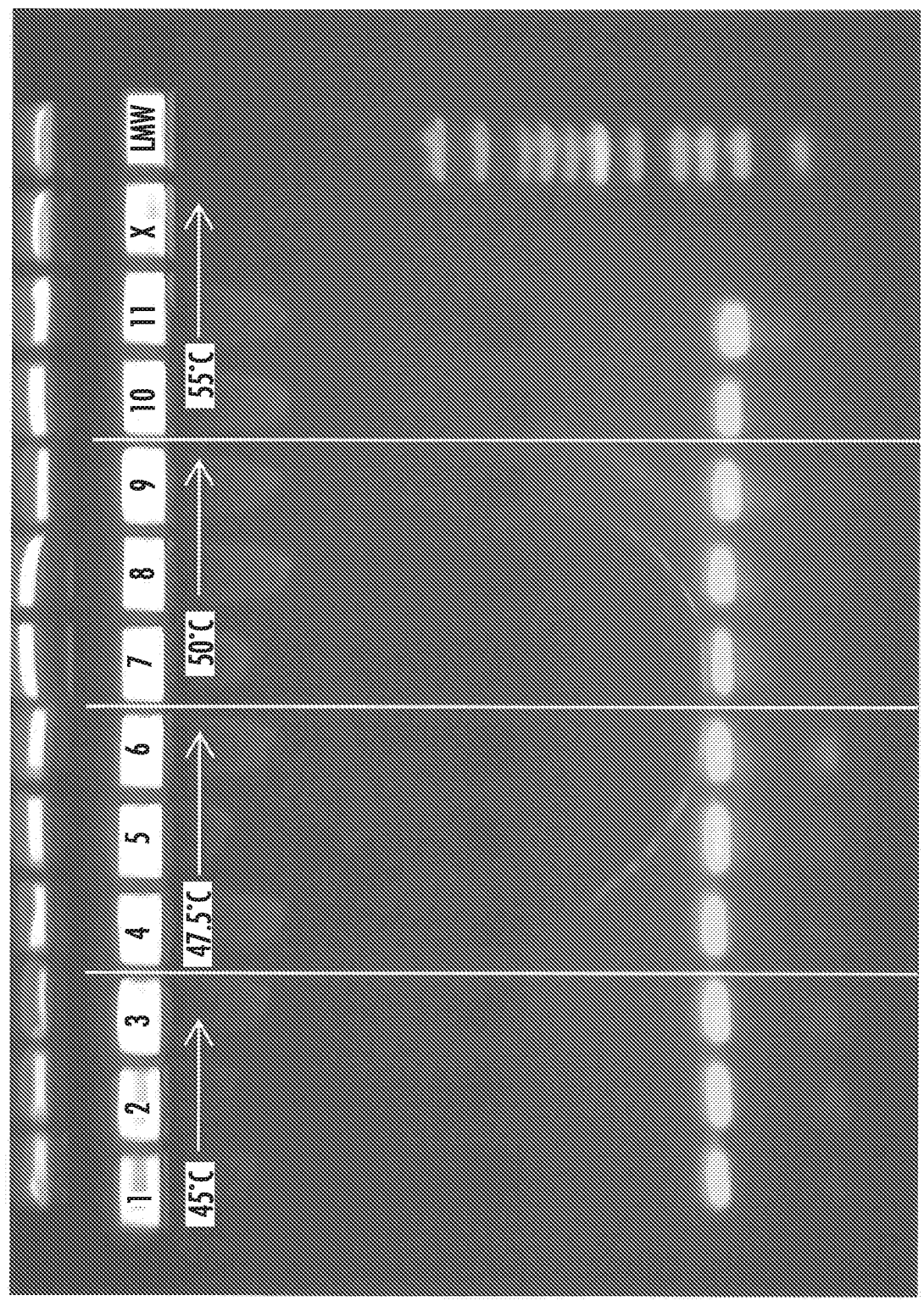
FIG. 18 is a gel of PCR products of RT-PCR using various temperatures and times for the RT step. Lanes 1-3 show a 45° C. incubation for 15, 20, and 25 seconds respectively, lanes 4-6 show a 47.5° C. incubation for 15, 20, and 25 seconds respectively, lanes 7-9 show a 50° C. incubation for 15, 20, and 25 seconds respectively, and lanes 10-11 show a 55° C. incubation for 15 and 20 seconds respectively.

Using a water bath/stepper motor PCR instrument similar to that shown in FIG. 1c, a one-step RT-PCR was performed using 8 times the normal primer concentrations in less than 1 minute. The 5 µl one step RT-PCR contained 4 µM of each ACTB primer, 25 ng of total leukocyte RNA, 50 U of the enzyme ISCRIPT™ RT (final concentration 10 U/µl) similar to Example 12 except that no random hexamers or poly (dT) were included, and 2 µM KLENTAQ® (a DNA polymerase) all in the rapid PCR master solution of Example 11, with the exception of anti-Taq antibody. The samples were incubated in a water bath 310 set at 45, 47.5, 50, or 55° C., each for 15, 20, or 24 seconds, and then cycled between 55° C. and 94° C. using water baths 313 and 314. Each cycle required 1.05 seconds and included two transfers between water baths 313 and 314, each transfer requiring 125 msec, and two stationary holds of 400 msec in each of water bath 313 and 314, for 35 cycles. The total time for RT and PCR for the samples with 15 seconds of RT was 53 seconds. All samples appeared to amplify equally as measured by agarose gels (FIG. 18). Although the stabilizers present in the enzyme ISCRIPT™ are not disclosed, it is believed that they include DTT.

Example 14

Figure 19B:
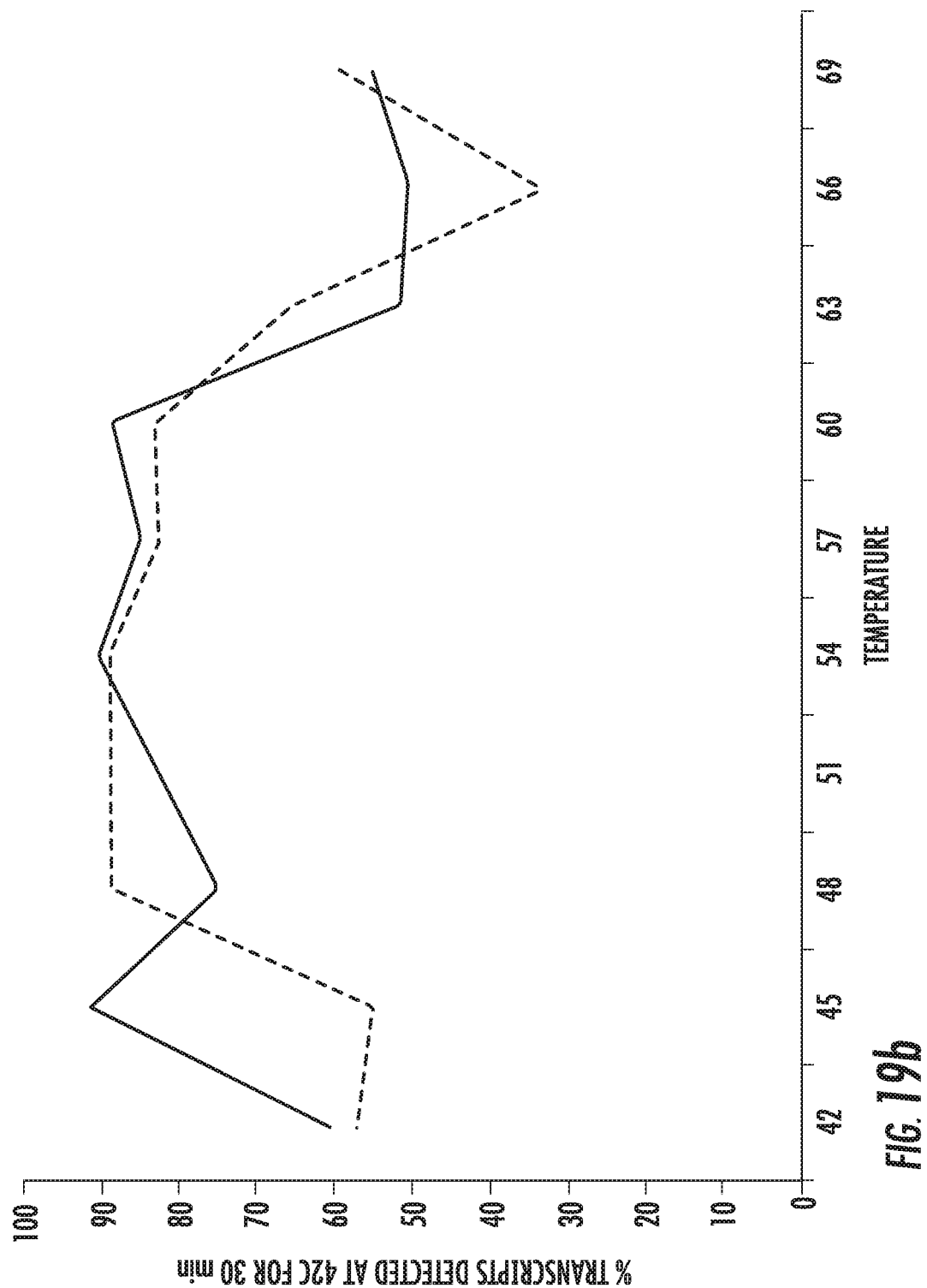

Trehalose is a sugar that has been used to thermostabilize and thermoactivate RT enzymes and can be used as an enhancer of PCR (63). The temperature profile of the enzyme ISCRIPT™ MMLV with and without 0.6 M trehalose was measured by two-step RT-PCR. Conditions were the same as in Example 13, except that the RNA source was a human reference total RNA sample obtained from multiple tissues (Stratagene) included at 5 ng/µl, and the reverse transcription incubation was for 20 seconds at temperatures from 42-69° C. RT was performed in capillaries in a water bath at varying temperatures, with immediate RT inactivation by moving the capillaries in 125 msec to an 85° C. water bath for 60 seconds. The samples were then diluted and transferred to a capillary LightCycler for qPCR, as described in Example 12. The no template controls were negative and samples were compared to a positive control with the RT run at 42° C. for 30 min. From 55-63° C. in the RT step, trehalose had a protective effect, increasing the amount of product as measured by qPCR by 20-40% (FIG. 19a).

In a similar experiment, the enzyme ISCRIPT™ MMLV RT was compared to the enzyme ROCKETSCRIPT™ MMLV RT (Bioneer). Set up and analysis were the same except that the enzyme ROCKETSCRIPT™ RT was performed in a 10 µl reaction with 100 U RT (final concentration 10 U/µl), 10 mM dithiothreitol, 0.25 mM each dNTP, and 0.5 U RNase inhibitor. Very similar results were obtained (FIG. 19B) for the two enzymes across the tested temperature range, suggesting that these engineered MMLV mutants may be the same or similar enzymes. Both manufacturers claim their MMLV mutants are more stable than the native enzyme and have RNase H activity.

Example 15

Using 0.6 M trehalose and 56° C. for reverse transcription as determined in Example 14, primer concentrations from 1-8 µM were studied by two-step RT-PCR. Reverse transcription was performed at 56° C. for 20 or 60 seconds, otherwise following the procedure of Example 14. With 60 s RT, the relative quantity increased through 4 µM of primer, then leveled off between 4-8 µM (FIG. 20). With 20 seconds of RT, the relative quantity continued to increase through 8 µM primer, suggesting that shorter times can be compensated for by higher concentrations of the RT primer.

In another set of experiments using the same 0.6 M trehalose, RT incubation for 20 seconds at 56° C. with 6 µM reverse primer, the amount of ISCRIPT™ MMLV RT enzyme was varied from 10 U/µl (normal) to 40 U/µl. The Cq decreased as the enzyme concentration increased, indicating that under these conditions, higher concentrations of enzyme resulted in greater cDNA yield.

In further experiments using 0.6 M trehalose and the higher concentrations of both RT (40 U/μl) and primers (6 RT times of 0.5, 1, 2, 4, 8, and 16 seconds were compared to 30 min at 42° C. Quantitative PCR revealed no difference between the 4, 8, and 16 second RT incubation times at 56° C. and the 30 min, 42° C. control, indicating that under these conditions, 4 seconds is sufficient for RT-PCR from total RNA.

Example 16

The above experiments amplified specific mRNA transcripts from total RNA. Another very common application of RT-PCR is in RNA virus detection and quantification. For example, viral load assays for HIV and HCV are much in demand, as are the detection of respiratory viruses such as respiratory syncytial virus (RSV).

Figure 21:
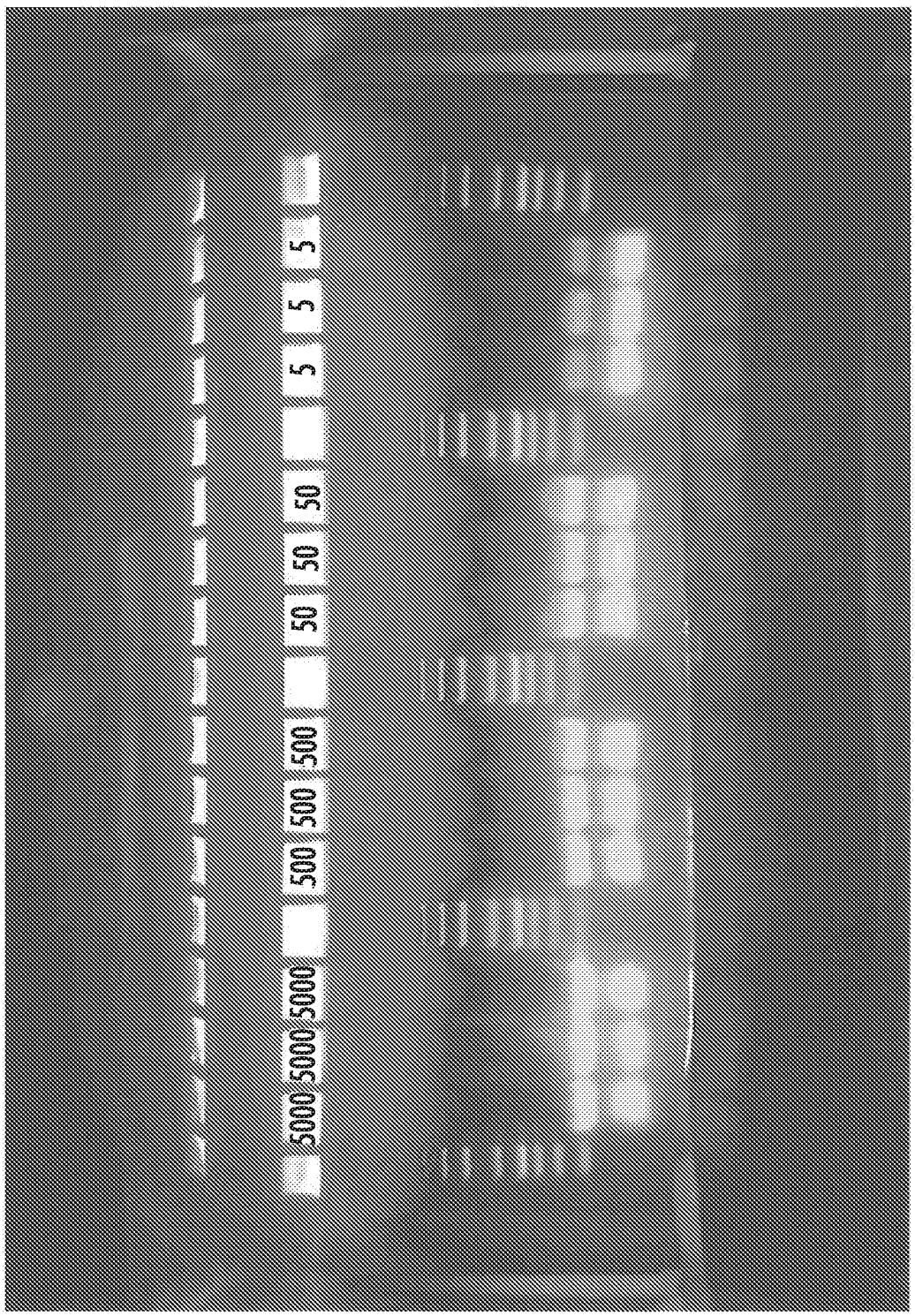
FIG. 21 is a gel showing one-step RT-PCR amplification of RSV RNA at 5,000, 500, 50, or 5 copies (from left to right, in triplicate).

One-step RT-PCR amplification of RSV RNA in less than 56 seconds was performed. RSV RNA was obtained from the ATCC, catalog #VR-3233SD. RSV primers were forward: TGGGGCAAATATGTCACGAAG (SEQ ID NO:30) and reverse: CCATTTAAGCAATGACCTCGAATTTCA (SEQ ID NO:31), with a resultant amplicon length of 63 bp. Reverse transcription and PCR were performed in 5 μl with 6 μM of each primer, (40 U/μl) the enzyme ISCRIPT™ RT, 2 μM KLENTAQ® (a DNA polymerase), 0.6 M trehalose and 5,000, 500, 50, or 5 copies of freshly diluted RSV RNA in the rapid PCR master solution of Example 11 with the exception of anti-Taq antibody. Reverse transcription was performed for 20 seconds at 56° C. followed by 35 cycles of PCR as described in Example 13. Gels of the PCR products (in triplicate) at different initial template copies numbers are shown in FIG. 21. Strong primer and product bands are seen in the left lanes with 5,000 and 500 initial copies of template. The product bands are slightly diminished at 50 copies, and definitely less intense at 5 initial copies, demonstrating sensitivity at least down to 5 copies. It may be possible to detect single copies using this illustrative one-step RT-PCR protocol.

Example 17

Figure 22:
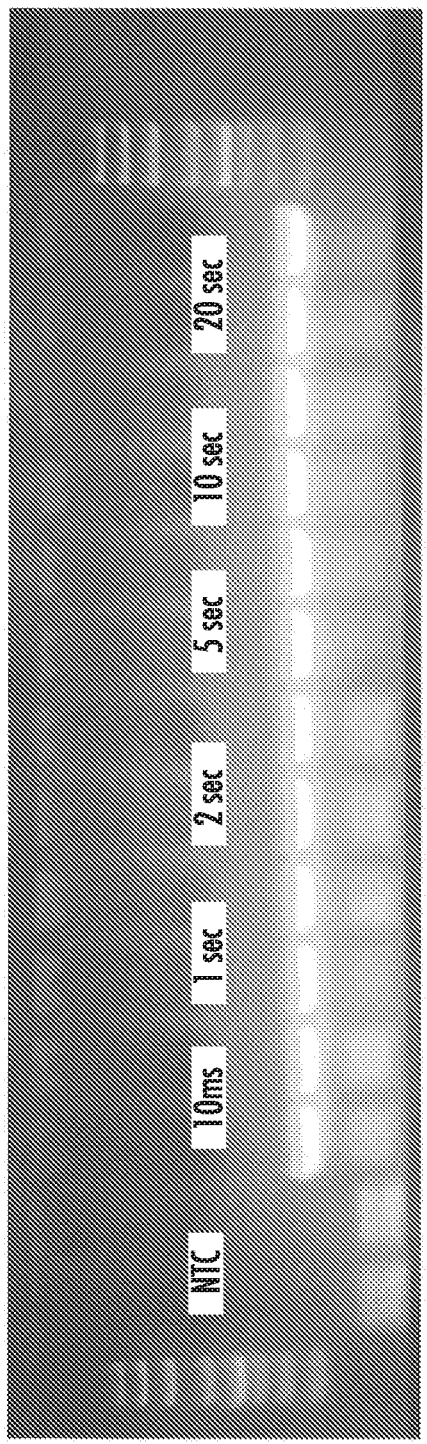
FIG. 22 is a gel showing RT-PCR with incubation times from 10 ms to 20 seconds.
Figure 23:
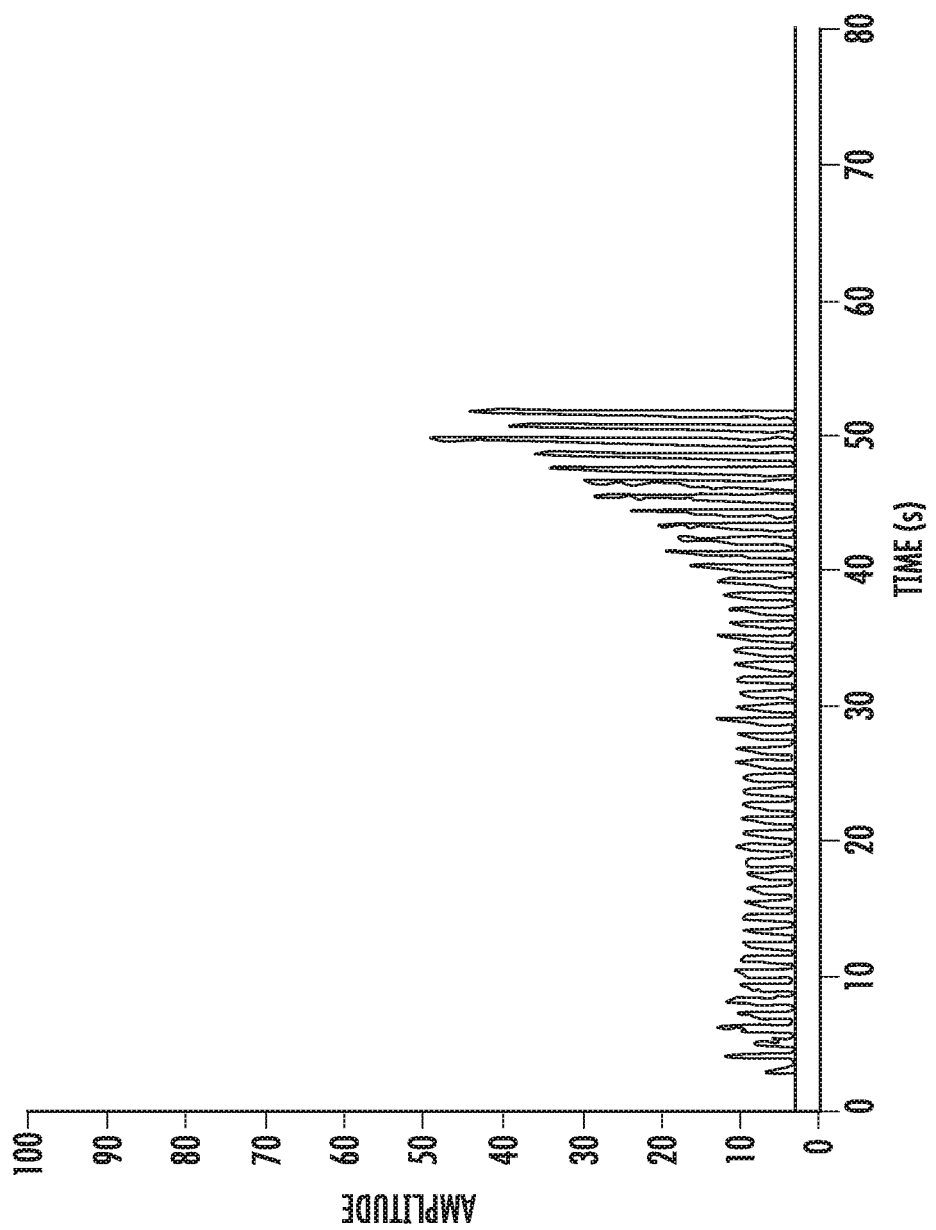
FIG. 23 shows the real-time results of a one-step RT-PCR using 5,000 initial template copies of RSV RNA with a 5 second RT step and 45 cycles of PCR.

One-step RT-PCR amplification of RSV RNA with reverse transcription incubations down to less than one second was performed. RT-PCR was performed as in Example 16, with 5,000 initial template copies of RSV RNA. All solutions were mixed on ice to limit any reverse transcription prior to initiation of the reaction at 56° C. The RT time at 56° C. was varied from 20 seconds down to less than 1 second. The shortest time period, labeled as "10 ms", indicates the time in the 56° C. water bath when the capillary was stationary. Time including the transition into and out of the water bath and the 10 msec stationary hold may not have been adequate exposure at 56° C. to bring the sample up to temperature. Surprisingly, all samples showed strong specific PCR products with RT times of 20, 10, 5, 2, 1 second, and "10 ms", while the NTC (no template control) remained negative (FIG. 22). Real-time monitoring of the sample with a 5 second RT step is shown in FIG. 23.

Figure 24:
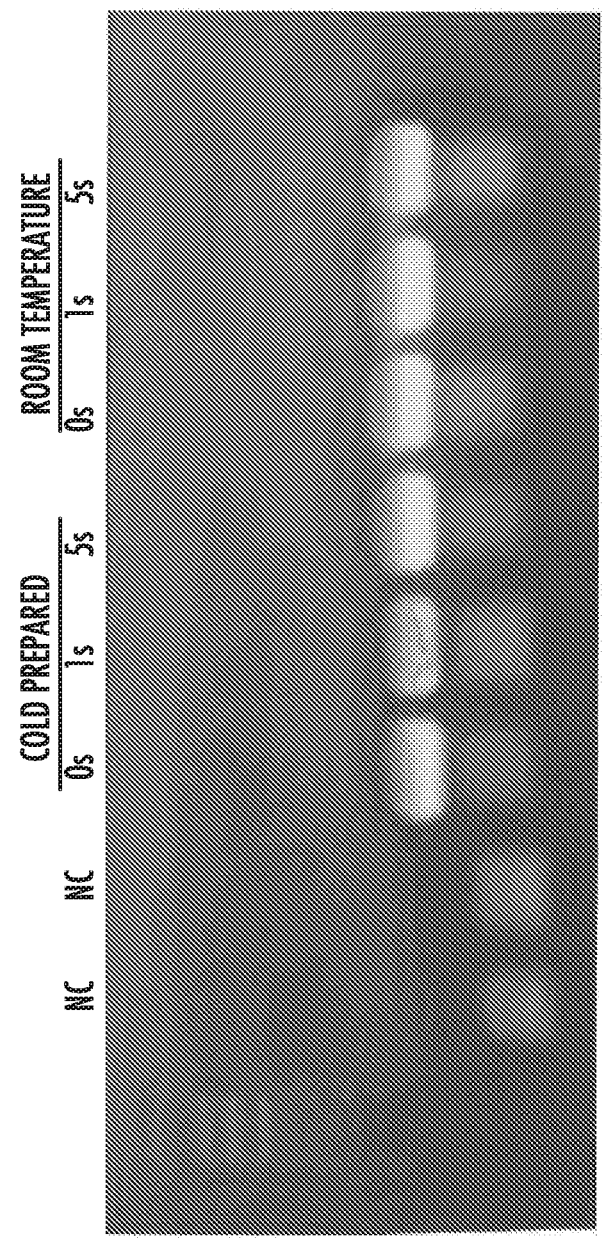
FIG. 24 is a gel showing very short times for an illustrative RT step. From left to right, the negative controls (NC) are the two left lanes, the cold prepared samples with 0, 1, and 5 s incubation at 56° C. in the next three lanes, and one minute at room temperature with 0, 1, and 5 s incubation at 56° C. in the last three lanes.

To further investigate very short times for RT, 5, 1, and 0 second incubations were compared, where the "0 s" incubation bypassed the 56° C. water bath. That is, the prepared sample was directly amplified by extreme PCR without a dedicated RT temperature incubation. All reactions were assembled on ice, and the final brief (20 second) centrifugation was performed in a centrifuge regulated at 2° C. One set of samples was immediately processed by extreme PCR, and the other set was left at room temperature for 60 seconds to simulate less care in maintaining a cold temperature throughout preparation. Results showed negative no template and no RT controls, with strong bands at all times and conditions (FIG. 24). From left to right, the negative controls are the two left lanes, the next three lanes are the cold prepared samples with 0, 1, and 5 second incubation at 56° C., and the last three lanes are the 1 min room temperature lanes with 0, 1, and 5 seconds incubation.

Example 18

Figure 25:
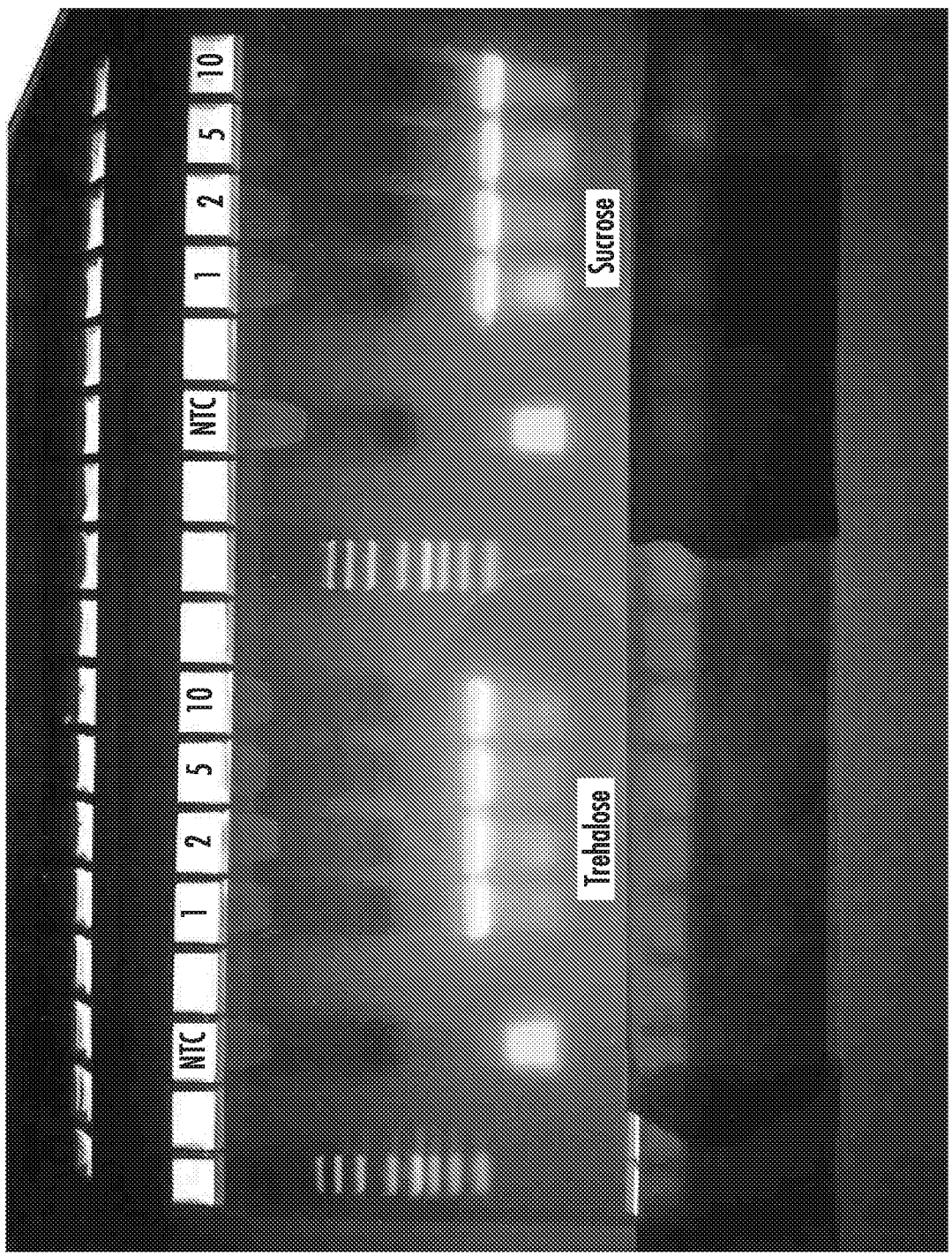
FIG. 25 is a gel comparing the effect of trehalose on an illustrative RT step. The trehalose set is on the left, with (left to right) the no template control, blank, 1, 2, 5, and 10 s of incubation, followed by the no trehalose in the same order.

The effect of trehalose and sucrose on RT were examined further. Using the conditions of Example 17, 1, 2, 5 and 10 second RT incubations with and without 0.6 M trehalose were tested with RSV RNA at 5,000 copies per reaction and 45 cycles of one-step PCR. The results are shown in FIG. 25. In FIG. 25, the trehalose set is on the left, with (left to right) the no template control, blank, 1, 2, 5, and 10 seconds of incubation, followed by the no trehalose set in the same order. Although the gel is taken at endpoint, it appears that trehalose increases final yield. When trehalose was compared against sucrose at 0.2, 0.4 and 0.6 M, sucrose, all samples amplified well with melting analysis indicating that the 0.4 M sucrose produced the highest yield (data not shown). Sucrose appears to be as good as or better than trehalose, suggesting that other sugars, including glucose and fructose may have similar effects. Other stabilizers may be used as well.

Example 19

AMV RT from New England Biolabs is a native, cloned RT usually run at 42° C. in the presence of a reducing agent such as dithiothreitol (10-250 mM), high Mg++ concentrations (8-13 mM), and high KCl (75 mM). The manufacturer's buffer (final concentration in the reaction) was: 50 mM Tris, pH 8.3, 75 mM K acetate, 8 mM Mg acetate, and 10 mM DTT. This mixture was supplemented with BSA (final concentration in the reaction of 500 μg/ml) for compatibility with glass capillary tubes. This buffer was compared to the rapid PCR master solution of Example 11 supplemented with 10 mM DTT and 10 mM Mg++(total 13 mM Mg++) in the final reaction. The main difference between the two buffers is that no K+ was in the rapid PCR mixture, while the manufacturer's buffer included 75 mM K+. The presence of potassium ions has previously been considered critical for RT reactions (64). Two-step RT-PCR reactions were performed. To each buffer, 250 copies of RSV RNA/μL, 2.5 U/μl AMV RT, and 15 μM reverse RSV primer were added and the RT performed at 42° C. for 1 s, 5 s, 20 s, 1 min, or 10 min. After RT, the reverse transcriptase was inactivated at 93° C. for 60 s, cooled to room temperature, and diluted 1:10 for PCR in a capillary LightCycler. Each 10 μl PCR included 0.5 μM RSV primers and 2 μl of 1:10 cDNA in the rapid PCR master solution. Real time PCR was performed by cycling for 45 cycles between 94 and 55° C. (no holds). The samples were then melted in the LightCycler by momentary denaturation at 95° C., cooling to 60° C., and finally fluorescence acquisition by heating to 95° C. at 0.2° C.

Real time results, melting curves, and gel analysis revealed that all reactions amplified a single product with a Tm of 79° C. Similar results across time (1 second, 2 seconds, 20 seconds, 1 min, 20 min) were seen for each buffer (data not shown). However, all amplifications in the commercial buffer (that included 75 mM K+) were delayed an average of 4.6 cycles compared to the amplifications performed in the supplemented rapid PCR master solution. That is, the quantification cycles (Cqs) in the rapid PCR solution without K+ were 4.6 cycles less than the Cqs in the commercial buffer, suggesting severe PCR inhibition by K+, despite its claimed necessity in the RT reaction.

Figure 26:
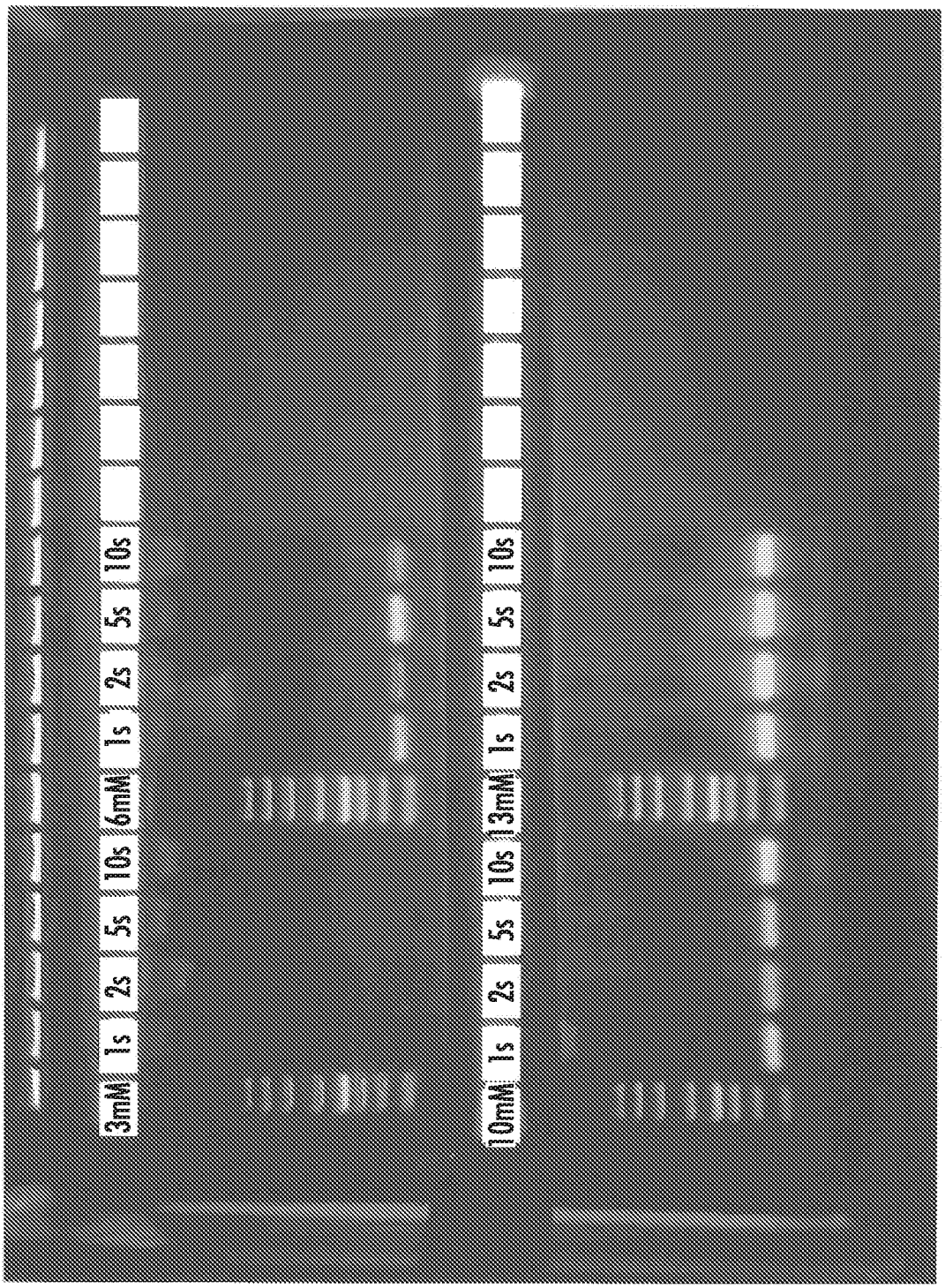
FIG. 26 is a gel showing one-step RT-PCR performed with AMV as the enzyme, at 42° C. with varying time and Mg++ concentration. Mg++ was included at 3 (top left), 6 (top right), 10 (bottom left), and 13 (bottom right) mM $MgCl_2$, each with RT times of 1, 2, 5, and 10 s (from left to right).

One-step RT-PCR was then performed with AMV at 42° C. to study the effects of RT time and $Mg^{++}$ concentration. $Mg^{++}$ was included at 3, 6, 10, and 13 mM, each with RT times of 1, 2, 5, and 10 seconds. The one-step reaction included the rapid PCR master solution of Example 11 (without anti-Taq antibody), 2.5 U/µl of AMV RT, 250 copies/µl of RSV RNA, 4 µM of each RSV primer, and 10 mM DTT. Cycling conditions were as in Example 13. Results are shown in FIG. 26. Panels include 3 (top left), 6 (top right), 10 (bottom left), and 13 (bottom right) mM $MgCl_2$. Within each panel, RT times were 1, 2, 5, and 10 seconds, left to right. No product was observed for AMV RT at 3 mM $MgCl_2$, variable intensity products were observed at 6 and 10 mM $MgCl_2$ without any clear trend for the time of RT incubation, and strong bands at all RT times were observed for 13 mM $MgCl_2$. Excellent amplification occurred with 13 mM $MgCl_2$, even in the complete absence of K+, contrary to expectations from prior art that suggests no amplification without K+. Thus, good results may be obtained using a one-step RT-PCR protocol wherein the reaction mixture is substantially free of potassium.

Example 20

Native MMLV from NEB was compared to the genetically modified MMLV enzyme ISCRIPT™ from Bio-Rad. The manufacturer of the enzyme ISCRIPT™ claims it to have greater RNase H activity and greater heat stability. Initial studies using the rapid PCR master solution of Example 11 with RSV RNA and 5 seconds of RT at 56° C. in 0.6 M trehalose showed good specific melting curves when the enzyme ISCRIPT™ (10 U/µl) was used, but no amplification with native MMLV (2.5 U/µl). Similar results were found when each enzyme was increased 4-fold. Finally, the RT temperature was lowered to 37, 42, or 47° C. with a 20 second RT step. Results were the same with the enzyme ISCRIPT™ showing good amplification, but native MMLV showed no amplification. The reactions did not contain any DTT or K+.

A two-step experiment similar to that of Example 19 was performed with 2 different buffers, one based on the manufacturer's buffer (50 mM Tris, pH 8.3, 3 mM $MgCl_2$, 75 mM KCl and 10 mM DTT) supplemented with BSA (500 µg/ml) and dNTPs (500 µM each), and the other based on the rapid PCR master solution of Example 11 (50 mM Tris, pH 8.3, 3 mM $MgCl_2$, 200 µM each dNTP, and 250 µg/ml BSA) supplemented with 10 µM DTT and 75 mM KCl. Instead of AMV, 20 U/µl of MMLV was used in each reaction, as well as 6 µM reverse RSV primer. Each reaction also included 250 copies of RSV RNA/µL. Both DTT and KCl were present in both buffers at the same concentration, although there were slight differences in dNTP and BSA concentrations that were not expected to affect the results. RT was performed at 42° C. for 1 second, 10 seconds, 1 min, or 10 min. After RT, the reverse transcriptase was inactivated at 93° C. for 60 seconds, cooled to room temperature, and diluted 1:20 for PCR in a capillary LightCycler. Each 10 µl PCR included 0.5 µM RSV primers and 2 µl of 1:20 cDNA in the rapid PCR master solution of Example 11. Real-time PCR and melting were performed as in the two-step procedure detailed in Example 19.

All time points from both buffers revealed specific melting curves and amplified with Cqs within 3 cycles of each other. However, the average Cq (29.4) was very delayed compared to samples in Example 19 that did not include KCl (average Cq=20), suggesting strong RT-PCR inhibition with K+. Without being bound to theory, it is believed that the KCl is the cause of the inhibition during PCR.

Figure 27:
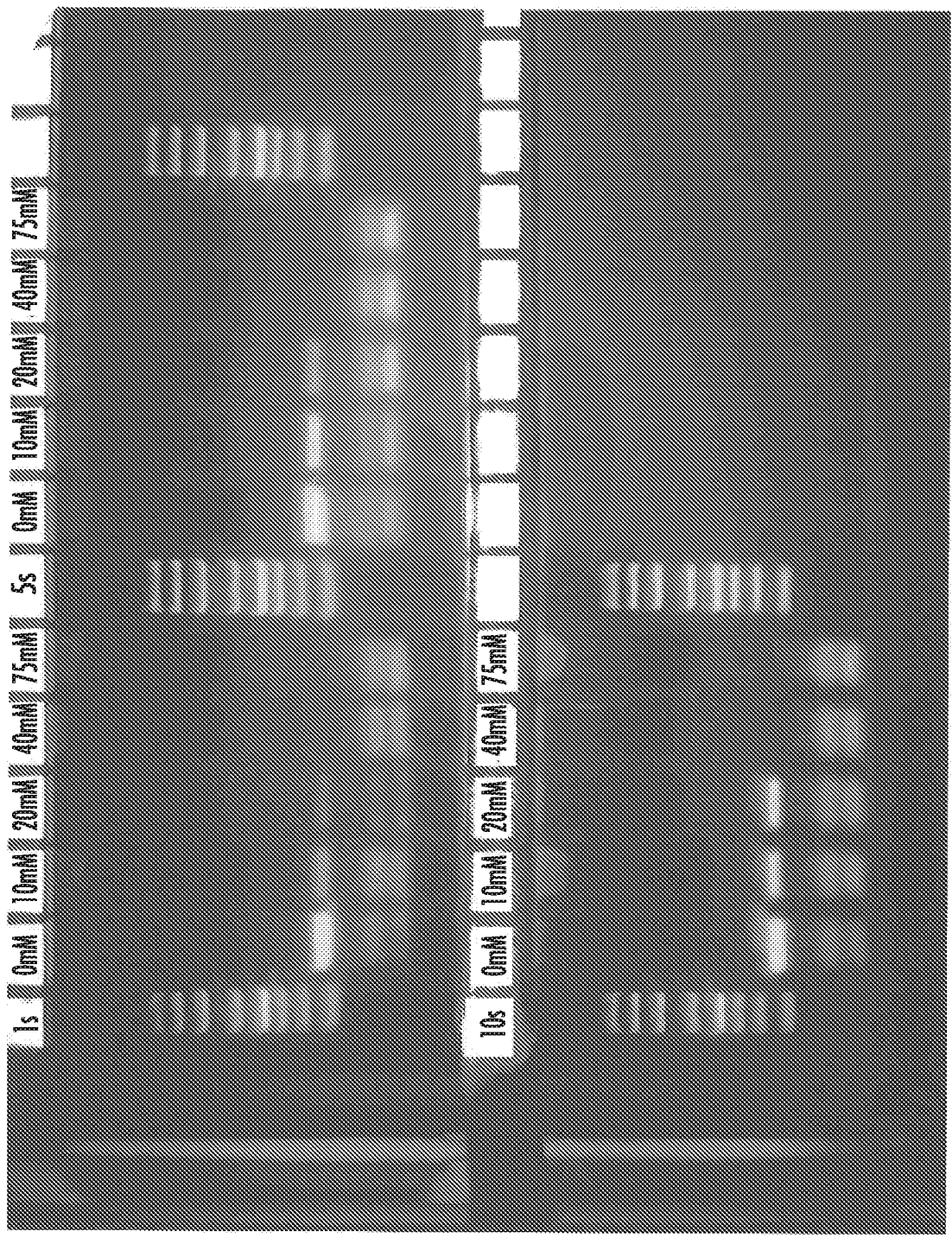
FIG. 27 is a gel showing results of an illustrative one-step RT-PCR protocol performed at 0, 10, 20, 40, and 75 (from right to left) mM KCl with a RT step at 42° C. lasting 1 (top left), 5 (top right), and 10 (bottom left) s.

To demonstrate inhibition with KCl, one-step RT-PCR was performed at 0, 10, 20, 40, and 75 mM KCl with a RT step at 42° C. lasting 1, 5 or 10 seconds. To the rapid PCR master solution, 250 copies/µl of RSV RNA, 20 U/µl MMLV, 4 µM of each RSV primer, 10 mM DTT, and 2 µM of KLENTAQ® (a DNA polymerase) were included, along with variable concentrations of KCl. Amplification was performed as in the one step protocol of Example 19. Agarose gels are shown in FIG. 27 for RT times of 1 (top left), 5 (top right) and 10 (bottom left) seconds, with increasing KCl concentrations within each panel. Strong amplification occurred at times of 1, 5 or 10 seconds with 0 mM KCl. Bands resulting from reactions with 10 and 20 mM KCl were weaker than at 0 mM KCl, but did increase with increased RT incubation times. No amplification was observed at 40 or 75 mM KCl.

Figure 28:
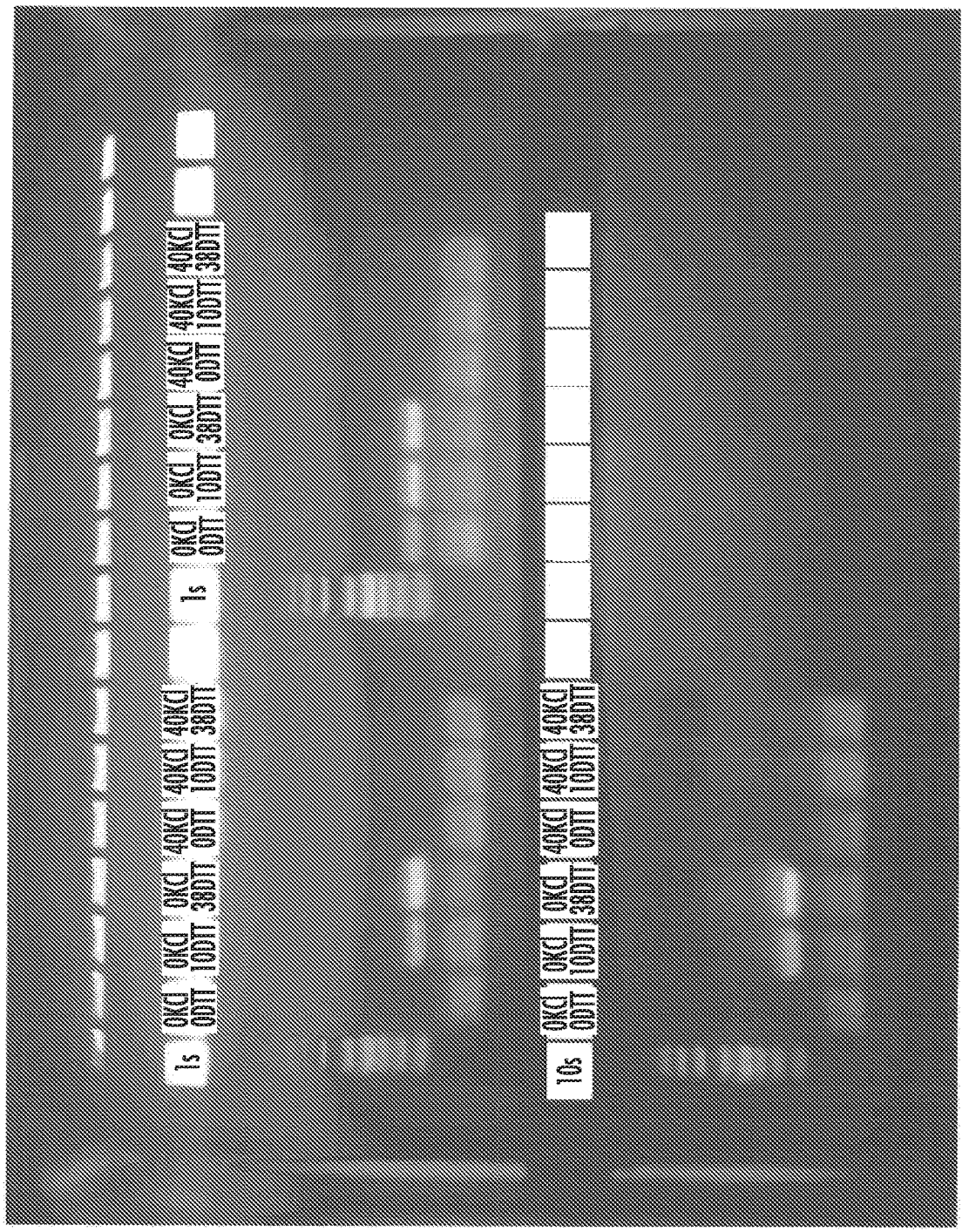
FIG. 28 is a gel showing results of an illustrative one-step RT-PCR protocol performed with 0, 10, or 38 mM DTT and 0 or 40 mM KCl (as indicated) with 1 s (top left), 5 s (top right), and 10 s (bottom left) sec RT incubation at 42° C.

DTT is a powerful sulfhydryl reducing agent required by some enzymes that have free sulfhydryl groups. One-step RT-PCR similar to the preceding paragraph was performed with 0, 10, or 38 mM DTT and 0 or 40 mM KCl with 1, 5, or 10 seconds RT incubation at 42° C. Results (FIG. 28) show panels for 1 second (top left), 5 seconds (top right), and 10 seconds (bottom left) with the different DTT/KCl treatments from left to right (0 mM KCl/0 mM DTT, 0 mM KCl/10 mM DTT, 0 mM KCl/38 mM DTT, 40 mM KCl/0 mM DTT, 40 mM KCl/10 mM DTT, and 40 mM KCl/38 mM DTT). When neither DTT nor KCl are added, amplification does not usually occur, although the 5 second panel does show a weak band. The activating effect of DTT is clearly seen in all panels with distinct 10 mM DTT bands that are even brighter at 38 mM. Whenever KCl is present at 40 mM, no amplification is visible, even when DTT is present. These data indicate that DTT activates and KCl suppresses RT-PCR amplification. Other reducing agents, illustratively beta-mercaptoethanol and others, may activate amplification as well.

Example 21

When PCR products are analyzed by gels or melting analysis after 45 cycles of extreme PCR (FIGS. 21, 22, 24, and 25), most quantitative information is lost. Even though gel bands may appear equal after a time series of reverse transcription (RT), this may be due to limiting concentrations of PCR components that may equalize any quantitative differences between samples. For quantitative results, real-time PCR is often much better than gels or melting analysis. The cycle of quantification (Cq) that is derived from each real-time curve is inversely proportional to the log of the initial template concentration. Therefore, a low Cq indicates a high amount of initial template, which, in reverse transcription, is equivalent to the amount of cDNA generated by the reverse transcription reaction.

Cloned native MMLV from New England Biolabs was titrated to examine the number of Units necessary to maximize the RT-PCR amplification, as indicated by the lowest Cq value. The manufacturer's protocol suggests 10 Units/µL of MMLV for the RT reaction. However, initial results suggested that lower amounts were optimal in extreme one-step RT-PCR, so 5, 2.5, 1.25, 0.625 and 0.313 Units/µL were examined under varying RT incubation times (2.5, 5, 10, 20, 40, and 80 seconds) at 45° C.

One-step RT-PCR reactions were performed with RSV RNA obtained from ATCC, catalog #VR-26D. RSV primers were TGGGGCAAATATGTCACGAAG (SEQ ID NO:30) and CCATTTAAGCAATGACCTCGA (SEQ ID NO:31). Reverse transcription and PCR were performed in glass capillaries in a 5 µL volume with 5 µM of each primer and an extreme PCR master solution (1×LCGreen Plus Dye, 0.2 µM each dNTP, 50 mM Tris (pH 8.3), 1.65 µM KLENTAQ® DNA polymerase, and 25 ng/µL bovine serum albumin) with 3.8 mM $MgCl_2$. Each positive sample included 6000 copies of RSV template in 5 Negatives samples did not include template (no template controls).

All solutions were mixed on ice to restrict any enzyme activity before the start of the reaction. The temperature of the samples was controlled with the 3 water bath system (FIG. 1c), first transferring the samples to a water bath at the desired RT temperature for the desired time, and then alternating between the other 2 water baths set at 95° C. and 55° C. with 400 ms holds in each water bath. The samples were cycled 33 times with fluorescence monitoring each cycle, taking about 30 seconds for PCR completion.

Figure 29:
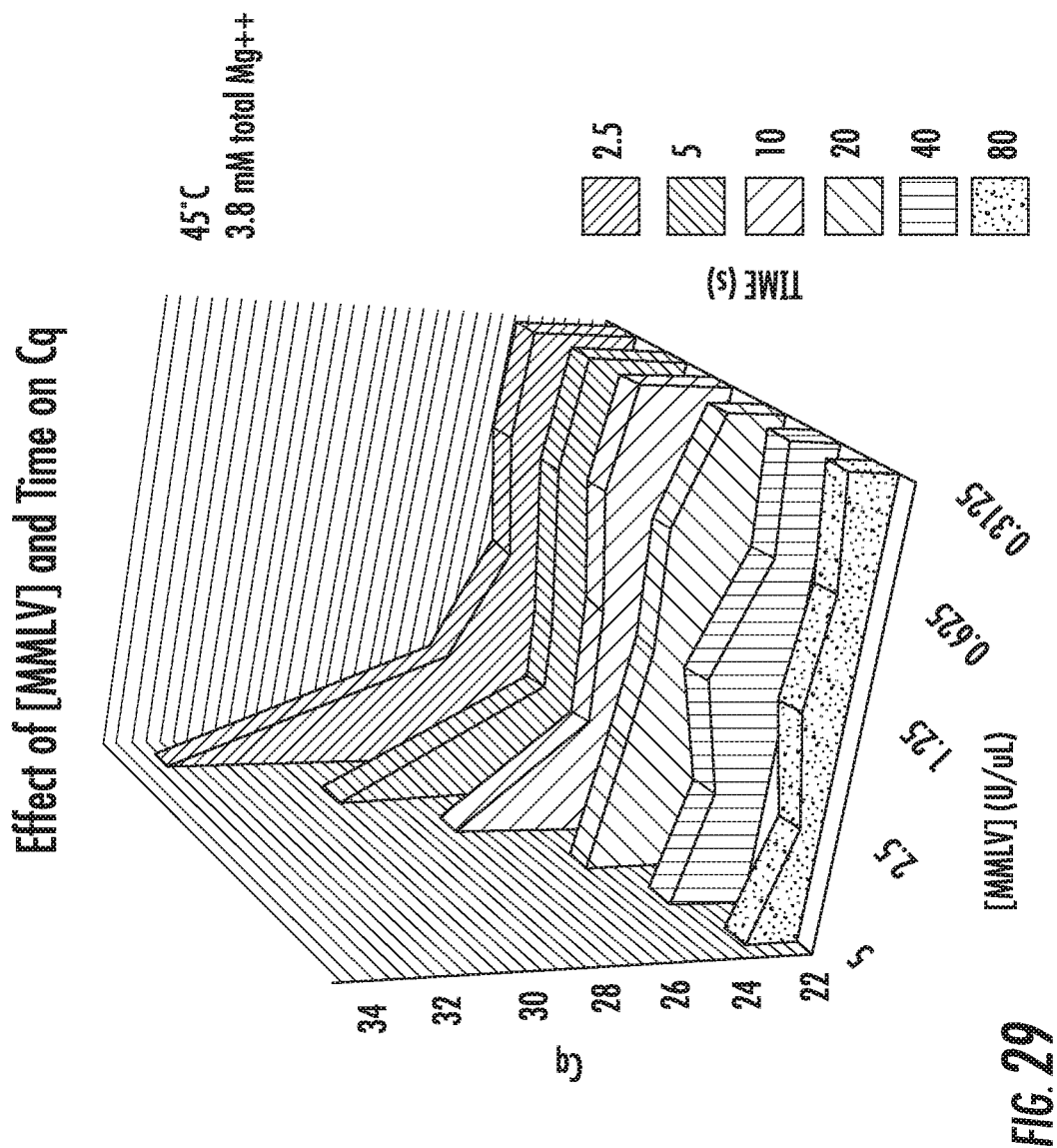
FIG. 29 is a graph showing the effect of MMLV concentration and RT time on Cq.

Results showed a minor decrease in Cq (<2 cycles) with increasing RT times (FIG. 29). However, at the shortest time (2.5 seconds), high concentrations of MMLV strongly inhibited (up to 10 cycles) the overall reaction. At 2.5 seconds, 1.25 U/µL appeared optimal, an 8-fold decrease from the recommended concentration of 10 U/µL. With the goal of reducing the overall time for RT-PCR, 2.5 seconds is small compared to the PCR time of about 30 seconds, only contributing <10% of the overall time. It is preferable that the RT time is less than 50% of the overall time in extreme RT-PCR, more preferable that it is less than 20% of the overall time, and most preferable that it is less than 10% of the overall time. The shorter RT time minimizes RNA degradation at high temperatures and high magnesium concentrations. For longer products, both the RT and PCR times may be proportionately increased. In addition, the amount of reverse transcriptase can be proportionately increased as the length of the intended product increases, but at the small lengths used here, lower amounts of RT are optimal. Reverse transcriptase has been reported to inhibit DNA polymerases such as Taq polymerase, another reason to limit the concentration of RT in one-step RT-PCR reactions.

Example 22

AMV in the cloned native form (NEB) was diluted to determine the optimal concentration as determined by low Cq values. The recommended concentration of AMV in RT-PCR by the manufacturer is 1.25 U/µL. However, initial experiments indicated that optimal concentrations were lower. Reactions were tested at AMV concentrations of 1.25, 0.63, 0.31, 0.156, 0.078, and 0.039 U/µL.

One-Step RT-PCR reactions were performed with RSV RNA as in Example 21 except that AMV was used (at the concentrations above) with 8 mM $MgCl_2$ and the RT reaction occurred for 2 seconds at 48° C. Samples were run in triplicate at each concentration of AMV.

Figure 30:
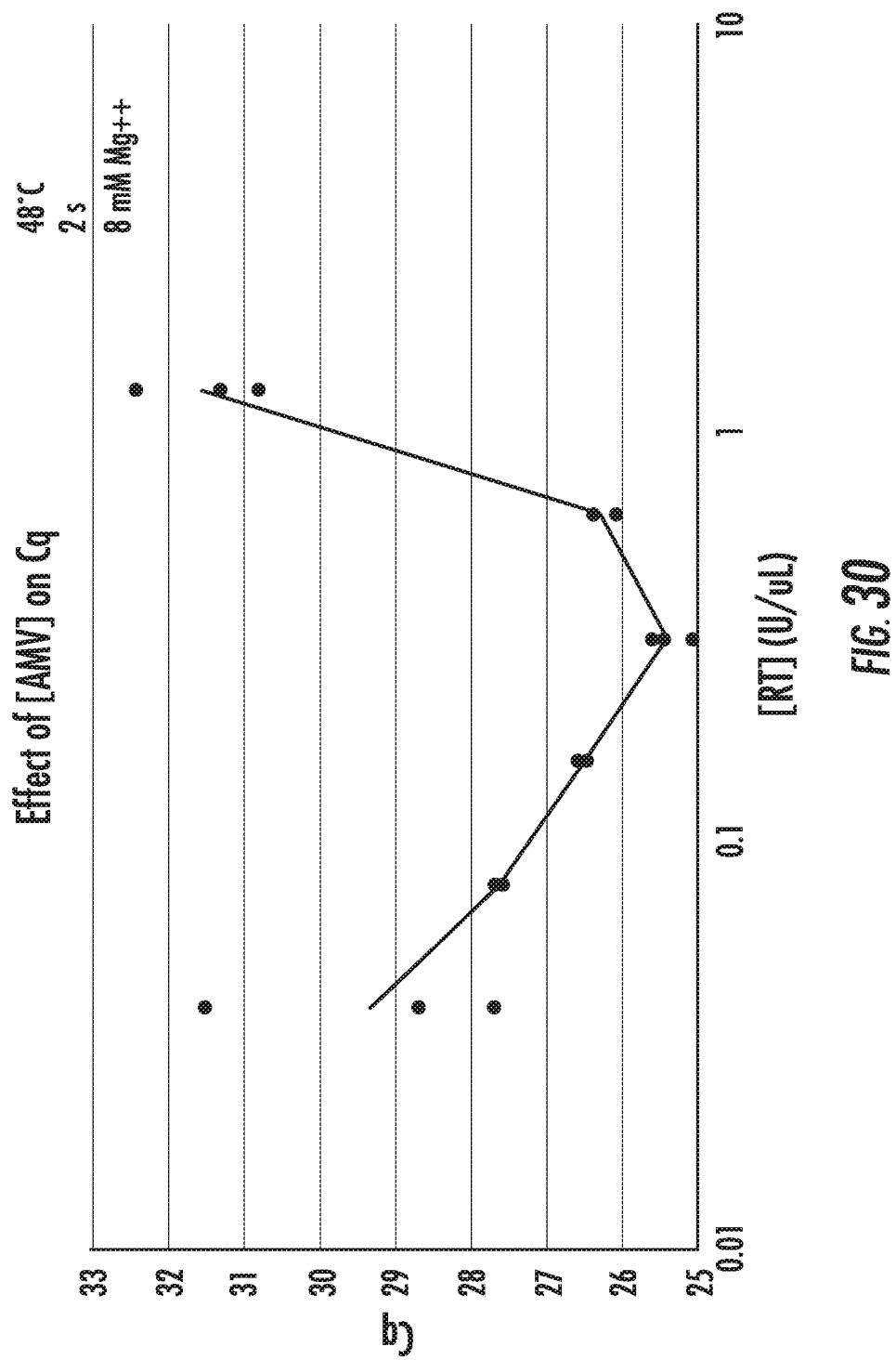
FIG. 30 is a graph showing the effect of AMV concentration on Cq at a 2 s RT reaction time.
Figure 31:
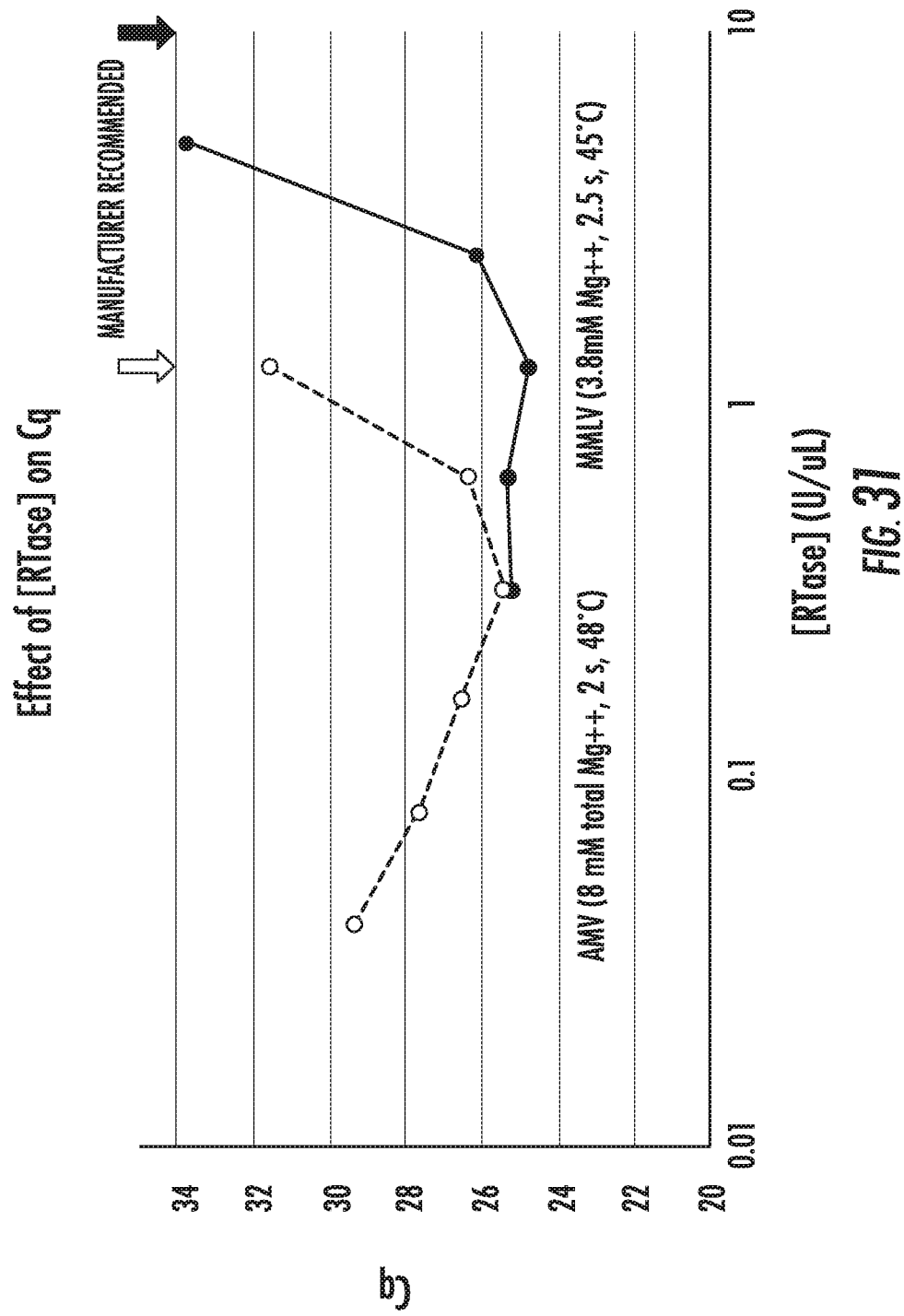
FIG. 31 is a graph showing the effect of MMLV and AMV concentration on Cq, with reactions using AMV containing 8 mM Mg++, 2 s reaction time at 48° C., and reactions using MMLV containing 3.8 mM Mg++, 2.5 s reaction time at 45° C.

AMV performed best at a concentration of 0.31 U/µL, 4 times lower than the recommended concentration of 1.25 U/µL (FIG. 30), although larger amounts may be used, illustratively 0.5, 0.8, and 1.0 Units/µL, particularly for larger amplicons. FIG. 31 combines the results for both Examples 21 and 22, with the manufacturer's recommended concentrations indicated.

Example 23

Figure 32:
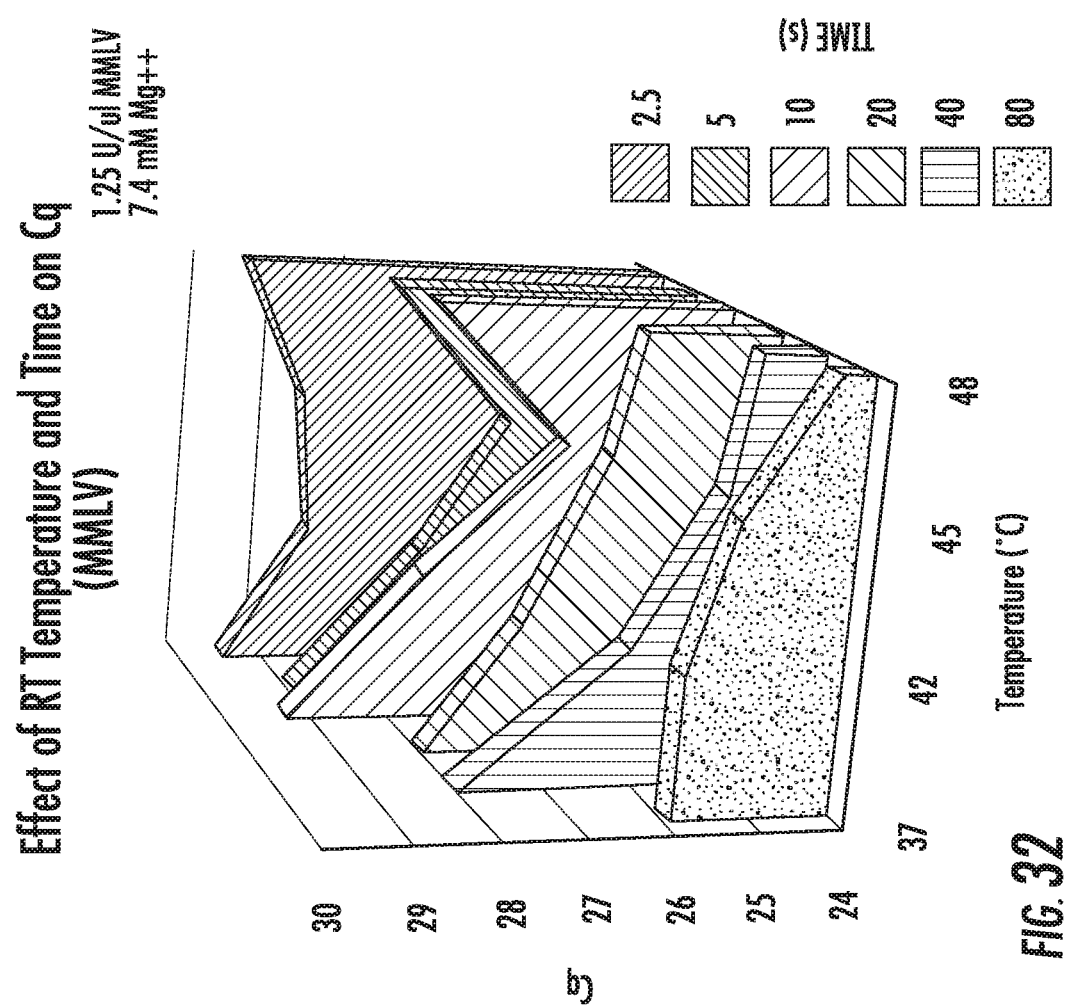
FIG. 32 is a graph showing the effect RT temperature and time on Cq.

Extreme one-step RT-PCR using MMLV was analyzed across a range of temperatures (37, 42, 45, and 48° C.) and hold times (2.5, 5, 10, 20, 40, and 80 seconds) for the RT step. RT-PCR followed Example 21, except that the $MgCl_2$ concentration was 7.4 mM and 1.25 U/µL MMLV was used. In general, the Cq decreased as the RT time increased, although not always (FIG. 32). Furthermore, no temperature optimum could be determined for MMLV.

Figure 33:
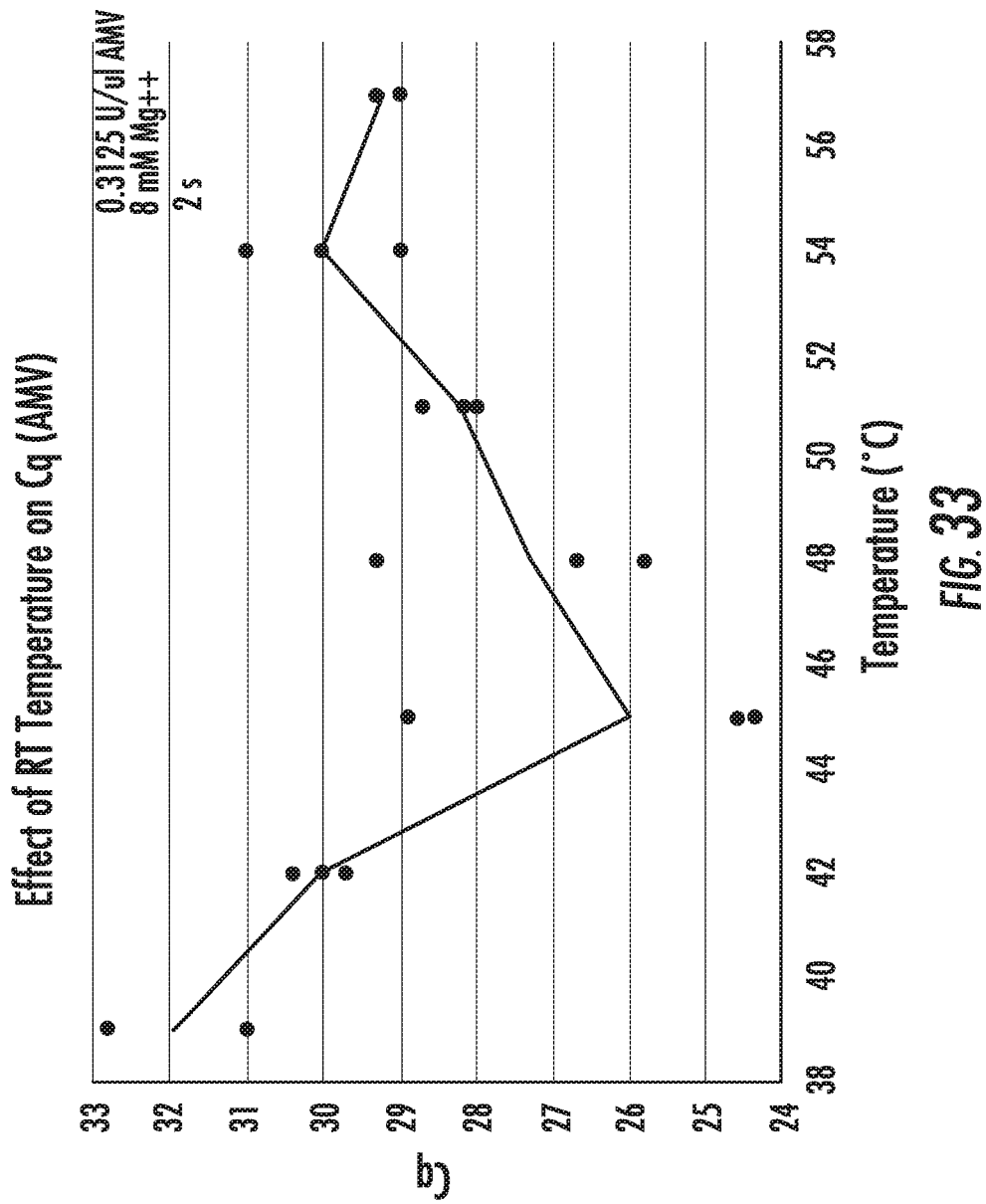
FIG. 33 is a graph showing the effect of RT temperature on Cq, with AMV as the RT enzyme.
Figure 34:
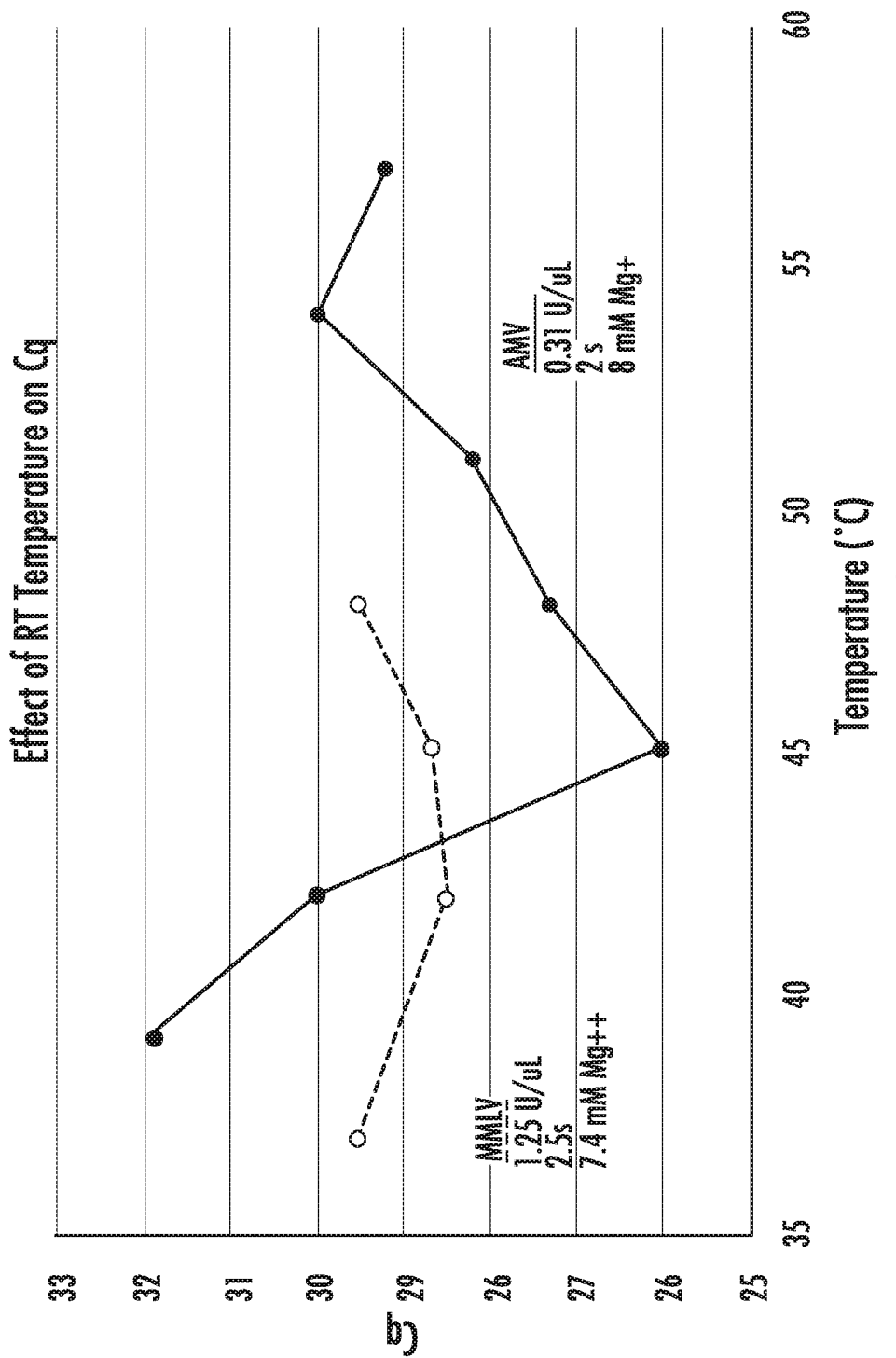
FIG. 34 is a graph showing the effect of RT temperature on Cq, showing results using both MMLV and AMV, wherein open circles represent MMLV and filled circles represent AMV.

Selecting a 2 second RT time, AMV was tested across a range of temperatures (39, 42, 45, 48, 51, 54, and 57° C.) using Cq as a measure of the amount of cDNA generated. The procedure of Example 22 was followed with 0.31 U/µL of AMV. Triplicate measurements showed a lot of variation (FIG. 33), making it difficult to identify the best temperature. The lowest average Cq was 45° C., which is also the manufacturer's recommended temperature for RT using AMV. FIG. 34 combines the data for MMLV and AMV. Optimal temperatures are not apparent. Indeed, similar RT activity appears over a wide range of temperatures.

Example 24

Due to the catalytic potential of magnesium to reduce reaction times, $MgCl_2$ concentrations were studied with both MMLV and AMV. One-step RT-PCR was performed with RSV as described previously (Examples 21 and 22). All samples were treated with a 45° C. RT hold for 2 seconds (AMV) or 2 and 5 seconds (MMLV), followed immediately by PCR amplification for 33 cycles.

Figure 35:
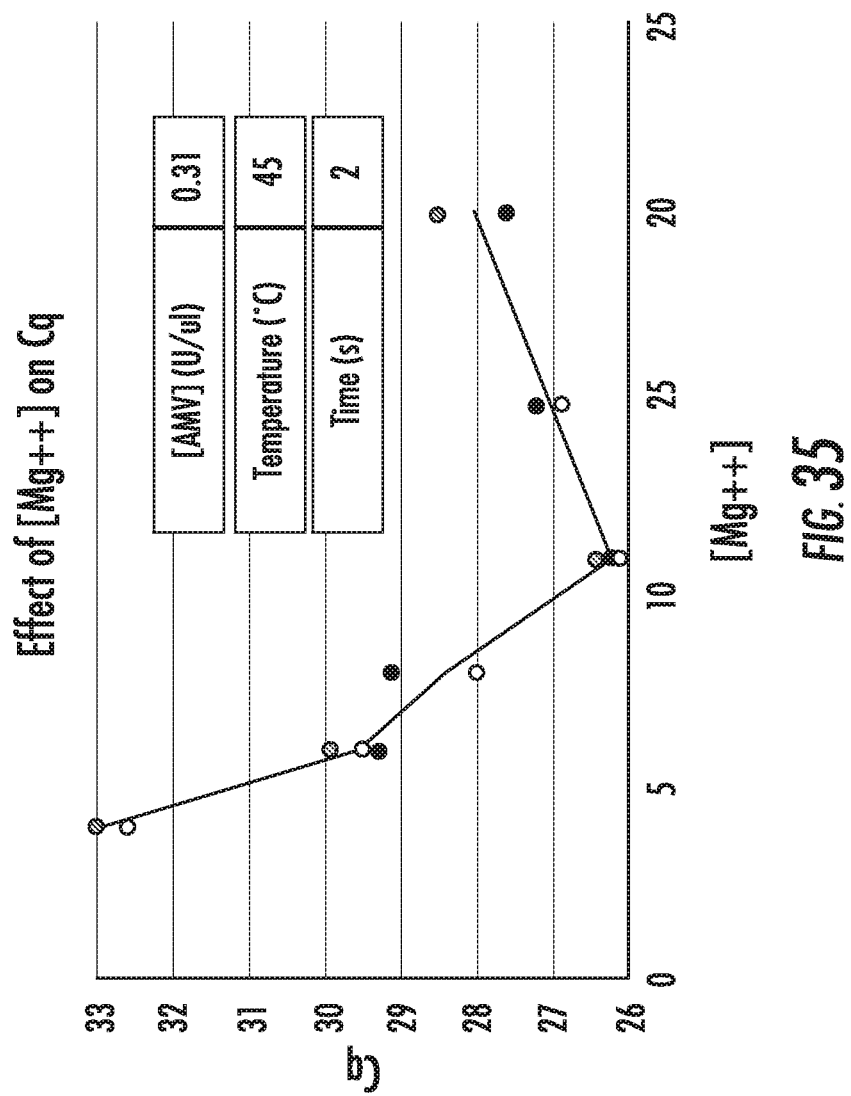
FIG. 35 is a graph showing the effect of Mg++ concentration on Cq using AMV using a 2 s RT reaction time.

Samples included RSV template and AMV at 0.31 U/µL in 1×PCR buffer as in Example 22. The $MgCl_2$ concentration was analyzed in varying increments between 3 mM and 20 mM. The lowest Cq value was measured at 11 mM (FIG. 35). Reactions with less than 11 mM $MgCl_2$ rapidly became less efficient, while Cq only rose slowly between 11 and 20 mM.

Figure 36:
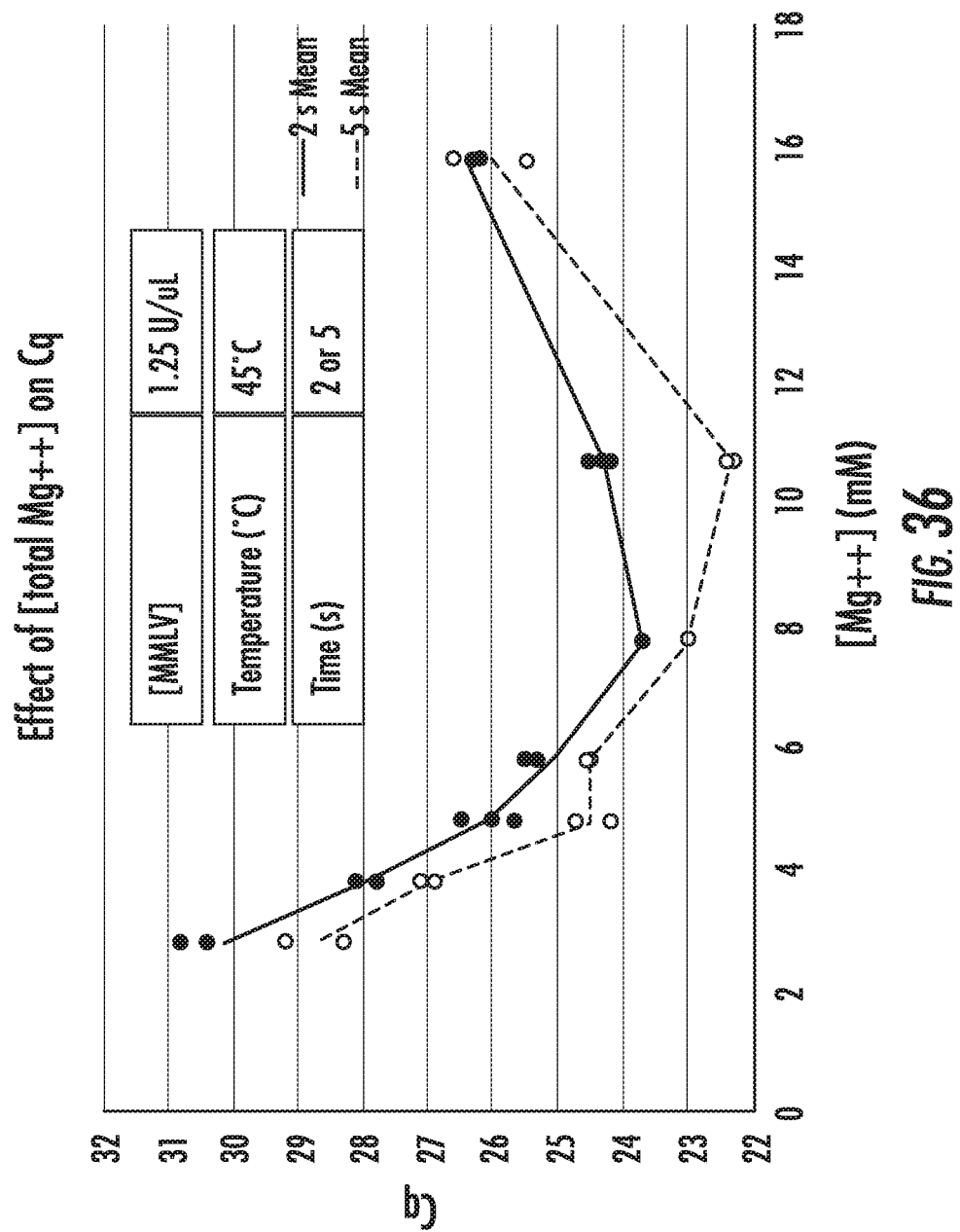
FIG. 36 is a graph showing the effect of Mg++ concentration on Cq using MMLV using 2 s and 5 s RT reaction times, wherein the solid line (filled circles) represents 2 s RT, and the dashed line (open circles) represents 5 s RT.
Figure 37:
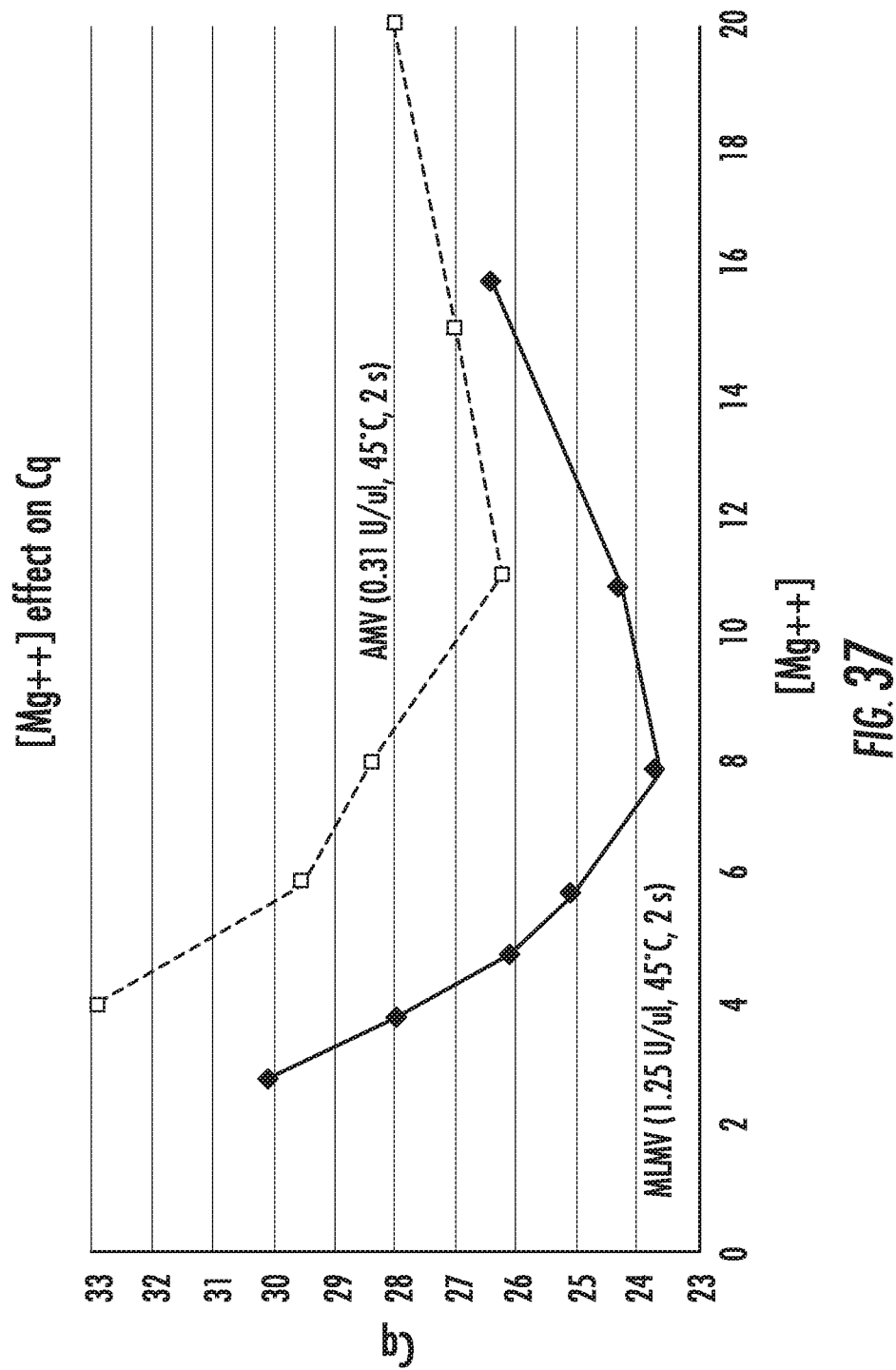
FIG. 37 is a graph showing the effect of Mg++ concentration on Cq using MMLV at 1.25 U/µL at 45° C. for 2 s (filled diamonds) and AMV at 0.31 U/µL at 45° C. for 2 s (open squares).

One-Step RT-PCR samples containing MMLV were performed with 1×PCR buffer (Example 21) and 1.25 Units/µL RT. $MgCl_2$ was titrated between 2 mM and 15 mM to determine the optimal concentration. In this case, both 2 and 5 second RT times were studied. The lowest Cq was found between 8 and 11 mM $MgCl_2$, depending on the RT time (FIG. 36), although between 6 and 12 mM the $MgCl_2$ was effective. The Cq increased about 1 cycle going from 5 second to 2 second RT times. Both enzymes are compared in FIG. 37 with 2 second RT times. MMLV was more active than AMV at all Mg++ concentrations.

Example 25

Reestablishing the minimum critical RT hold necessary for one-step RT-PCR was performed under AMV and MMLV reaction conditions determined in prior examples. Having optimized the majority of the RT-PCR reaction for AMV and MMLV, the effect of the RT hold time on Cq was analyzed again. Both reverse transcriptase reactions were performed with a RT temperature of 45° C. and cycling 33 times between 95° C. and 55° C.

Figure 38:
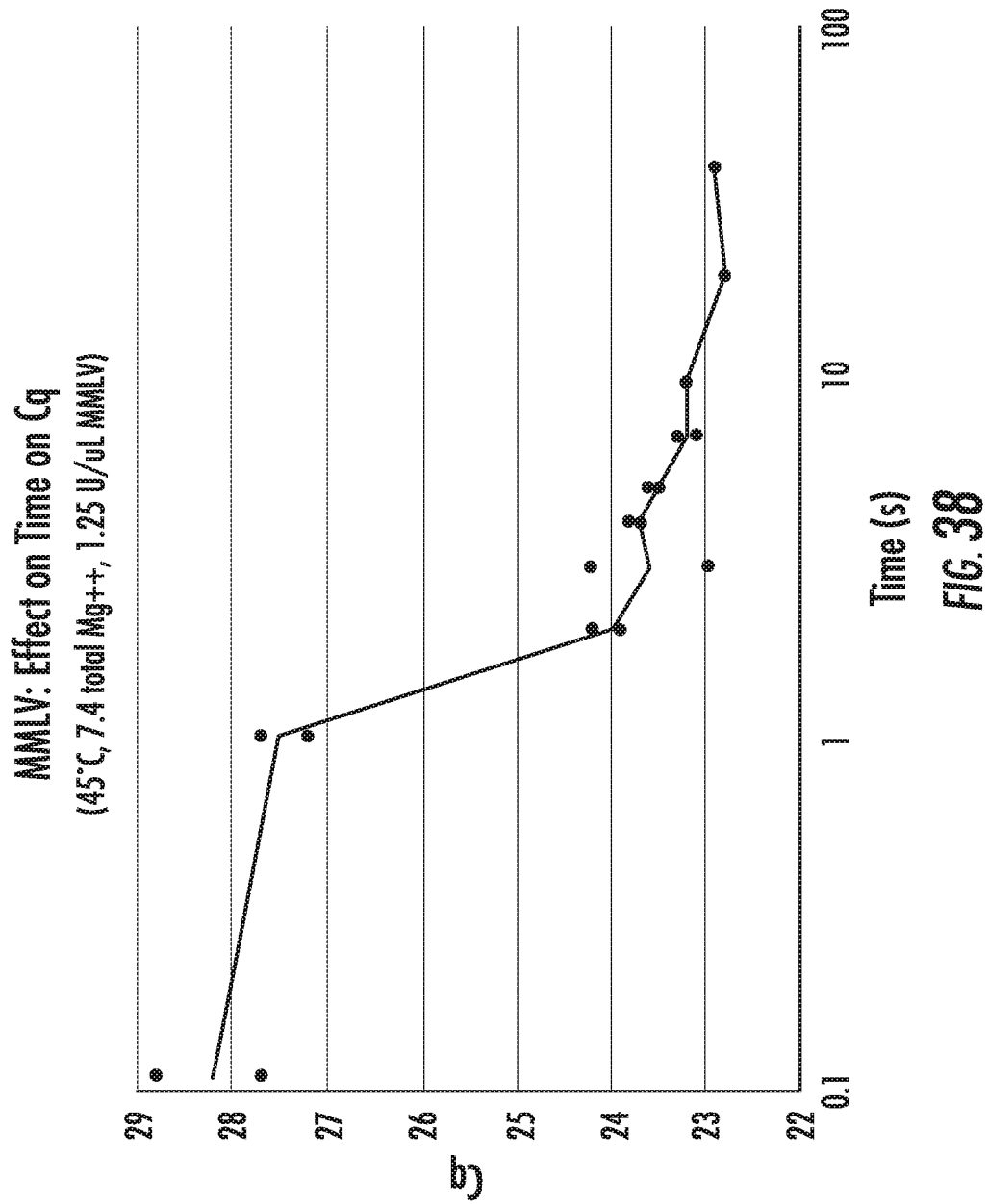
FIG. 38 is a graph showing the effect of RT reaction time on Cq using MMLV at 1.25 U/μL at 45° C. for 2 s with 7.4 mM MgCl$_2$.

MMLV reactions contained 1.25 U/µL of enzyme, 1×PCR buffer (Example 21), and 7.4 mM $MgCl_2$. Results are shown in duplicate in FIG. 38 with a logarithmic X-axis. There is a large Cq drop between 1 and 2 seconds, and less than a 1-cycle difference between a 2 and 40 seconds. The majority of the cDNA appears to be made within the first few seconds of RT.

Figure 39:
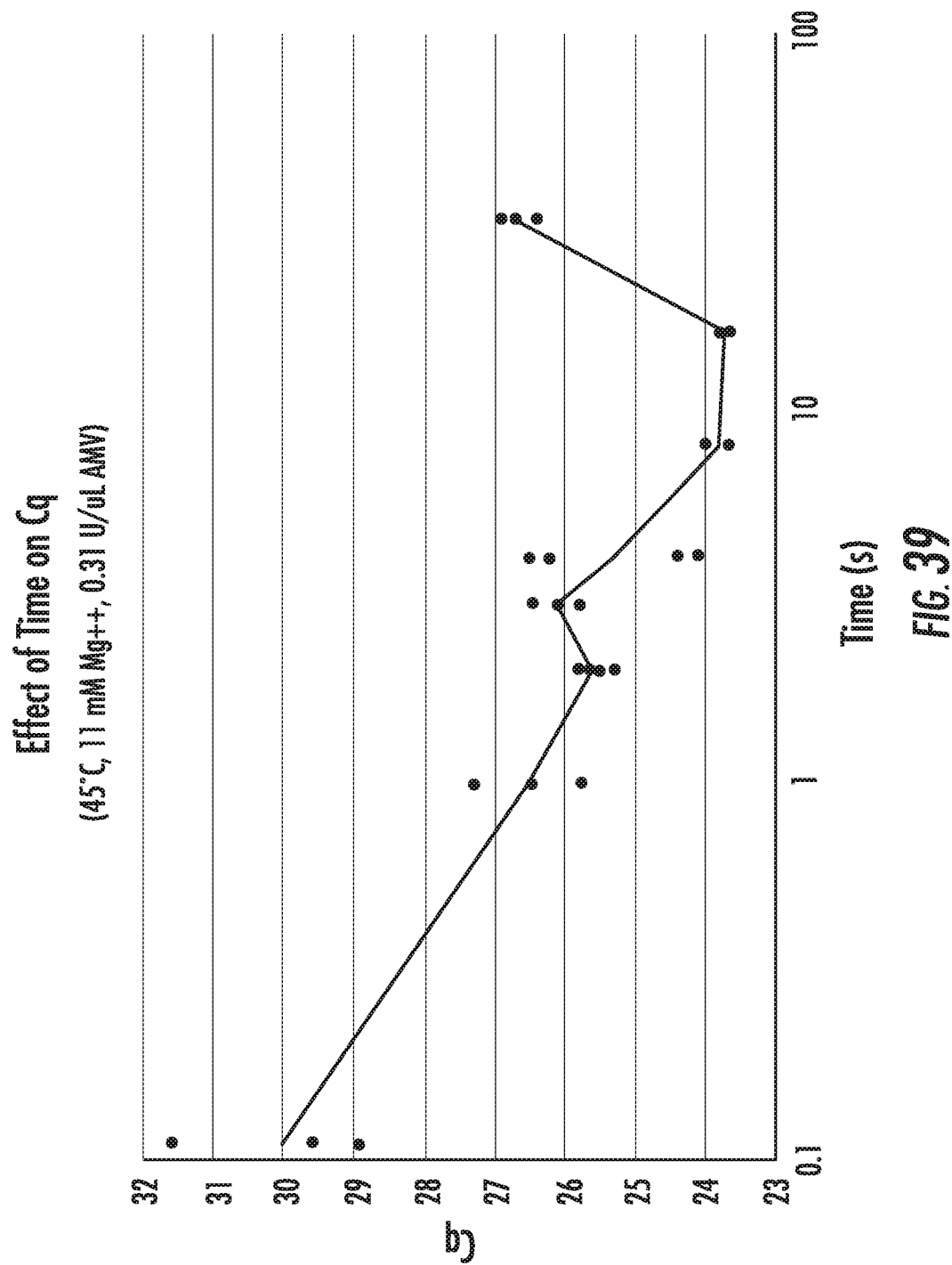
FIG. 39 is a graph showing the effect of RT reaction time on Cq using AMV at 0.31 U/μL at 45° C. for 2 s with 11 mM MgCl$_2$.

AMV reactions contained 0.31 U/μL enzyme, 1×PCR buffer, and 11 mM $MgCl_2$. Results are shown in triplicate in FIG. 39 with a logarithmic X-axis. Again, most of the Cq drop appears by 2 seconds, suggesting that under these conditions, the majority of the cDNA appears to be made within the first few seconds of RT.

Figure 40:
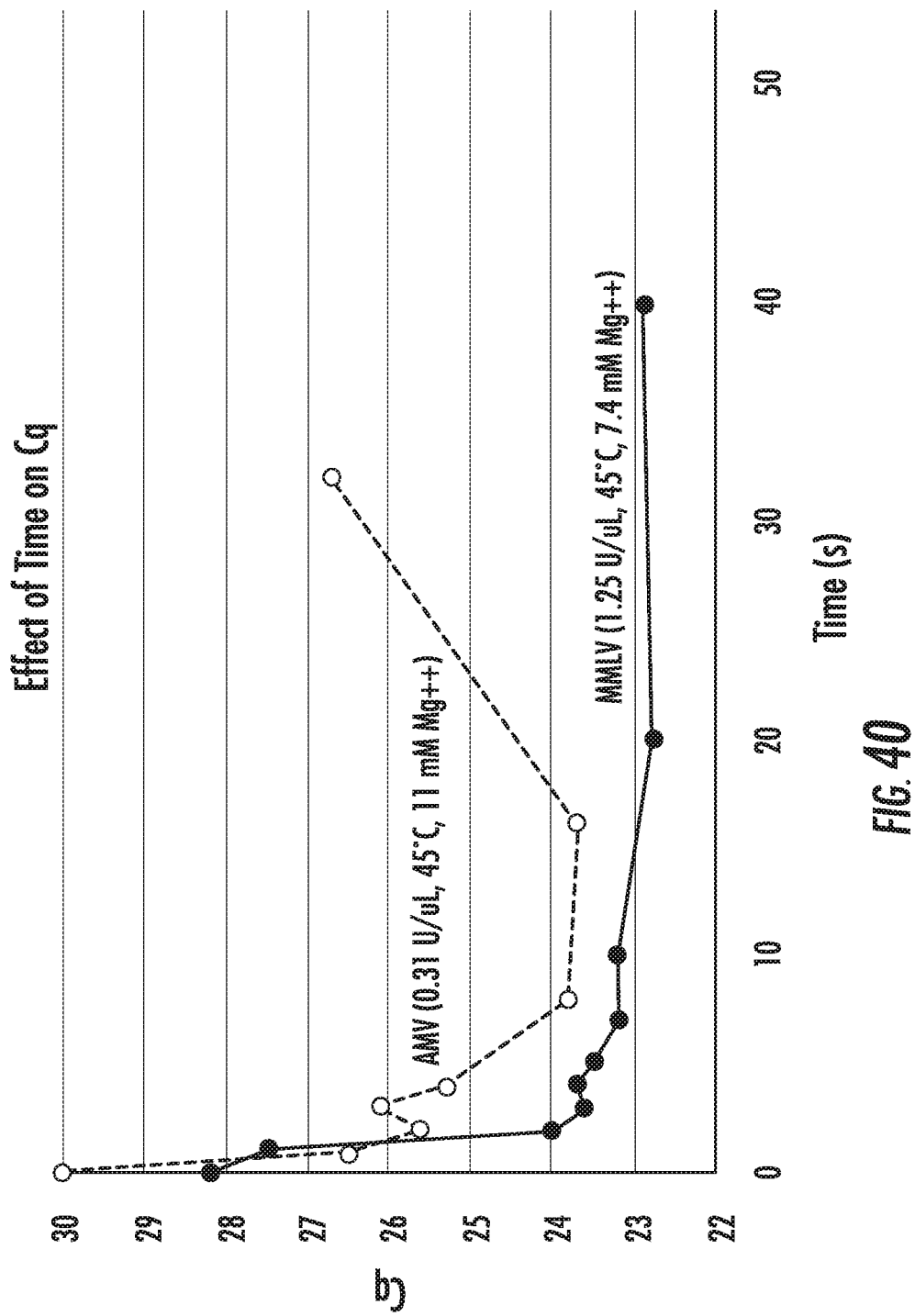
FIG. 40 is a graph that combines the results shown in FIGS. 38-39, with AMV (open circles) and MMLV (filled circles).

The combined data from MMLV and AMV are shown in FIG. 40. While some cDNA is still generated without a RT hold, increasing the hold time to 2 seconds substantially boosts cDNA synthesis, with only minor gains thereafter. Again, MMLV appears more efficient than AMV in generating cDNA at most time points. The ability to perform reverse transcription in 2 seconds or less significantly reduces RT reaction times, especially useful in one-step PCR where no reagent additions are necessary, particularly useful in diagnostic testing.

Example 26

The sensitivity of one-step RT-PCR under extreme conditions with increased primer and polymerase concentrations may be limited because of poor specificity. Depending on the target, apparent amplification of no-template controls may be observed, with little difference in Cq between the no-template controls and low copy number positive samples. Furthermore, the primer dimers generated in such reactions may melt at or close to the specific product melting temperature, making primer dimers hard to distinguish from the desired product. To mitigate these effects, hot start techniques were considered. Heat activated polymerases, primers, and dNTPs are available commercially, but all take minutes to activate, longer than the time required for extreme RT-PCR, and such hot start techniques may reduce much of the value of the method. Antibodies against polymerases are also available, but the amount of antibody needed and cost are both high when the polymerase concentration is increased 10-20 fold, as in extreme PCR. Another option is to mix the components within an instrument that holds the solutions at a high temperature during mixing, such as the FilmArray (BioFire Diagnostics, LLC). The high temperature reduces or eliminates primer binding prior to the start of the reaction, but this requires a specialized instrument that may not be needed for many applications.

When all RT-PCR components are present, non-specific template amplification or non-template amplification (primer dimer) may occur at room temperature during preparation. Therefore, critical reaction components, like the polymerase or dNTPs are typically withheld from the reaction mixture during preparation as long as possible. Primer dimer formation occurs more readily with the high primer and polymerase concentrations that are found in extreme PCR. However, primer dimers do not occur when only one primer is exposed to a polymerase; two different primers are necessary for primer dimer formation (65). The present work demonstrates that primer dimer formation in extreme RT-PCR can be reduced by separating the primers into two half reactions that are mixed immediately before RT. The Cq of no template control reactions was higher (better specificity and hence better sensitivity) when the primers were separated into the two half reactions until just before RT-PCR than when they were prepared together.

Primer dimers can also be decreased or prevented by keeping the fully mixed reactions cold and limiting the amount of time after mixing prior to RT-PCR. For example, it has been found that keeping the samples on ice after mixing and centrifuging the samples in the cold before PCR increased the Cqs of no template controls. In general, better results may be obtained by minimizing both the time and temperature after final mixing but before RT-PCR. In addition, rapidly ramping the temperature from the mixing temperature (illustratively 0 to 25° C.) to the RT temperature (37 to 90° C.) lowers primer dimer formation. The temperature change after mixing to the RT temperature illustratively may be performed in less than one second, more illustratively in less than 0.5 s, and most illustratively in less than 200 ms. In contrast to other studies, the present work shows that at short RT times, there is a broad range of acceptable RT temperatures.

Furthermore, when both a polymerase such as KLENTAQ® and a reverse transcriptase are present in the same reaction tube, inhibition of PCR can occur (66-68). The present work shows that separation of the DNA-directed polymerase (e.g., KLENTAQ®) and the RNA-directed polymerase (reverse transcriptase) into the 2 separate half reactions also lowers primer dimers as evidenced by an increase in delta Cq, the difference in Cq between positive control and negative control amplifications. Additional experiments have shown better results when the half reaction that contains the reverse transcriptase contains the reverse primer, that is, the primer that can anneal to any template present and extend the primer if dNTPs and Mg++ are present.

In summary, control of primer dimers was obtained by separating the one-step RT-PCR preparation into two half-reactions. In one embodiment, the first half-reaction contains the DNA directed polymerase (e.g., KLENTAQ®), the primer that does not anneal to the template (the forward primer), and 1× buffer (e.g., Tris, BSA, and 1× fluorescent dye, e.g., LCGreen plus). The second half reaction contains the reverse transcriptase, the primer that does anneal to the template (the reverse primer), 1× buffer, $Mg^{++}$, dNTPs, and template). After mixing, the solution is kept as cold as practical (illustratively <25° C., more illustratively <5° C., and even more illustratively <2) for as short a time as possible (illustratively <60 s, more illustratively <30 s, and even more illustratively <10 s) before the RT reaction and raised as quickly as possible to the RT temperature (illustratively <1 s, more illustratively <500 ms, and even more illustratively <200 msec).

An exemplary one-step RT-PCR included components separated into a first frozen half-reaction and a second chilled (but liquid) half-reaction. The two half reaction portions were combined immediately before running one-step RT-PCR, hereinafter called the "glaciate" technique.

Demonstration of the glaciate technique utilized RSV RNA obtained from ATCC, catalog #VR-26D. The RSV primers were forward: TGGGGCAAATATGTCACGAAG (SEQ ID NO:30) and reverse: CCATTTAAGCAATGACCTCGA (SEQ ID NO:31). Both half reactions contained 1×LCGreen Plus Dye, 50 mM Tris (pH 8.3), and 25 ng/μL bovine serum albumin. Working on ice, the half reaction to be frozen contained in addition, 0.2 mM each dNTP, 3.2 mM KLENTAQ® (a DNA polymerase) and 10 μM forward primer. Two and a half μL of this sample was pipetted into each glass capillary and briefly centrifuged (<5 seconds) and frozen at −20° C. for a minimum of 20 minutes.

While the frozen portion of reaction was in the −20° C. freezer, the chilled portion was prepared on ice. The chilled portion included 10 µM reverse primer, 12 mM MgCl$_2$, 2.5 Units/µL MMLV, and 2400 copies/µL of RSV. MMLV was not added to the chilled solution until right before addition to the frozen capillaries. Two to three frozen reaction capillaries were removed from the freezer and immediately placed into an ice water bath. Addition of 2.5 µL of the chilled solution was then pipetted into the top of each capillary and quickly pulsed in a table top centrifuge (<3 seconds) and promptly placed back into the ice bath. RT-PCR was then performed with a 2 second RT hold at 50° C. and cycled 45 times between 95° C. and 55° C.

This same experiment was also performed with inactivated Zika virus RNA obtained from ATCC (catalog #VR-1838DQ). The Zika forward primer was CAGGTTG-GAGTGGGAGTCAT (SEQ ID NO:32) and reverse primer was TTTGTAACGTGCCACATGGT (SEQ ID NO:33). 1250 copies of Zika RNA were used per 5 µL RT-PCR reaction.

Figure 41:
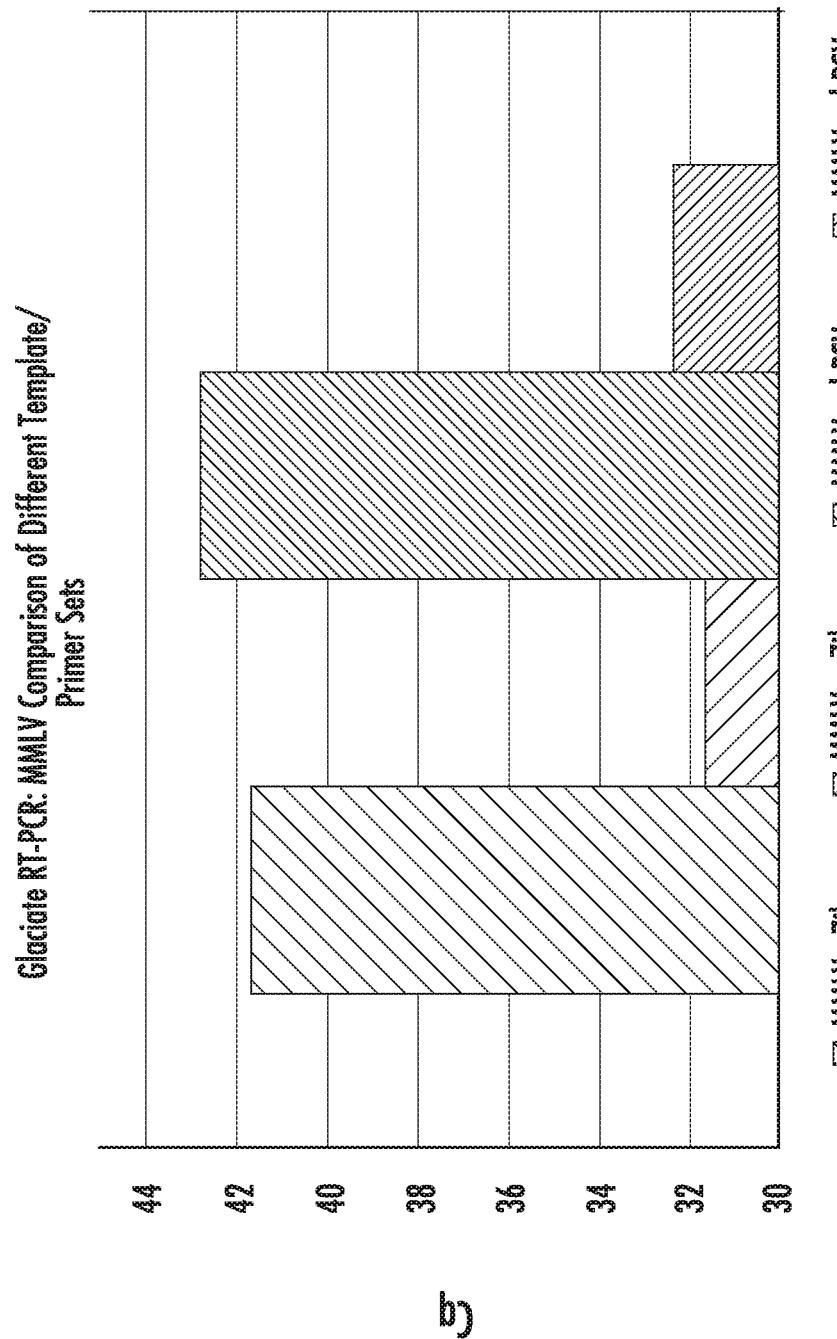
FIG. 41 is a graph showing the difference between Cqs using the glaciate technique with and without Zika template (two left bars) and with and without hRSV template (two right bars).

Results from both the RSV and Zika virus experiments showed a substantial increase in ΔCq (about 10 cycles, or a sensitivity increase of 1000) for no template controls of RT-PCR reactions made by the glaciate techniques as compared to those mixed on ice (FIG. 41). Furthermore, the melting curves of the no-template controls were shifted to lower temperatures and became easily distinguished from positive samples.

A series of three experiments were conducted to determine the effect of placing MgCl$_2$ and dNTPs into either the frozen or chilled portions of the glaciate RT-PCR procedure (Tables 4-6). Samples were made by freezing 2.5 µL of one half reaction at −20° C. into capillaries. The frozen sample was then placed in an ice bath where 2.5 µL of the chilled solution was added as in Example 26. In all experiments the 2 primers were separated into different solutions and the KLENTAQ® (a DNA polymerase) and MMLV were separated. The reverse primer was combined with the RNA and MMLV so that they could bind before mixing of the 2 solutions. This gave better results than combining the forward primer with MMLV and RNA.

TABLE 4

| Freeze Solution | | Chilled Solution | |
|---|---|---|---|
| Dye, buffer, BSA | 1X dye, 50 mM Tris, pH 8.3, 25 ng/µl BSA | Dye, buffer, BSA | 1X dye, 50 mM Tris, pH 8.3, 25 ng/µl BSA |
| Forward Primer | 10 µM | Reverse Primer | 10 µM |
| KLENTAQ® (a DNA polymerase) | 3.2 µM | MgCl$_2$ | 6 mM |
| Total dNTPs | 1.6 mM | MMLV | 2.5 Units/µL |
| MgCl$_2$ | 6 mM | (+/−) RNA | 2400 copies/µL |

TABLE 5

| Freeze Solution | | Chilled Solution | |
|---|---|---|---|
| Dye, buffer, BSA | 1X dye, 50 mM Tris, pH 8.3, 25 ng/µl BSA | Dye, buffer, BSA | 1X dye, 50 mM Tris, pH 8.3, 25 ng/µl BSA |
| Forward Primer | 10 µM | Reverse Primer | 10 µM |
| KLENTAQ® (a DNA polymerase) | 3.2 µM | MgCl$_2$ | 12 mM |
| Total dNTPs | 1.6 mM | MMLV | 2.5 Units/µL |
| | | (+/−) RNA | 2400 copies/µL |

TABLE 6

| Freeze Solution | | Chilled Solution | |
|---|---|---|---|
| Dye, buffer, BSA | 1X dye, 50 mM Tris, pH 8.3, 25 ng/µl BSA | Dye, buffer, BSA | 1X dye, 50 mM Tris, pH 8.3, 25 ng/µl BSA |
| Forward Primer | 10 µM | Reverse Primer | 10 µM |
| KLENTAQ® (a DNA polymerase) | 3.2 µM | Total dNTPs | 1.6 mM |
| | | MgCl$_2$ | 12 mM |
| | | MMLV | 2.5 Units/µL |

Figure 42:
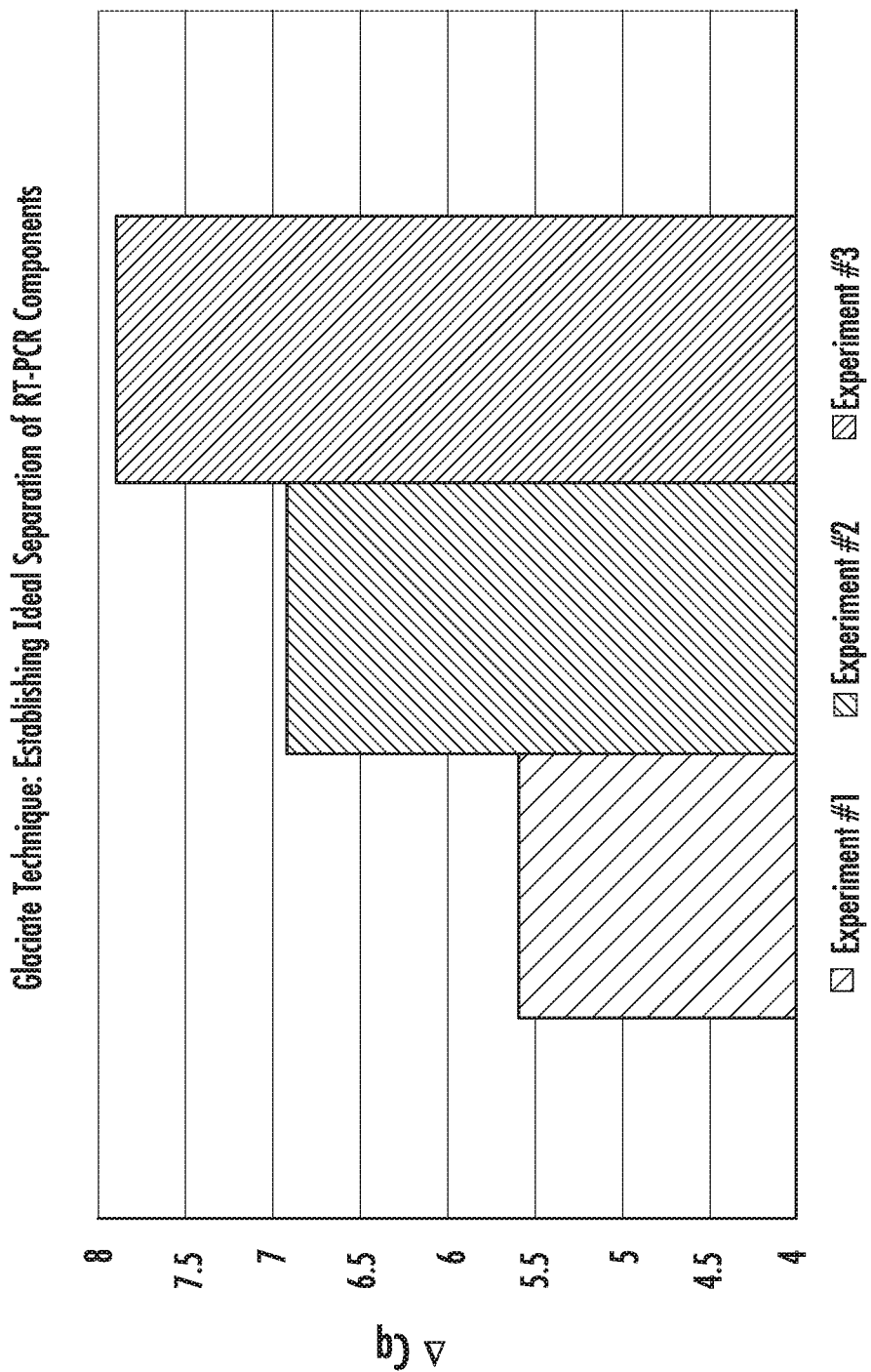
FIG. 42 is a graph comparing different frozen and chilled portions using the glaciate technique wherein Experiments #1, #2, #3 are described in Example 26 and Experiment #1 corresponds to Table 4, Experiment #2 corresponds to Table 5, and Experiment #3 corresponds to Table 6.

In Experiment 1 (Table 4), the MgCl$_2$ was included equally in both solutions. In Experiment 2 (Table 5), all of the MgCl$_2$ was placed into the chilled half reaction to see if separation of the Mg$^{++}$ from the KLENTAQ® (a DNA polymerase) would reduce no template control amplification. Finally, in Experiment 3 (Table 6) both dNTPs and MgCl$_2$ were placed in the chilled solution. Hypothetically, if the reverse transcriptase was responsible for no-template control amplification, such amplification might increase in the presence of dNTPs and MgCl$_2$. Alternatively, if the no-template control amplification was mediated by KLENTAQ® (a DNA polymerase), no Mg$^{++}$ or dNTPs would be available for extension by KLENTAQ® (a DNA polymerase), although positive samples would have perfect conditions for cDNA synthesis. Based on ΔCq values of the one-step RT-PCR reactions, experimental parameters outlined in experiment 3 lead to optimal conditions (FIG. 42).

Example 27

Figure 43:
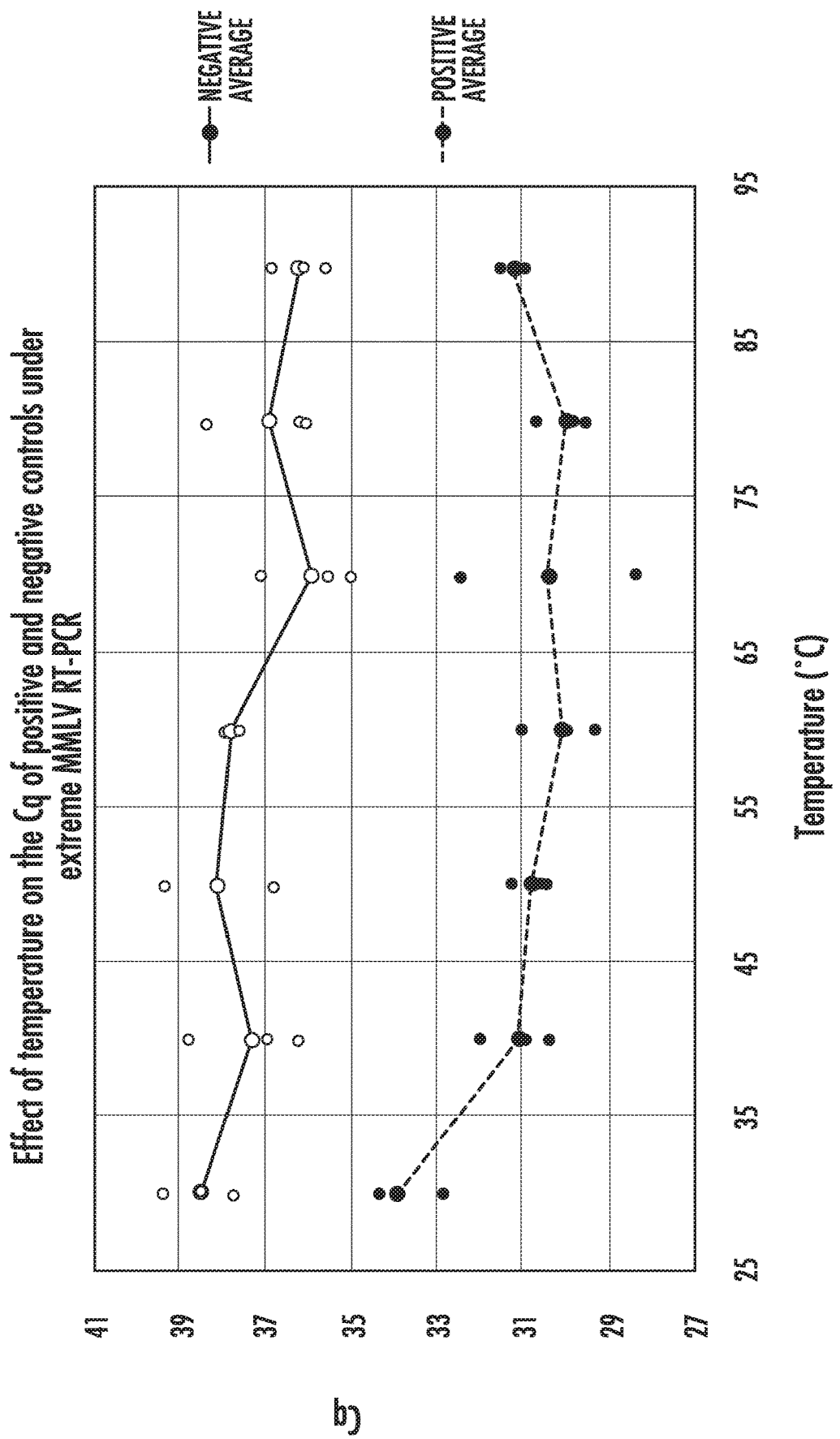
FIG. 43 is a graph showing the effect of temperature on Cq of positive and negative controls using the glaciate technique described in Example 26.

The effect of the RT temperature on RT-PCR was studied with the glaciate technique using 2 seconds of RT. The procedure outlined in experiment 3 of Example 26 was performed, using Zika primers and analyzing both positive (1250 copies per 5 µL RT-PCR) and no template controls over a range of RT temperatures from 30 to 90° C. The Cq values were very constant over a 60° C. range of temperatures with ΔCqs of 4-8 cycles (FIG. 43). The optimum was 50-60° C. for MMLV using extreme RT-PCR conditions. Even using the glaciate technique, there is still room for improvement. Greater ΔCqs between positive and no template controls would further improve sensitivity.

Example 28

Aptamers were investigated as a means to decrease no-template control "primer-dimer" amplification in extreme RT-PCR. Aptamers have been used in the past to inhibit polymerization reactions, specifically both DNA-directed DNA polymerases (69-70) and RNA-directed DNA polymerases (71). Aptamers are derived by in vitro evolutionary selection. The basic sequence of the aptamers studied herein are listed below (5'-3'):

Taq Aptamer Sequences (70):
6-10:
(SEQ ID NO: 34)
CAAGACGGGCGGGTGTGGTAGGCGCCCGTG 4-1:
(SEQ ID NO: 35)
ACTTGATGGCGGGTGTGGTAGGCGCCATCT -continued Stoffel (KlenTaq) Aptamer Sequences (69):
Trnc.A-30:
(SEQ ID NO: 36)
AAGACCAGACAATGTACAGTATTGGCCTGA Trnc.2-30:
(SEQ ID NO: 37)
GCCGGCCAATGTACAGTATTGGCCGGC Tctw.A-30:
(SEQ ID NO: 38)
CCGGACAATGTACAGTATTGGCCCGG MuLV Aptamer Sequences (71):
dm.1.1:
(SEQ ID NO: 39)
UUACCACGCGCUCUUAACUGCUAGCGCCAUGGC m.1.1:
(SEQ ID NO: 40)
CUUACCACGCGCUCUUAACUGCUAGCGCCAUGGCCAAAACU.

Each of the DNA aptamers above was synthesized by standard phosphoroamidite synthesis in 3 forms: the first was unmodified at the 3'-end, the second was modified with a 3'-phosphate, and the third was modified with a C6-amino terminal modifier at the 3'-end (Glen Research). The names of each of these oligonucleotides, along with its template, 3'-blocker and literature reference are given in Table 7. The 3'-blocks were added to prevent possible extension from the DNA aptamers. While aptamer blocking with phosphate and C6 amino groups are described herein, additional 3'-blockers are contemplated, including amino modifiers with different carbon chain lengths, illustratively those with two carbon (C2), three carbon (C3), and up to twelve carbon (C12) linkers. Any 3'-blocker with a positive charge is also contemplated and thought to increase the binding and effectiveness of the aptamers described herein, although other blockers may be used. The oligonucleotides Tctw.A-30, Tctw.A-30 Phos, and Tctw.A-30 amino are novel aspects of this application because they maintain the hairpin loop and the asymmetric internal loop of the hairpin stem of aptamer Trnc.A-30, while adding stability by changing one of the stem base pairs from A::T to G::C and increasing the length of the stem by an additional G::C base pair. Additionally, other modifications to Trnc.A-30 that maintain its secondary structure (hairpin loop and asymmetrical internal loop) while increasing the stem stability are expected to produce useful aptamers, with or without a 3'-amino modifier for the applications described herein. The secondary structures of Trnc.A-30 and Trnc.2-30 have been published (69). The RNA aptamers for MMLV are not blocked because they should not be extended by DNA polymerases.

TABLE 7

| Name | Template | 3'-Blocker | Reference |
| --- | --- | --- | --- |
| 6-10 | DNA | None | 70 |
| 6-10 Phos | | Phosphate | |
| 6-10 Amino | | C6-Amino | |
| 4-1 | DNA | None | 70 |
| 4-1 Phos | | Phosphate | |
| 4-1 Amino | | Amino | |
| Trnc.2-30 | DNA | None | 69 |
| Trnc.2-30 Phos | | Phosphate | |
| Trnc.2-30 Amino | | Amino | |
| Tctw.A-30 | DNA | None | Novel |
| Tctw.A-30 Phos | | Phosphate | |
| Tctw.A-30 Amino | | Amino | |
| dm.1.1 | RNA | None | 71 |
| m.1.1 | RNA | None | 71 |

The DNA aptamers were first tested with rapid cycle PCR. The human genomic DNA target was defined by the following PUM1 (intron 2) primers: AGGTAGGTGAGGAGACTTAAG (SEQ ID NO:41) and TAACCAGCTGGTGGTGA (SEQ ID NO:42). In 10 μL reactions, 50 ng of DNA template was present with 0.5 μM of each primer in 3 mM MgCl$_2$, 50 mM Tris, pH 8.3, 200 μM each dNTP, 500 μg/mL BSA, LCGreen Plus, 0.064 μM KLENTAQ1™ DNA polymerase, and variable amounts of aptamer Trnc.2-30. Samples were mixed at room temperature without cooling or any other means of primer-dimer prevention. Samples were amplified by heating to 95° C. for 5 seconds for genomic denaturation, followed by 45 cycles of 95° C. for 0 seconds and 55° C. for 0 seconds to determine quantification cycle values (Cqs) on a capillary LightCycler 1.5 (Roche). The PCR products were then melted from 60-95° C. at 0.2° C./s with continuous fluorescence acquisition.

Figure 44:
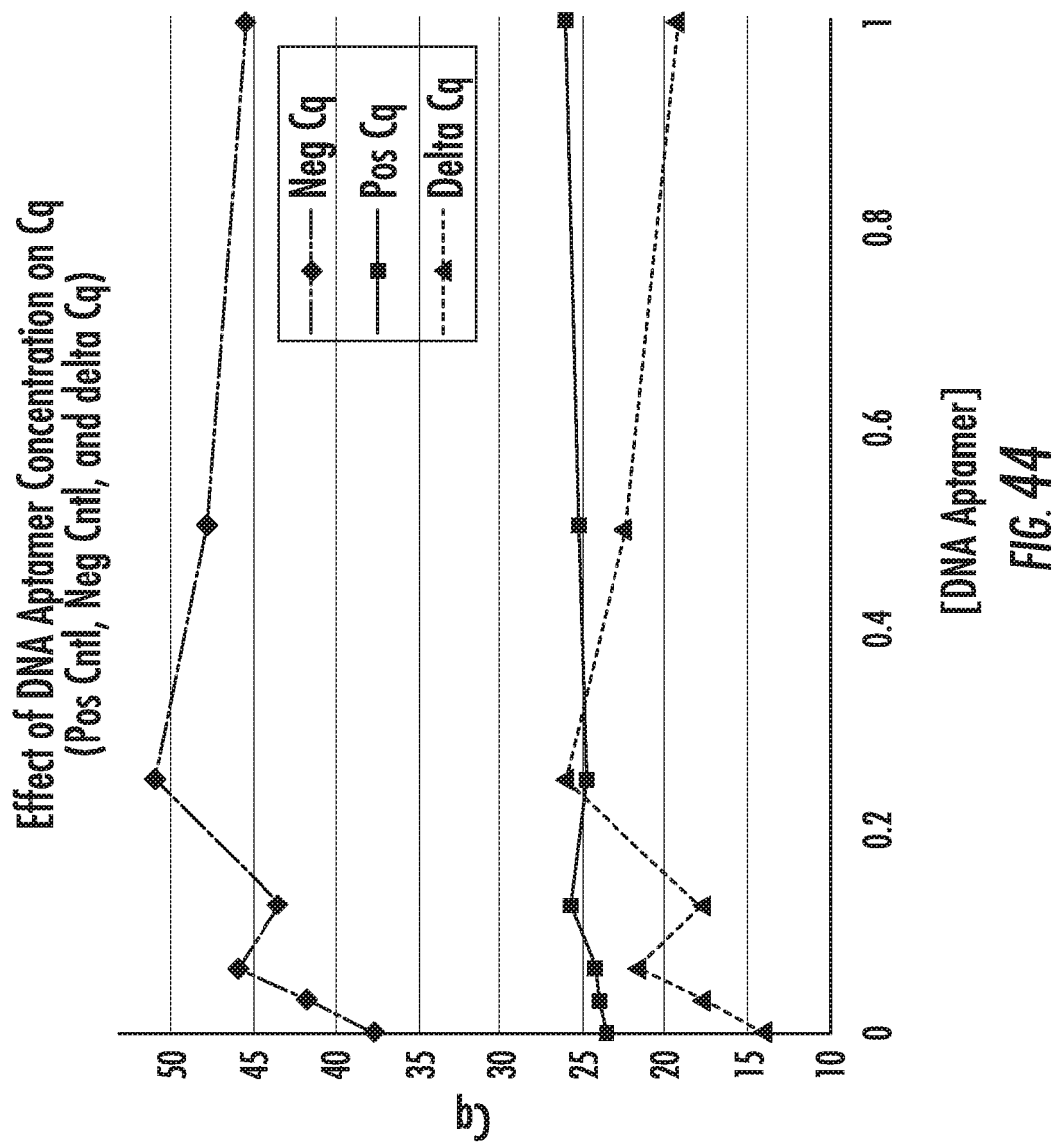
FIG. 44 is a graph of the effect of the aptamer Trnc.2-30 on the Cq of positive controls, negative controls, and their difference (delta Cq) using human genomic DNA and rapid cycle PCR, wherein diamonds represent the Cq for the negative control, squares represent the Cq for the positive control, and triangles represent the delta Cq.

The effect on Cq of different Trnc.2-30 concentrations is shown in FIG. 44. Delta Cq (ΔCq) is used as a measure of sensitivity; wherein the higher the ΔCq, the better the sensitivity of the assay. In the absence of aptamer, the ΔCq is about 14 cycles, rising to 26 cycles at 0.25 μM. At higher concentrations, although the Cq of the positive control stays about constant, the Cq of the negative control drops, also decreasing ΔCq.

Figure 45:
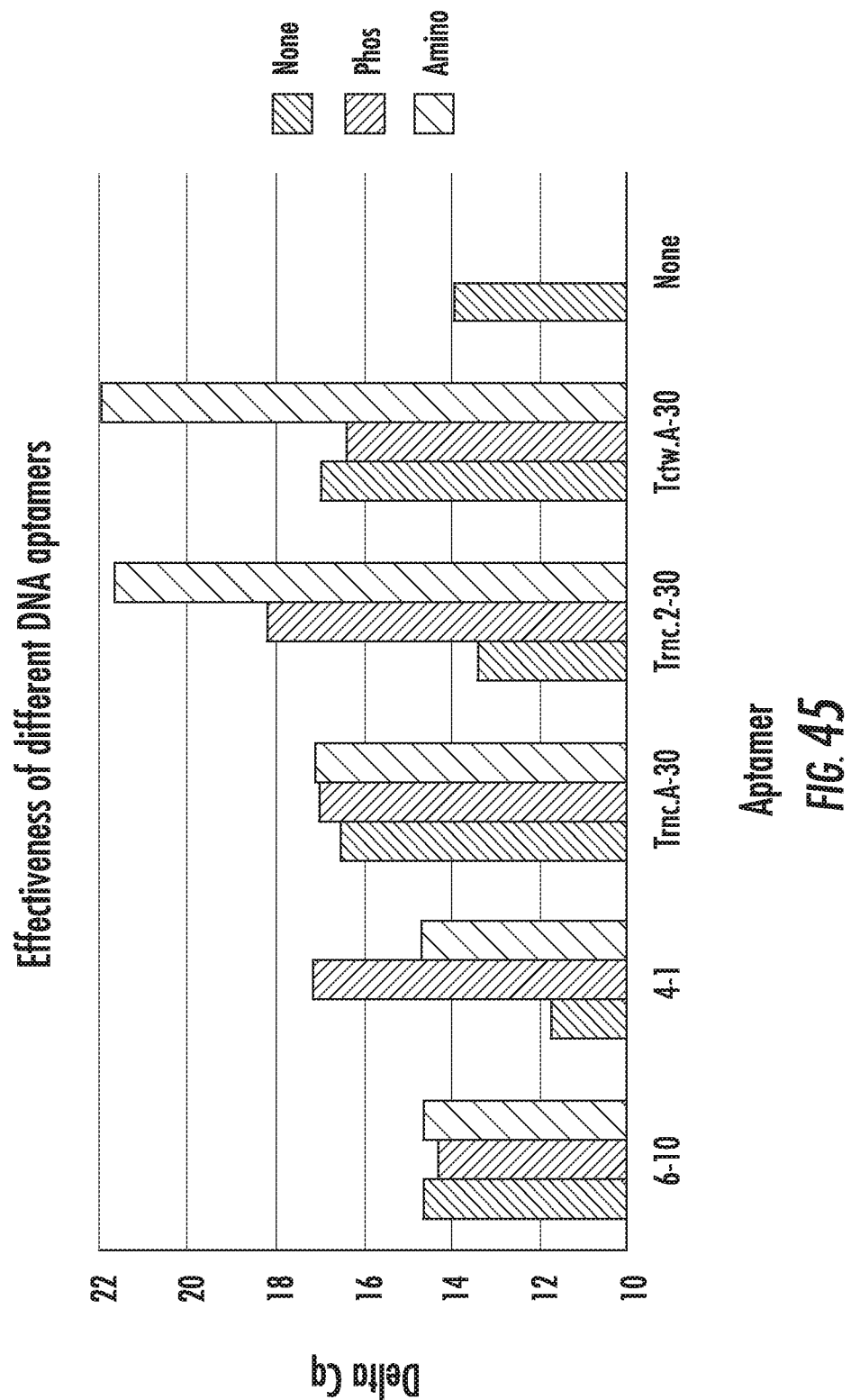
FIG. 45 is a graph comparing the effect of different DNA aptamers, with and without 3'-blockers, where None is no blocker, Phos has a 3'-phosphate, and Amino is modified with a C6-amino terminal modifier at the 3'-end.

Using the apparent optimal aptamer concentration of 0.25 μM determined above, the ΔCq of all DNA aptamers in Table 7 were determined using the same LightCycler PUM1 PCR assay. The positive controls varied less than 1.4 cycles with Cqs around 24-25 cycles, while the negative controls varied widely (data not shown). Results for the ΔCq values are shown in FIG. 45. The addition of the 6-10 and 4-1 aptamers did not provide much better results than the negative (no aptamer control). The best aptamers were C6 amino terminated at the 3'-end with the highest ΔCq aptamer being Tctw.A-30 amino. This aptamer is unique from the published literature in its C6 amino termination and it sequence (69).

Figure 46:
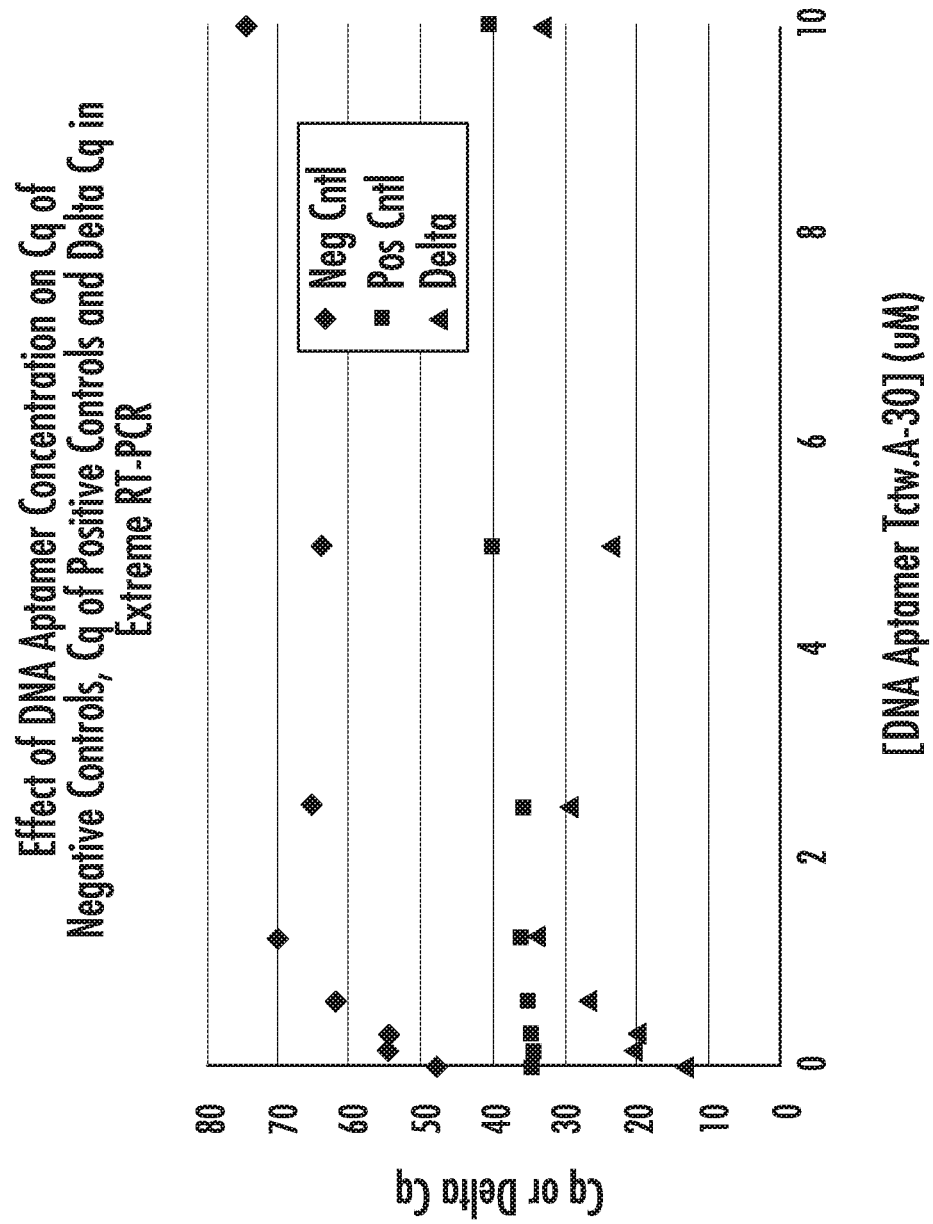
FIG. 46 is a graph showing the effect of DNA aptamer concentration on Cq, wherein diamonds represent the Cq for the negative control, squares represent the Cq for the positive control, and triangles represent the delta Cq.

Using the Tctw.A-30 Amino aptamer found optimal above for 15 min LightCycler PCR, its concentration was optimized for extreme PCR. Since the primer concentrations in some embodiments are 10-fold higher in extreme RT-PCR than in the LightCycler experiments, the aptamer concentration may need to be increased. The conditions for the PUM1 (intron 2) amplification above were used except for extreme chemistry (5 μM primers and 1.6 μM polymerase) and extreme amplification (approximately 1 second cycles between 90° C. and 60° C.). Results are shown in FIG. 46. The Cq of positive control reactions slowly rose as the DNA aptamer concentration increased, while the Cq of both the negative controls and the ΔCq rose quickly between 0 and 1.25 μM and then appeared to level off. The optimal concentration of TctwA-30 under exptreme conditions appeared to be about 2 μM. Because certain DNA aptamers partly inhibit some reverse transcriptases, including MMLV (72), one DNA aptamer could be used to inhibit both enzymes in RT-PCR. Alternatively, two aptamers, one specific to the reverse transcriptase and one specific to the DNA-directed polymerase can be used in RT-PCR.

Figure 47:
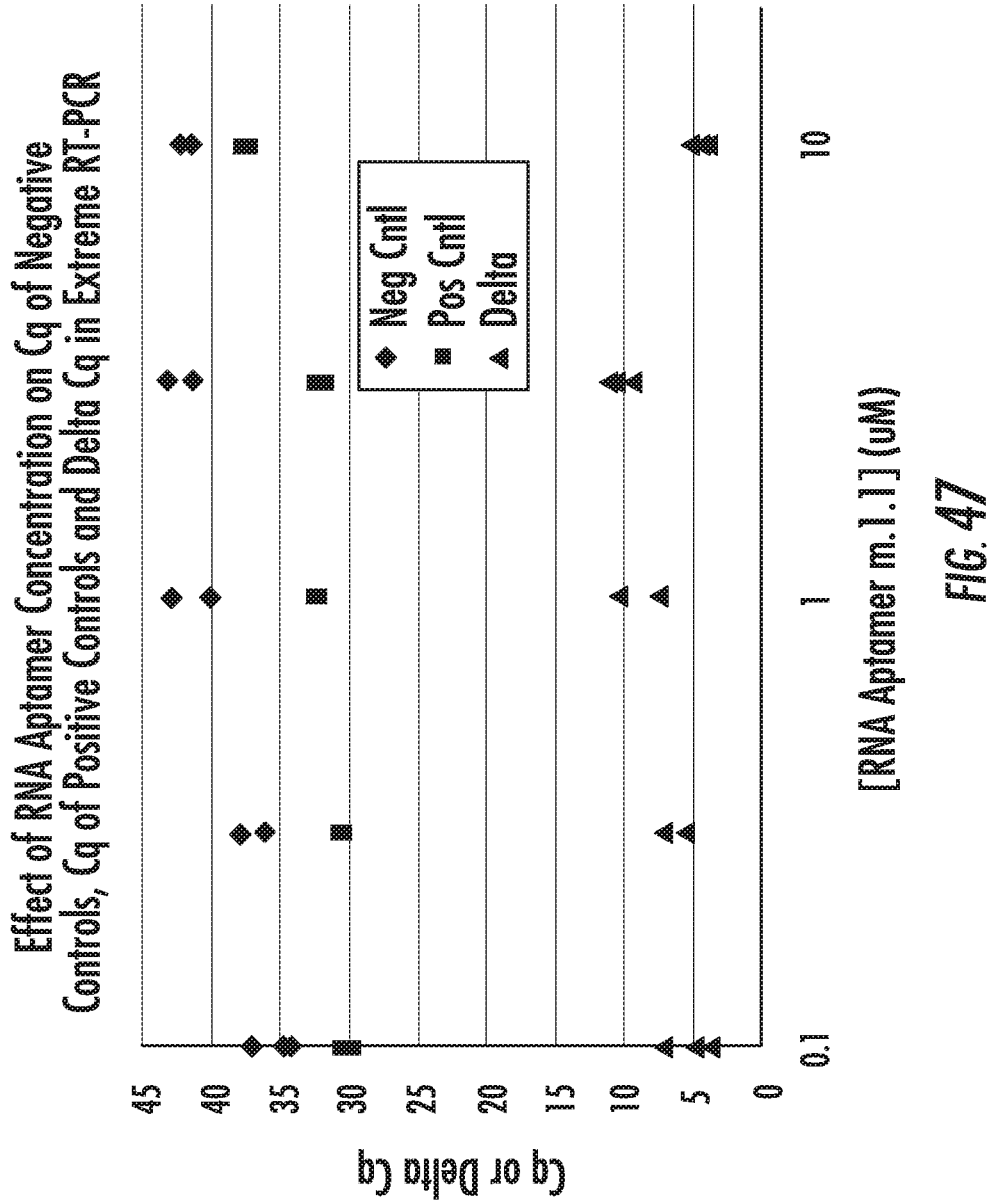
FIG. 47 is a graph showing the effect of RNA aptamer concentration on Cq, wherein diamonds represent the Cq for the negative control, squares represent the Cq for the positive control, and triangles represent the delta Cq.

Since specific RNA aptamers are available to inhibit MMLV, RNA aptamers dm1.1 and m.1.1 listed in Table 7 were used to inhibit primer-dimer formation in RT-PCR. First, these RNA aptamers were studied without any DNA aptamer. Conditions followed the PUM1 (intron 2) amplification above, with 2 seconds of RT at 60° C. The results for m.1.1 are shown in FIG. 47, showing the effect of aptamer concentration on Cq. Both the negative control and ΔCq were maximal at 3 µM of aptamer. Next, aptamer m.1.1 was compared to aptamer dm1.1, each at 3 µM, using the same system. The ΔCq for m.1.1 (9.0) was superior to the ΔCq for dm1.1 (7.5). Therefore, when RNA aptamers are used in isolation (without DNA aptamers) in RT-PCR, primer dimers can be decreased, and aptamer m.1.1 is a good choice.

When both RNA and DNA aptamers were optimized separately under extreme conditions, from the set tested, the best choice for the RNA aptamer was m.1.1 at 3 µM and the best choice for the DNA aptamer was Tctw.A-30 amino at 2 µM. In preliminary experiments, when both aptamers were tested together and compared against controls of just one aptamer and no aptamers at all, the ΔCq values were highest when both aptamers were present. It is anticipated that conditions where the ΔCqs resulting from RNA and DNA aptamers will be additive or synergistic, greatly increasing the resistance to primer dimer formation in extreme RT-PCR.

REFERENCES

1. Wittwer C T, Reed G B, Ririe K M. Rapid cycle DNA amplification. In: Mullis I K, Ferre F, Gibbs R, eds. *The polymerase chain reaction*, Vol. Deerfield Beach, Fla.: 174-181, 1994.
2. Wittwer C T, Fillmore G C, Hillyard D R. Automated polymerase chain reaction in capillary tubes with hot air. *Nucleic Acids Res* 1989; 17:4353-7.
3. Wittwer C T, Fillmore G C, Garling D J. Minimizing the time required for DNA amplification by efficient heat transfer to small samples. *Anal Biochem* 1990; 186:328-31.
4. Wittwer C T, Garling D J. Rapid cycle DNA amplification: time and temperature optimization. *Biotechniques* 1991; 10:76-83.
5. Wittwer C T, Marshall B C, Reed G H, Cherry J L. Rapid cycle allele-specific amplification: studies with the cystic fibrosis delta F508 locus. *Clin Chem* 1993; 39:804-9.
6. Schoder D, Schmalwieser A, Schauberger G, Hoorfar J, Kuhn M, Wagner M. Novel approach for assessing performance of PCR cyclers used for diagnostic testing. *J Clin Microbiol* 2005; 43:2724-8.
7. Herrmann M G, Durtschi J D, Wittwer C T, Voelkerding K V. Expanded instrument comparison of amplicon DNA melting analysis for mutation scanning and genotyping. *Clin Chem* 2007; 53:1544-8.
8. Herrmann M G, Durtschi J D, Bromley L K, Wittwer C T, Voelkerding K V. Amplicon DNA melting analysis for mutation scanning and genotyping: cross-platform comparison of instruments and dyes. *Clin Chem* 2006; 52:494-503.
9. Raja S, El-Hefnawy T, Kelly L A, Chestney M L, Luketich J D, Godfrey T E. Temperature-controlled primer limit for multiplexing of rapid, quantitative reverse transcription-PCR assays: application to intraoperative cancer diagnostics. *Clin Chem* 2002; 48:1329-37.
10. Wittwer C T, Ririe K M, Andrew R V, David D A, Gundry R A, Balis U J. The LightCycler: a microvolume multisample fluorimeter with rapid temperature control. *Biotechniques* 1997; 22:176-81.
11. Wittwer C T, Ririe K M, Rasmussen R P. Fluorescence monitoring of rapid cycle PCR for quantification. In: Ferre F, ed. *Gene Quantification*, New York: Birkhauser, 1998:129-44.
12. Elenitoba-Johnson O, David D, Crews N, Wittwer C T. Plastic vs. glass capillaries for rapid-cycle PCR. *Biotechniques* 2008; 44:487-8,490,492.
13. Roper M G, Easley C J, Landers J P. Advances in polymerase chain reaction on microfluidic chips. *Anal Chem* 2005; 77:3887-93.
14. Zhang C, Xing D. Miniaturized PCR chips for nucleic acid amplification and analysis: latest advances and future trends. *Nucleic Acids Res* 2007; 35:4223-37.
15. Cheng J, Shoffner M A, Hvichia G E, Kricka L J, Wilding P. Chip PCR. II. Investigation of different PCR amplification systems in microfabricated silicon-glass chips. *Nucleic Acids Res* 1996; 24:380-5.
16. Woolley A T, Hadley D, Landre P, deMello A J, Mathies R A, Northrup M A. Functional integration of PCR amplification and capillary electrophoresis in a microfabricated DNA analysis device. *Anal Chem* 1996; 68:4081-6.
17. Neuzil P, Zhang C, Pipper J, Oh S, Zhuo L. Ultra fast miniaturized real-time PCR: 40 cycles in less than six minutes. *Nucleic Acids Res* 2006; 34:e77.
18. Oda R P, Strausbauch M A, Huhmer A F, Borson N, Jurrens S R, Craighead J, et al. Infrared-mediated thermocycling for ultrafast polymerase chain reaction amplification of DNA. *Anal Chem* 1998; 70:4361-8.
19. Roper M G, Easley C J, Legendre L A, Humphrey J A, Landers J P. Infrared temperature control system for a completely noncontact polymerase chain reaction in microfluidic chips. *Anal Chem* 2007; 79:1294-300.
20. Friedman N A, Meldrum D R. Capillary tube resistive thermal cycling. *Anal Chem* 1998; 70:2997-3002.
21. Heap D M, Herrmann M G, Wittwer C T. PCR amplification using electrolytic resistance for heating and temperature monitoring. *Biotechniques* 2000; 29:1006-12.
22. Kopp M U, Mello A J, Manz A. Chemical amplification: continuous-flow PCR on a chip. *Science* 1998; 280:1046-8.
23. Hashimoto M, Chen P C, Mitchell M W, Nikitopoulos D E, Soper S A, Murphy M C. Rapid PCR in a continuous flow device. *Lab Chip* 2004; 4:638-45.
24. Crews N, Wittwer C, Gale B. Continuous-flow thermal gradient PCR. *BiomedMicrodevices* 2008; 10; 187-95.
25. Chiou J T, Matsudaira P T, Ehrlich D J. Thirty-cycle temperature optimization of a closed-cycle capillary PCR machine. *Biotechniques* 2002; 33:557-8, 60, 62.
26. Frey O, Bonneick S, Hierlemann A, Lichtenberg J. Autonomous microfluidic multi-channel chip for real-time PCR with integrated liquid handling. *Biomed Microdevices* 2007; 9:711-8.
27. Chen J, Wabuyele M, Chen H, Patterson D, Hupert M, Shadpour H, et al. Electrokinetically synchronized polymerase chain reaction microchip fabricated in polycarbonate. *Anal Chem* 2005; 77:658-66.
28. Sun Y, Kwok Y C, Nguyen N T. A circular ferrofluid driven microchip for rapid polymerase chain reaction. *Lab Chip* 2007; 7:1012-7.
29. Agrawal N, Hassan Y A, Ugaz V M. A pocket-sized convective PCR thermocycler. *Angew Chem Int Ed Engl* 2007; 46:4316-9.
30. Zhang C, Xu J, Ma W, Zheng W. PCR microfluidic devices for DNA amplification. *Biotechnol Adv* 2006; 24:243-84.
31. Wheeler E K, Benett W, Stratton P, Richards J, Chen A, Christian A, et al. Convectively driven polymerase chain reaction thermal cycler. *Anal Chem* 2004; 76:4011-6.

32. Belgrader P, Benett W, Hadley D, Long G, Mariella R, Jr., Milanovich F, et al. Rapid pathogen detection using a microchip PCR array instrument. *Clin Chem* 1998; 44:2191-4.
33. Terazona H, Takei, H, Hattori A, Yasuda K. Development of a high-speed real-time polymerase chain reaction system using a circulating water-based rapid heat exchange. *Jap J Appl Phys* 2010; 49:06GM05.
34. Wheeler E K, Hara C A, Frank J, Deotte J, Hall S B, Benett W, Spadaccini C, Beer N R. Under-three minute PCR: Probing the limits of fast amplification. *Analyst* 2011; 136(16):3707-12.
35. Fuchiwaki Y, Nagai H, Saito M, Tamiya E. Ultra-rapid flow-through polymerase chain reaction microfluidics using vapor pressure. *Biosens Bioelect* 2011; 27:88-94.
36. Maltezos G, Johnston M, Taganov K, Srichantaratsamee C, Gorman J, Baltimore D, Chantratita W and Scherer A, Exploring the limits of ultrafast polymerase chain reaction using liquid for thermal heat exchange: A proof of principle. *Appl. Phys. Lett.,* 2010; 97: 264101.
37. Wilhelm J, Hahn M, Pingoud A. Influence of DNA target melting behavior on real-time PCR quantification. *Clin Chem* 2000; 46:1738-43.
38. Zuna J, Muzikova K, Madzo J, Krejci O, Trka J. Temperature non-homogeneity in rapid airflow-based cycler significantly affects real-time PCR. *Biotechniques* 2002; 33:508, 10, 12.
39. von Kanel T, Adolf F, Schneider M, Sanz J, Gallati S. Sample number and denaturation time are crucial for the accuracy of capillary-based LightCyclers. *Clin Chem* 2007; 53:1392-4.
40. Wittwer C T, Herrmann M G. Rapid thermal cycling and PCR kinetics. In: Innis M, Gelfand D, Sninsky J, eds. *PCR Methods Manual*, Vol. San Diego: Academic Press, 1999:211-29.
41. Wittwer C T, Reed G H, Gundry C N, Vandersteen J G, Pryor R J. High-resolution genotyping by amplicon melting analysis using LCGreen. *Clin Chem* 2003; 49:853-60.
42. von Ahsen N, Wittwer C T, Schutz E. Oligonucleotide melting temperatures under PCR conditions: nearest-neighbor corrections for Mg(2+), deoxynucleotide triphosphate, and dimethyl sulfoxide concentrations with comparison to alternative empirical formulas. *Clin Chem* 2001; 47:1956-61.
43. Ririe K M, Rasmussen R P, Wittwer C T. Product differentiation by analysis of DNA melting curves during the polymerase chain reaction. *Anal Biochem* 1997; 245: 154-60.
44. Wittwer C T, Herrmann M G, Moss A A, Rasmussen R P. Continuous fluorescence monitoring of rapid cycle DNA amplification. *Biotechniques* 1997; 22:130-1, 4-8.
45. Weis J H, Tan S S, Martin B K, Wittwer C T. Detection of rare mRNAs via quantitative RT-PCR. *Trends Genet* 1992; 8:263-4.
46. Brown R A, Lay M J, Wittwer C T. Rapid cycle amplification for construction of competitive templates. In: Horton R M, Tait R C, eds. *Genetic Engineering with PCR*, Vol. Norfolk: Horizon Scientific Press, 1998:57-70.
47. Ausubel et al., *Current Protocols in Molecular Biology*, John Wiley & Sons, New York, N.Y., 1998
48. Whitney S E, "Analysis of rapid thermocycling for the polymerase chain reaction," Ph.D. thesis, University of Nebraska, 2004.
49. Lawyer F C, Stoffel S, Saiki R K, Chang S Y, Landre P A, Abramson R D, Gelfand D H. High-level expression, purification and enzymatic characterization of full-length *Thermus aquaticus* DNA polymerase and a truncated form deficient of 5' to 3' exonuclease activity. *PCR Meth Appl.* 1993; 2:275-287.
50. Innis M A, Myamo K B, Gelfand D H, Brow M A D. DNA sequencing with *Thermus aquaticus* DNA polymerase and direct sequencing of polymerase chain reaction-amplified DNA. *Proc. Natl. Acad. Sci USA* 1988; 85:9436-40.
51. Terazono H, Hattori A, Takei H, Takeda K, Yasuda K. Development of 1480 nm photothermal high-speed real-time polymerase chain reaction system for rapid nucleotide recognition. *Jpn J Appl Phys.* 2008; 47:5212-6.
52. Wittwer C T, Rasmussen R P, Ririe K M. Rapid PCR and melting curve analysis. In: *The PCR Revolution: Basic Technologies and Applications*, Bustin S A, ed. Cambridge Univ Press, New York, 48-69, 2010.
53. Fuchiwaki Y, Saito M, Wakida S, Tamiya E, Nagai H. A practical liquid plug flow-through polymerase chain-reaction system based on a heat-resistant resin chip. *Anal Sci.* 2011; 27:225-30.
54. Kim H, Dixit S, Green C J, Faris G W. Nanodroplet real-time PCR system with laser assisted heating. *Optics Express* 2009; 17:218-27.
55. Obeid P J, Christopoulos T K, Crabtree H J, Backhouse C J. Microfabricated device for DNA and RNA amplification by continuous-flow polymerase chain reaction and reverse transcription-polymerase chain reaction with cycle number selection. *Anal Chem* 2003; 75:288-95.
56. Giordano B C, Ferrance J, Swedberg S, Huhmer A F R, Landers J P. Polymerase chain reaction in polymeric microchips: DNA amplification in less than 240 seconds. *Anal Biochem* 2001; 291:124-132.
57. Pal, D., Venkataraman, V., Mohan, K. N., Chandra, H. S., & Nataraj an, V. (2004). A power-efficient thermocycler based on induction heating for DNA amplification by polymerase chain reaction. *Review of Scientific Instruments,* 75(9), 2880-2883.
58. Yuanzhi Lao, F. E. H., Tay, F. E. H., Guolin Xu, Hartono, D., & Lee, Y. Y. (2003). A Non-Contact Micro Thermocycling Chip for Polymerase Chain Reactions. *International Journal of Computational Engineering Science,* 4(3), 651-654.
59. Shen F, Sun, B, Kreutz J E. Davydova E K, Du W, Reddy P L, Joseph L J, and. Ismagilov R F. Multiplexed Quantification of Nucleic Acids with Large Dynamic Range Using Multivolume Digital RT-PCR on a Rotational SlipChip Tested with HIV and Hepatitis C Viral Load. *J. Am. Chem. Soc.* 2011, 133, 17705-17712.
60. Bustin, S. et al., Variability of the reverse transcription step: practical implications, *Clinical Chemistry* 61, 201-12, 2015.
61. J L Montgomery and CT Wittwer, Influence of PCR reagents on DNA polymerase extension rates measured on real-time PCR instruments, *Clin Chem* 60:334-340 (2014).
62. S Mifatovic-Rustempasic et al., Sensitive and specific quantitative detection of rotavirus A by one-step real-time reverse transcription-PCR assay without antecedent double-stranded-RNA denaturation, *J Clin Microbiol* (2013), 51, 3047-54.
63. P Carninci et al., Thermostabilization and thermoactivation of thermolabile enzymes by trehalose and its application for the synthesis of full length cDNA, *PNAS,* 1998:95:520-4 and AN Spiess et al., Trehalose is a potent enhancer: Lowering of DNA melting temperature and thermal stabilization of Taq polymerase by the disaccharide trehalose, *Clin Chem,* 2004; 50: 1256-9.

64. Gerard G F, D'Alessio J M. Chapter 6 (73-93) From: *Methods in Molecular Biology*, Vol. 16, *Enzymes of Molecular Biology*, Edited by MM Burell, 1993, Humana Press, Inc., Totowa, N.J.
65. Brownie J et al., The elimination of primer-dimer accumulation in PCR. *Nucl Acid Res,* 1997; 25:3235-41.
66. Sellner L N et al., Reverse transcriptase inhibits Taq polymerase activity. *Nucl Acid Res,* 1992; 20:1487-90.
67. Chandler D P et al., Reverse Transcriptase (RT) inhibition of PCR at low concentrations of template and its implications for quantitative RT-PCR, *Appl Environ Microbiol,* 1998; 64:669-77.
68. Suslov O et al., PCR inhibition by reverse transcriptase leads to an overestimation of amplification efficiency, *Nucl Acid Res,* 2005; 33:e181.
69. Lin Y and Jayasena S D, Inhibition of multiple thermostable DNA polymerases by a heterodimeric aptamer, *J Mol Biol,* 1997; 271:100-111.
70. Noma T and Ikebukuro K, Aptamer selection based on inhibitory activity using an evolution-mimicking algorithm, *Biochem Biophys Res Comm,* 2006, 347, 226-31.
71. Chen H and Gold L, Selection of high-affinity RNA ligands to reverse transcriptase: Inhibition of cDNA synthesis and RNase h activity, *Biochemistry,* 1994, 33, 8746-56.
72. Dang C and Jayasena S D, Oligonucleotide inhibitors of Taq DNA polymerase facilitate detection of low copy number targets by PCR, *J Mol Biol,* 1996; 264:268-78.

Several patents, patent publications and non-patent documents are cited throughout the specification in order to describe the state of the art to which this invention pertains. Each of these documents and citations is incorporated herein by reference as though set forth in full.

Although the invention has been described in detail with reference to certain embodiments, variations and modifications exist within the scope and spirit of the invention as described and defined in the following claims.

What is claimed is:

1. A method for amplifying a target RNA in a biological sample during amplification comprising the steps of:
provoding a reaction mixture comprising the biological sample, a reverse transcription enzyme, a thermostable polymerase, and primers configured for amplification of the target RNA in the biological sample, wherein the reverse transcription enzyme is provided at a reduced concentration, the polymerase is provided at a concentration of at least 0.5 µM and primers are each provided at a concentration of at least 2 µM, wherein the reduced concentration of the reverse transcription enzyme is below a manufacturer's recommended concentration for a reverse transcription (RT) reaction for the reverse transcription enzyme;
reverse transcribing the RNA to DNA by incubating for a reverse transcription time of no longer than 5 minutes, and
amplifying the DNA by polymerase chain reaction by thermally cycling the biological sample between at least a denaturation temperature and an elongation temperature through a plurality of amplification cycles using an extreme temperature cycling profile, wherein each cycle is completed in a cycle time less than 20 seconds per cycle.

2. The method of claim 1, wherein the reverse transcription time is no longer than 16 seconds.

3. The method of claim 1, wherein the amplifying step takes place in the same reaction mixture as the reverse transcribing step.

4. The method of claim 1, wherein the reaction mixture has a KCl concentration of no more than 10 mM.

5. The method of claim 1, wherein the reaction mixture is substantially free of potassium.

6. The method of claim 1, wherein the reaction mixture further comprises a reducing agent.

7. The method of claim 1, wherein the transcription enzyme is MMLV provided at a concentration of no more than 4.0 Units/µL.

8. The method of claim 1, wherein the reverse transcription enzyme is AMV provided at a concentration of no more than 0.8 Units/µL.

9. The method of claim 1, wherein
the amplifying step has an amplification time equal to the cycle time times the number of cycles,
the method has an overall time equal to the sum of the reverse transcription time and the amplification time, and
the reverse transcription time is no more than 50% of the overall time.

10. The method of claim 9, wherein the reverse transcription time is no more than 10% of the overall time.

11. The method of claim 1, wherein a first portion of the reaction mixture is provided frozen and a second portion of the reaction mixture is provided chilled, wherein one of the first and second portions comprises the thermostable polymerase and the other of the first and second portions comprises the reverse transcriptase enzyme, and further comprising mixing the first portion and second portion prior to the reverse transcribing step.

12. The method of claim 11, wherein the first portion of the reaction mixture is provided with a first primer and the second portion of the reaction mixture is provided with a second primer, and further comprising mixing the first portion and second portion prior to the reverse transcribing step.

13. The method of claim 11, wherein the reverse transcribing step begins within one second of completion of the mixing step.

14. The method of claim 1, wherein the reaction mixture further comprises an aptamer.

15. The method of claim 14, wherein the aptamer is an RNA aptamer.

16. The method of claim 14, wherein the aptamer is a mixture of an RNA aptamer and a DNA aptamer.

17. The method of claim 14, wherein the aptamer is modified with a 3'-blocker.

18. The method of claim 14, wherein the aptamer has a stabilized hairpin loop.

19. The method of claim 1, wherein the reverse transcription time is 2.5 seconds or less.

* * * * *

UNITED STATES PATENT AND TRADEMARK OFFICE
CERTIFICATE OF CORRECTION

PATENT NO. : 10,900,074 B2
APPLICATION NO. : 15/771968
DATED : January 26, 2021
INVENTOR(S) : Wittwer et al.

It is certified that error appears in the above-identified patent and that said Letters Patent is hereby corrected as shown below:

In the Specification

Column 25, Line 55: Please correct "8 polymerase" to read -- 8 μM polymerase --

Column 25, Line 60: Please correct "1 and 8 and" to read -- 1 and 8 μM, and --

Column 25, Line 61: Please correct "8 depending" to read -- 8 μM, depending --

Column 25, Line 66: Please correct "2-8 and" to read -- 2-8 μM, and --

Column 26, Line 19: Please correct "0.5 and more illustratively about 1.0 for" to read -- 0.5 μM, and more illustratively about 1.0 μM, for --

Column 26, Line 55: Please correct "4 while" to read -- 4 μM, while --

Column 27, Line 8: Please correct "2-4 yield" to read -- 2-4 μM, yield --

Column 30, Line 35: Please correct "was 1 with" to read -- was 1 μl, with --

Column 41, Line 2: Please correct "(6" to read -- (6 μM), --

Column 45, Line 14: Please correct "in 5 Negatives" to read -- in 5 μL. Negatives --

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*